United States Patent
Walsh et al.

(10) Patent No.: US 11,865,534 B2
(45) Date of Patent: Jan. 9, 2024

(54) IMAGING ANALYZER FOR TESTING ANALYTES

(75) Inventors: Bruce Walsh, Londonderry, NH (US);
Boris Blanter, Lexington, MA (US);
Matthew Barra, Hingham, MA (US);
Brian Connolly, Winthrop, MA (US);
Greg Yantz, Somerville, MA (US);
Paul Gervasio, North Billerica, MA (US); Don Straus, Charlestown, MA (US)

(73) Assignee: FIRST LIGHT DIAGNOSTICS, INC., Chelmsford, MA (US)

( * ) Notice: Subject to any disclaimer, the term of this patent is extended or adjusted under 35 U.S.C. 154(b) by 0 days.

(21) Appl. No.: 13/120,533

(22) PCT Filed: Sep. 24, 2009

(86) PCT No.: PCT/US2009/058274
§ 371 (c)(1),
(2), (4) Date: Nov. 7, 2011

(87) PCT Pub. No.: WO2010/036829
PCT Pub. Date: Apr. 1, 2010

(65) Prior Publication Data
US 2012/0046203 A1    Feb. 23, 2012

Related U.S. Application Data

(60) Provisional application No. 61/099,830, filed on Sep. 24, 2008.

(51) Int. Cl.
*B01L 3/00*    (2006.01)
*G01N 35/00*   (2006.01)
(Continued)

(52) U.S. Cl.
CPC ........ *B01L 3/502715* (2013.01); *A61B 5/157* (2013.01); *A61B 5/150022* (2013.01);
(Continued)

(58) Field of Classification Search
None
See application file for complete search history.

(56) References Cited

U.S. PATENT DOCUMENTS

| | | |
|---|---|---|
| 2,672,431 A | 3/1954 | Goetz |
| 2,761,813 A | 9/1956 | Goetz |

(Continued)

FOREIGN PATENT DOCUMENTS

| | | |
|---|---|---|
| AU | 760425 B2 | 3/2000 |
| CN | 101254482 A | 9/2008 |

(Continued)

OTHER PUBLICATIONS

Al-Hakiem et al., "Development of Fluoroimmunoassays for the Determination of Individual or Combined Levels of Procainamide and N-Acetylprocainamide in Serum." *J. Immunoassay* 3(1):91-110, 1982.

(Continued)

*Primary Examiner* — Neil N Turk
(74) *Attorney, Agent, or Firm* — BALLARD SPAHR LLP

(57) ABSTRACT

The invention provides analyzers that improve tests for detecting specific cellular, viral, and molecular targets in clinical, industrial, or environmental samples. The invention permits efficient and specific selection and sensitive imaging detection of individual microscopic targets at low magnification. Automated embodiments allow efficient walk-away, on-demand, random-access high-throughput testing. The analyzers perform tests without requiring wash steps thus streamlining engineering and lowering costs. Thus, the invention provides analyzers that can deliver rapid, accurate, (Continued)

Imaging and optics system diagram (Example 1)

and quantitative, easy-to-use, and cost-effective tests for analytes.

27 Claims, 77 Drawing Sheets

(51) Int. Cl.
    *G01N 35/02*     (2006.01)
    *G01N 33/543*     (2006.01)
    *A61B 5/157*     (2006.01)
    *G01N 21/03*     (2006.01)
    *G01N 21/25*     (2006.01)
    *G01N 21/64*     (2006.01)
    *A61B 5/15*     (2006.01)
    *A61B 5/151*     (2006.01)
    *B01L 7/00*     (2006.01)
    *B01L 9/00*     (2006.01)
    *A61B 5/117*     (2016.01)
    *G01N 35/04*     (2006.01)

(52) U.S. Cl.
    CPC ...... *A61B 5/15113* (2013.01); *A61B 5/15186* (2013.01); *A61B 5/150213* (2013.01); *A61B 5/150221* (2013.01); *A61B 5/150274* (2013.01); *A61B 5/150305* (2013.01); *A61B 5/150343* (2013.01); *A61B 5/150351* (2013.01); *A61B 5/150412* (2013.01); *A61B 5/150503* (2013.01); *A61B 5/150786* (2013.01); *B01L 3/5027* (2013.01); *B01L 3/5029* (2013.01); *B01L 3/5082* (2013.01); *B01L 3/502738* (2013.01); *B01L 3/502761* (2013.01); *G01N 21/03* (2013.01); *G01N 21/253* (2013.01); *G01N 21/6452* (2013.01); *G01N 21/6458* (2013.01); *G01N 33/54373* (2013.01); *G01N 35/0098* (2013.01); *G01N 35/02* (2013.01); *G01N 35/025* (2013.01); *A61B 5/117* (2013.01); *A61B 5/151* (2013.01); *B01L 7/00* (2013.01); *B01L 9/52* (2013.01); *B01L 2200/025* (2013.01); *B01L 2200/026* (2013.01); *B01L 2200/027* (2013.01); *B01L 2200/0605* (2013.01); *B01L 2200/10* (2013.01); *B01L 2300/022* (2013.01); *B01L 2300/042* (2013.01); *B01L 2300/043* (2013.01); *B01L 2300/046* (2013.01); *B01L 2300/048* (2013.01); *B01L 2300/0654* (2013.01); *B01L 2300/0681* (2013.01); *B01L 2300/0864* (2013.01); *B01L 2400/043* (2013.01); *B01L 2400/0406* (2013.01); *B01L 2400/0409* (2013.01); *B01L 2400/0415* (2013.01); *B01L 2400/0457* (2013.01); *B01L 2400/0472* (2013.01); *B01L 2400/0481* (2013.01); *B01L 2400/0677* (2013.01); *B01L 2400/0683* (2013.01); *G01N 21/6428* (2013.01); *G01N 2021/0325* (2013.01); *G01N 2021/0346* (2013.01); *G01N 2035/0401* (2013.01); *G01N 2035/0429* (2013.01)

(56) References Cited

U.S. PATENT DOCUMENTS

| | | | |
|---|---|---|---|
| 3,694,317 A | 9/1972 | Scher | |
| 3,981,776 A | 9/1976 | Saxholm | |
| 4,097,586 A | 6/1978 | Gross | |
| 4,098,876 A | 7/1978 | Piasio et al. | |
| 4,115,535 A | 9/1978 | Giaever | |
| 4,125,375 A | 11/1978 | Hunter | |
| 4,129,419 A * | 12/1978 | Hermann, Jr. | ............ 422/64 |
| 4,141,687 A | 2/1979 | Forrest et al. | |
| 4,157,323 A | 6/1979 | Yen et al. | |
| 4,177,253 A | 12/1979 | Davies et al. | |
| 4,222,744 A | 9/1980 | McConnell | |
| 4,436,826 A | 3/1984 | Wang | |
| 4,438,068 A | 3/1984 | Forrest | |
| 4,454,233 A | 6/1984 | Wang | |
| 4,455,370 A | 6/1984 | Bartelsman et al. | |
| 4,477,578 A | 10/1984 | Miles et al. | |
| 4,537,861 A | 8/1985 | Elings et al. | |
| 4,562,157 A | 12/1985 | Lowe et al. | |
| 4,565,783 A | 1/1986 | Hansen et al. | |
| 4,582,810 A | 4/1986 | Rosenstein | |
| 4,587,213 A | 5/1986 | Malecki | |
| 4,614,585 A | 9/1986 | Mehra et al. | |
| 4,693,972 A | 9/1987 | Mansour et al. | |
| 4,731,337 A | 3/1988 | Luotola et al. | |
| 4,745,077 A | 5/1988 | Holian et al. | |
| 4,750,820 A | 6/1988 | Pareigat | |
| 4,777,137 A | 10/1988 | Lemonnier | |
| 4,777,145 A * | 10/1988 | Luotola | ............ G01N 33/54326 436/525 |
| 4,912,037 A | 3/1990 | Lemonnier | |
| 4,922,092 A | 5/1990 | Rushbrooke et al. | |
| 4,959,301 A | 9/1990 | Weaver et al. | |
| 4,988,302 A | 1/1991 | Smith et al. | |
| 4,988,618 A | 1/1991 | Li et al. | |
| 5,073,497 A | 12/1991 | Schwartz | |
| 5,089,413 A | 2/1992 | Nelson et al. | |
| 5,130,733 A | 7/1992 | Taniguchi et al. | |
| 5,137,812 A | 8/1992 | Matner | |
| 5,166,079 A * | 11/1992 | Blackwood | ......... G01N 21/6428 435/7.1 |
| 5,190,666 A | 3/1993 | Bisconte | |
| 5,232,838 A | 8/1993 | Nelson et al. | |
| 5,238,810 A | 8/1993 | Fujiwara et al. | |
| 5,258,284 A | 11/1993 | Morris, Jr. et al. | |
| 5,262,526 A | 11/1993 | Sasamoto et al. | |
| 5,292,644 A | 3/1994 | Berg | |
| 5,306,420 A | 4/1994 | Bisconte | |
| 5,321,545 A | 6/1994 | Bisconte | |
| 5,355,215 A | 10/1994 | Schroeder et al. | |
| 5,366,867 A | 11/1994 | Kawakami et al. | |
| 5,464,749 A | 11/1995 | Schwarzberg et al. | |
| 5,474,910 A | 12/1995 | Alfano | |
| 5,510,246 A | 4/1996 | Morgan | |
| 5,538,857 A | 7/1996 | Rosenthal et al. | |
| 5,541,069 A | 7/1996 | Mortensen et al. | |
| 5,552,272 A | 9/1996 | Bogart | |
| 5,558,839 A | 9/1996 | Matte et al. | |
| 5,582,982 A | 12/1996 | Cubbage et al. | |
| 5,585,241 A | 12/1996 | Lindmo | |
| 5,604,351 A | 2/1997 | Bisconte | |
| 5,606,413 A | 2/1997 | Bellus et al. | |
| 5,624,850 A | 4/1997 | Kumar et al. | |
| 5,652,939 A | 7/1997 | Verlinden et al. | |
| 5,653,939 A | 8/1997 | Hollis et al. | |
| 5,663,057 A | 9/1997 | Drocourt et al. | |
| 5,672,880 A | 9/1997 | Kain | |
| 5,681,530 A | 10/1997 | Kuster et al. | |
| 5,681,712 A | 10/1997 | Nelson | |
| 5,694,478 A | 12/1997 | Braier et al. | |
| 5,705,402 A | 1/1998 | Leland et al. | |
| 5,736,405 A | 4/1998 | Alfano et al. | |
| 5,744,322 A | 4/1998 | Krejcarek et al. | |
| 5,766,868 A | 6/1998 | Seto | |
| 5,792,617 A | 8/1998 | Rotman | |
| 5,814,454 A | 9/1998 | Ju | |
| 5,821,066 A | 10/1998 | Pyle et al. | |
| 5,828,716 A | 10/1998 | Bisconte de Saint Julien | |
| 5,843,766 A | 12/1998 | Applegate et al. | |
| 5,852,498 A | 12/1998 | Youvan et al. | |
| 5,861,251 A | 1/1999 | Park et al. | |
| 5,861,270 A | 1/1999 | Nelis | |
| 5,891,394 A | 4/1999 | Drocourt et al. | |
| 5,914,245 A | 6/1999 | Bylina et al. | |
| 5,958,790 A | 9/1999 | Cerny | |
| 5,968,766 A | 10/1999 | Powers | |

(56) References Cited

U.S. PATENT DOCUMENTS

| | | | |
|---|---|---|---|
| 5,976,892 A | 11/1999 | Bisconte | |
| 5,981,180 A | 11/1999 | Chandler et al. | |
| 5,985,675 A | 11/1999 | Charm et al. | |
| 5,989,835 A | 11/1999 | Dunlay et al. | |
| 5,993,740 A | 11/1999 | Niiyama et al. | |
| 6,048,723 A | 4/2000 | Banes | |
| 6,051,395 A | 4/2000 | Rocco | |
| 6,121,055 A | 9/2000 | Hargreaves | |
| 6,122,396 A | 9/2000 | King et al. | |
| 6,130,931 A * | 10/2000 | Laurila et al. | 378/45 |
| 6,140,653 A | 10/2000 | Che | |
| 6,165,742 A | 12/2000 | Ofjord et al. | |
| 6,171,780 B1 | 1/2001 | Pham et al. | |
| 6,200,762 B1 | 3/2001 | Zlokarnik et al. | |
| 6,214,560 B1 | 4/2001 | Yguerabide et al. | |
| 6,258,326 B1 | 7/2001 | Modlin | |
| 6,259,807 B1 | 7/2001 | Ravkin | |
| 6,268,222 B1 | 7/2001 | Chandler et al. | |
| 6,274,384 B1 | 8/2001 | Starzl et al. | |
| 6,306,589 B1 | 10/2001 | Muller et al. | |
| 6,309,822 B1 | 10/2001 | Fodor et al. | |
| 6,345,115 B1 | 2/2002 | Ramm et al. | |
| 6,358,730 B1 | 3/2002 | Kane | |
| 6,472,166 B1 | 10/2002 | Wardlaw et al. | |
| 6,473,698 B1 * | 10/2002 | Albert | G06V 20/698 702/45 |
| 6,582,912 B1 | 6/2003 | Rousseau et al. | |
| 6,623,983 B1 | 9/2003 | Terstappen et al. | |
| 6,664,528 B1 | 12/2003 | Cartlidge et al. | |
| 6,710,879 B1 | 3/2004 | Hansen et al. | |
| 6,727,071 B1 | 4/2004 | Dunlay et al. | |
| 6,764,648 B1 * | 7/2004 | Roach et al. | 422/63 |
| 6,792,132 B1 | 9/2004 | Hara et al. | |
| 6,852,527 B2 | 2/2005 | Chan et al. | |
| 6,919,960 B2 | 7/2005 | Hansen et al. | |
| 7,068,365 B2 | 6/2006 | Hansen et al. | |
| 7,160,687 B1 | 1/2007 | Kapur et al. | |
| 7,582,415 B2 | 9/2009 | Straus | |
| 7,763,405 B2 | 7/2010 | Wu et al. | |
| 7,820,430 B2 | 10/2010 | Weng et al. | |
| 8,021,848 B2 | 9/2011 | Straus | |
| 2001/0039060 A1 | 11/2001 | Siiman et al. | |
| 2002/0028471 A1* | 3/2002 | Oberhardt | 435/7.21 |
| 2002/0055092 A1* | 5/2002 | Hochman | 435/4 |
| 2002/0137106 A1 | 9/2002 | Leung et al. | |
| 2002/0155033 A1* | 10/2002 | Strand | G01N 30/88 436/178 |
| 2003/0068638 A1* | 4/2003 | Cork | G01N 21/253 435/6.12 |
| 2003/0082516 A1 | 5/2003 | Straus | |
| 2003/0143580 A1 | 7/2003 | Straus | |
| 2003/0170613 A1* | 9/2003 | Straus | 435/5 |
| 2004/0010192 A1* | 1/2004 | Benaron | A61B 5/0075 600/431 |
| 2004/0048395 A1 | 3/2004 | Lee et al. | |
| 2004/0171121 A1 | 9/2004 | Leppla et al. | |
| 2004/0172000 A1 | 9/2004 | Roe et al. | |
| 2004/0246483 A1 | 12/2004 | Hansen et al. | |
| 2005/0013737 A1* | 1/2005 | Chow et al. | 422/63 |
| 2005/0148085 A1 | 7/2005 | Larsen | |
| 2005/0191687 A1 | 9/2005 | Wang et al. | |
| 2005/0220670 A1* | 10/2005 | Palmieri et al. | 422/64 |
| 2005/0221403 A1 | 10/2005 | Gazenko | |
| 2005/0225766 A1 | 10/2005 | Hansen et al. | |
| 2005/0226779 A1 | 10/2005 | Oldham et al. | |
| 2006/0006067 A1 | 1/2006 | Unger | |
| 2006/0051816 A1 | 3/2006 | Hsieh et al. | |
| 2006/0121055 A1 | 6/2006 | Campbell et al. | |
| 2006/0129327 A1 | 6/2006 | Kim et al. | |
| 2006/0188967 A1 | 8/2006 | Nalin et al. | |
| 2006/0210435 A1* | 9/2006 | Alavie et al. | 422/65 |
| 2006/0216696 A1 | 9/2006 | Goguen | |
| 2006/0256340 A1 | 11/2006 | Hansen et al. | |
| 2006/0292552 A1 | 12/2006 | Haquette et al. | |
| 2007/0014695 A1 | 1/2007 | Yue et al. | |
| 2007/0184546 A1* | 8/2007 | Farrelly et al. | 435/286.3 |
| 2007/0212681 A1 | 9/2007 | Shapiro et al. | |
| 2007/0212747 A1 | 9/2007 | Browne et al. | |
| 2008/0003571 A1 | 1/2008 | McKernan et al. | |
| 2008/0014576 A1 | 1/2008 | Jovanovich et al. | |
| 2008/0032328 A1* | 2/2008 | Cline et al. | 435/40.5 |
| 2008/0038738 A1* | 2/2008 | Weigum et al. | 435/6 |
| 2008/0200343 A1* | 8/2008 | Clemens et al. | 506/9 |
| 2008/0206099 A1* | 8/2008 | Aruga et al. | 422/68.1 |
| 2009/0137029 A1 | 5/2009 | Breidenthal et al. | |
| 2009/0315987 A1 | 12/2009 | Straus | |
| 2010/0248281 A1 | 9/2010 | Straus | |
| 2012/0045826 A1 | 2/2012 | Yantz et al. | |
| 2012/0149007 A1 | 6/2012 | Abrams et al. | |
| 2013/0011566 A1 | 1/2013 | Colin et al. | |

FOREIGN PATENT DOCUMENTS

| | | |
|---|---|---|
| DE | 19608320 A1 | 8/1997 |
| DE | 19631997 A1 | 2/1998 |
| DE | 19940810 A1 | 5/2000 |
| EP | 0171174 A2 | 2/1986 |
| EP | 0574977 A1 | 12/1993 |
| EP | 0753732 A2 | 1/1997 |
| EP | 1207394 A2 | 5/2002 |
| EP | 1508374 A2 | 2/2005 |
| JP | S62-501647 A | 7/1987 |
| JP | H02-502405 A | 8/1990 |
| JP | H02-278155 A | 11/1990 |
| JP | 3102240 A | 4/1991 |
| JP | H3-83598 A | 4/1991 |
| JP | 6-501311 A | 2/1994 |
| JP | H08-201391 A | 8/1996 |
| JP | 10-295362 A | 11/1998 |
| JP | H11-148901 A | 6/1999 |
| JP | H11-346795 A | 12/1999 |
| JP | 2000-508778 A | 7/2000 |
| JP | 2000-509827 A | 8/2000 |
| JP | 2000-275258 A | 10/2000 |
| JP | 2001-224355 A | 8/2001 |
| JP | 2001-512875 A | 8/2001 |
| JP | 2002-125656 A | 5/2002 |
| JP | 2003-294596 A | 10/2003 |
| JP | 2004-070039 A | 3/2004 |
| JP | 2004-125799 A | 4/2004 |
| JP | 2006-087336 A | 4/2006 |
| JP | 2006-162466 A | 6/2006 |
| JP | 2007-526807 A | 9/2007 |
| JP | 2008-96223 A | 4/2008 |
| JP | 2008-513022 A | 5/2008 |
| WO | WO-83/01581 A1 | 5/1983 |
| WO | WO-86/04684 A1 | 8/1986 |
| WO | WO-89/05456 A1 | 6/1989 |
| WO | WO-92/05448 A2 | 4/1992 |
| WO | WO-97/40181 A1 | 10/1997 |
| WO | WO-97/44664 A1 | 11/1997 |
| WO | WO-98/38490 A1 | 9/1998 |
| WO | WO-98/50577 A1 | 11/1998 |
| WO | WO-99/08233 A1 | 2/1999 |
| WO | WO-99/20789 A1 | 4/1999 |
| WO | WO-99/35483 A1 | 7/1999 |
| WO | WO-99/36577 A1 | 7/1999 |
| WO | WO-99/40176 A1 | 8/1999 |
| WO | WO-99/58948 A2 | 11/1999 |
| WO | WO-00/04382 A1 | 1/2000 |
| WO | WO-00/47766 A1 | 8/2000 |
| WO | WO-01/57522 A2 | 8/2001 |
| WO | WO-01/61348 A1 | 8/2001 |
| WO | WO-03/036290 A1 | 5/2003 |
| WO | WO-03/073817 A2 | 9/2003 |
| WO | WO-2005/082254 A2 | 9/2005 |
| WO | WO-2006/032044 A2 | 3/2006 |
| WO | WO-2006/106962 A1 | 10/2006 |
| WO | WO-2007/038478 A1 | 4/2007 |
| WO | WO-2007/145091 A1 | 12/2007 |
| WO | WO-2008/005998 A2 | 1/2008 |
| WO | WO-2010/036808 A1 | 4/2010 |
| WO | WO-2010/036827 A1 | 4/2010 |

(56) References Cited

FOREIGN PATENT DOCUMENTS

| WO | WO-2011/117545 A1 | 9/2011 |
|----|-------------------|--------|
| WO | WO-2013/070730 A2 | 5/2013 |
| WO | WO-2013/158666 A1 | 10/2013 |

OTHER PUBLICATIONS

Allman et al., "Fluoroimmunoassay of Progesterone in Human Serum or Plasma" *Clin. Chem.* 27: 1176-1179, 1981.
The brain, <http://www.enchantedlearning.com/subjects/anatomy/brain/neuron.html>, retrieved Nov. 4, 2007 (4 pages).
Clean Technology, 5(8), 60-61 (1995) (No english translation provided).
Colony Counter (<http://www.topac.com/acolyte.html>), retrieved Apr. 12, 2005 (3 pages).
Colony Counter Models and Specifications (<http://biologics-inc.com/cc-models.htm>), retrieved Apr. 15, 2005 (3 pages).
Corkidi et al., "COVASIAM: An Image Analysis Method That Allows Detection of Confluent Microbial Colonies and Colonies of Various Sizes for Automated Counting," *Appl. Environ. Microbiol.* 64(4):1400-1404, 1998.
Definition and Procedure for the Determination of the Method Detection Limit, Appendix B to 40 C.F.R. § 136, available at <http://access.gpo.gov> (retrieved Nov. 20, 2007), pp. 343-346.
Digital Multi-Purpose High-Resolution Colony and Plaque Counter (<http://www.loats.com/mla.html>), retrieved Apr. 12, 2005 (3 pages).
Esteban et al., "Improved Direct Epifluorescent Filter Technique for Rapid Bioburden Control in Intravenous Solutions," *J. Parenter. Sci. Technol.* 46: 146-149, 1992.
Frost, "Improved Technic for the Micro or Little Plate Method of Counting Bacteria in Milk," *J. Infect. Dis.* 28(2):176-184, 1921.
"Innovative Plate Holder for Colony Counter," <http://www.laboratorytalk.com> retrieved Oct. 16, 2002 (2 pages).
"Innovative Plate Holder for ProtoCOL," <http://www.synbiosis.com> retrieved Oct. 16, 2002 (2 pages).
Kamentsky, "Laser Scanning Cytometry," *Methods Cell Biol.* 63: 51-87, 2001.
Kroll et al. "A Laser-Light Pulse Counting Method for Automatic and Sensitive Counting Of Bacteria Stained with Acridine Orange", *J. Appl. Bacteriol.* 66: 161-167, 1989.
Lamture et al., "Direct Detection of Nucleic Acid Hybridization on the Surface of a Charge Coupled Device," *Nucleic Acids Res.* 22(11): 2121-5, 1994.
Loats et al., "LAI High-Resolution Automated Colony Counting System—Mouse Lymphoma Assay: Performance Analysis," (<http://loats.com/docs/HRCCval/HRCCval.htm>), p. 1-11 (1990).
Logtenberg et al., "Enumeration of (Auto)Antibody Producing Cells in Human Using the 'Spot-ELISA,'" *Immunol. Lett.* 9: 343-347, 1985.
London et al., "An Automated System for Rapid Non-Destructive Enumeration of Growing Microbes," PLoS One 5(1):e8609 (16 pages) (2010).
Masuko et al., "A Novel Method for Detection and Counting of Single Bacteria in a Wide Field Using an Ultra-High-Sensitivity TV Camera Without a Microscope," *FEMS Microbiol. Lett.* 81: 287-290, 1991.
Masuko et al., "Rapid Detection and Counting of Single Bacteria in a Wide Field Using a Photon-Counting TV Camera," *FEMS Microbiol. Lett.* 83: 231-238, 1991.
Mignon-Godefroy et al., "Solid Phase Cytometry for Detection of Rare Events," *Cytometry* 27: 336-344, 1997.
Miraglia et al., "Homogeneous Cell-and Bead-Based Assays for High Throughput Screening Using Fluorometric Microvolume Assay Technology," *J. Biomol. Screen.* 4: 193-204, 1999.
Moore et al., "Lymphocyte fractionation using immunomagnetic colloid and a dipole magnet flow cell sorter," *J. Biochem. Biophys. Methods* 37: 11-33, 1998.

Nargessi et al., "Magnetizable Solid-Phase Fluoroimmunoassay of Thyroxine by a Sequential Addition Technique." *Clin Chem* 26(12): 1701-1703, 1980.
Nargessi et al., "Immunoassays for Serum C-Reactive Protein Employing Fluorophore-Labelled Reactants." *J. Immunol. Methods* 71: 17-24, 1984.
Nealson, "Isolation, identification, and manipulation of luminous bacteria," *Methods Enzymol.* 57:153-166, 1978.
Nelis et al. "Enzymatic Detection of 1-15 Coliforms and *Escherichia coli* Within 4 Hours," *Water Air And Soil Pollut.* 123: 43-52, 2000.
PerkinElmer, Inc., GeneScreenTM Hybridization Transfer Membranes: transfer and detection protocols, Application Notes, available at <http://las.perkinelmer.com/>, retrieved Feb. 27, 2007.
Rousseau et al., "New Miniaturized Highly Sensitive Immunoassay Device for Quantitative Measurement of Soluble or Particular Antigen or Antibodies in a Liquid Sample," *Clin. Chem.* 45(9): 1685-1687, 1999.
Schultz et al., "Single Target Molecule Detection with Nonbleaching Multicolor Optical Immunolabels," *Proc. Natl. Acad. Sci. U.S.A.* 97(3): 996-1001, 2000.
Sorcerer Automated Colony Counting, Perceptive Instruments, 2002 (2 pages).
Susa et al., "Legionella Pneumophila Infection in Intratracheally Inoculated T Cell-Depleted or -Nondepleted A/J Mice," *J. Immunol.* 160: 316-321, 1998.
Loates Associates Inc., System Specifications (<http://www.loats.com/order_info.html>), retrieved Apr. 12, 2005, (1999) (7 pages).
Technical Specification (<http://www.perceptive.co.uk/products/scc/techspec.html>), retrieved Apr. 12, 2005 (2 pages).
Thomas et al., "Making Gold Nanoparticles Glow: Enhanced Emission from a Surface-Bound Fluoroprobe," *J. Am. Chem. Soc.* 122: 2655-2656, 2000.
Tibbe et al., "Optical Tracking and Detection of Immunomagnetically Selected and Aligned Cells," *Nature Biotechnol.* 17: 1210-1213, 1999.
Van Poucke et al. "Solid Phase Cytometry-Based Enzymatic Detection of Coliforms in Drinking Water Within 4 h", *Water Supply* 17: 67-72, 1999.
Van Poucke et al. "Rapid Detection of Fluorescent and Chemiluminescent Total Coliforms and *Escherichia coli* on Membrane Filters" *J. Microbiol. Methods* 42: 233-244, 2000.
Van Poucke et al., "A 210-min Solid Phase Cytometry Test for the Enumeration of *Escherichia coli* in Drinking Water," *J. Appl. Microbiol.* 89: 390-396, 2000.
Vidon et al., "A Simple Chemiluminescence-Based Method for Rapid Enumeration of *Listeria* spp. Microcolonies," *J. Appl. Microbiol.* 90: 988-993, 2001.
Viinikka et al., "A Two-Site Immunofluorometric Assay for Human Placental Lactogen," *Clin. Chim. Acta.* 114: 1-9, 1981.
Watanabe et al., "Analysis of synchronous photon emissions from the bacterium Photobacterium phosphoreum during colony formation from a single cell," *J. Biolumin. Chemilumin.* 6:13-18, 1991.
Watanabe et al., "Bioluminescence and cell growth of Photobacterium phosphoreum," *J. Biochem.* 88(3):815-817, 1980.
Wellman et al., "Magnetically-Assisted Transport Evanescent Field Fluoroimmunoassay," *Anal. Chem.* 78: 4450-6, 2006.
Wilson, "Use of the IUL Countermat Automatic Colony Counter for Spiral Plated Total Viable Counts," *Appl. Environ. Microbiol.* 61: 3158-3160, 1995.
Wolniak, 2004. BSCI 427 Principles of Microscopy Fall 2004 Syllabus, (<http://www.life.umd.edu/cbmg/faculty/wolniak/wolniakmicro.html>), retrieved Nov. 8, 2007 (8 pages).
Yasui et al., "Imaging of *Lactobacillus brevis* Single Cells and Microcolonies Without a Microscope by an Ultrasensitive Chemiluminescent Enzyme Immunoassay with a Photon-Counting Television Camera," *Appl. Environ. Microbiol.* 63: 4528-4533, 1997.
Zhao et al., "Competitive Immunoassay for Microliter Protein Samples with Magnetic Beads and Near-infrared Fluorescence Detection." *Anal. Chem.* 76: 1871-1876, 2004.
Extended Search Report for European Patent Application No. 09816873, dated Apr. 11, 2012 (12 pages).

(56) References Cited

OTHER PUBLICATIONS

International Search Report for PCT/US2009/058274, dated Nov. 20, 2009 (3 pages).
Patterson, "A wide angle camera for photographic search of the ocean bottom," SPIE. C-XII-1-8 (1966).
Batchelor, Light and Optics. Machine Vision Handbook. Springer-Verlag, 157-258 (2012).
Crowther, Methods in Molecular Biology. The ELISA Guidebook. Humana Press (425 pages)(2000).
Findlay et al., "Automated closed-vessel system for in vitro diagnostics based on polymerase chain reaction," Clin Chem. 39(9): 1927-33 (1993).
Sage et al., "A rapid and nondestructive method for microbiological testing in pharmaceutical manufacturing." American Biotechnology Laboratory. (5 pages) (2006).
Nebe-von-Caron et al., "Analysis of bacterial function by multicolour fluorescence flow cytometry and single cell sorting," J Microbiol Methods. 42(1):97-114 (2000).
Kepner et al., "Use of fluorochromes for direct enumeration of total bacteria in environmental samples: past and present," Microbiol Rev. 58(4):603-15 (1994).
Waggoner, "Fluorescent Probes for Cytometry," Flow Cytometry and Sorting, Wiley-Liss, 209-225 (1990).

\* cited by examiner

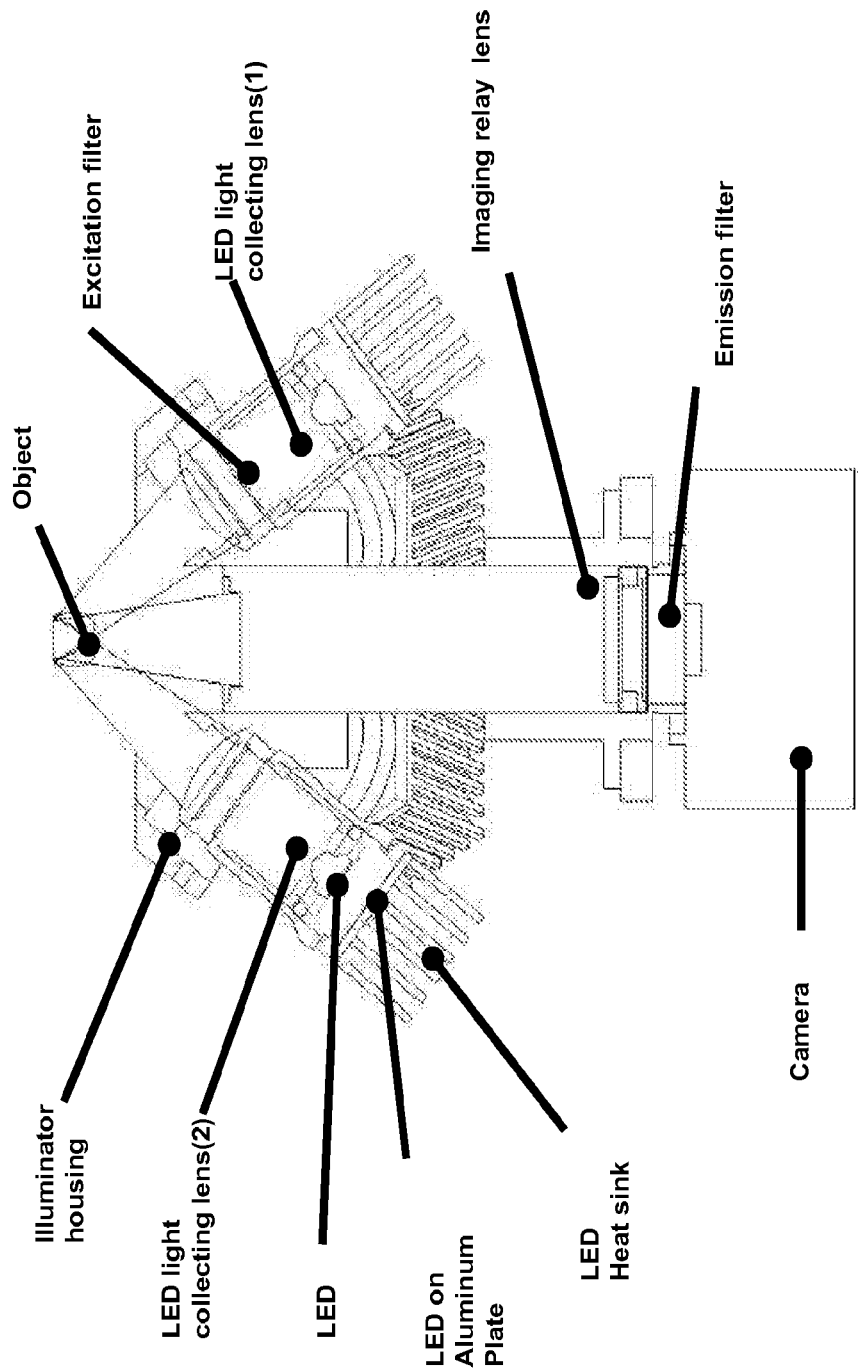
Fig. 1  Imaging and optics system diagram (Example 1)

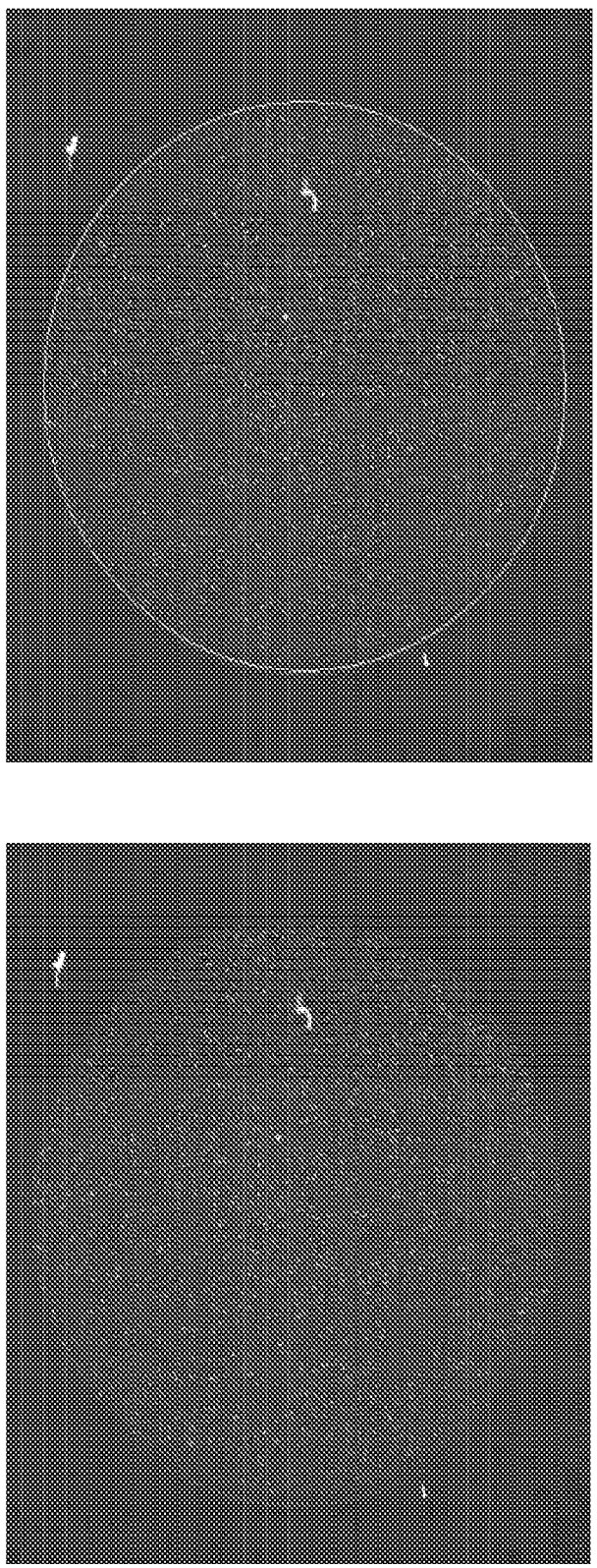
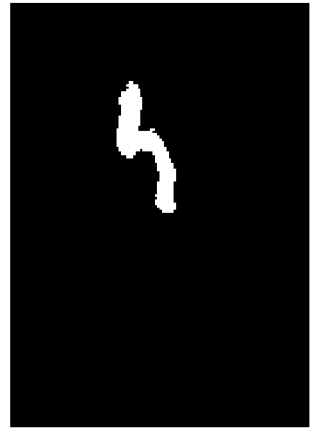
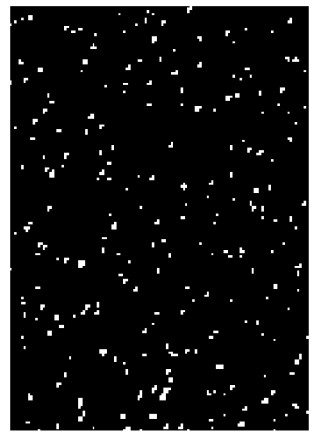
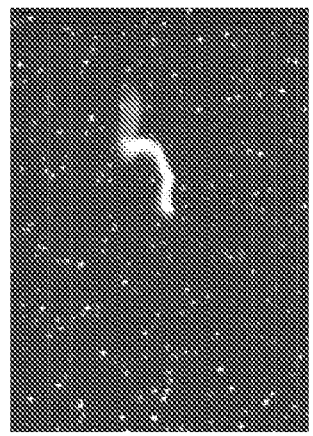
Fig. 2 Image analysis: counter clockwise from top left - input, ROI, zoomed input, detected signal, detected debris. (Example 3)

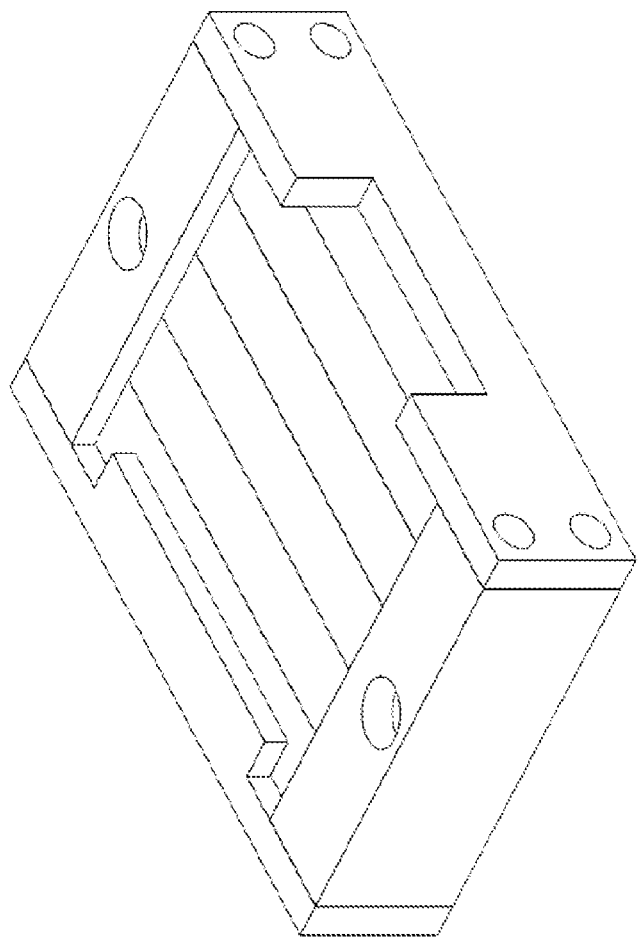
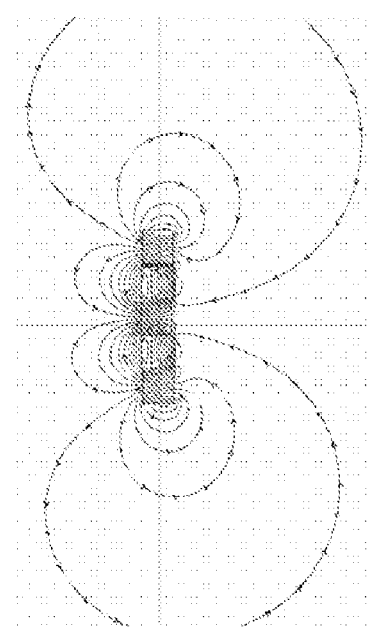
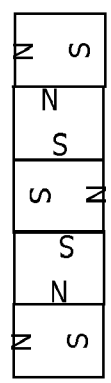
Fig. 3   Bar magnetic assembly. (Example 2)

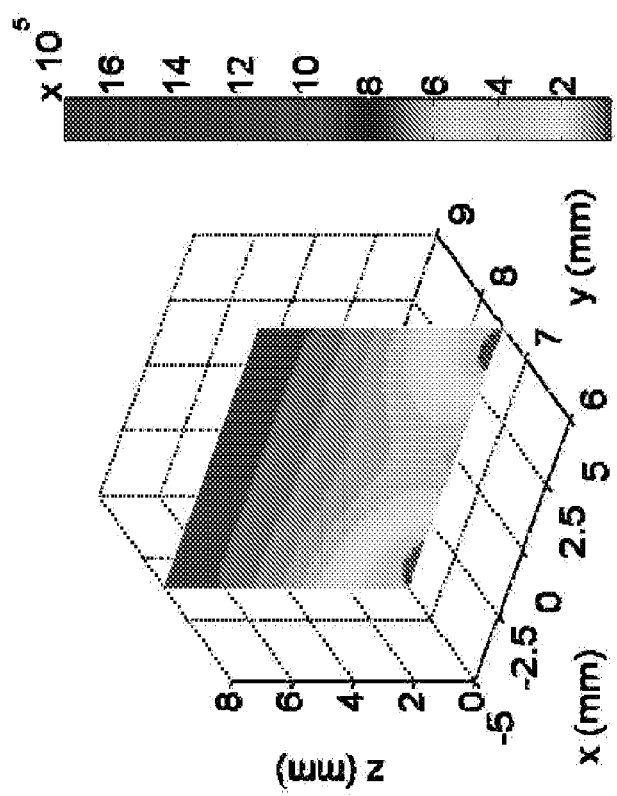
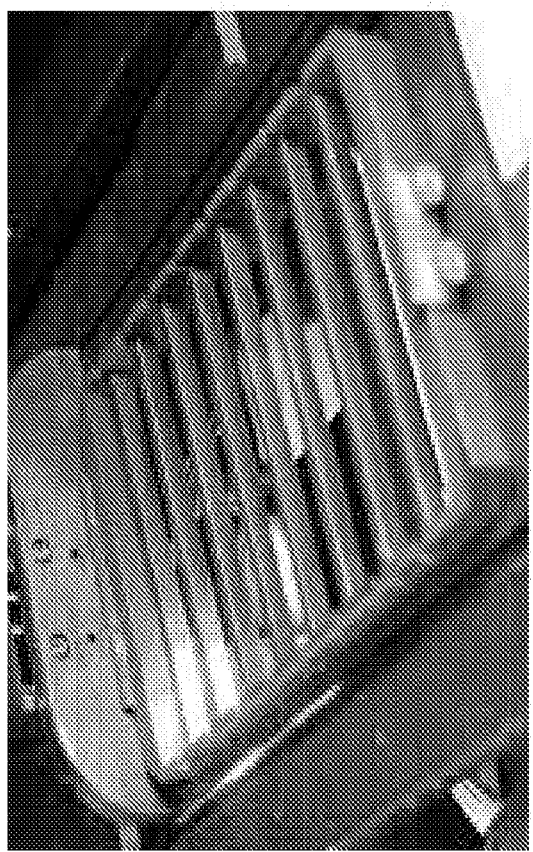
Fig. 4 Imaging between parallel bar magnets. (Example 2)

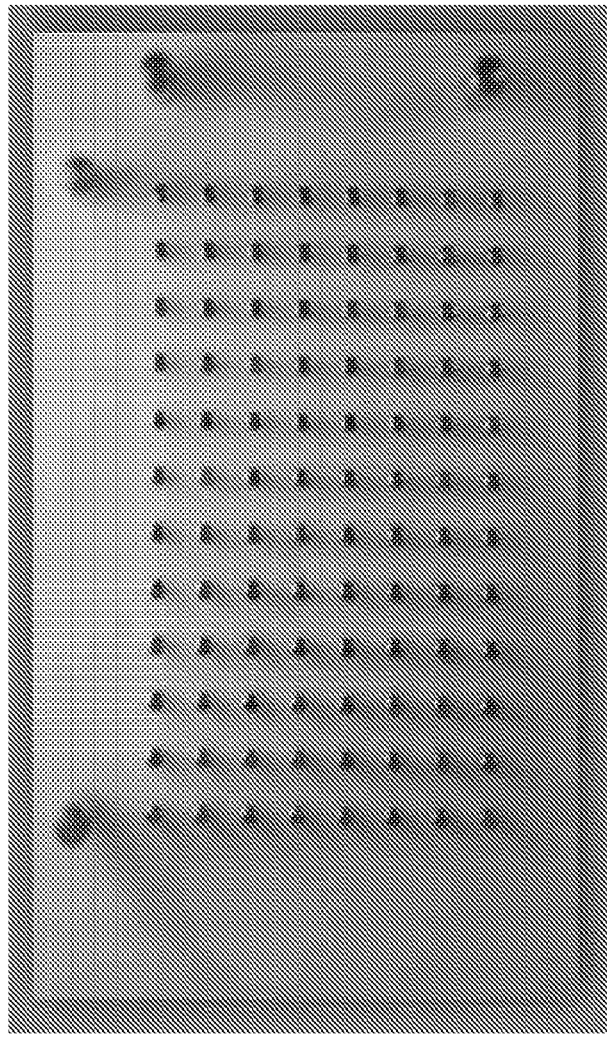
Fig. 5   Array of cylindrical magnets. (Example 2)

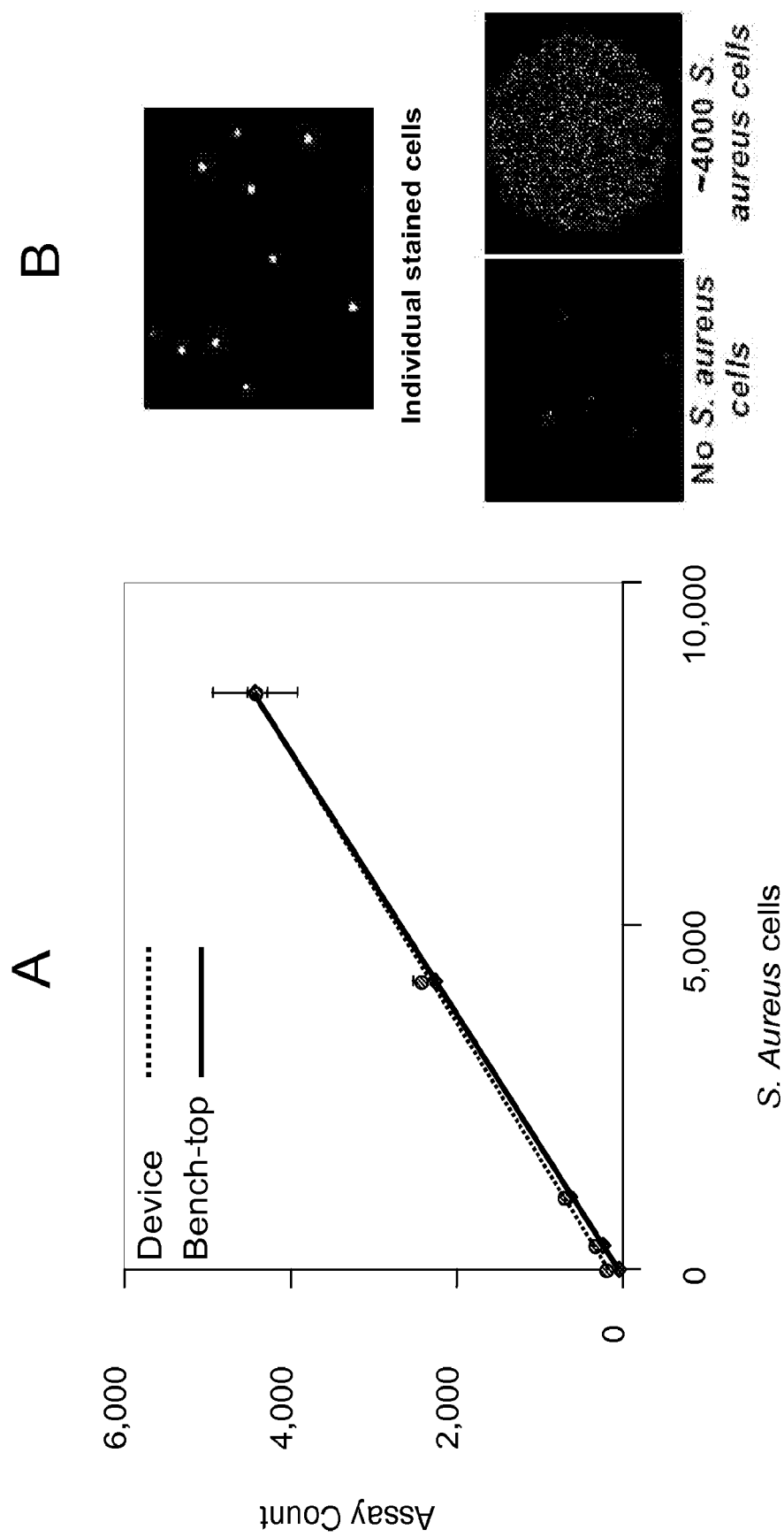
Fig. 6 Comparison of assay results from a device with integrated growth and reagent modules and a bench-top assay. (Example 9)

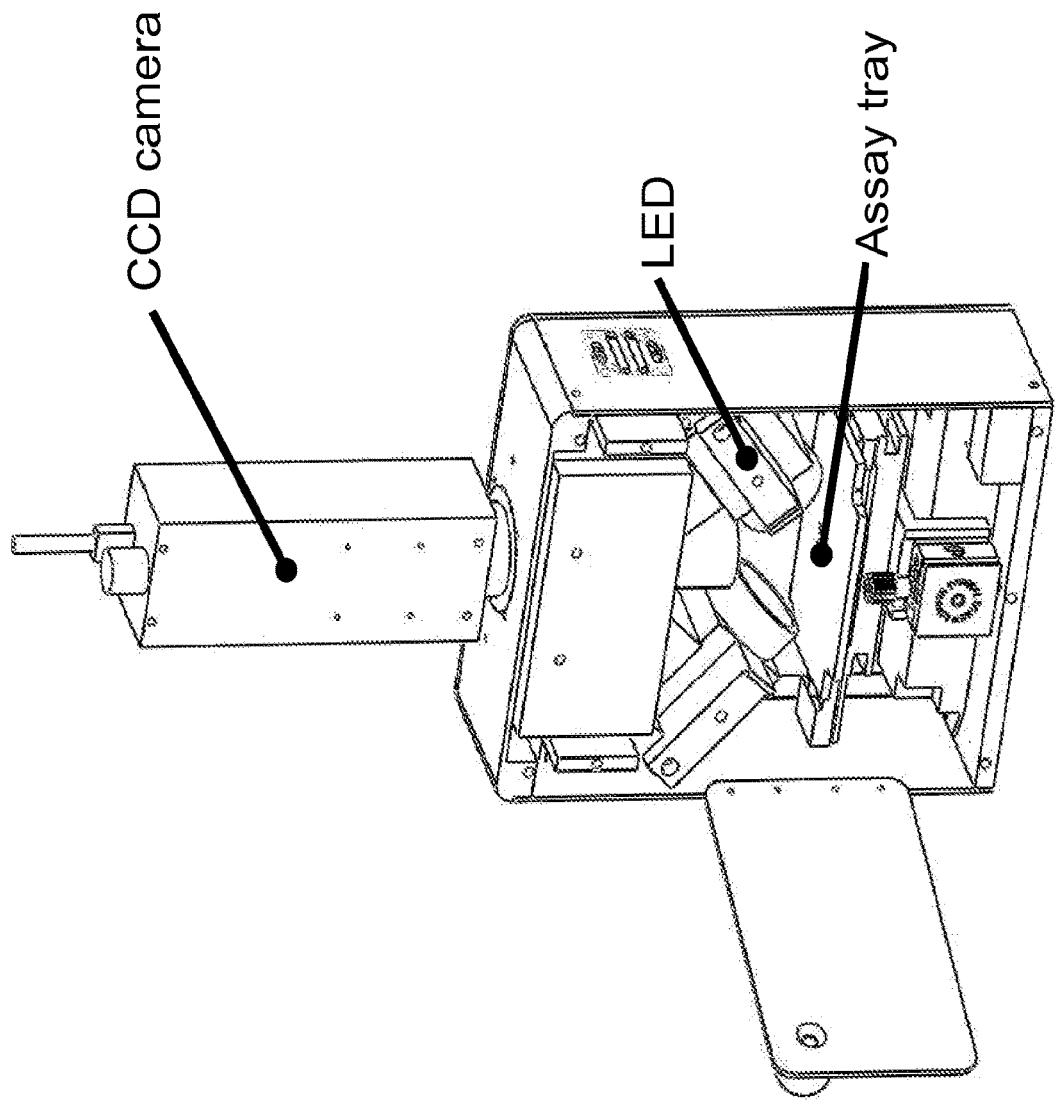
Fig. 7  System diagram of a simple non-automated analyzer. (Example 4)

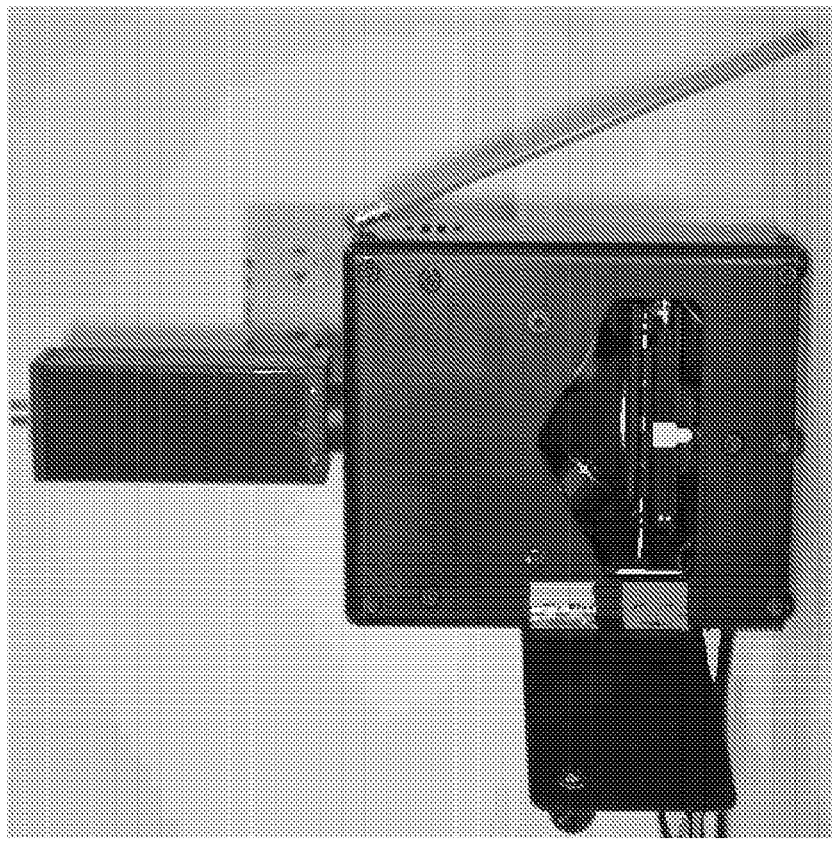
Fig. 8  Photograph of a simple non-automated analyzer. (Example 4)

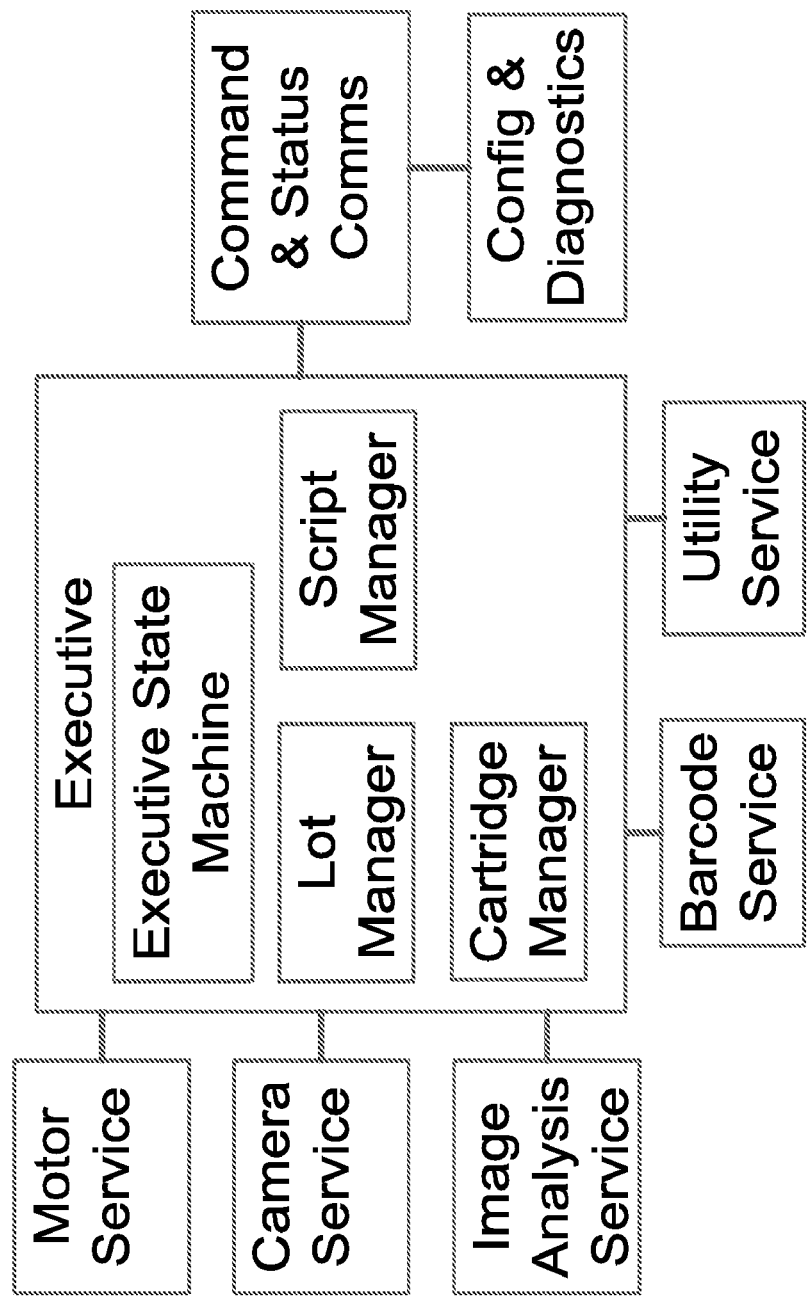
Fig. 9    Automated analyzer software diagram. (Example 6)

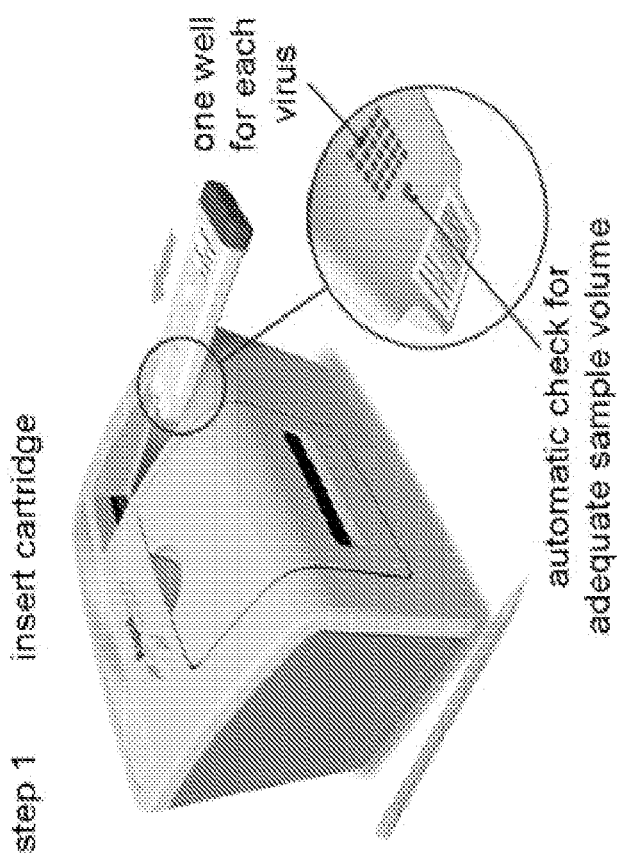
Fig. 10  Automated single sample instrument cartridge insertion (Example 7)

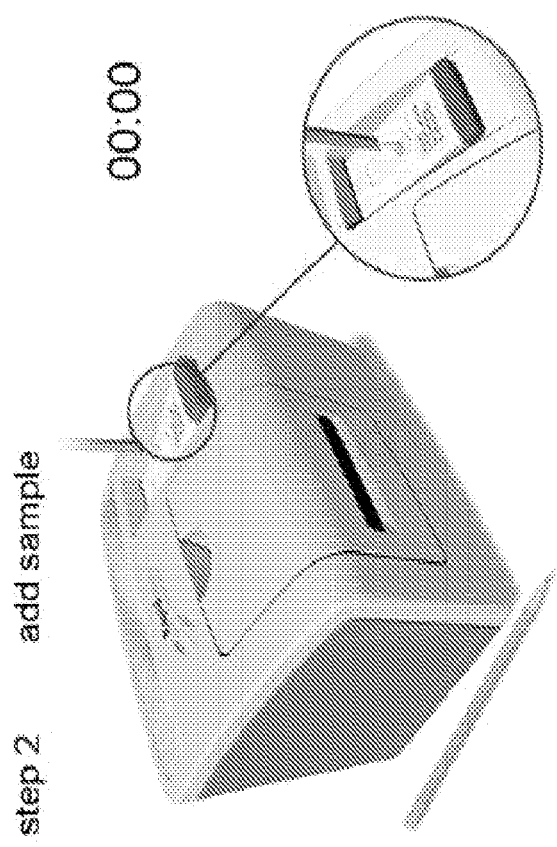
Fig. 11  Automated single sample instrument sample addition. (Example 7)

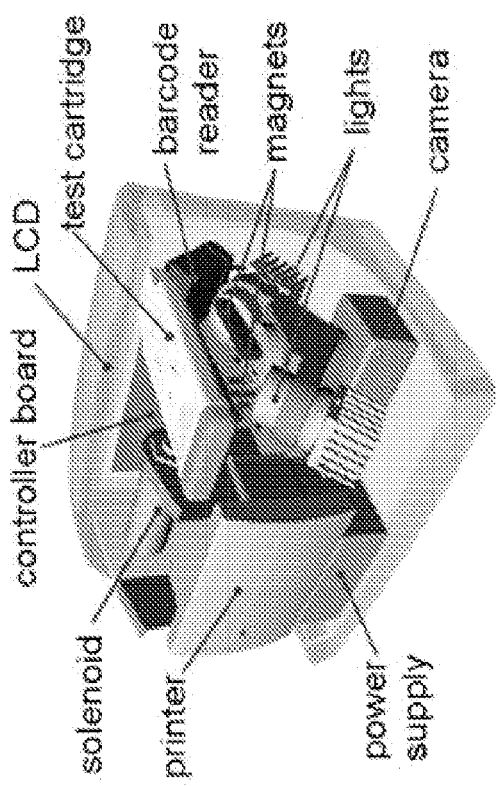
Fig. 12  Automated single sample instrument system diagram. (Example 7)

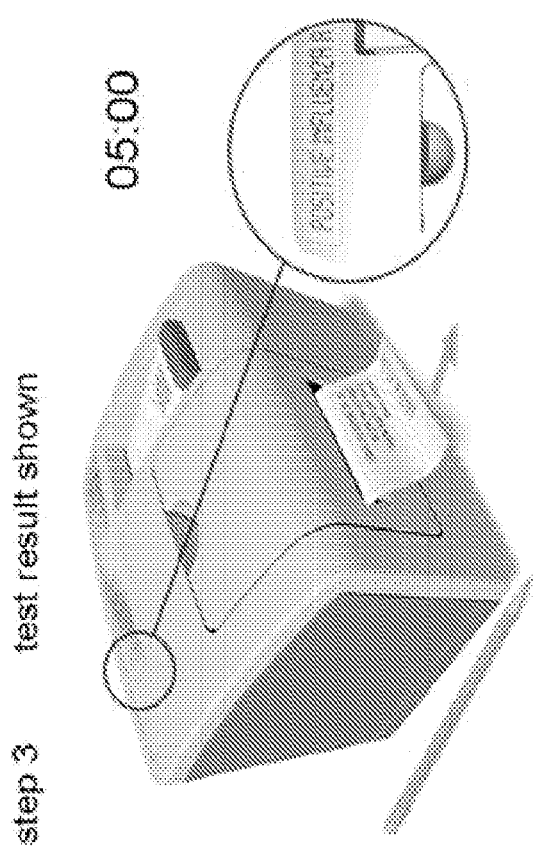
Fig. 13 Automated single sample instrument results output. (Example 7)

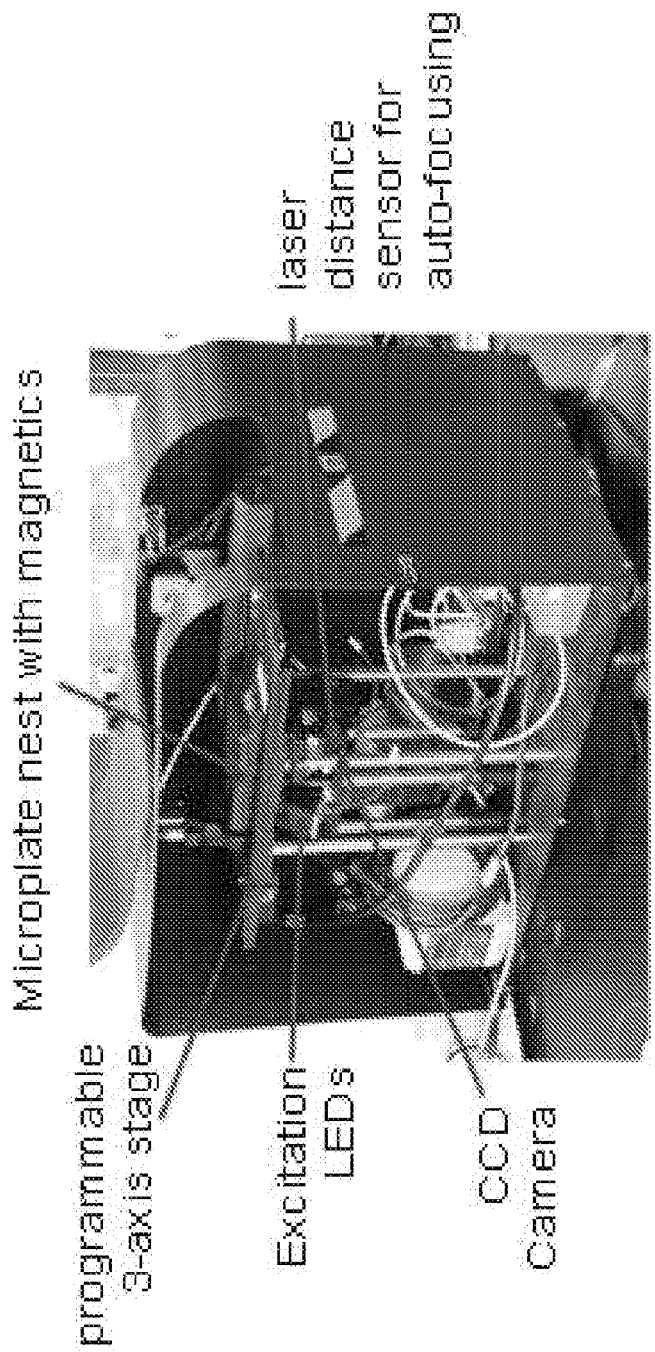
Fig. 14  High throughput automated analyzer. (Example 8)

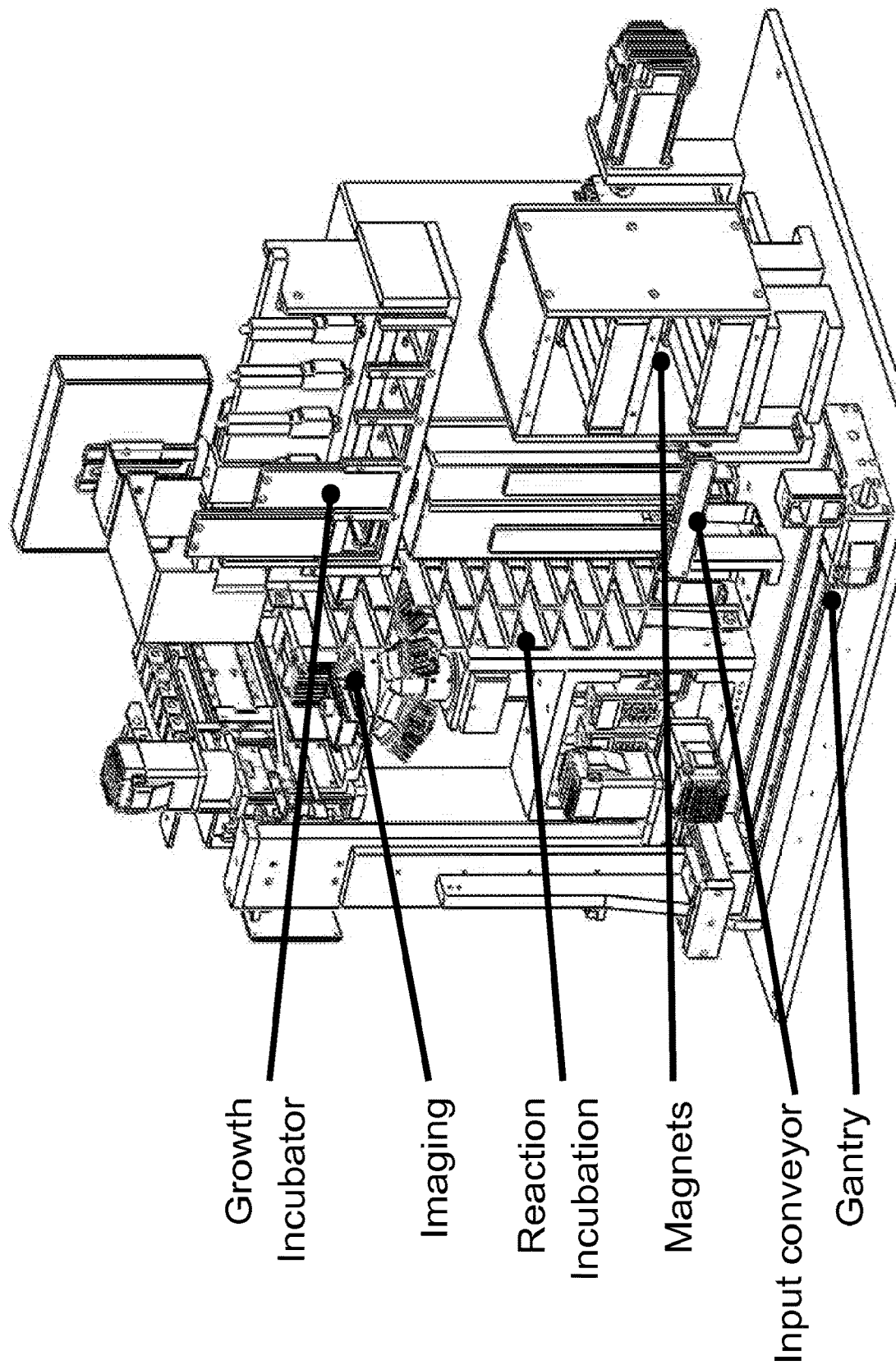
Fig. 15  On-demand analyzer CAD Subassemblies. (Example 9)

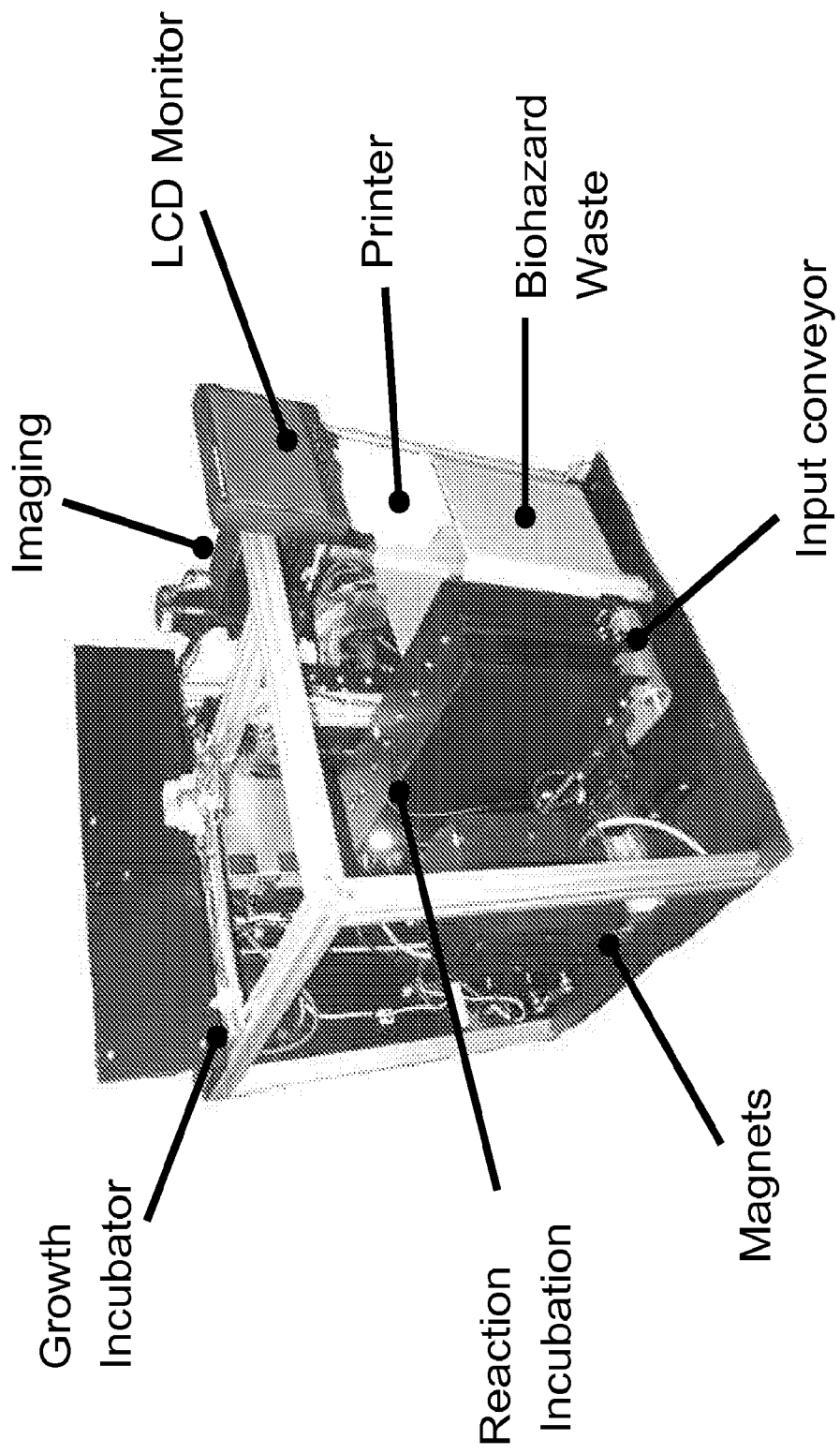
Fig. 16 On-demand analyzer photograph. (Example 9)

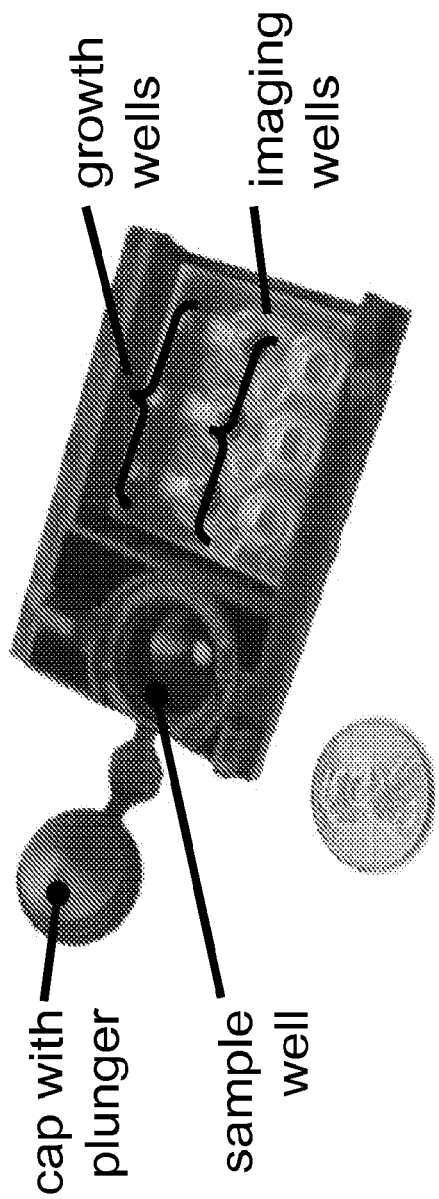
Fig. 17  Cartridge embodiment. (Example 9)

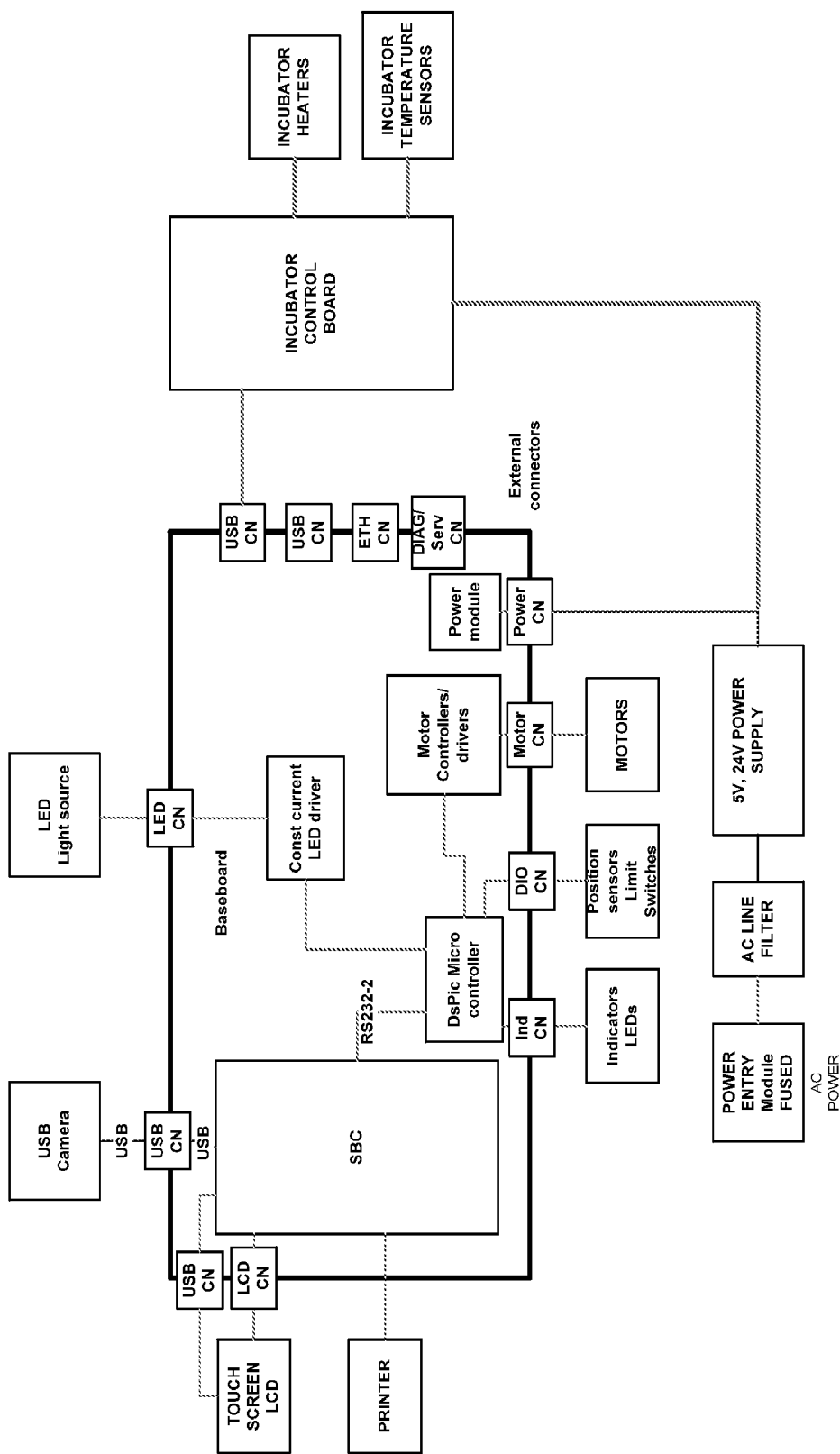
Fig. 18 On-demand analyzer electrical system. (Example 9)

Fig. 19 Exported spreadsheet from automated image analysis software. (Example 8)

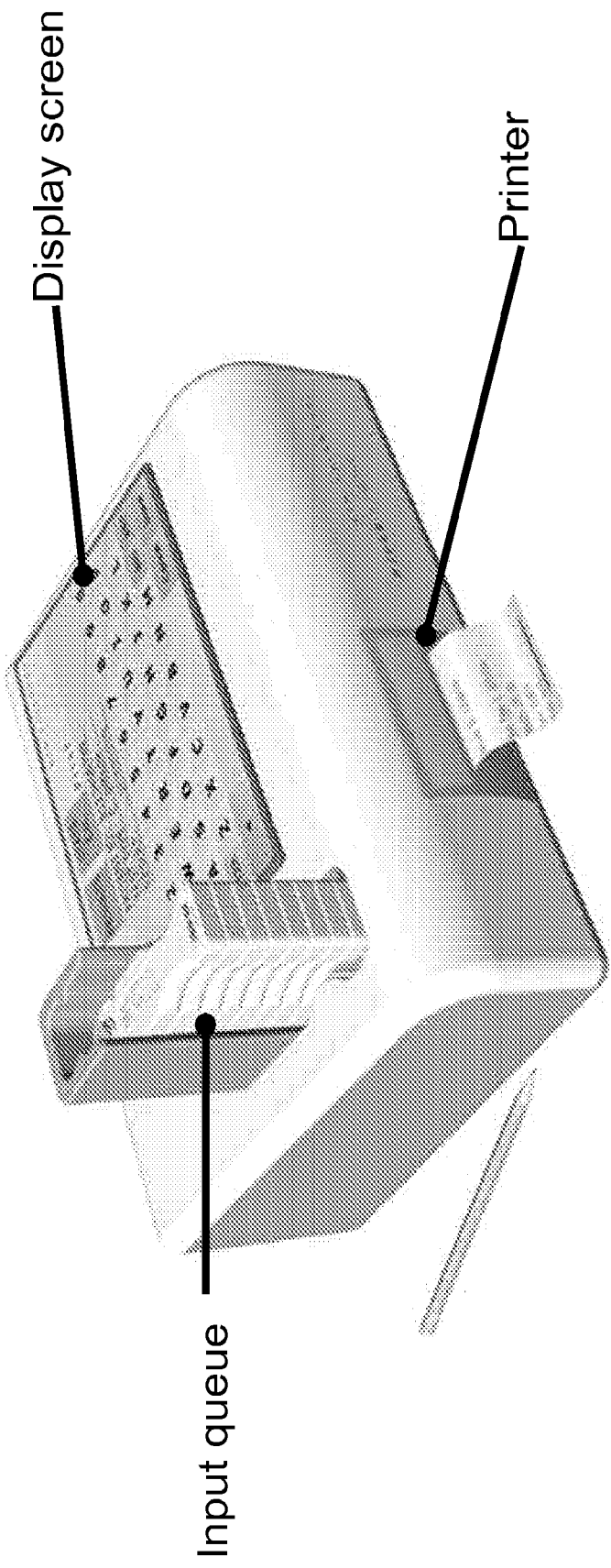
Fig. 20  External view of On-Demand Automated Analyzer using a cleated belt drive. (Example 10)

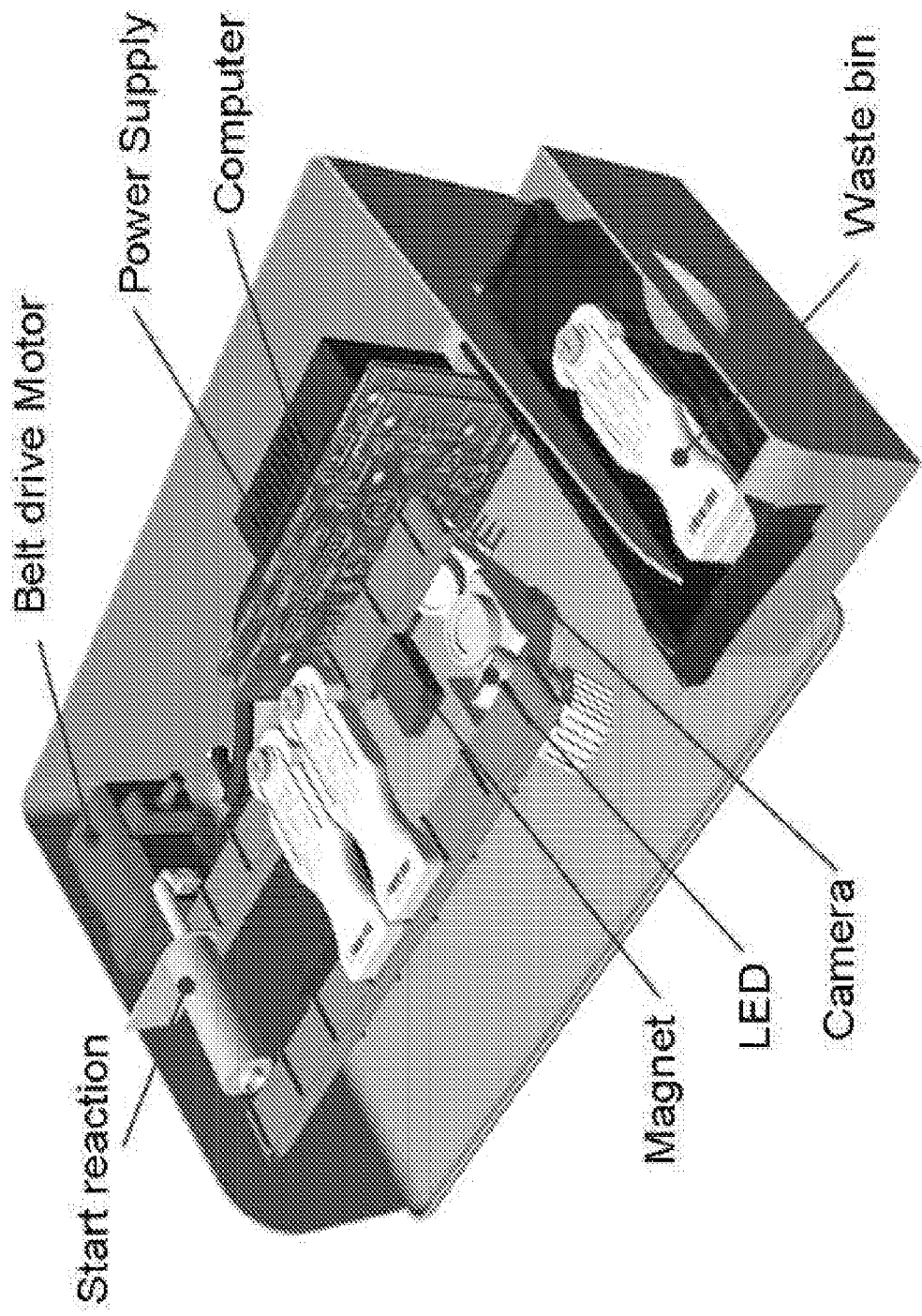
Fig. 21 Internal view of On-Demand Automated Analyzer (Example 10)

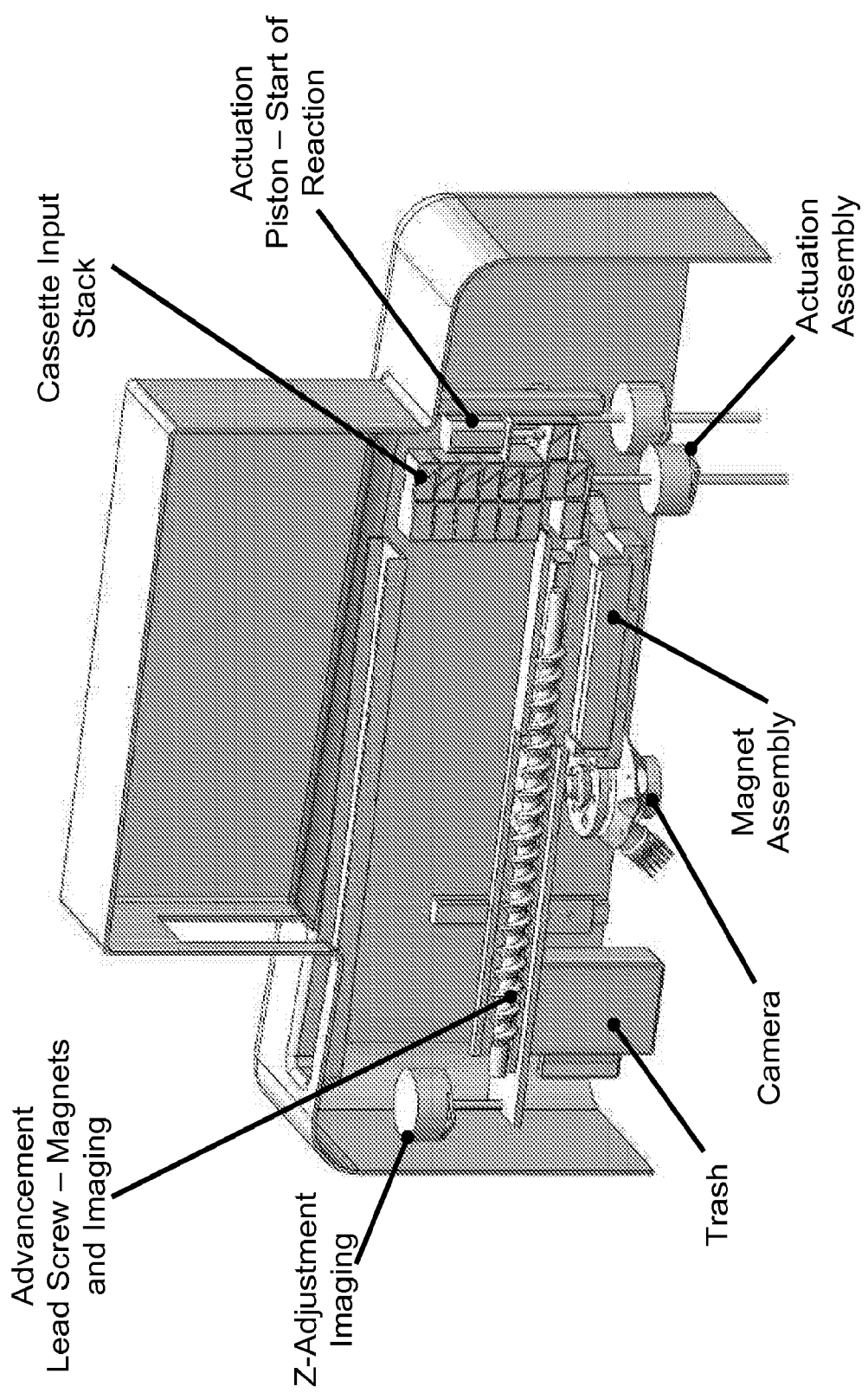
Fig. 22  Front view of conceptual drawing for Automated on-demand cartridge analyzer. (Example 11)

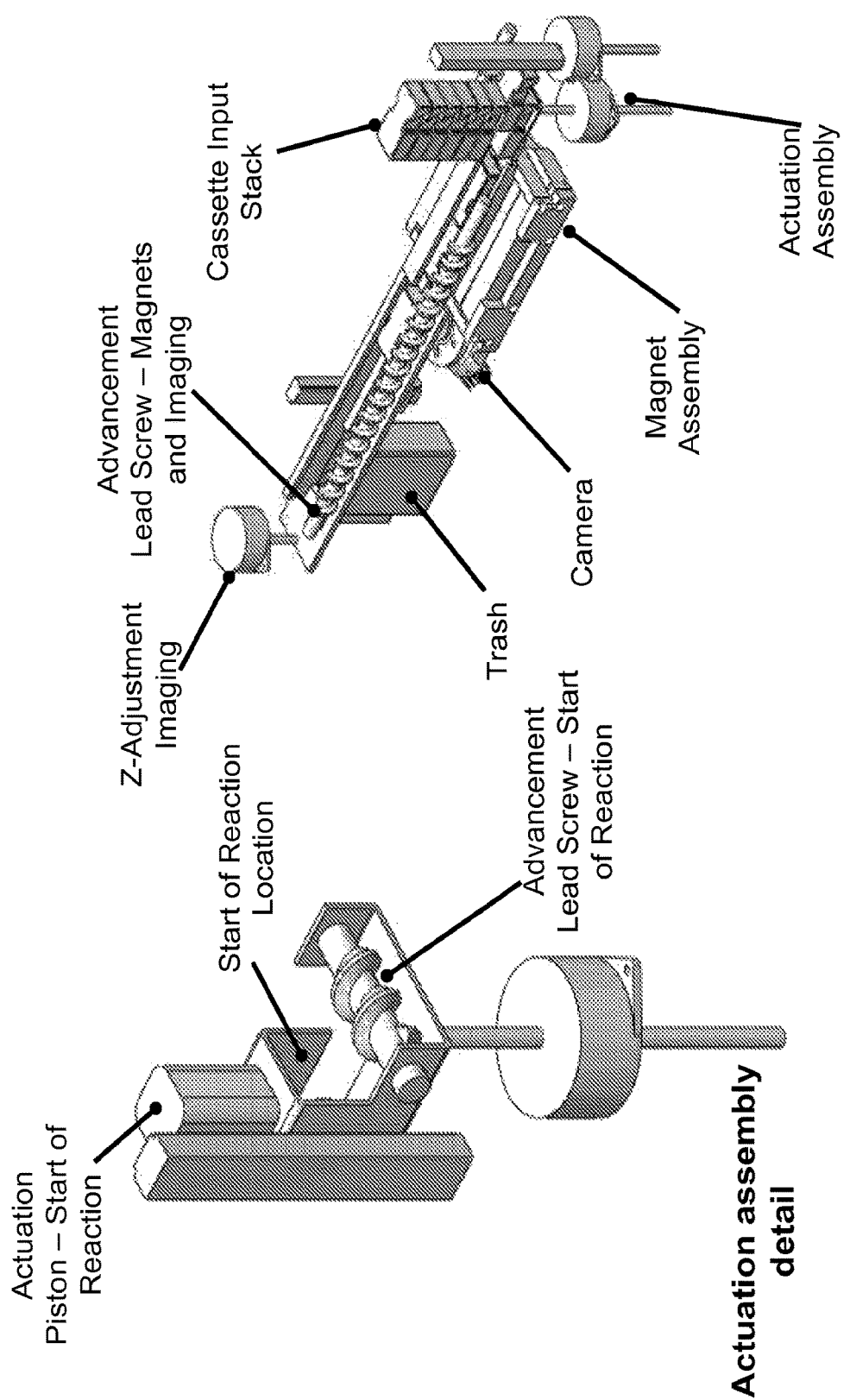
Fig. 23 Rear view of conceptual drawing for Automated on-demand cartridge analyzer. (Example 11)

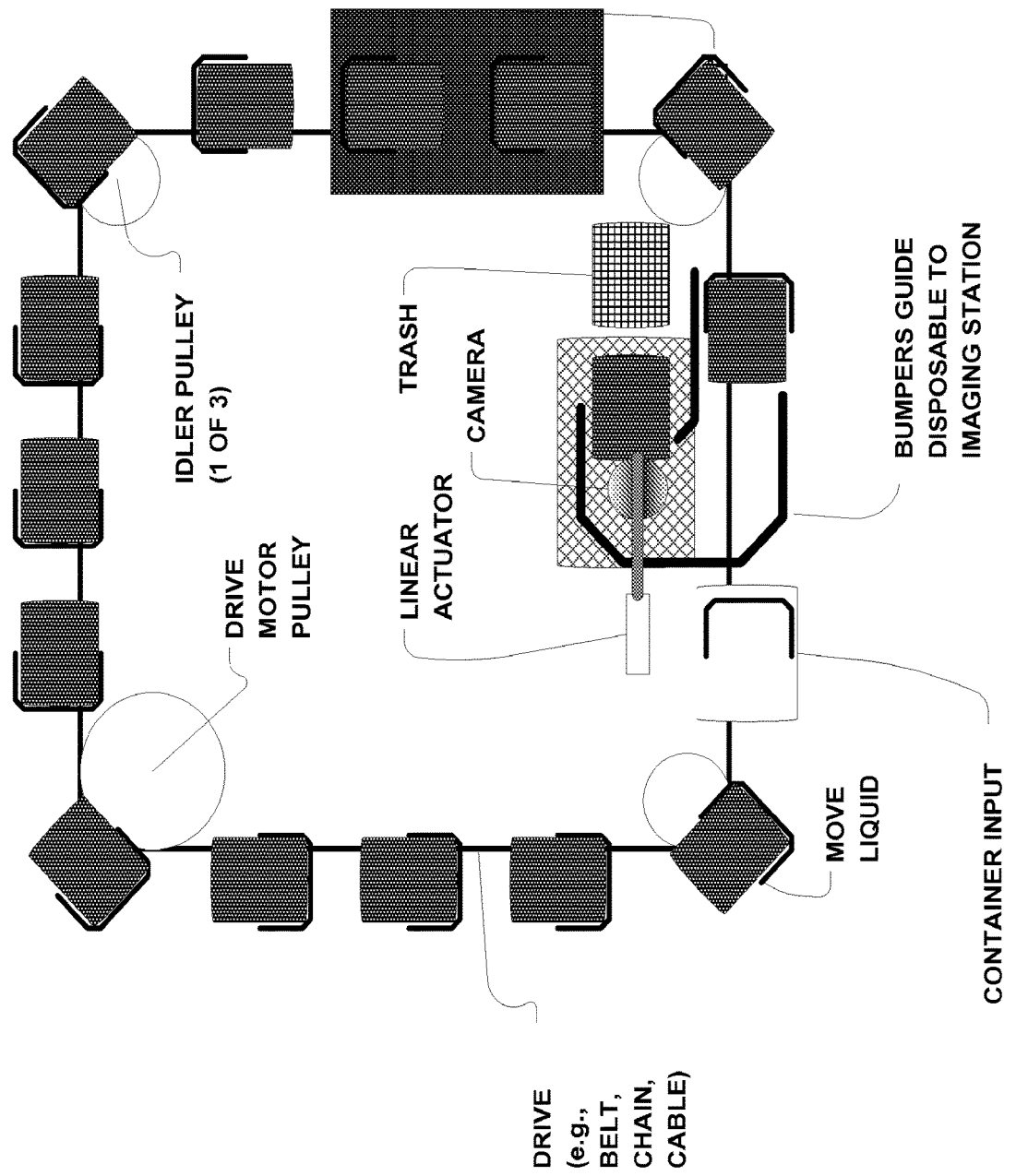
Fig. 24 A single plane conveyor drive mechanism. (Example 12)

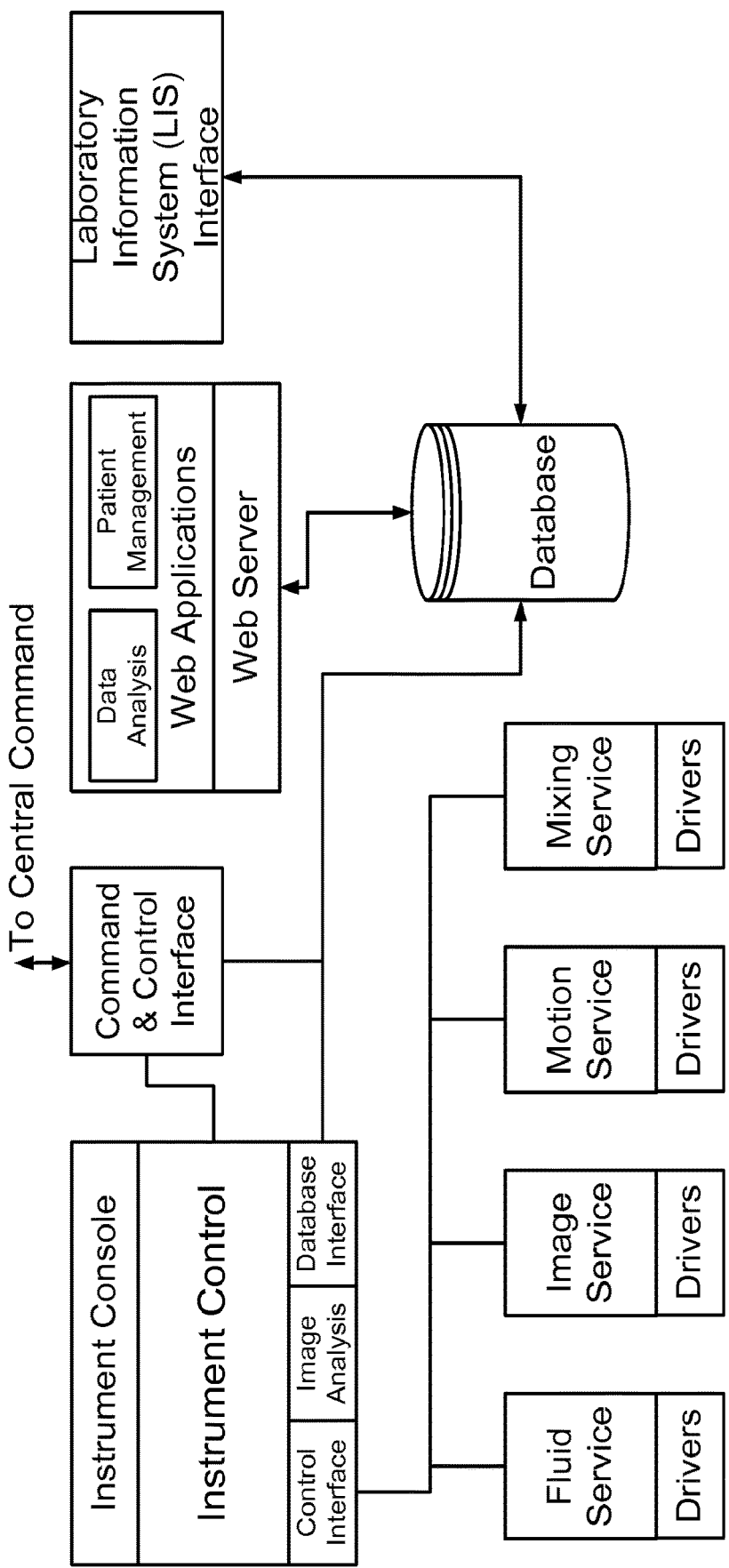
Fig. 25 Surge System Software Diagram. (Example 13)

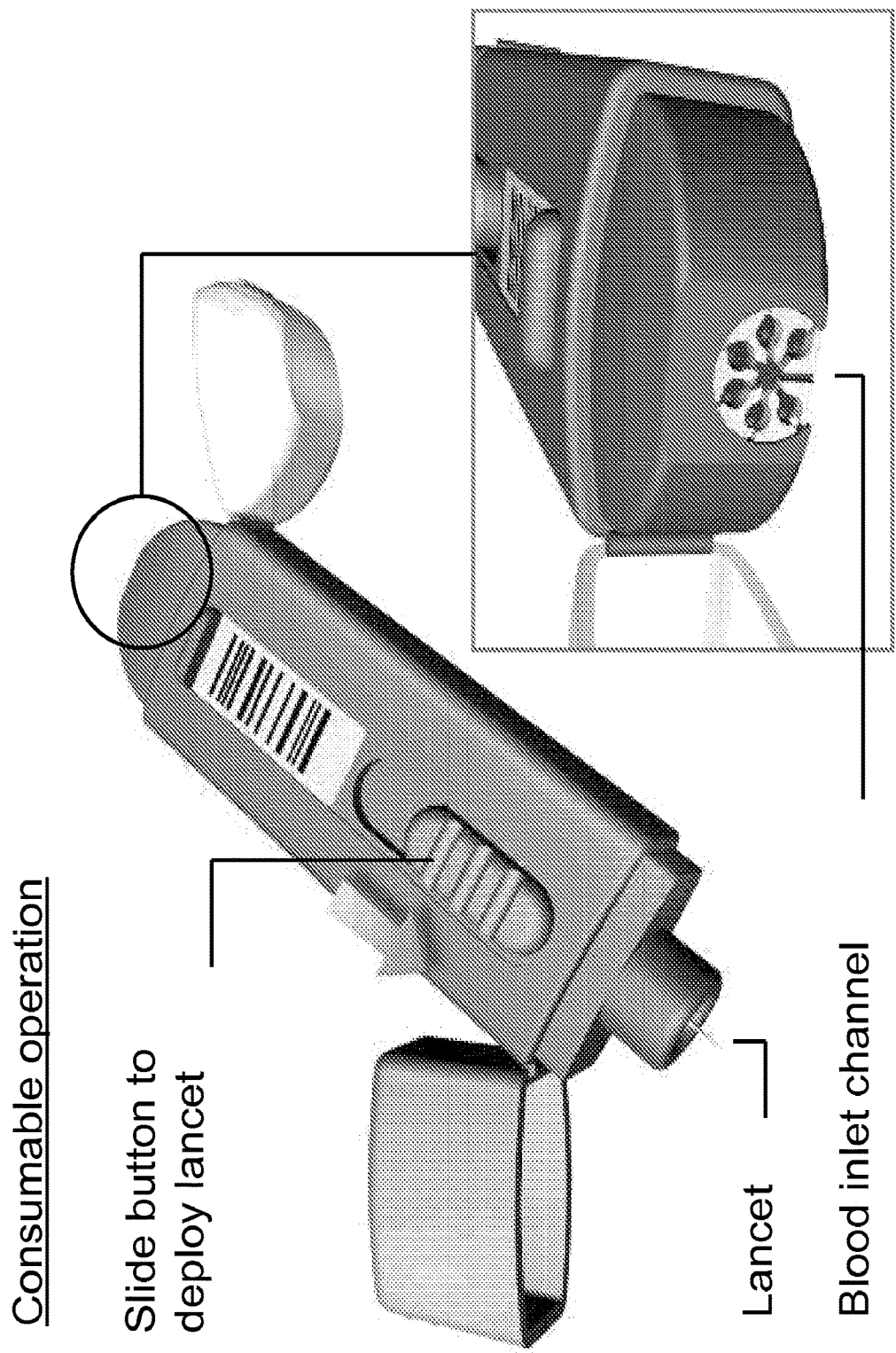
Fig. 26 Cartridge used in automated cartridge analyzer for high throughput surge testing. (Example 15)

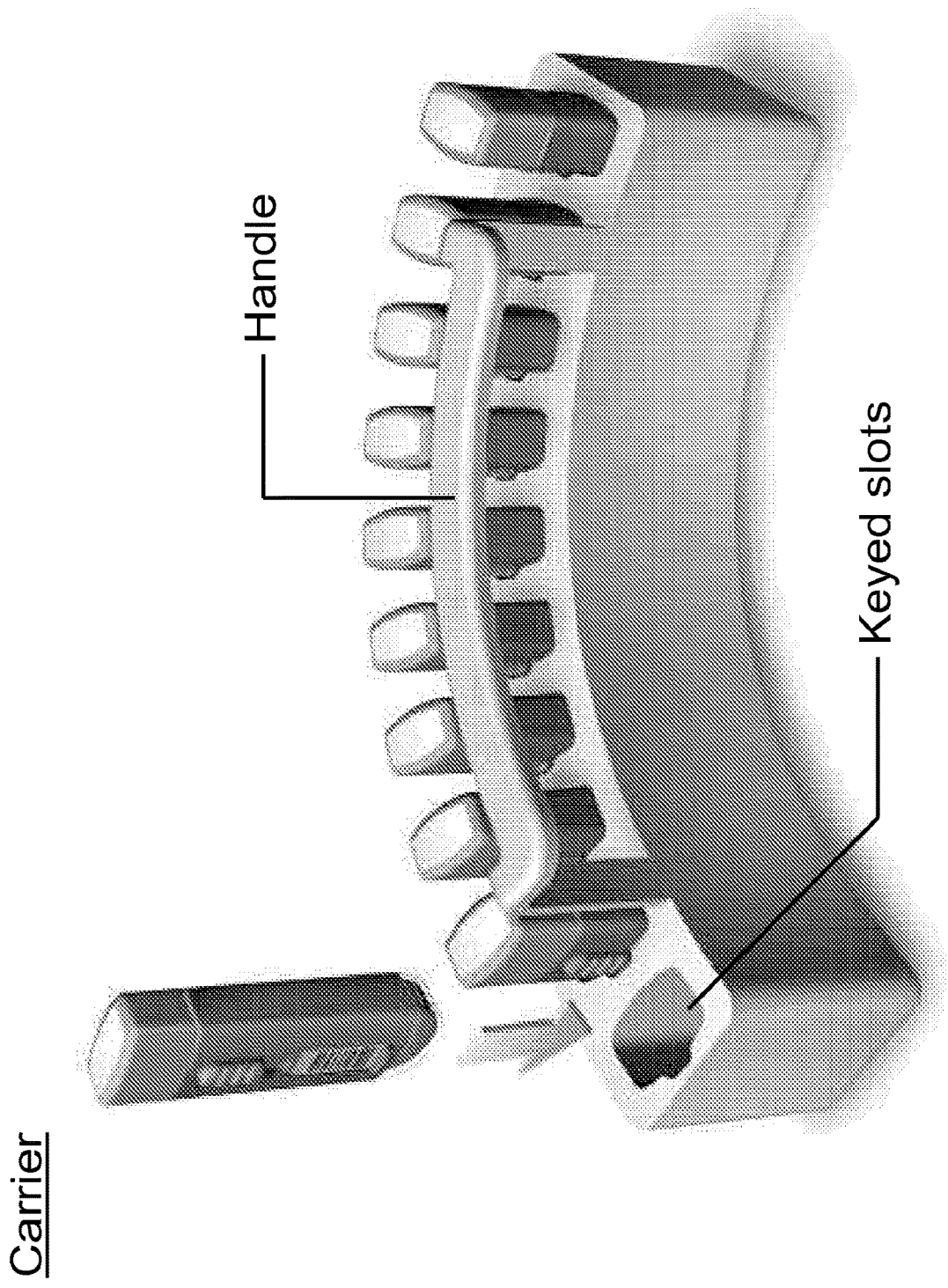
Fig. 27  Carrier for the cartridge in Figure 26. (Example 15)

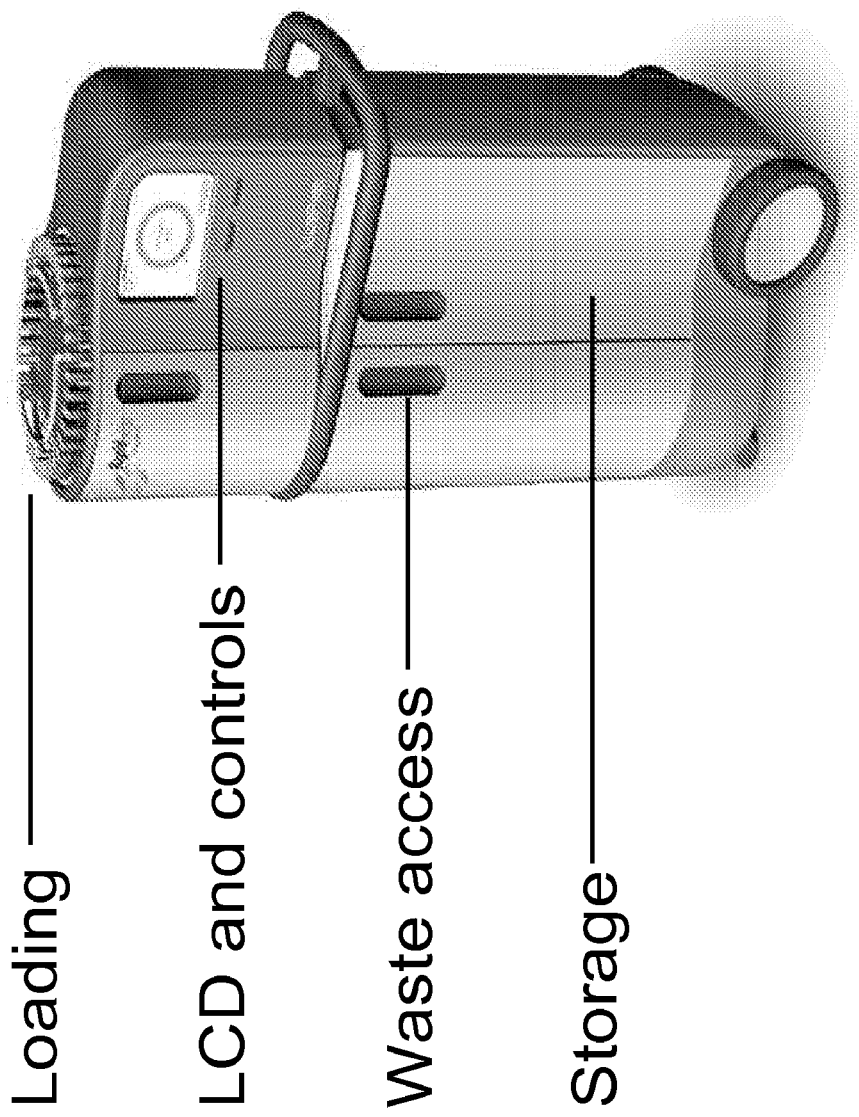
Fig. 28 Automated cartridge analyzer for high throughput surge testing. (Example 15)

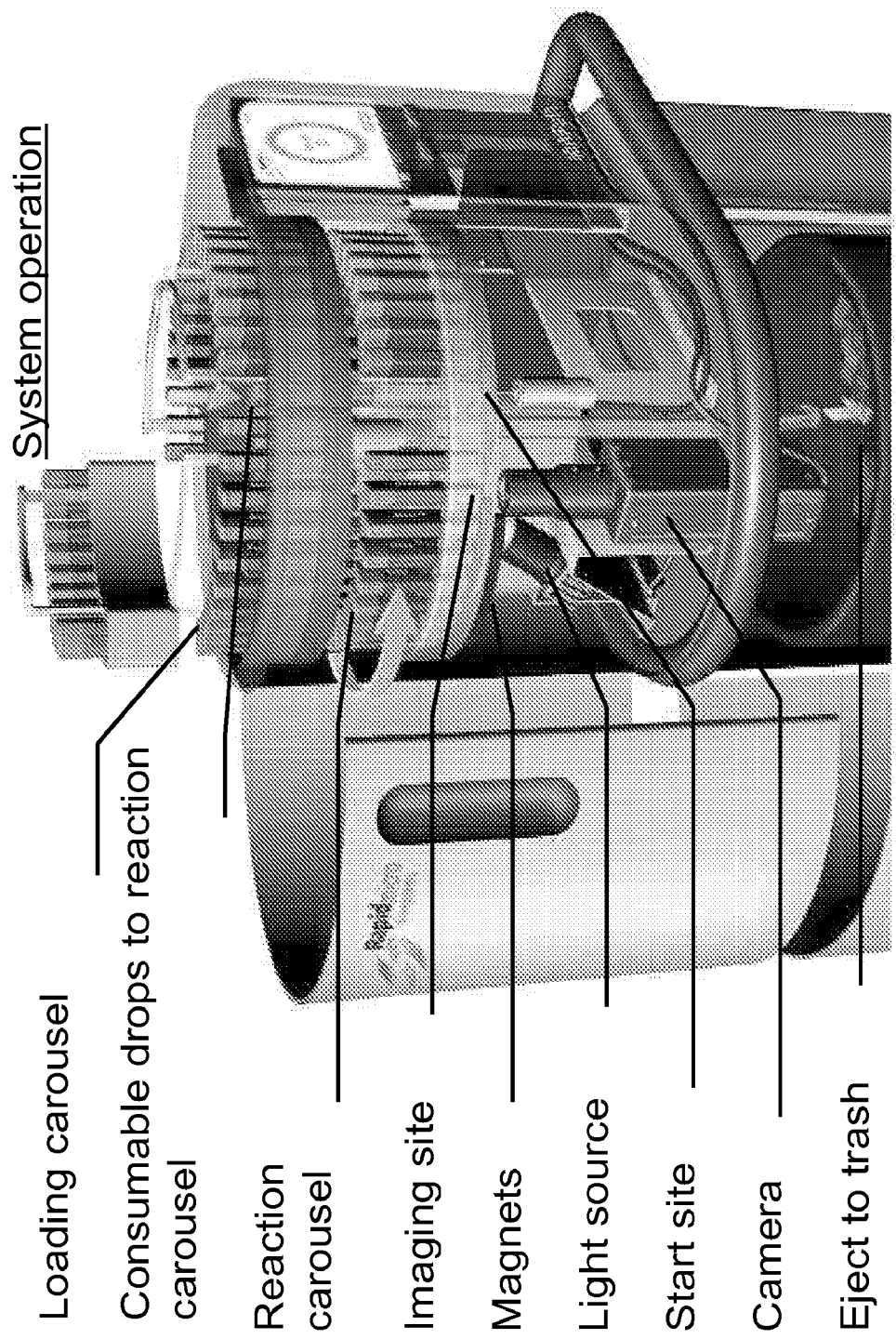
Fig. 29  Internal view of high throughput surge testing analyzer. (Example 15)

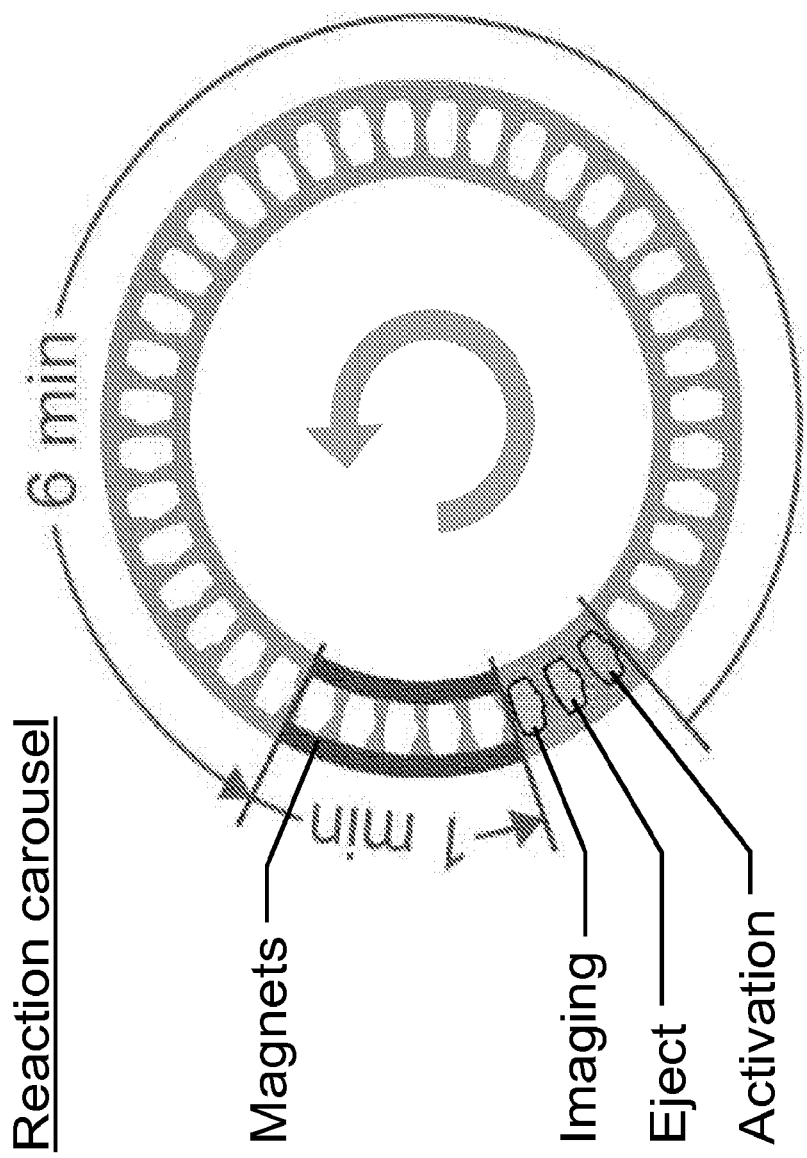
Fig. 30 Processing steps on the high throughput surge testing analyzer. (Example 15)

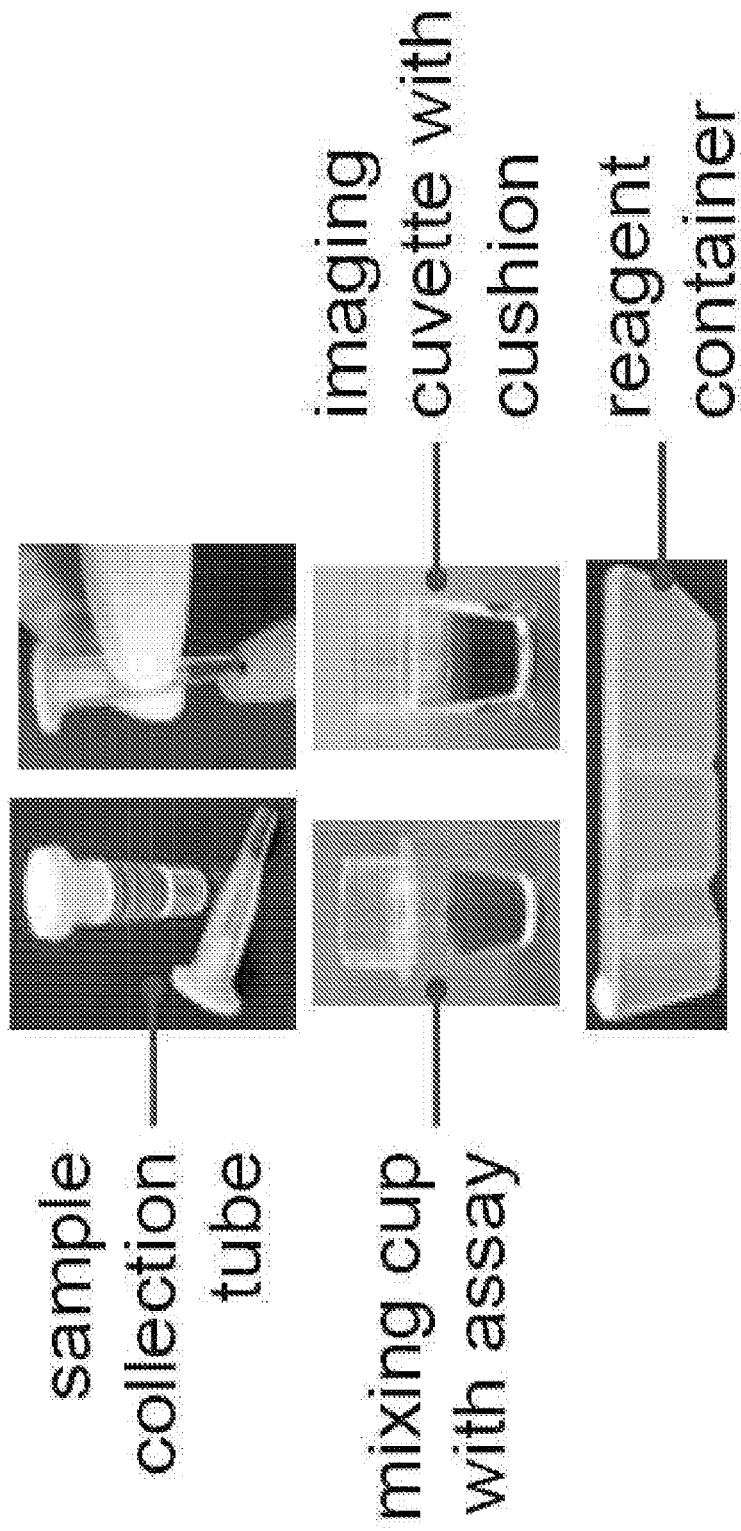
Fig. 31  Fluidic containers. (Example 14)

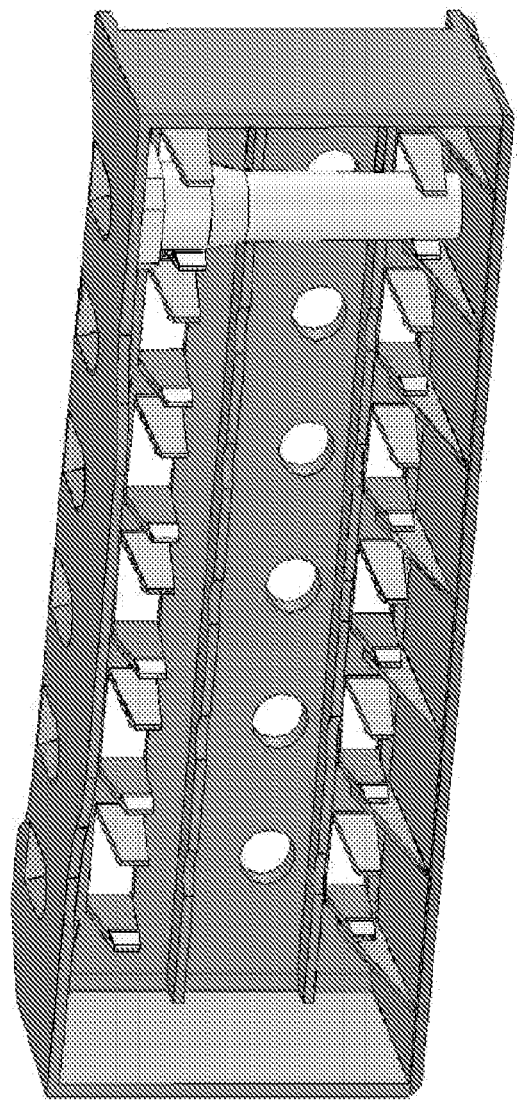
Fig. 32 Sample rack with one sample consumable. (Example 14)

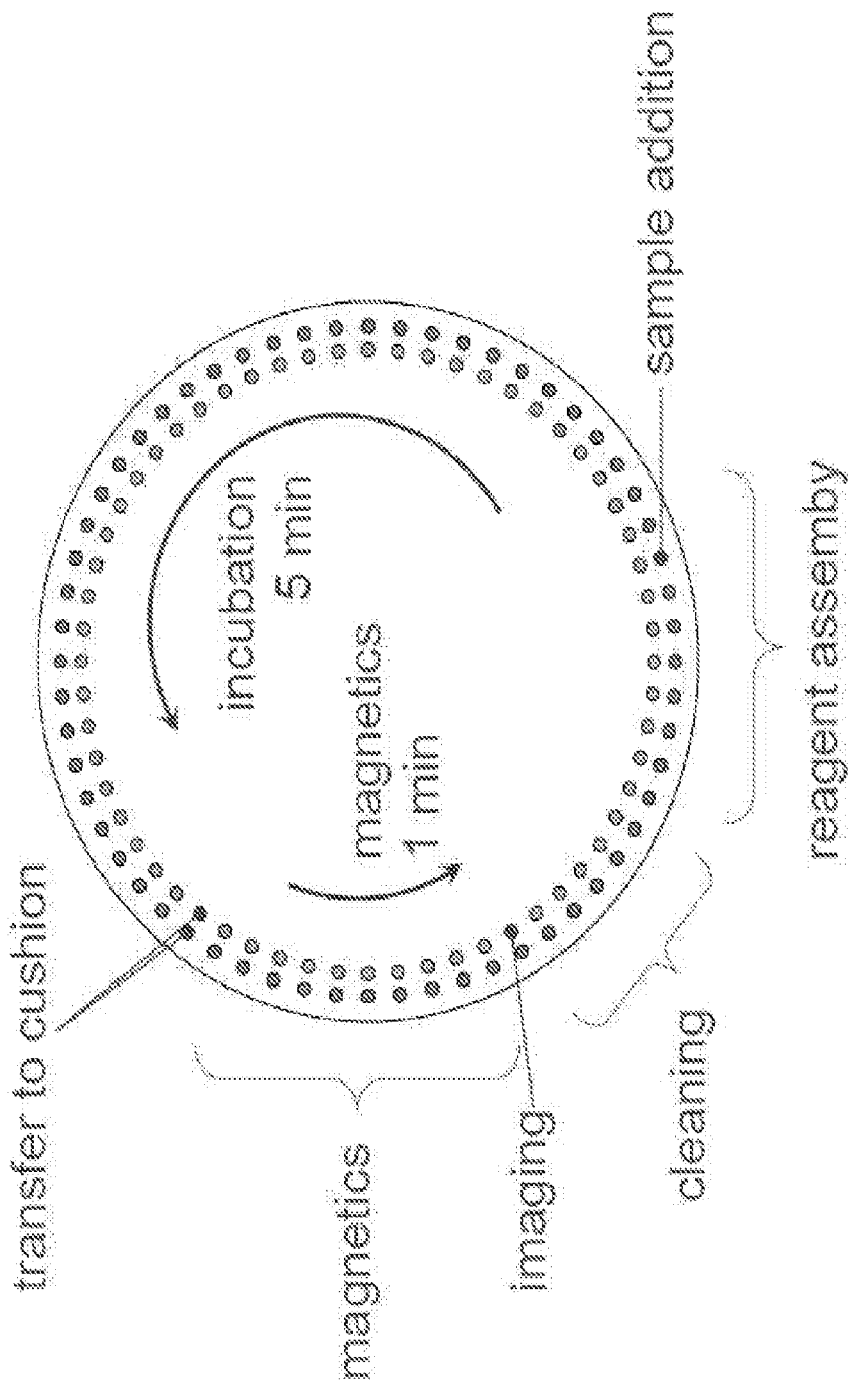
Fig. 33  Functional organization of the platform carousel. (Example 14)

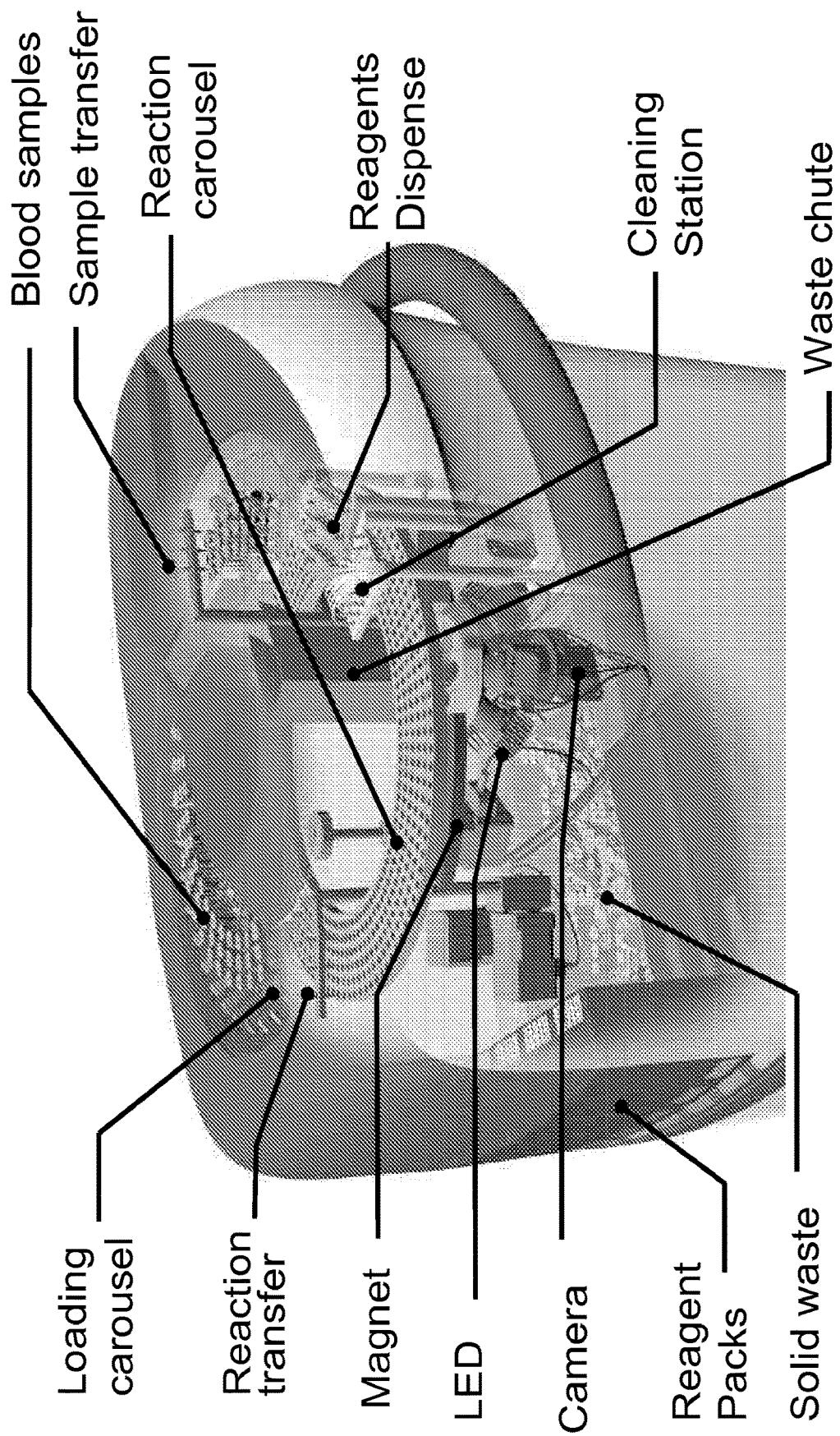
Fig. 34 Commercial Surge detection Platform Architecture. (Example 16)

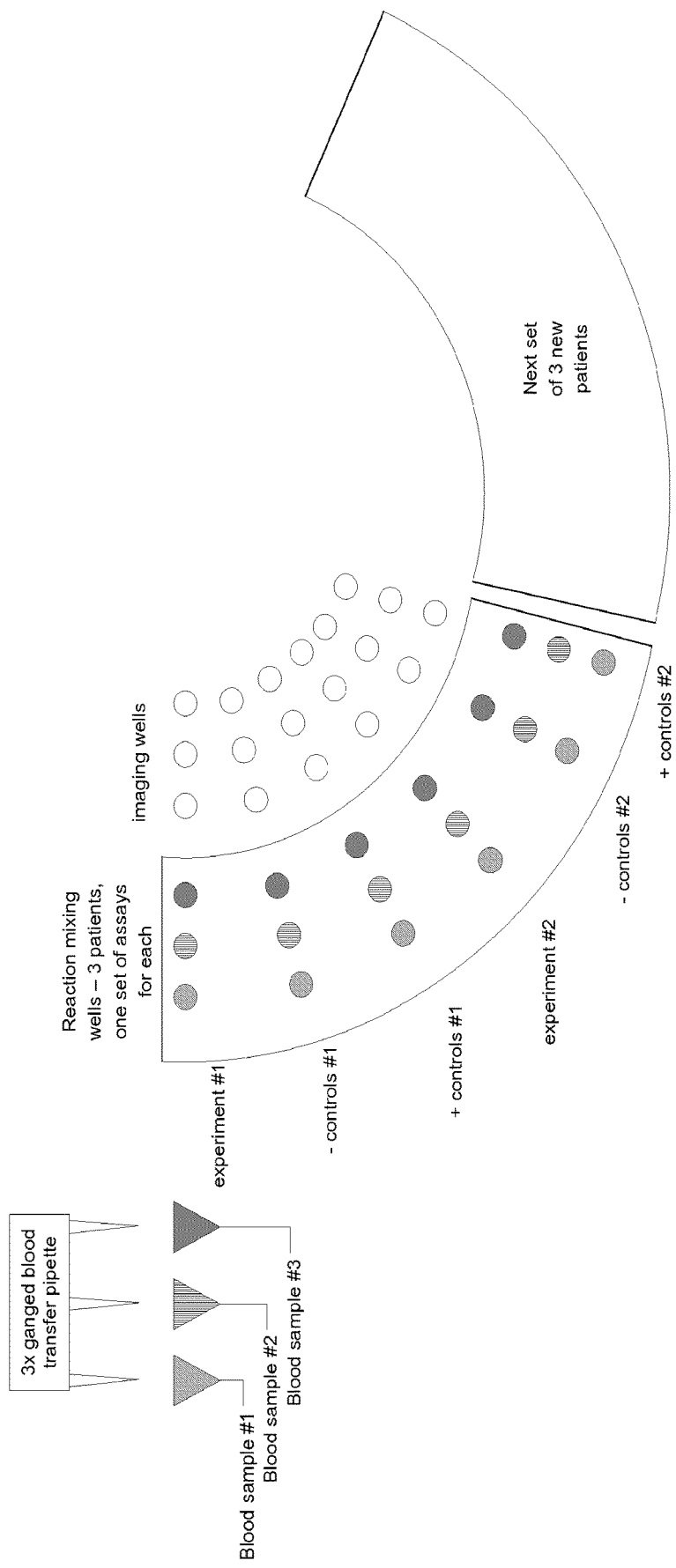
Fig. 35  Illustration of pipetting three patient samples at once. (Example 16)

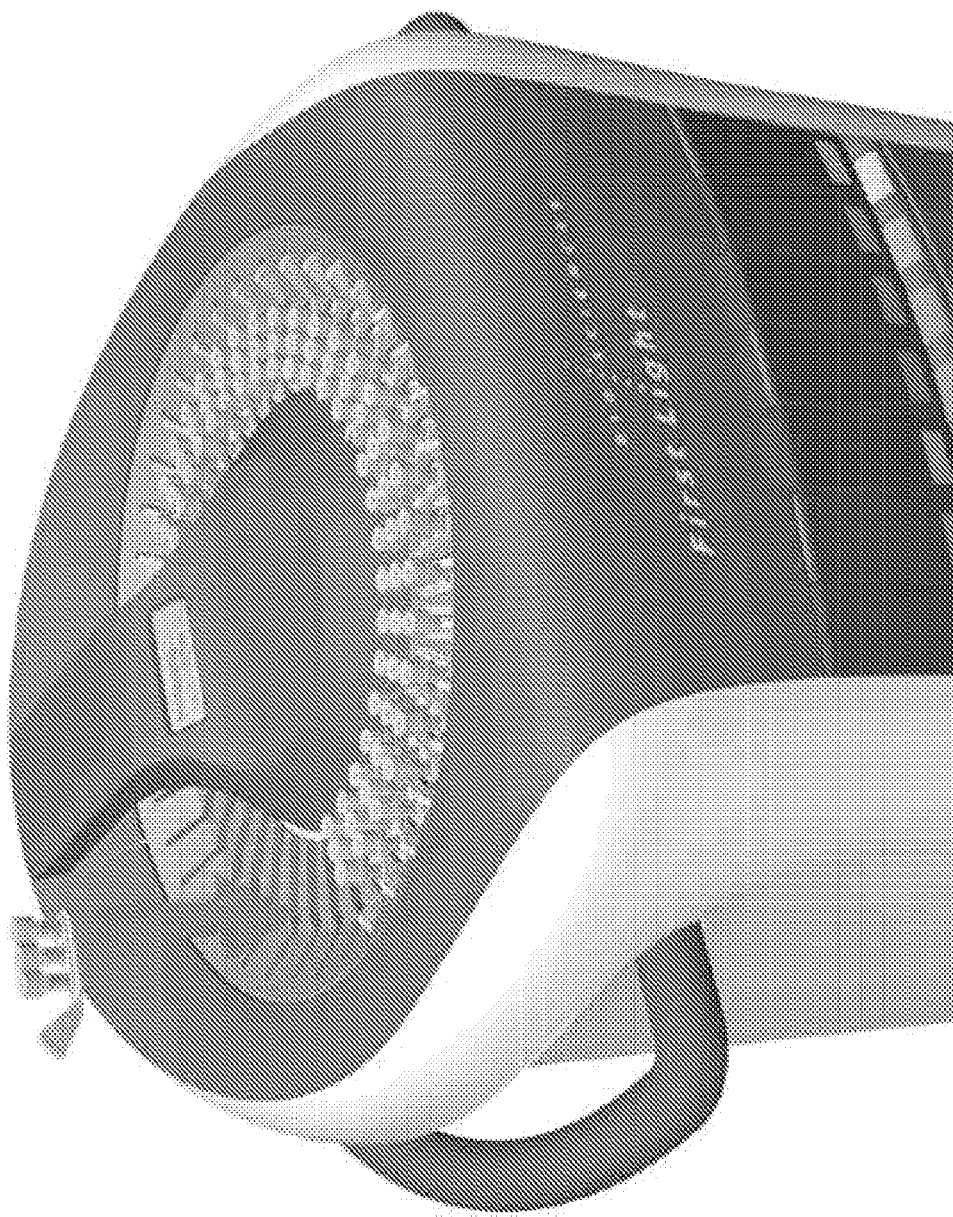
Fig. 36 Loading a sample rack. (Example 16)

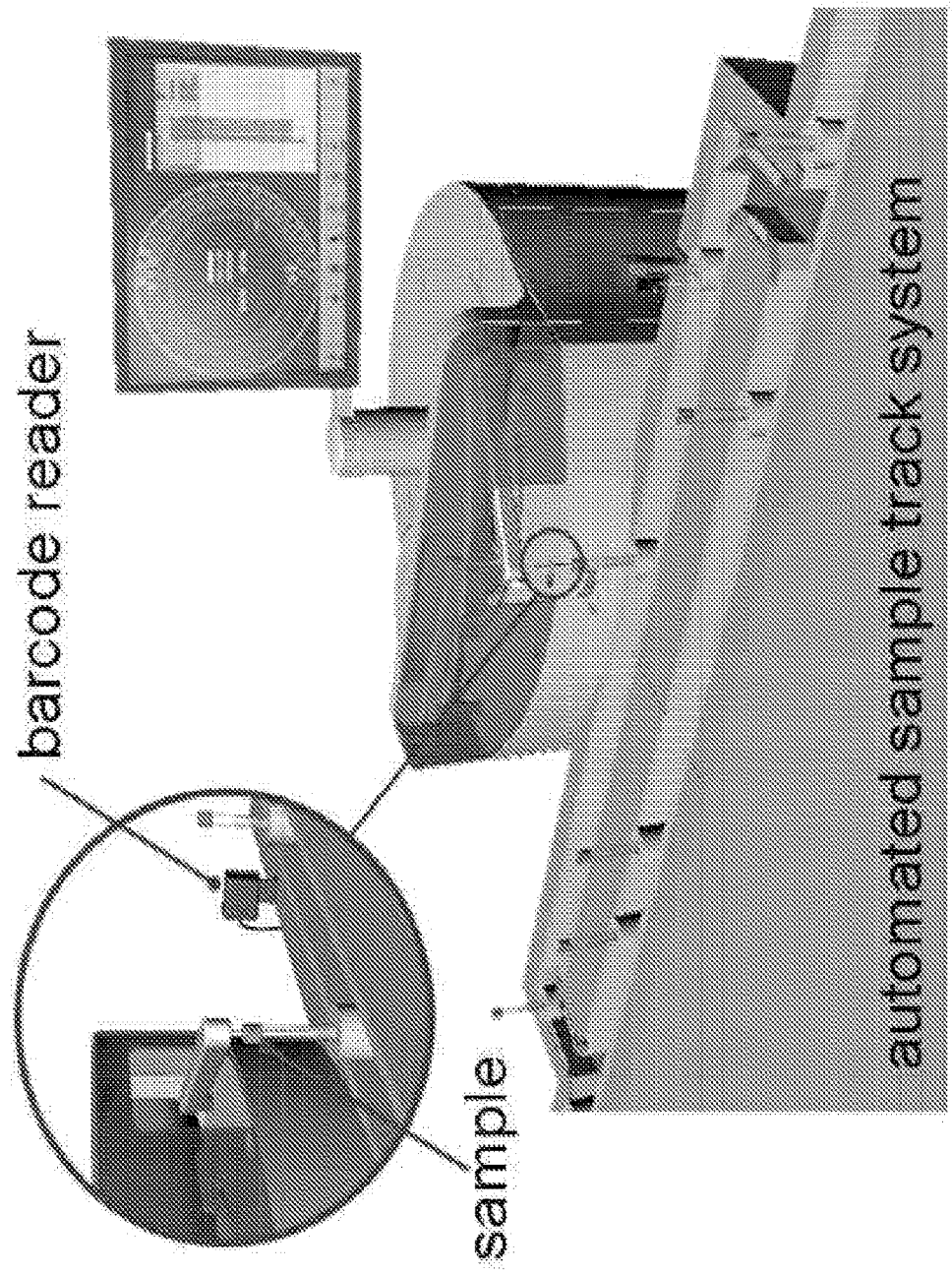
Fig. 37 Samples are delivered to the instrument by a sample track system. (Example 17)

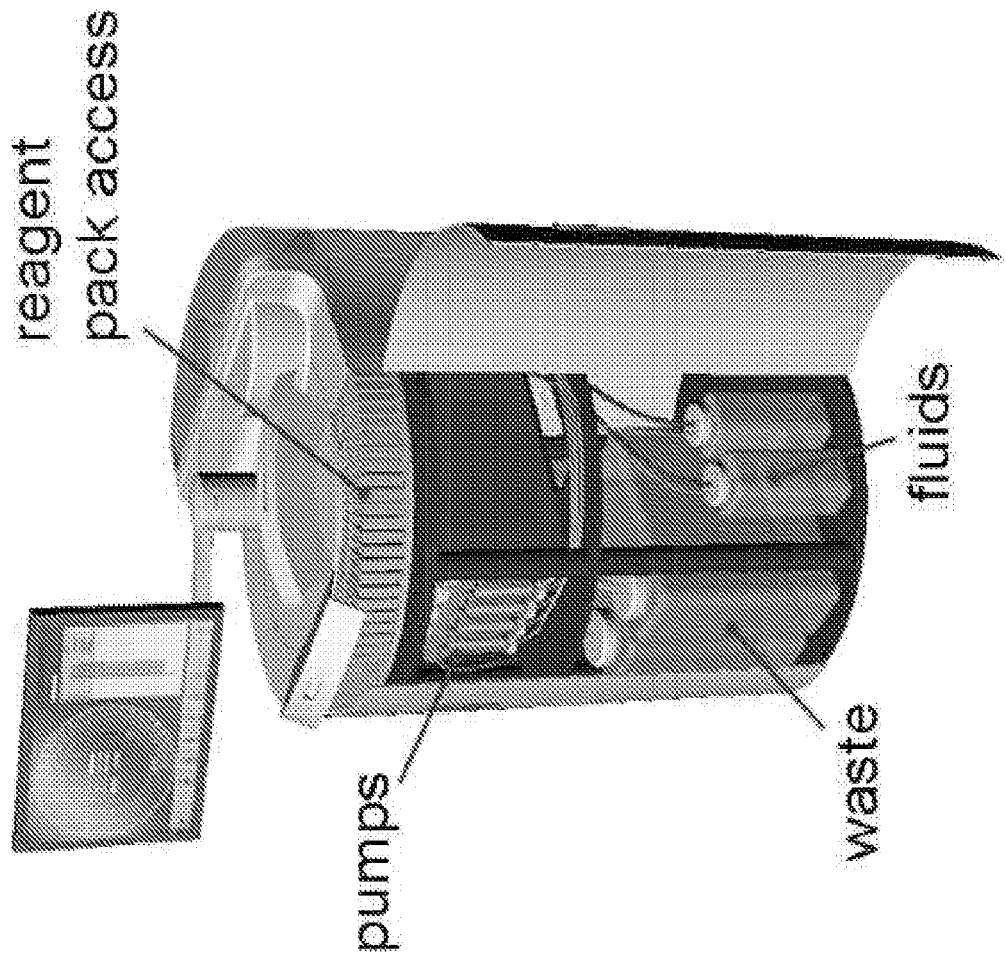
Fig. 38 Simple architecture and small footprint relative to comparable machines. (Example 17)

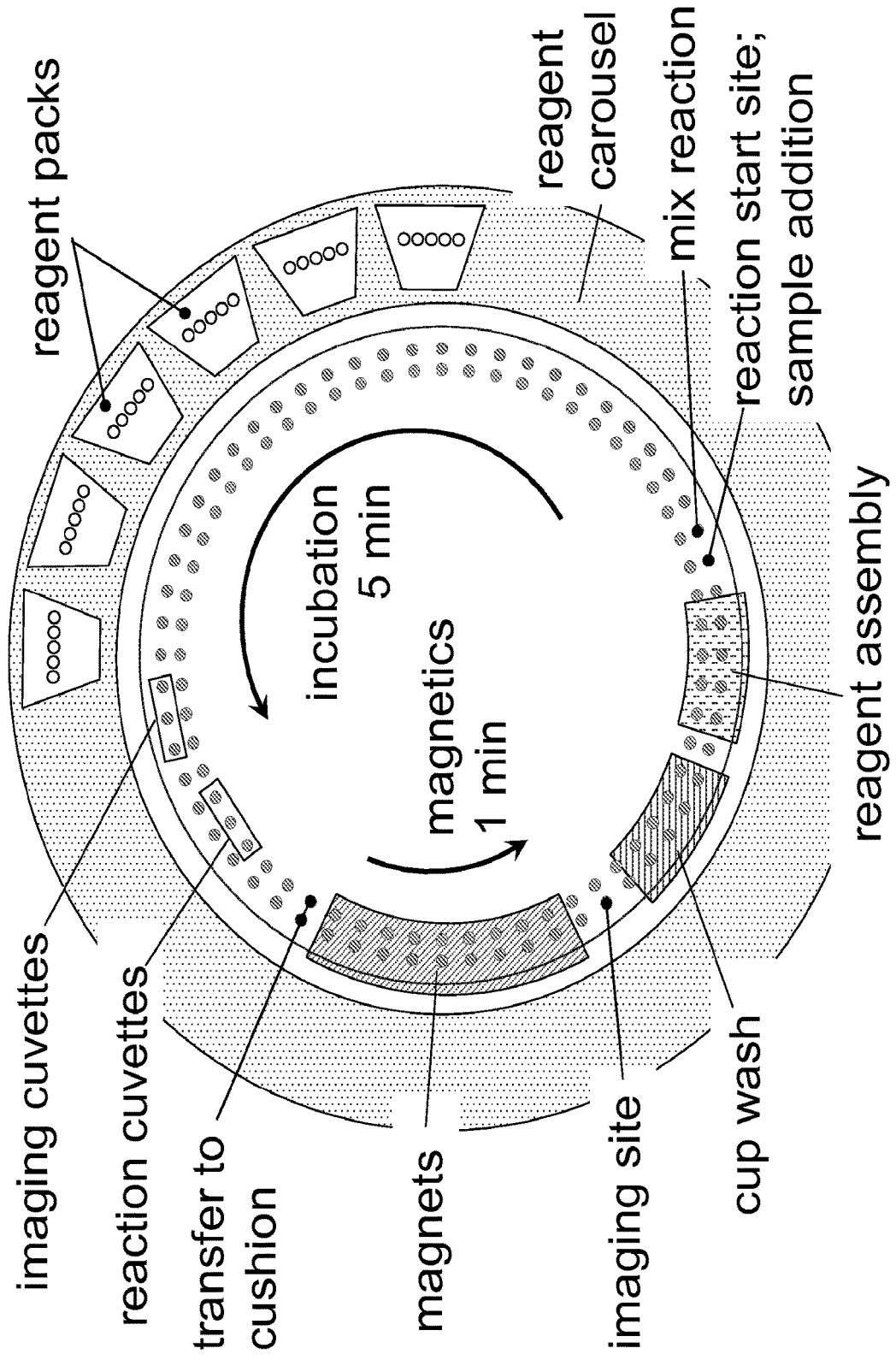
Fig. 39 Functional organization of central lab analyzer. (Example 17)

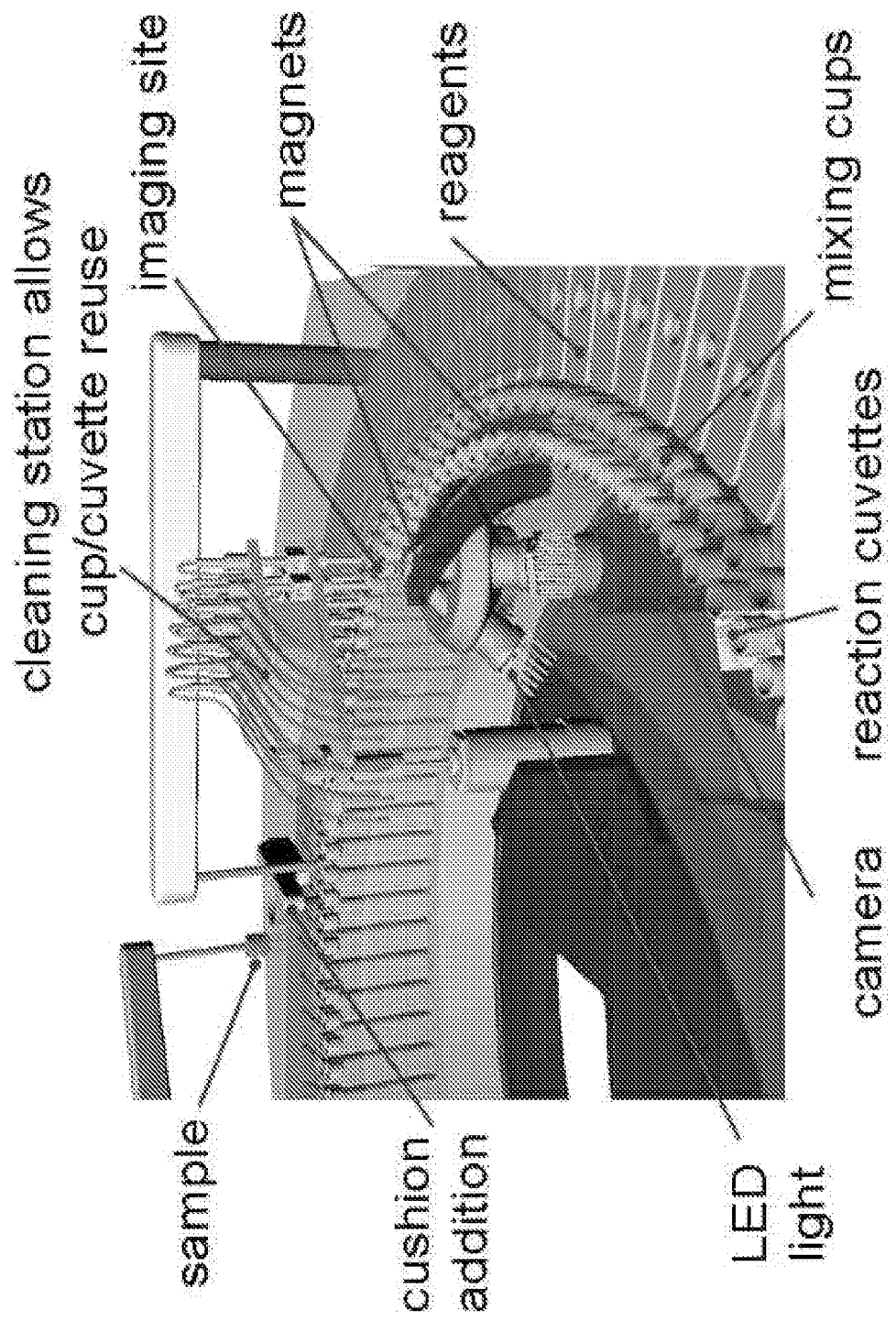
Fig. 40 Key elements of central lab analyzer. (Example 17)

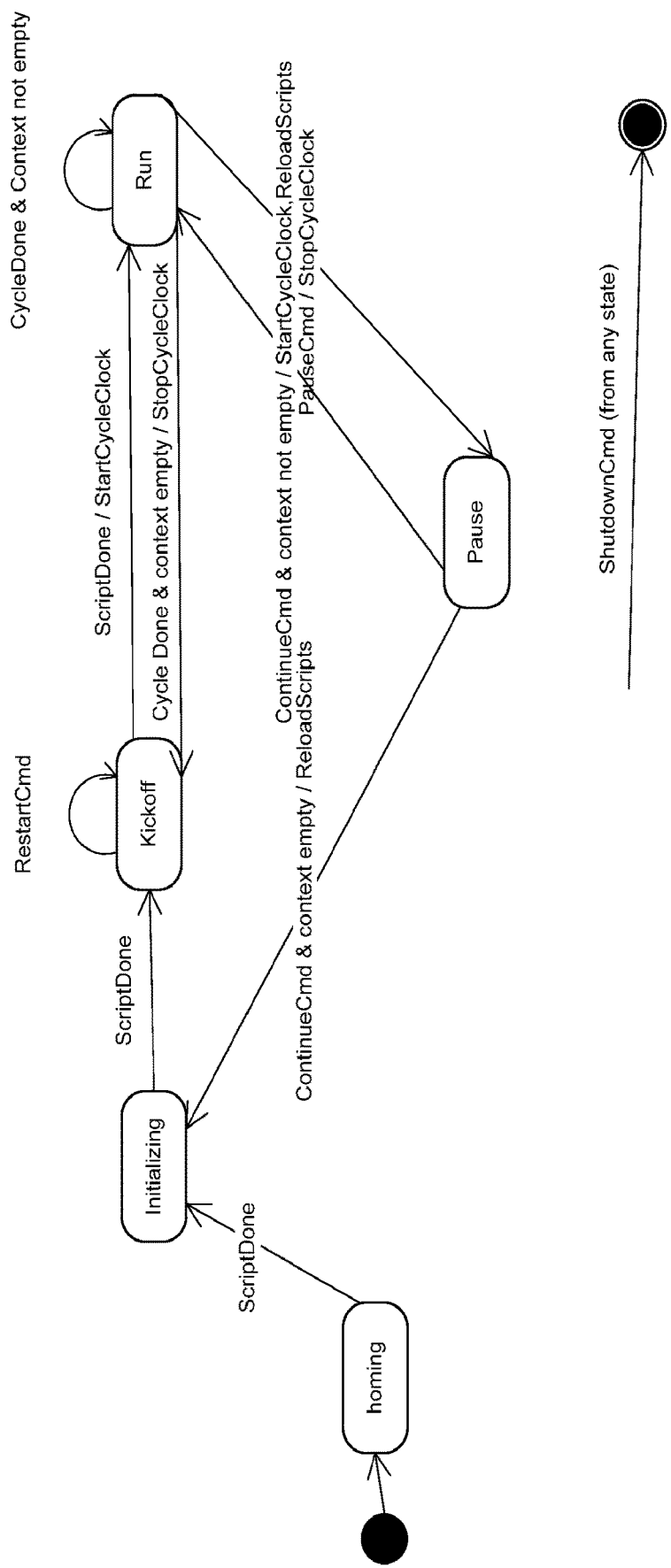
Fig. 41  Software state diagram. (Example 6)

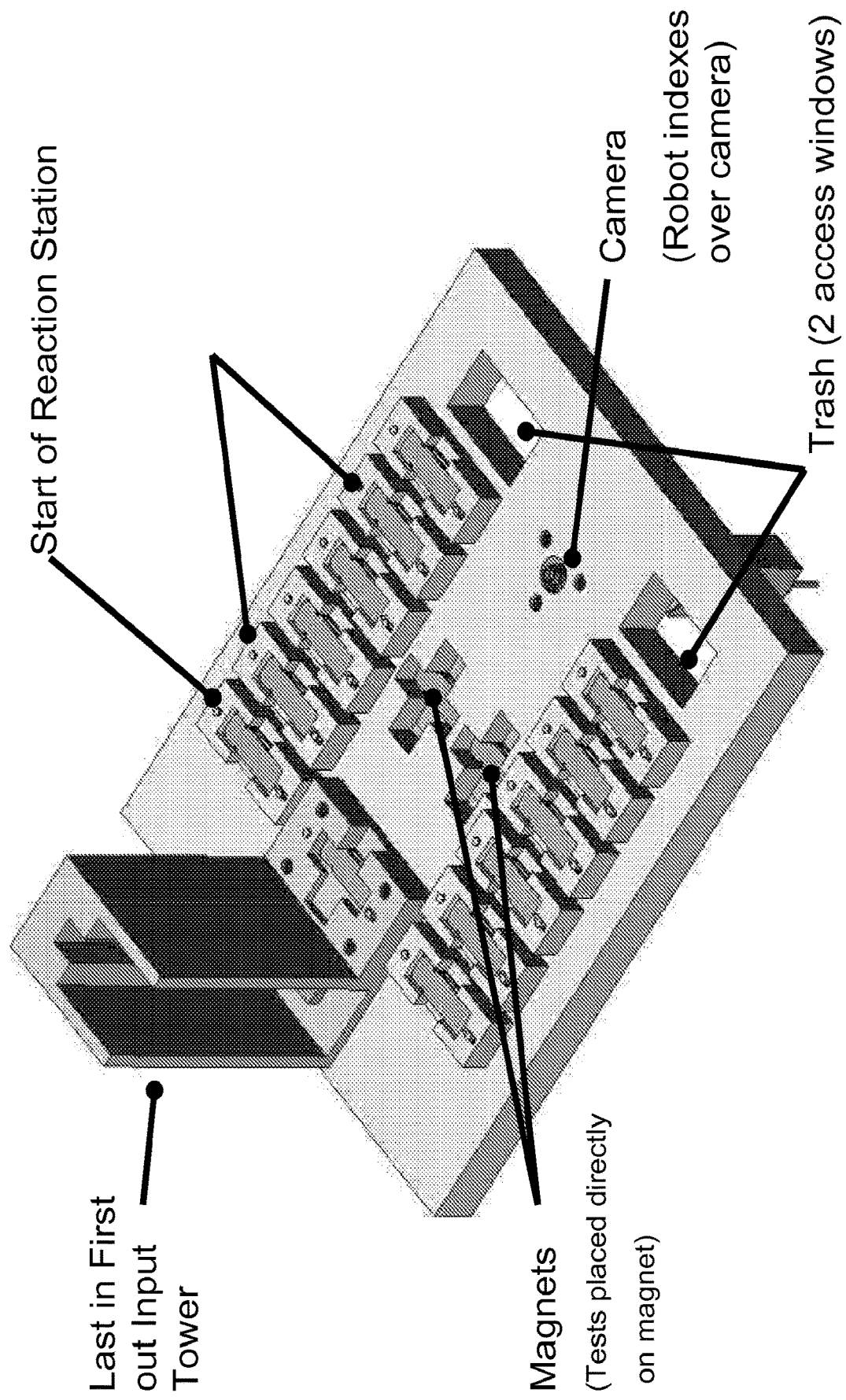
Fig. 42 Pick and place robot layout.

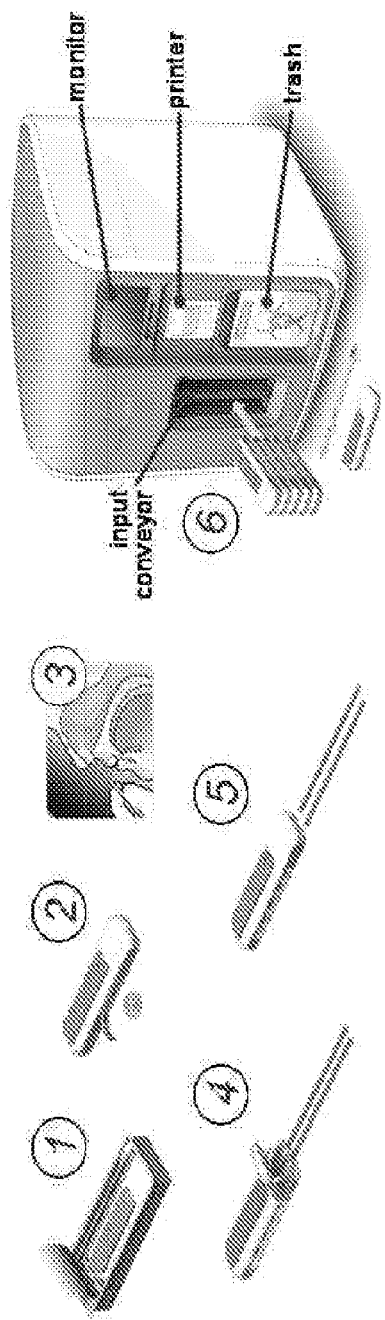
Fig. 43   Example sample workflow.

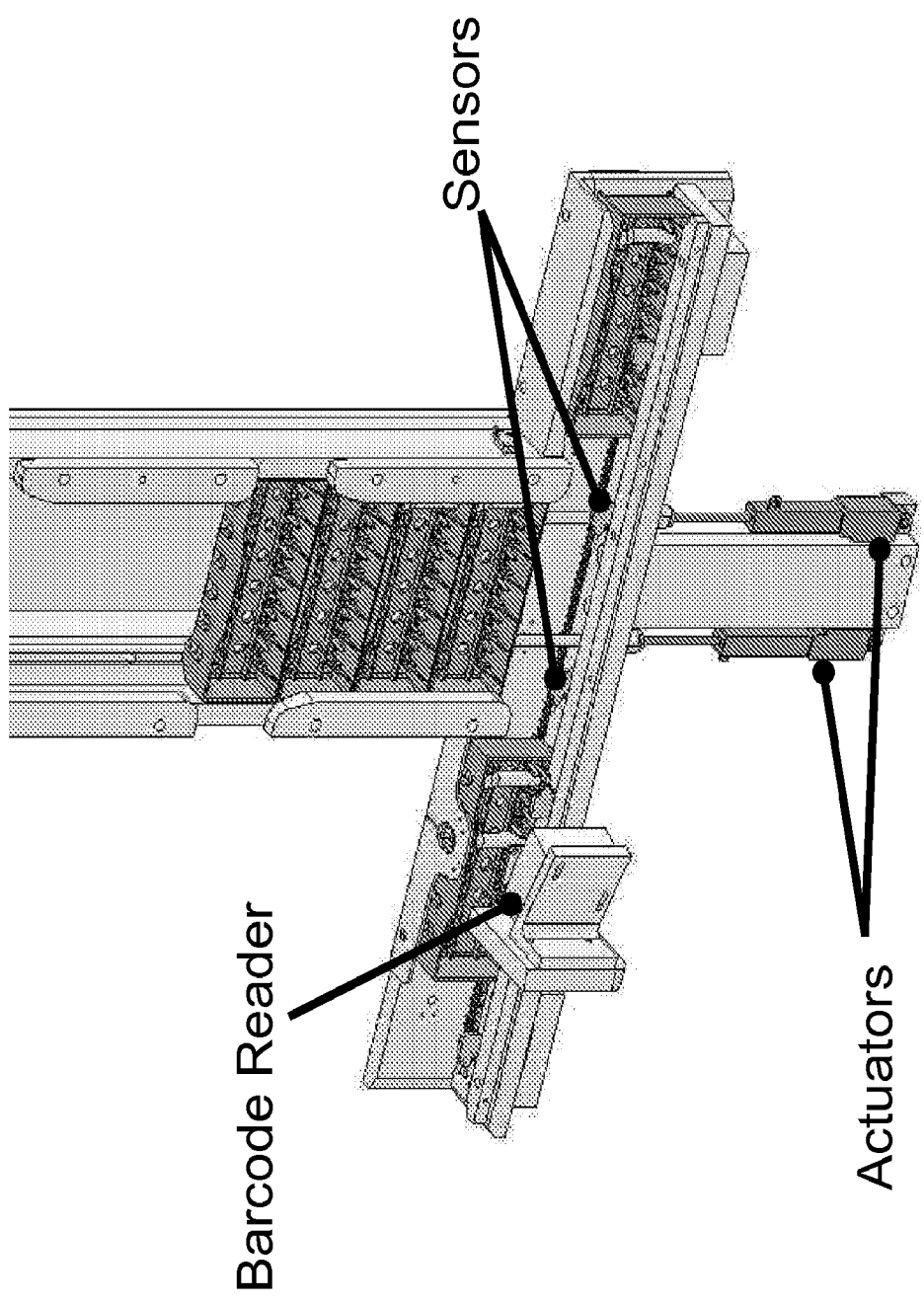
Fig. 44  Queuing subassembly populated with sample racks (Example 14)

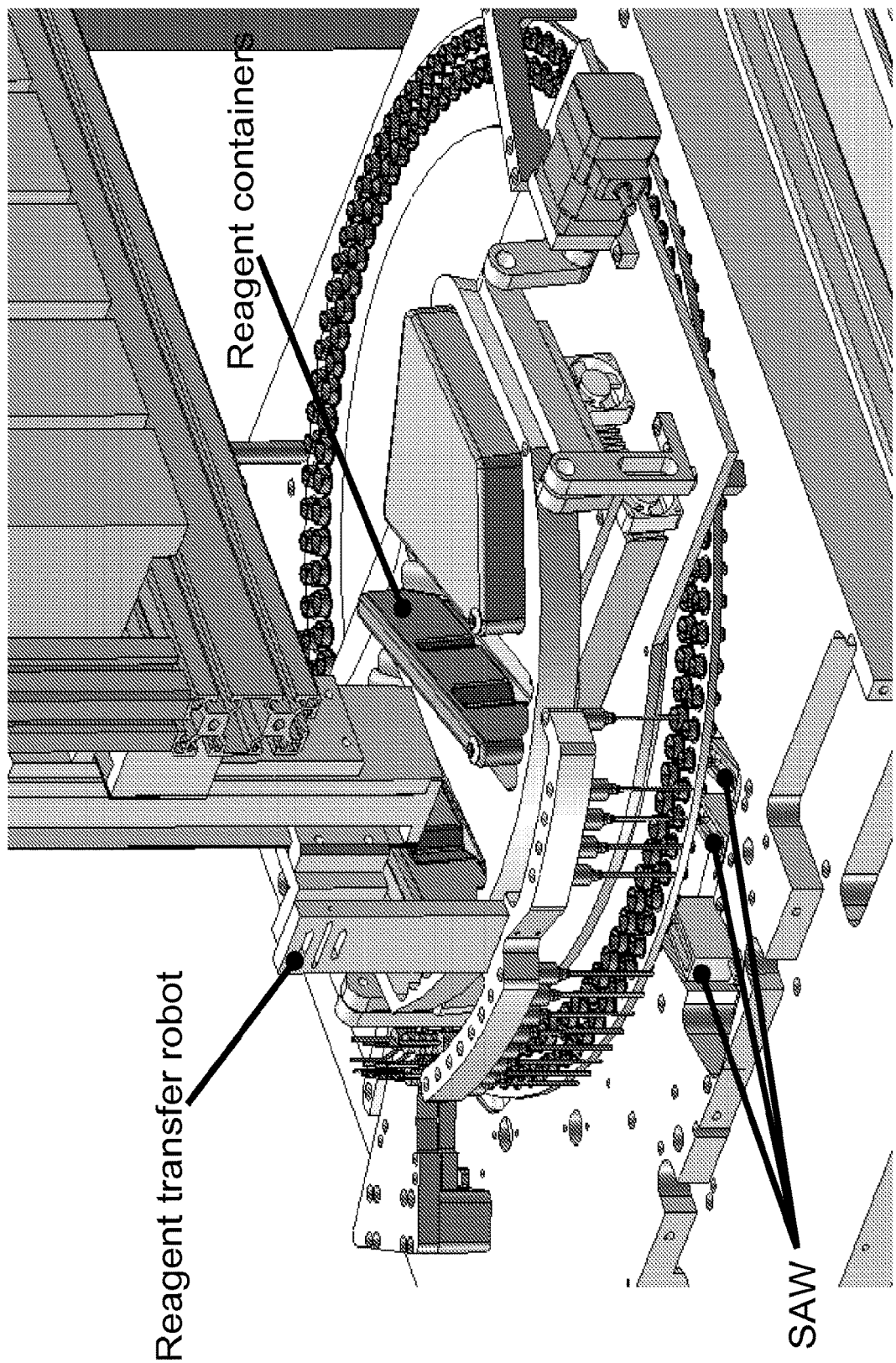
Fig. 45 View of liquid handling and reagent handling subsystem. (Example 14)

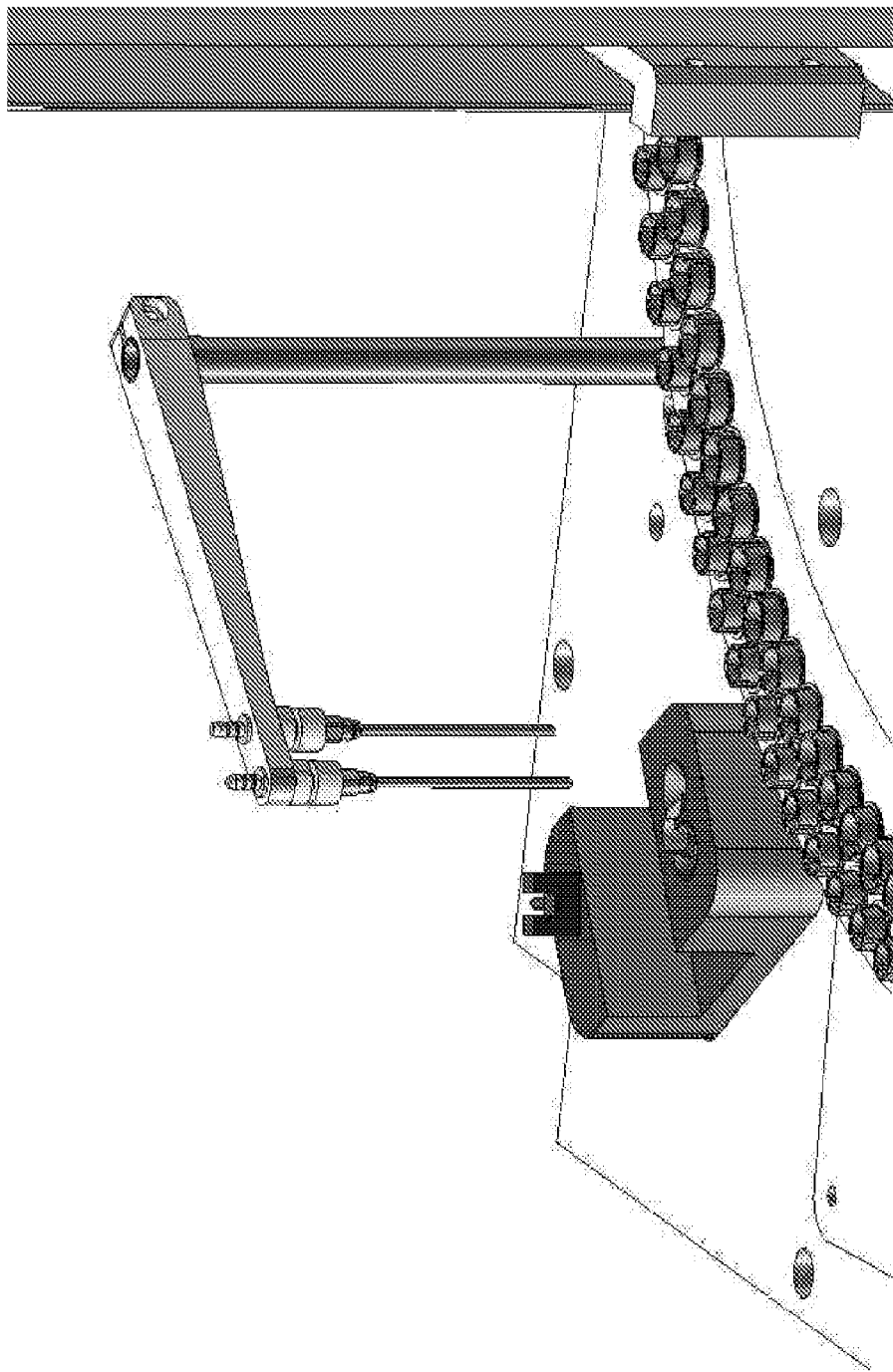
Fig. 46 Transfer pipette assembly. (Example 14)

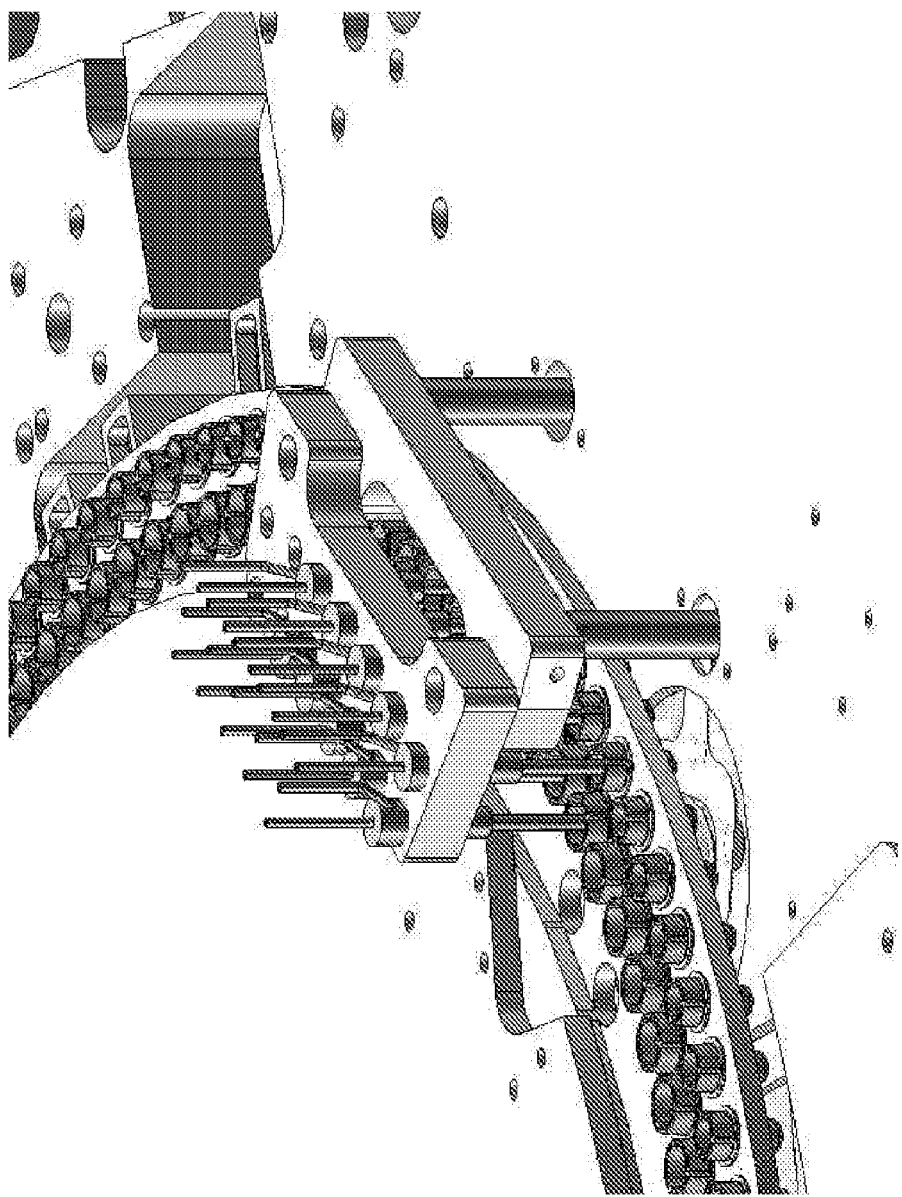
Fig. 47  Cup cleaning assembly. (Example 14)

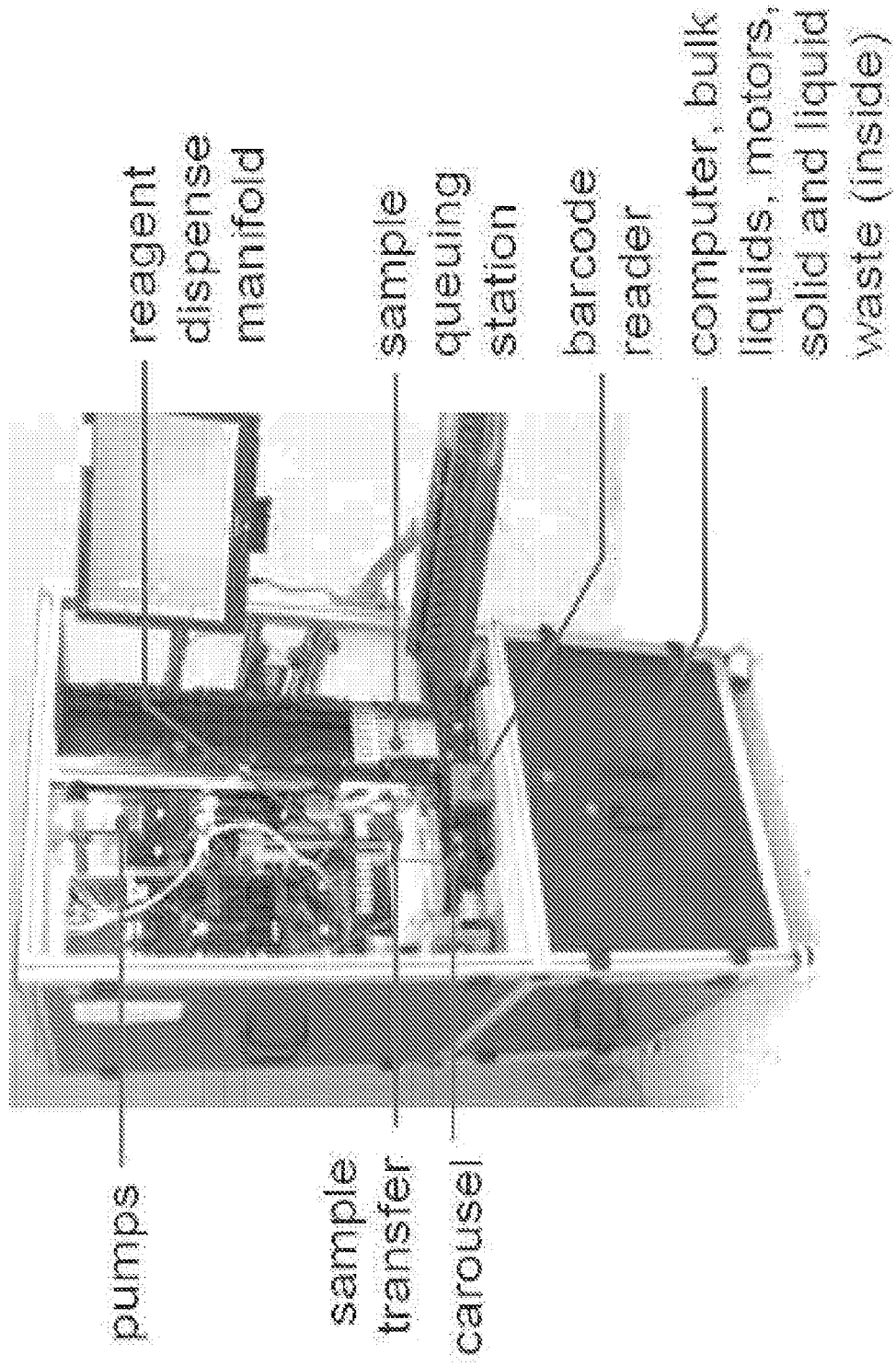
Fig. 48 Surge detection prototype platform. (Example 14)

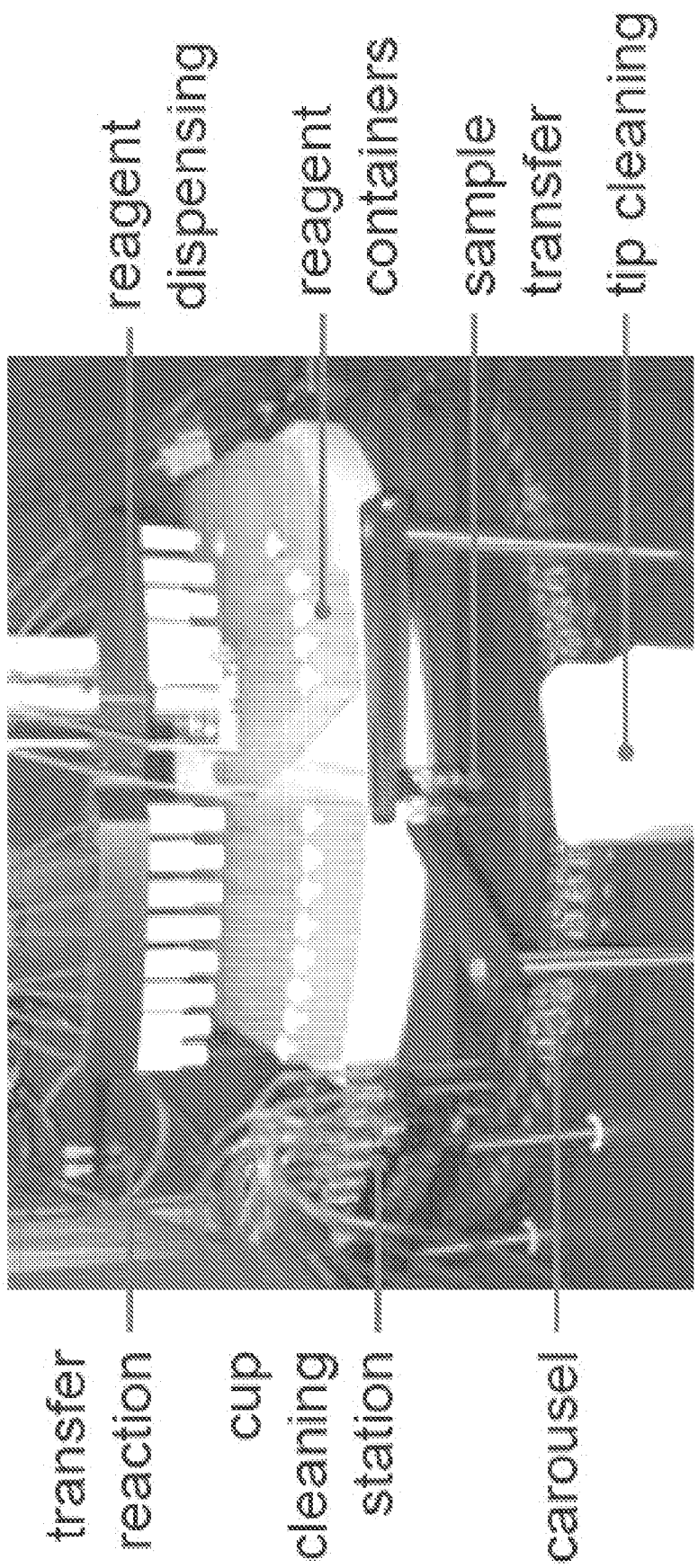
Fig. 49   Close up view of liquid handling subsystem. (Example 14)

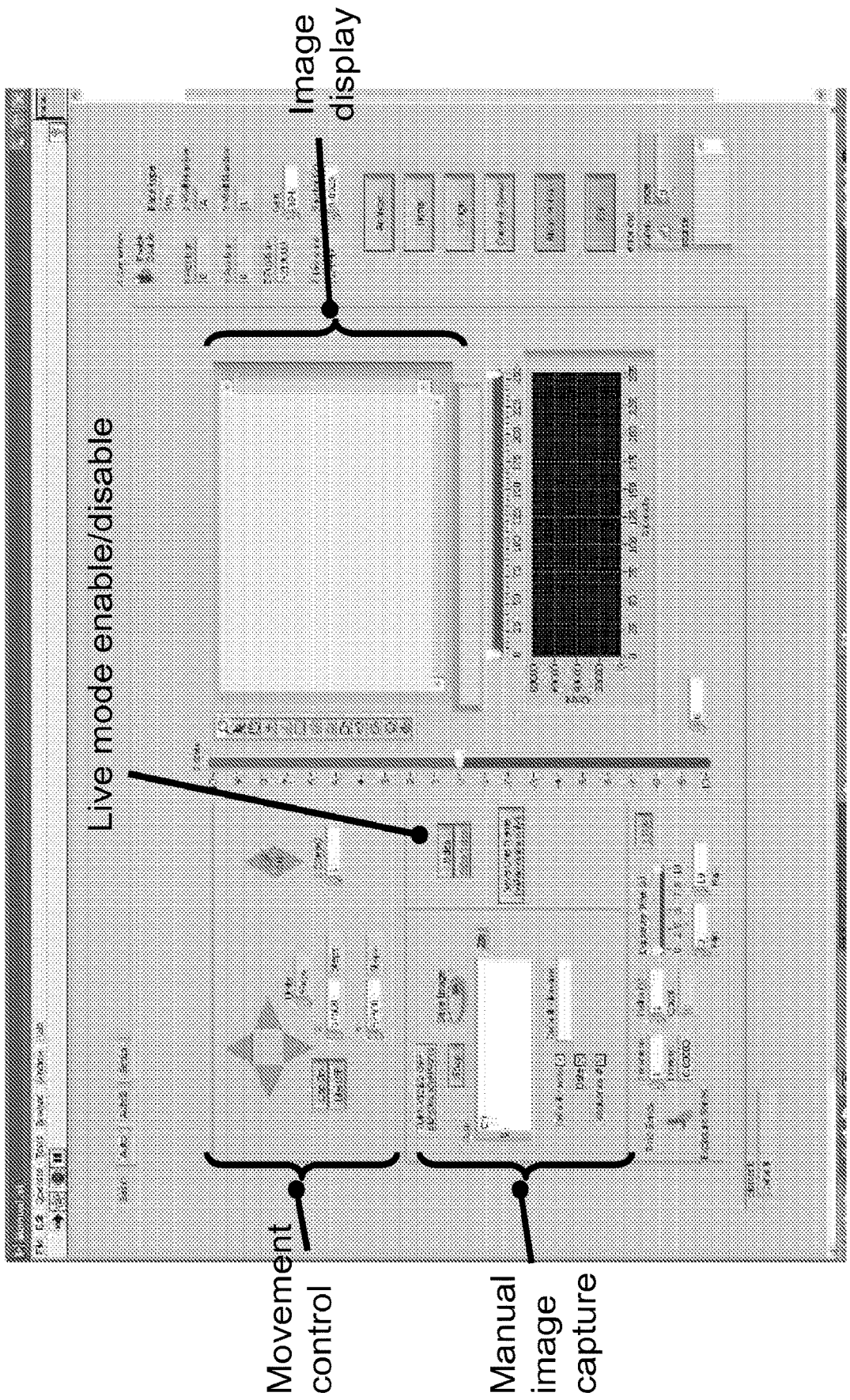
Fig. 50   System control interface tab 1. (Example 8)

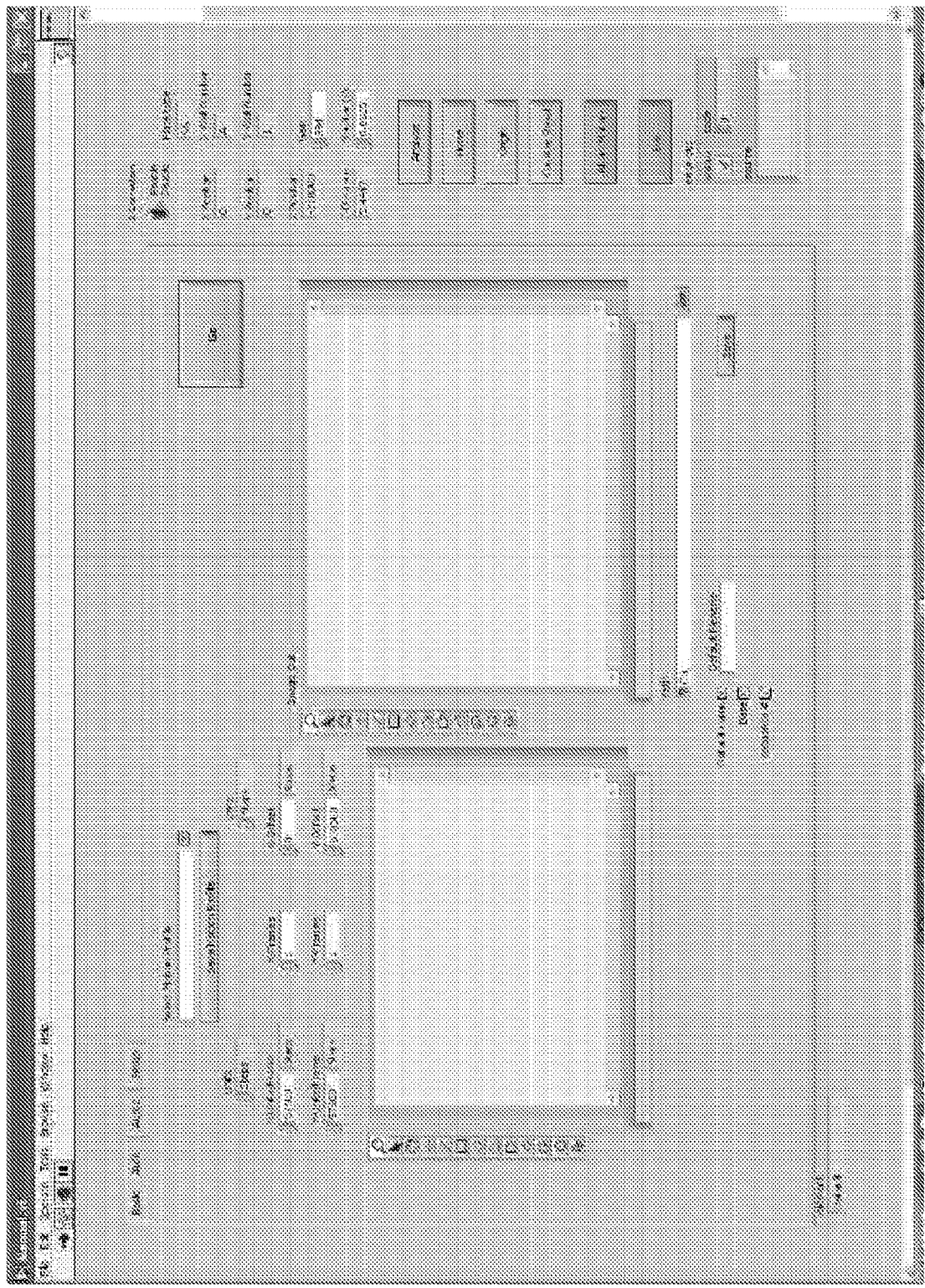
Fig. 51   System control interface tab 2. (Example 8)

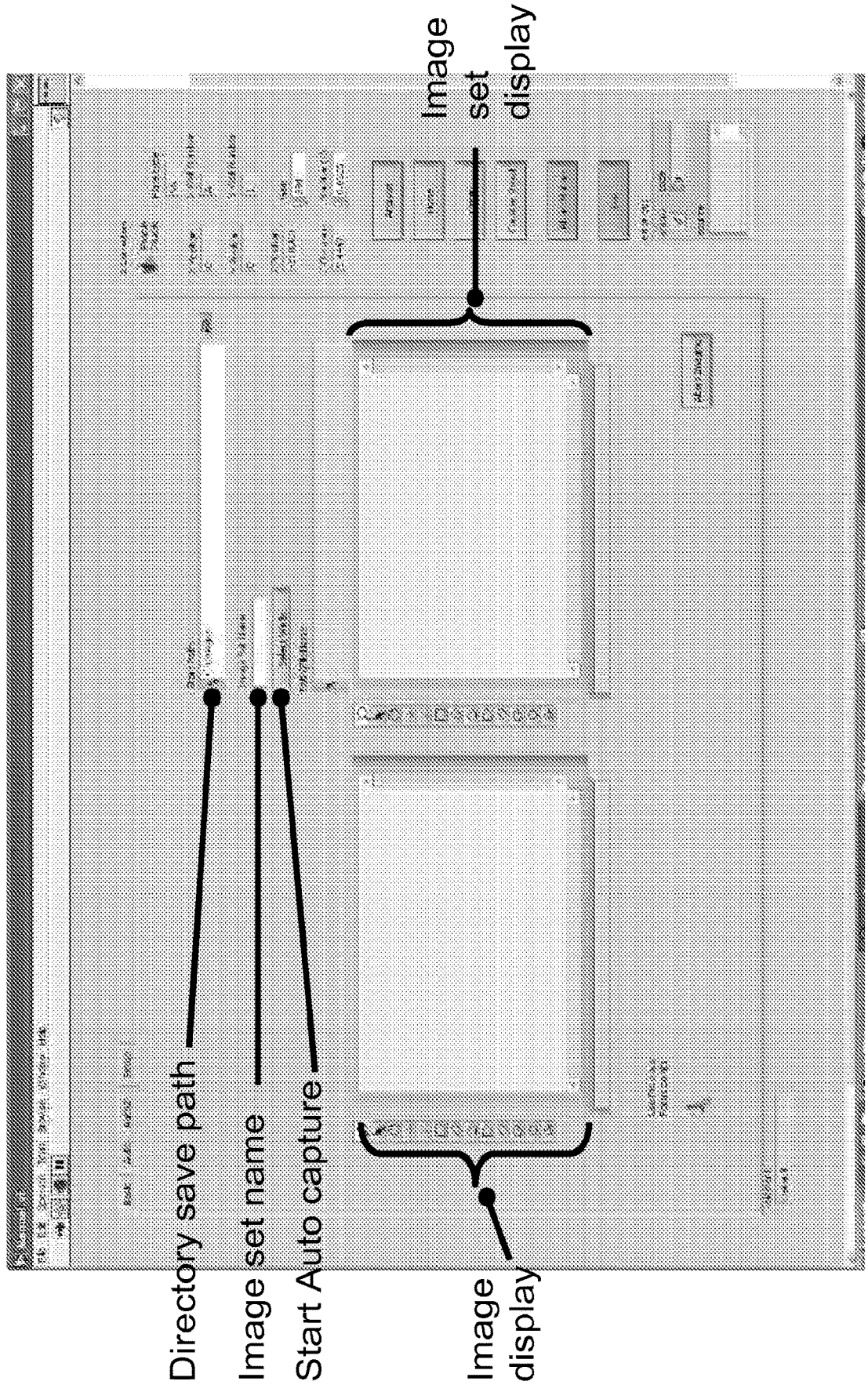
Fig. 52  System control interface tab 3. (Example 8)

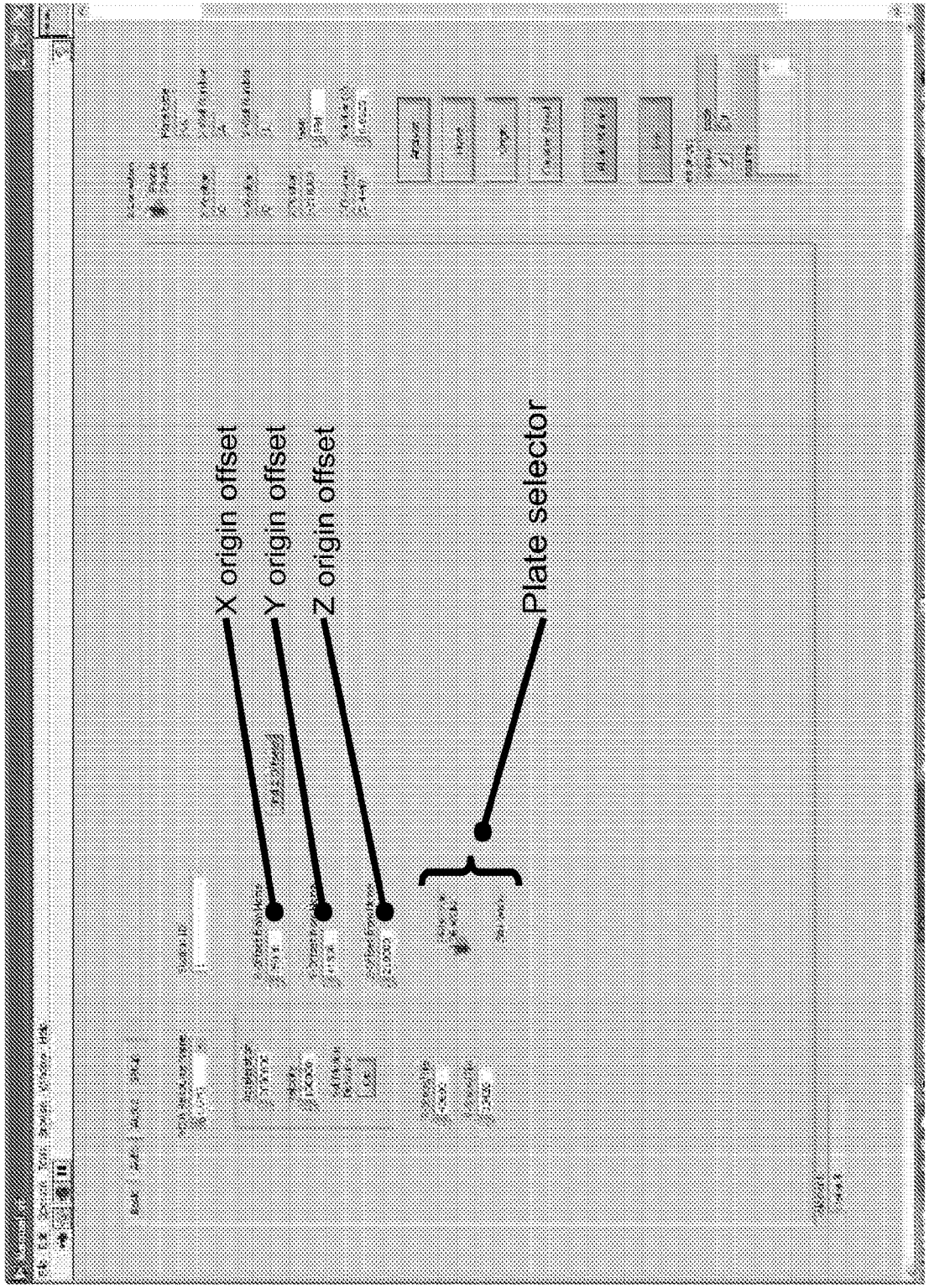
Fig. 53 System control interface tab 4. (Example 8)

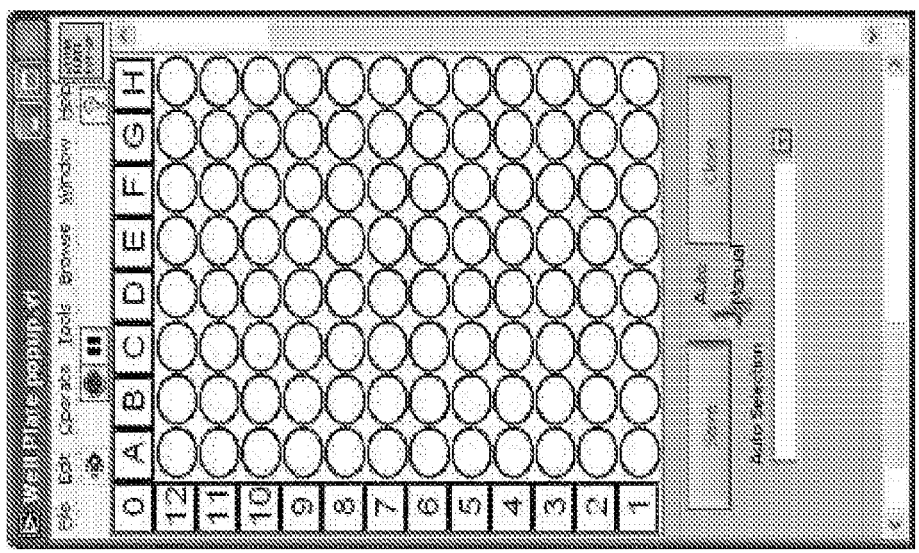
Fig. 54. Plate position selection window for Auto 2. (Example 8)

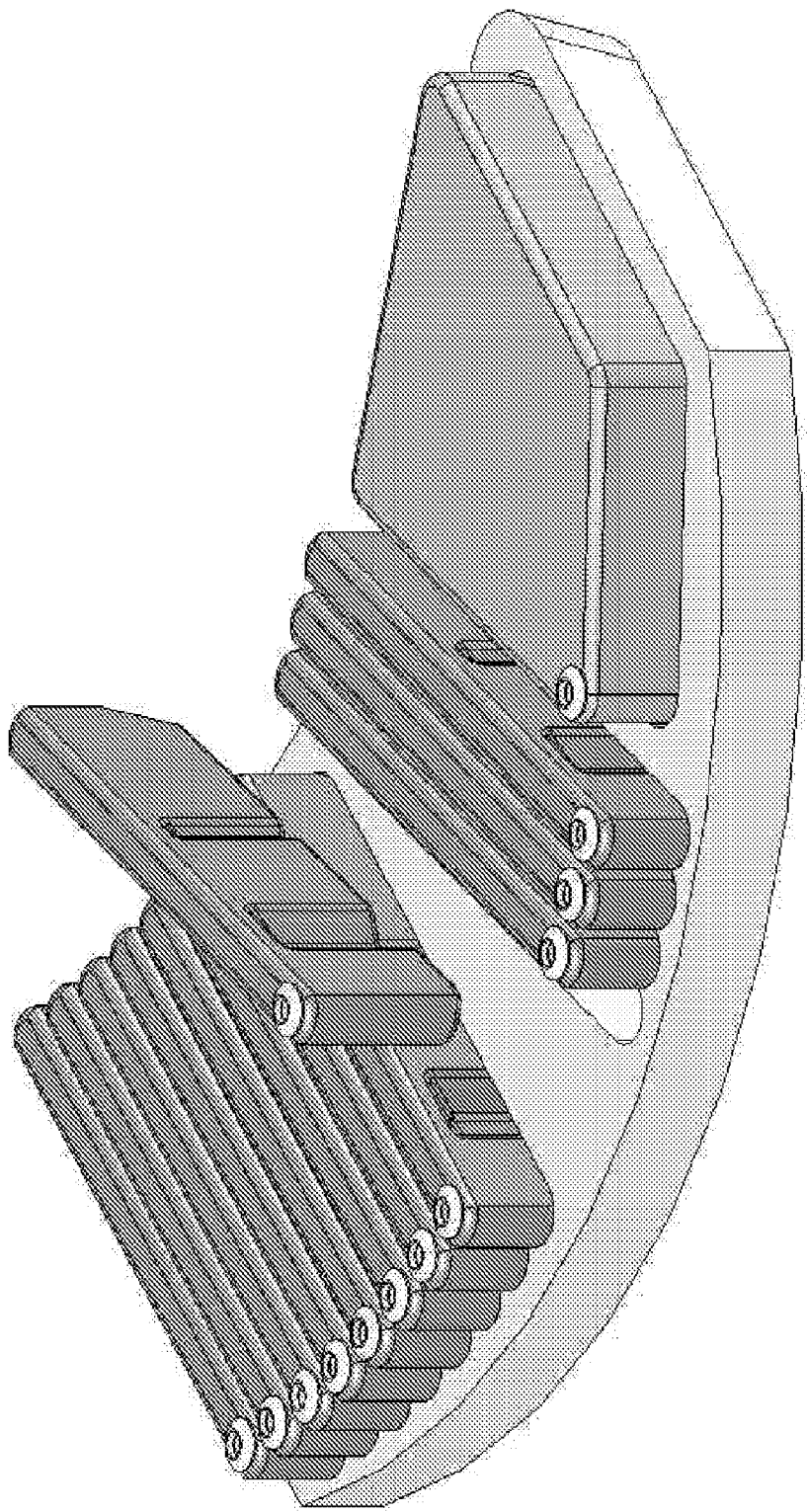
Fig. 55 Bulk reagent container examples showing turbulence-inducing baffles and keying. (Example 14)

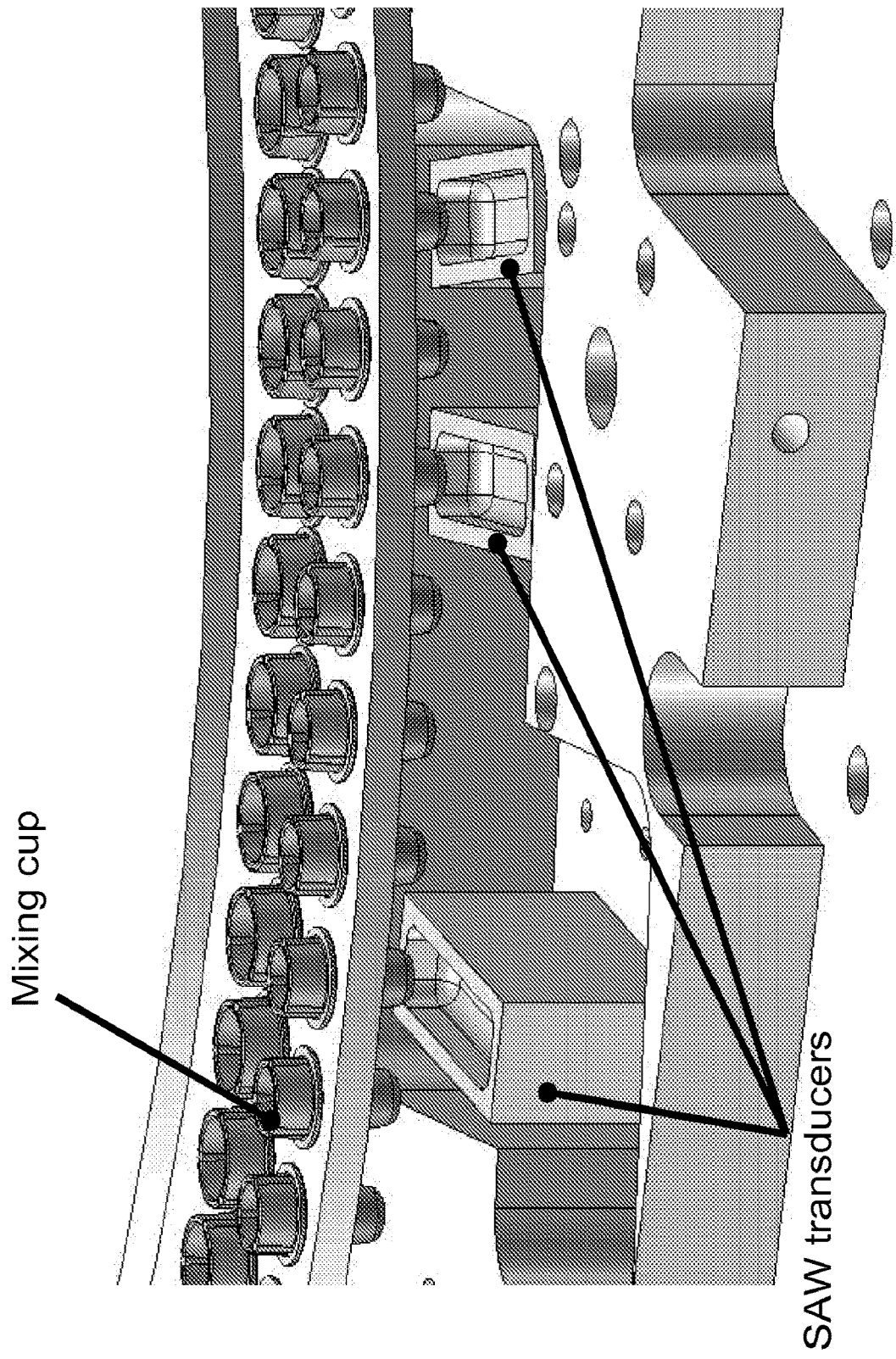
Fig. 56  Mixing cups and SAW transducer subassemblies. (Example 14)

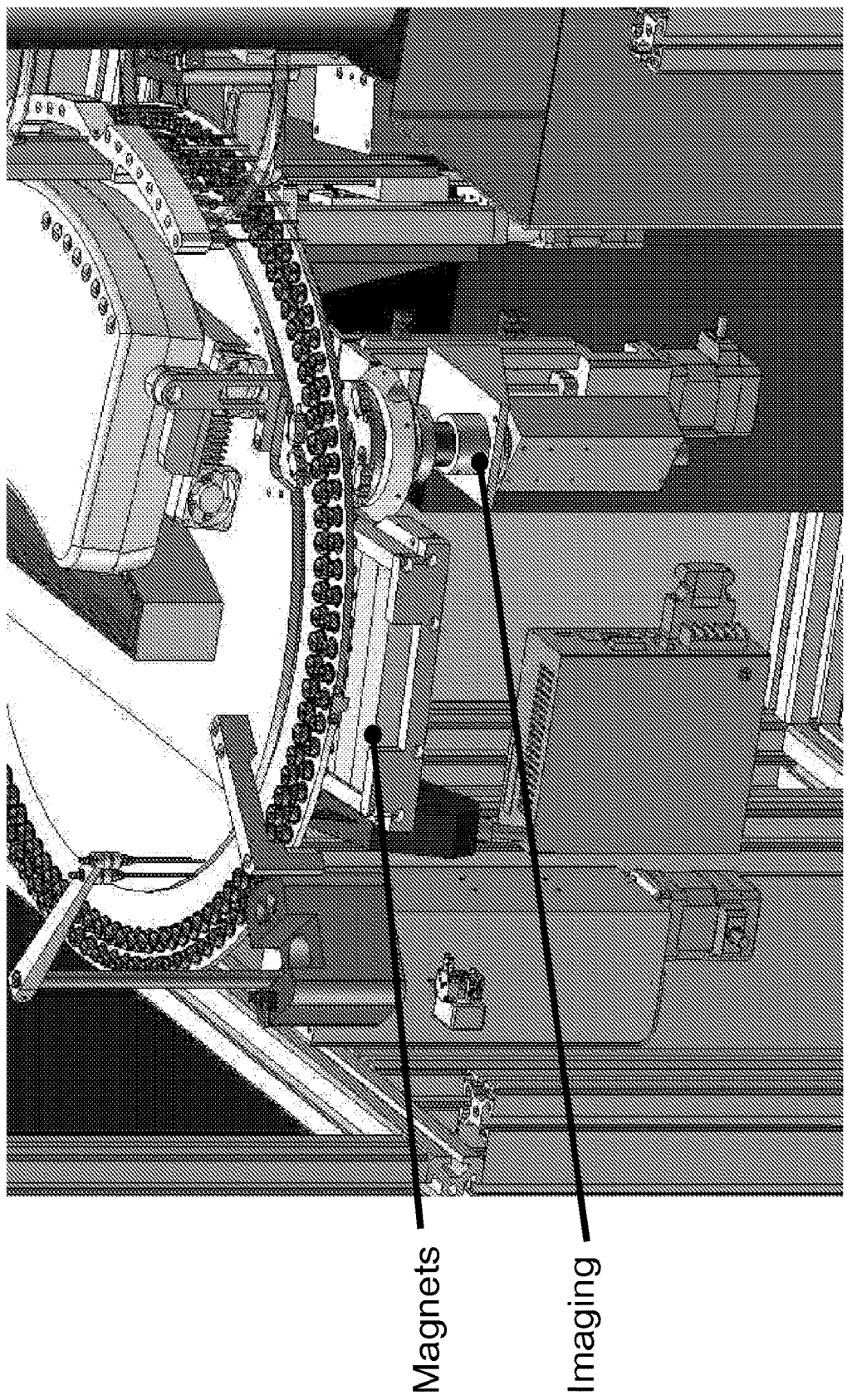
Fig. 57  Magnet and optical subassemblies. (Example 14)

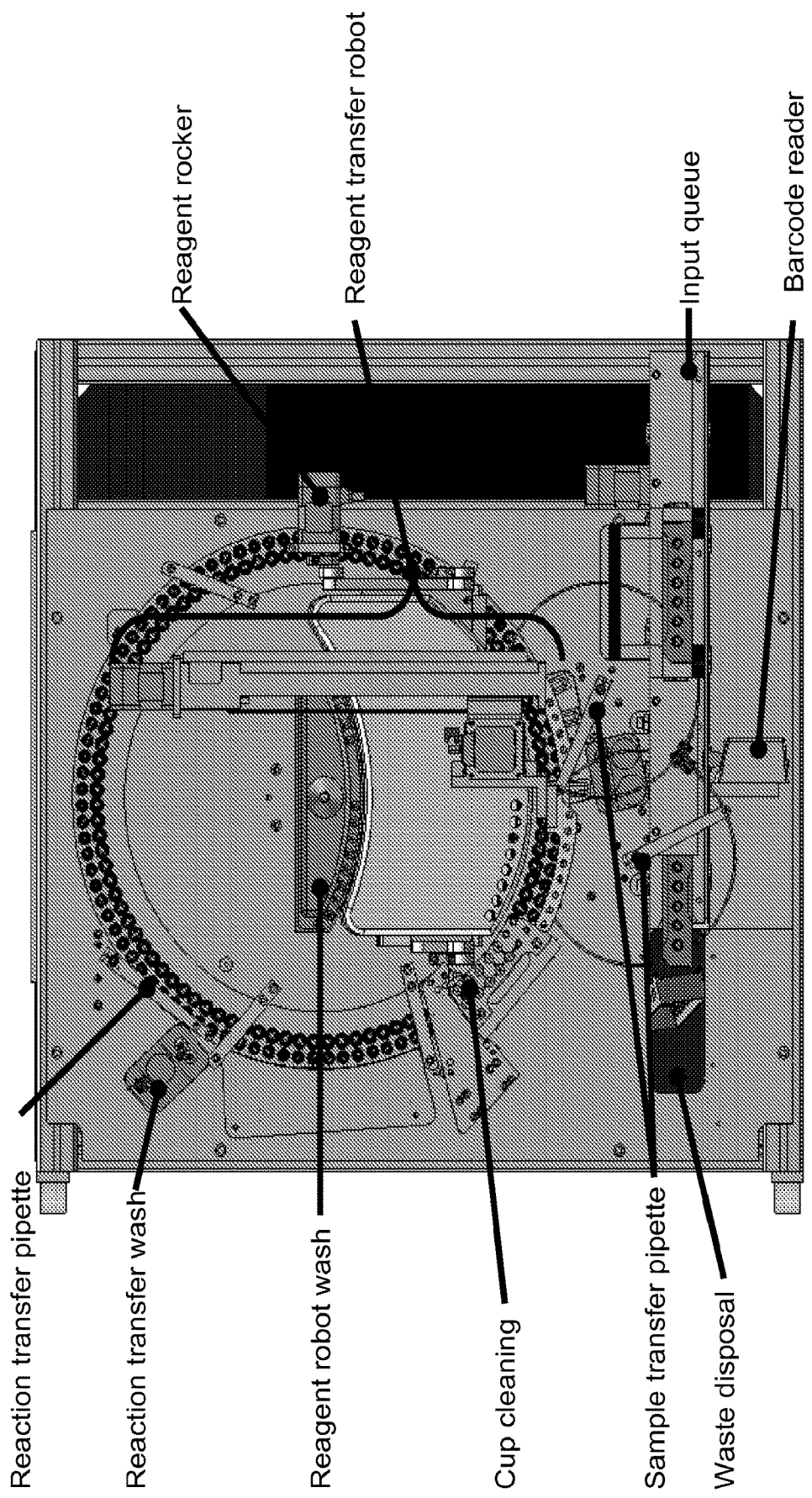
Fig. 58　Carousel top view. (Example 14)

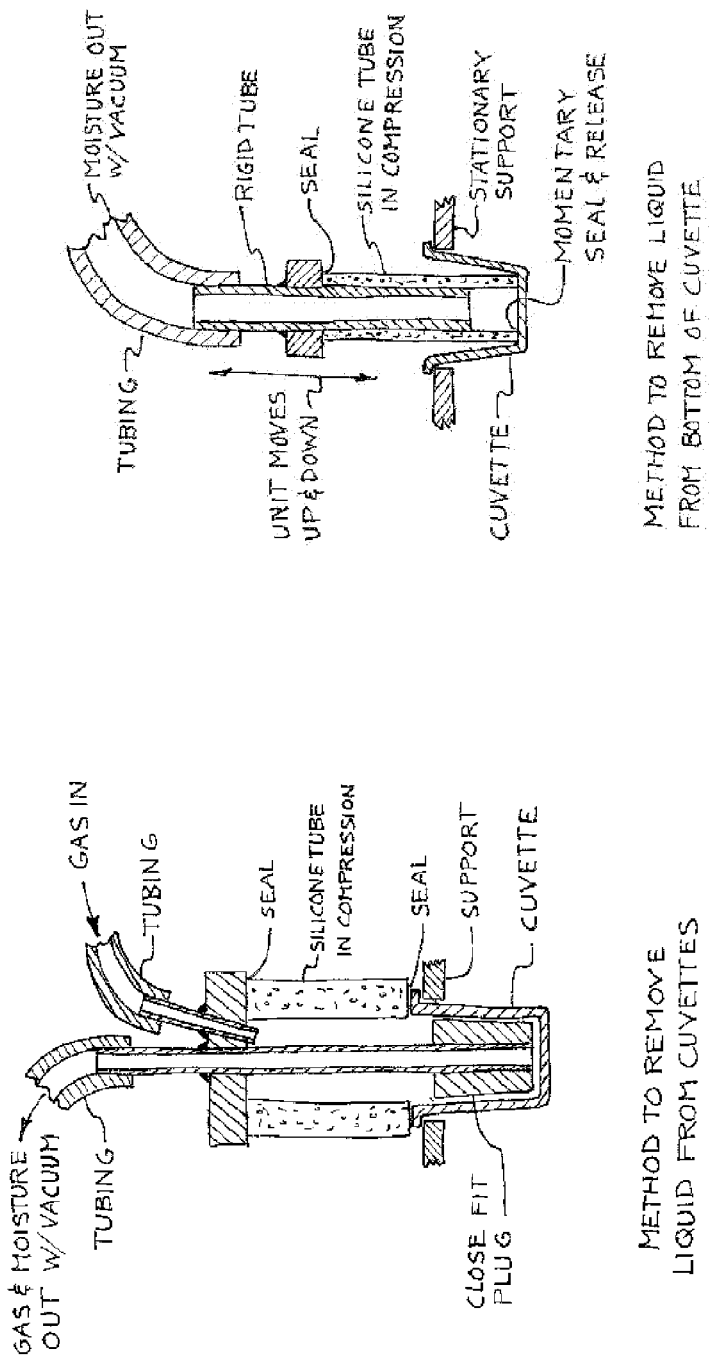
Fig. 59   Methods for removing liquid from cups. (Example 14)

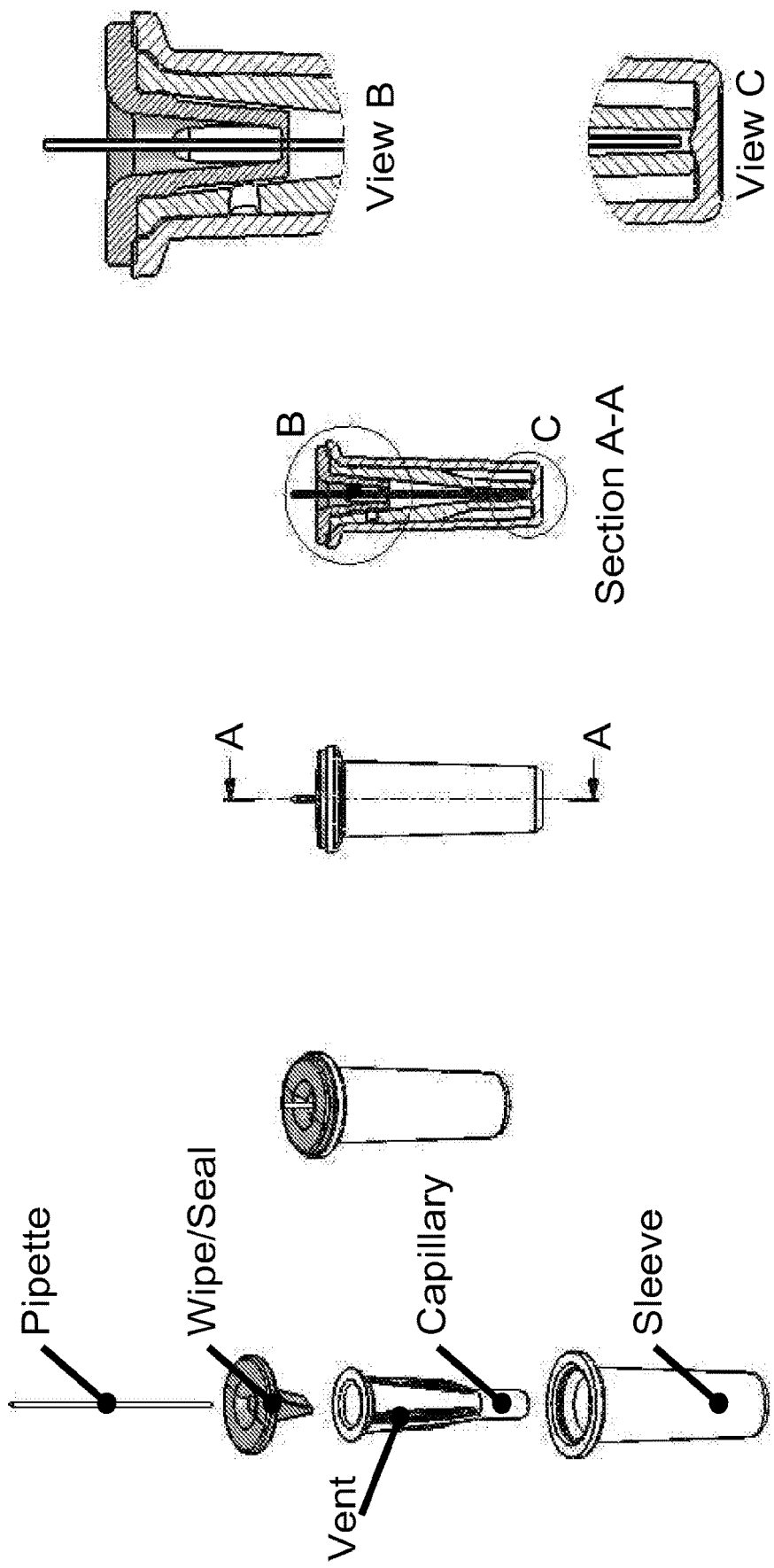
Fig. 60　Capillary sample collection consumable. (Example 14)

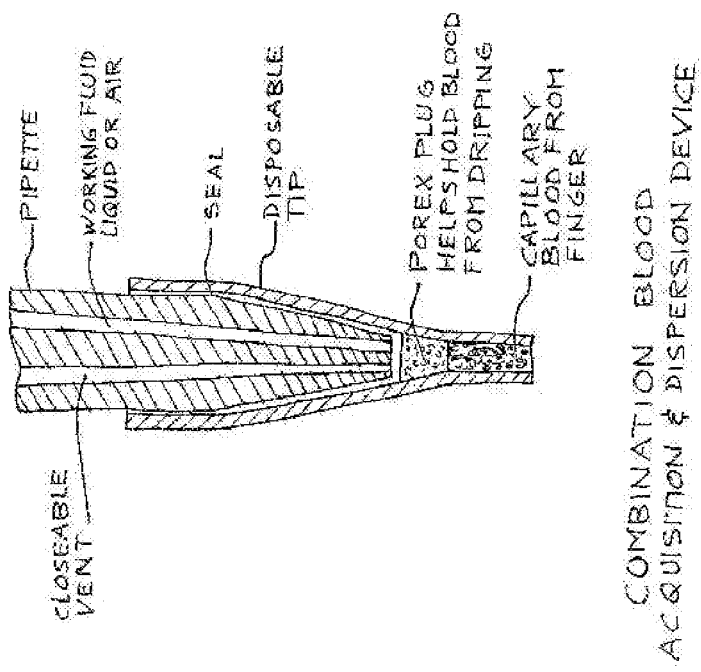
Fig. 61 Combination sample acquisition and dispense consumable. (Example 14)

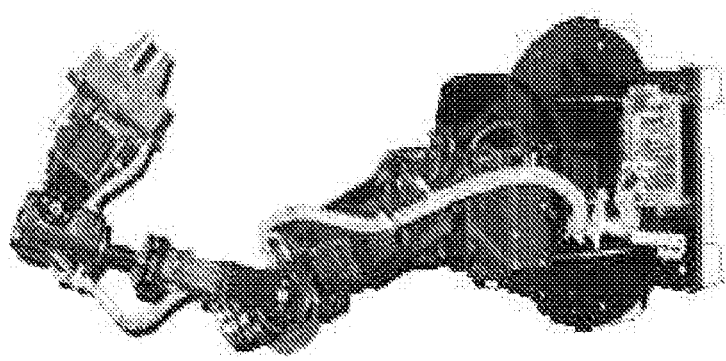
Fig. 62　Four axis manipulator

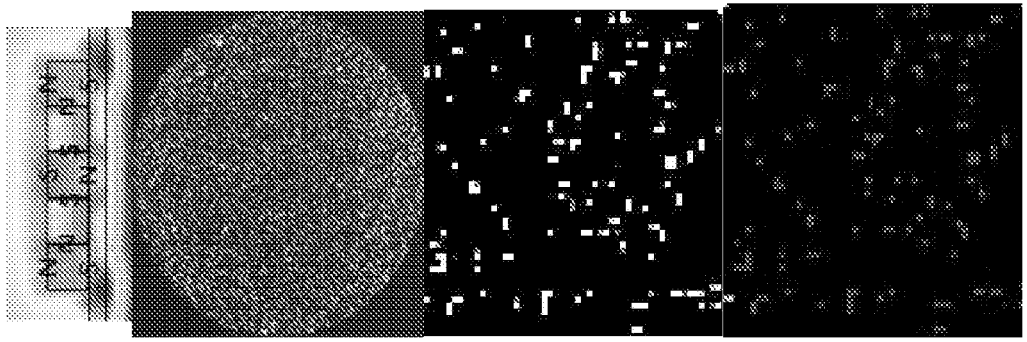
Fig. 63 Example of even magnetic selection. (Example 14)

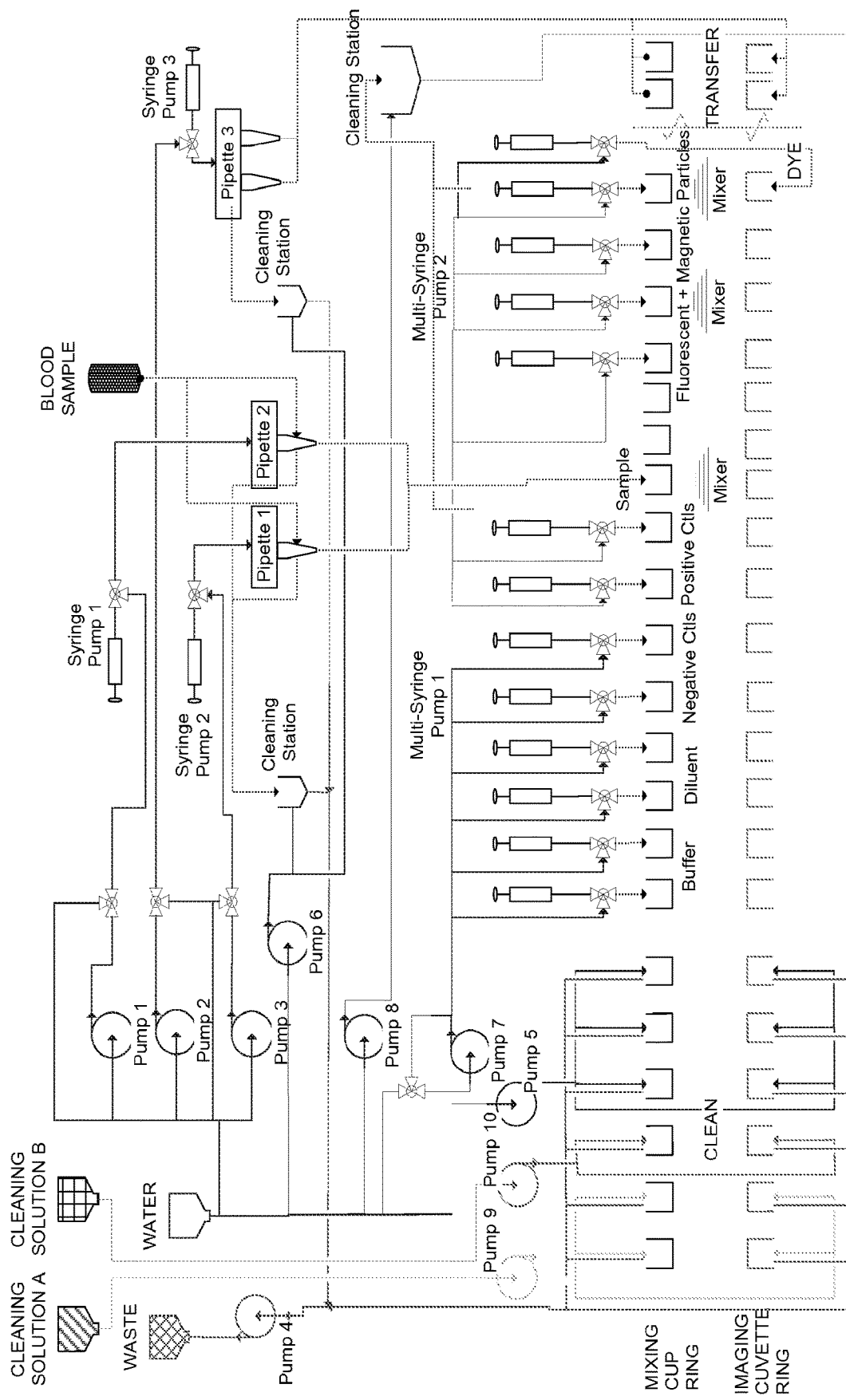
Fig. 64    Fluid Handling Diagram. (Example 14)

Fig. 65  Photograph of surge testing cartridge. (Example 15)

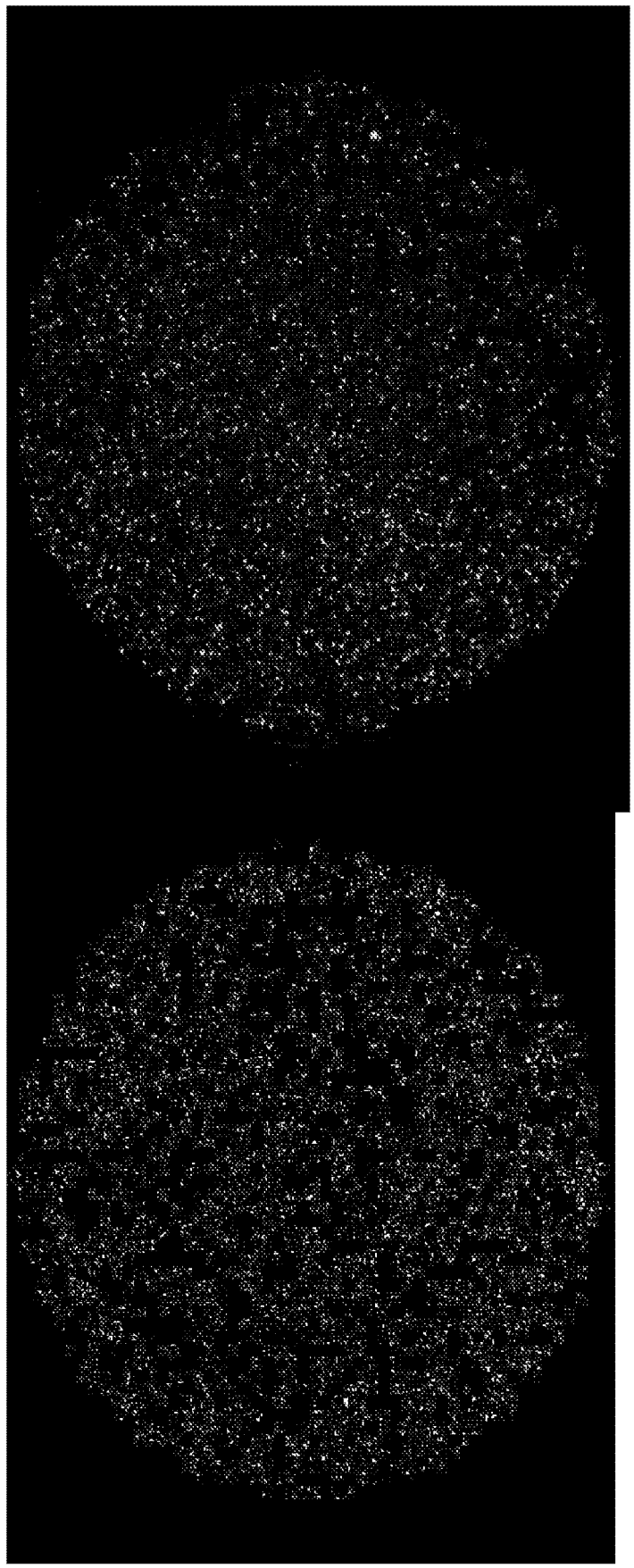
Fig. 66 Images with various magnetic selection. (Example 2)

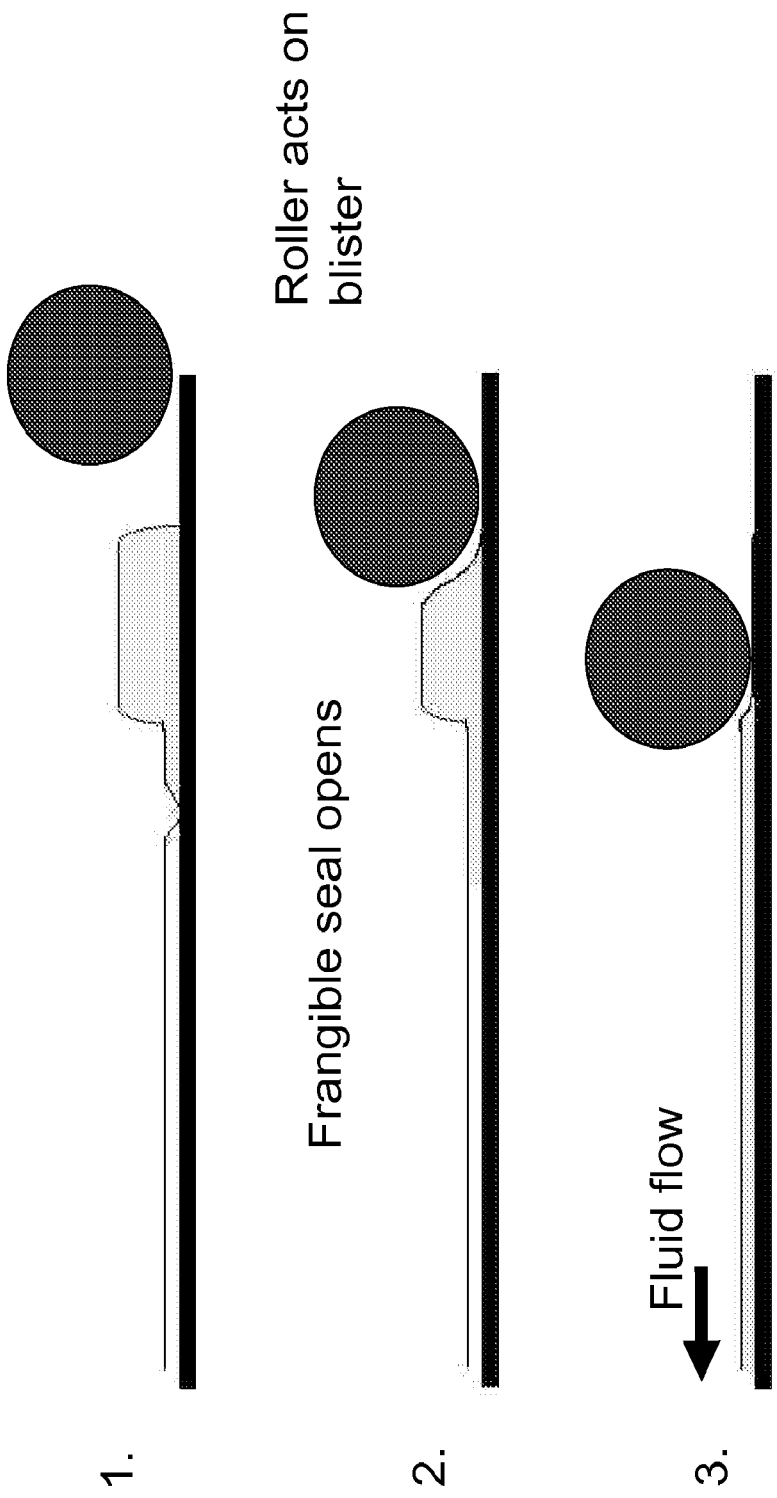
Fig. 67  Example of a deformable pouch with a frangible seal acted upon by a roller mechanism.

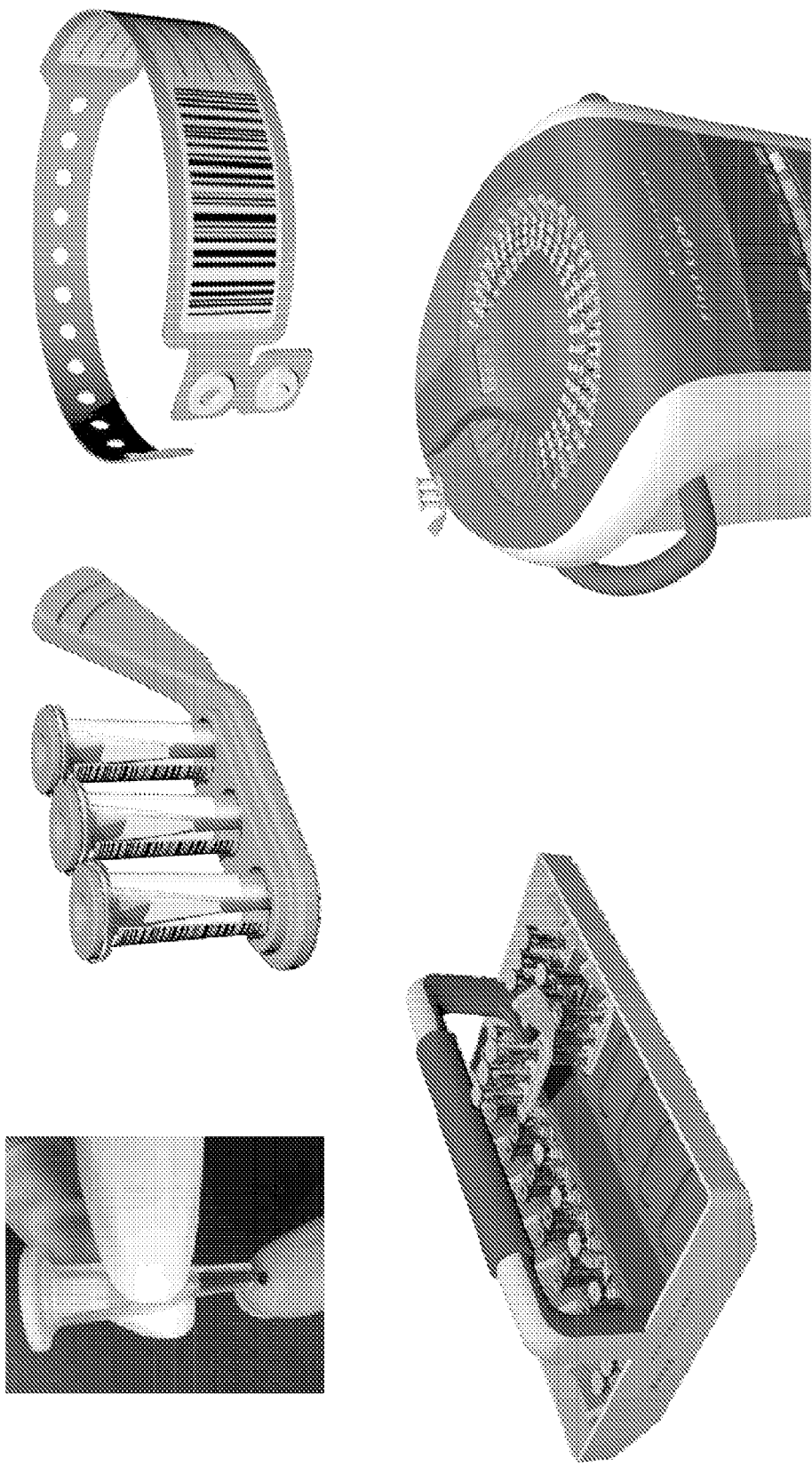
Fig 68. Surge system sample collection. (Example 16)

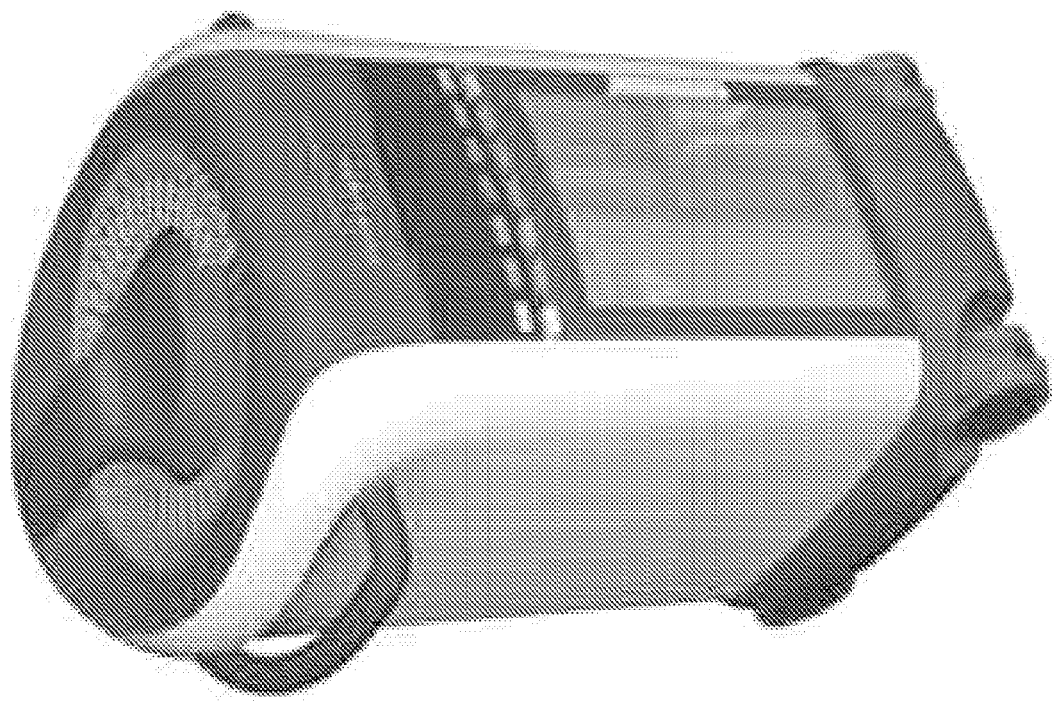
Fig. 69  Mobile surge analyzer. (Example 16)

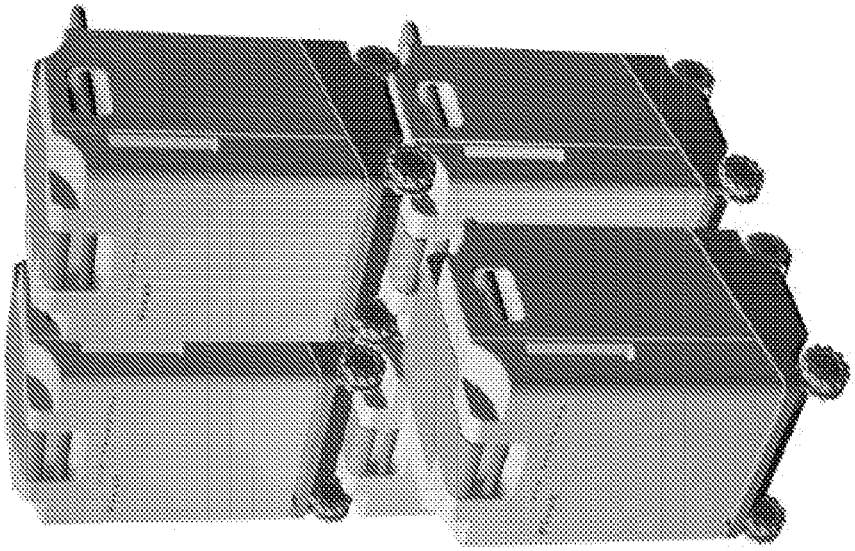
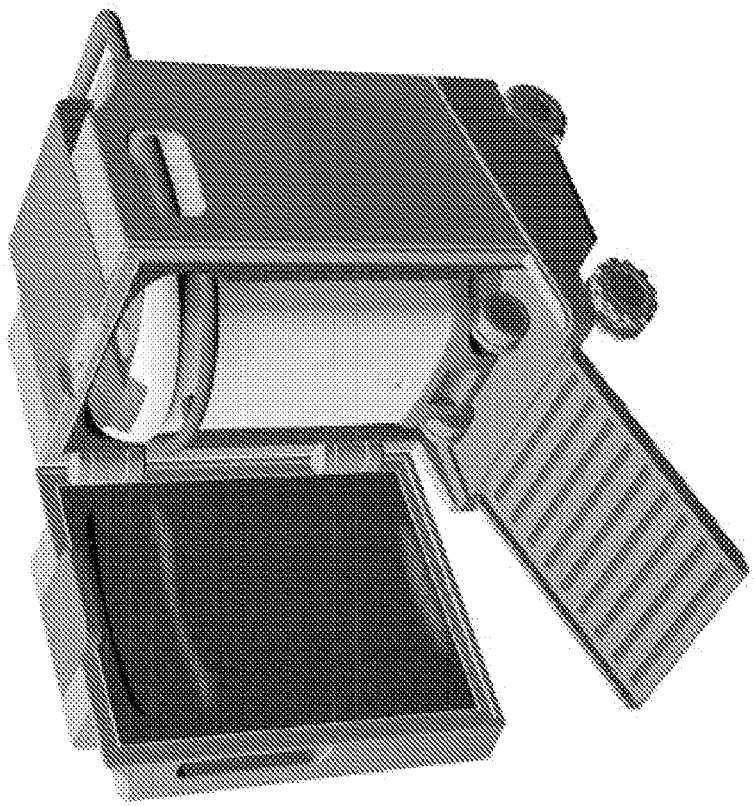
Fig. 70 Surge system secure crating, transport (left), and stacking storage (right). (Example 16)

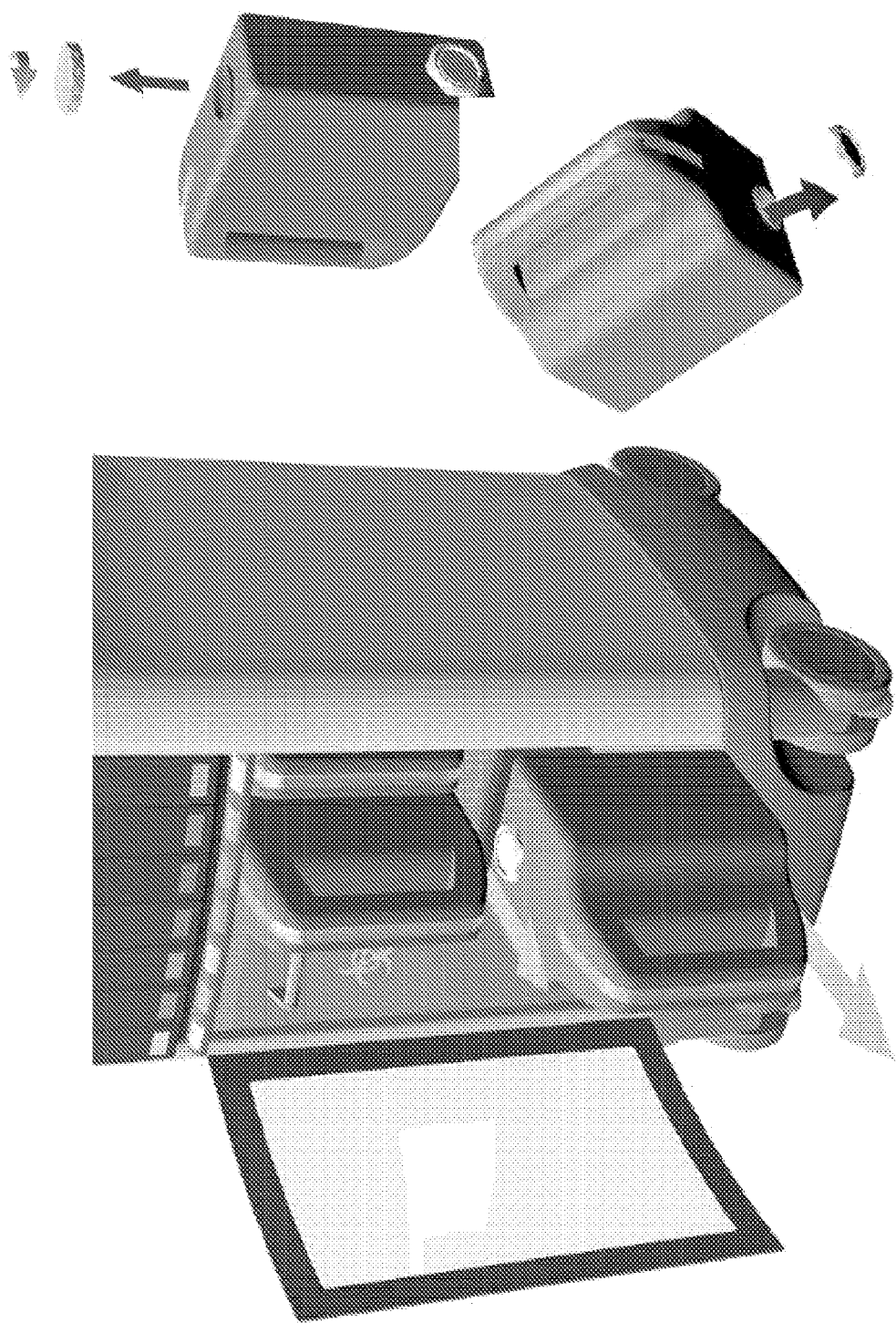
Fig. 71 Liquid replacement utilizing quick disconnect fittings. (Example 16)

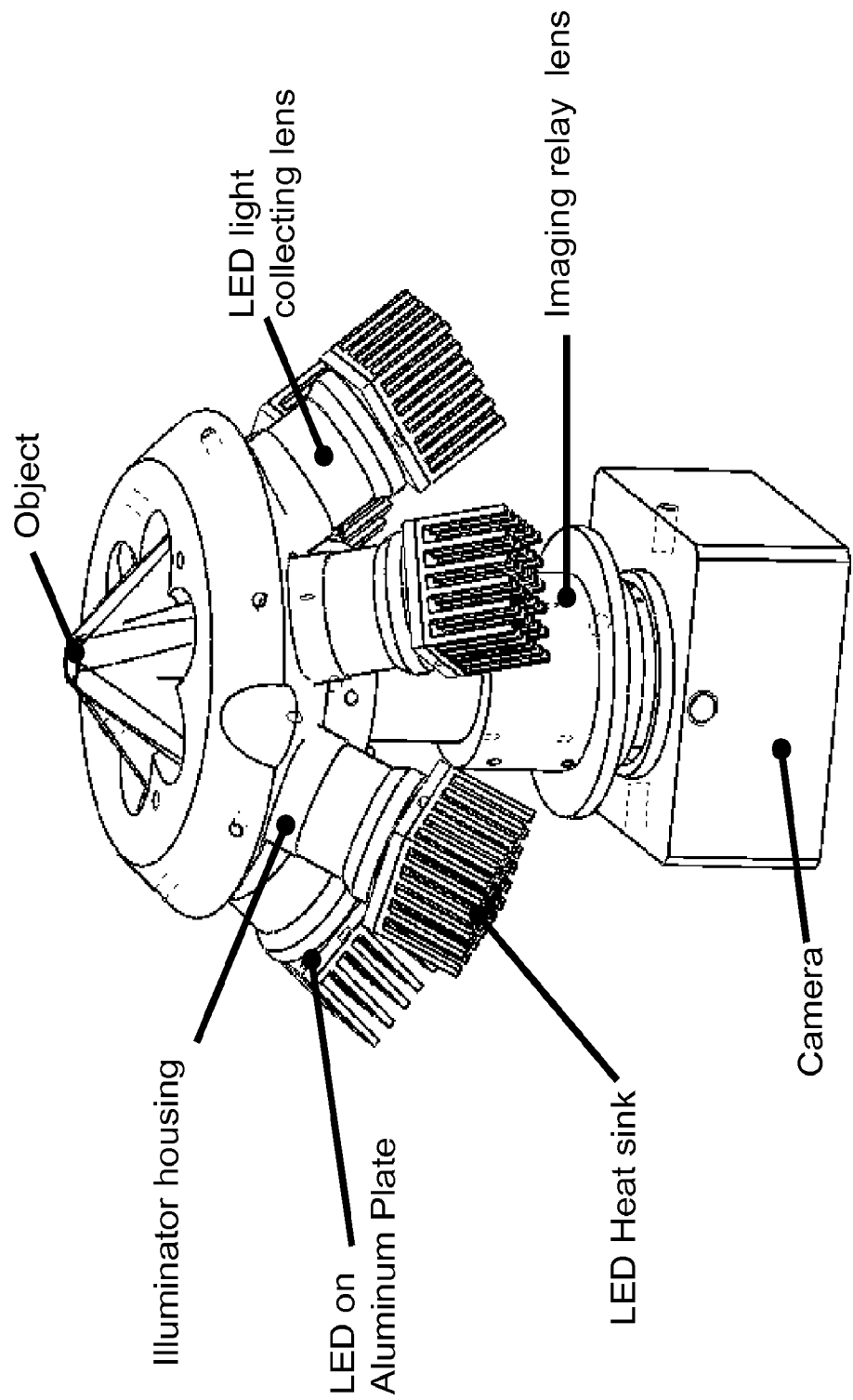
Fig. 72 Imaging optics system diagram of automated analyzer with robotics. (Example 1 and Example 9)

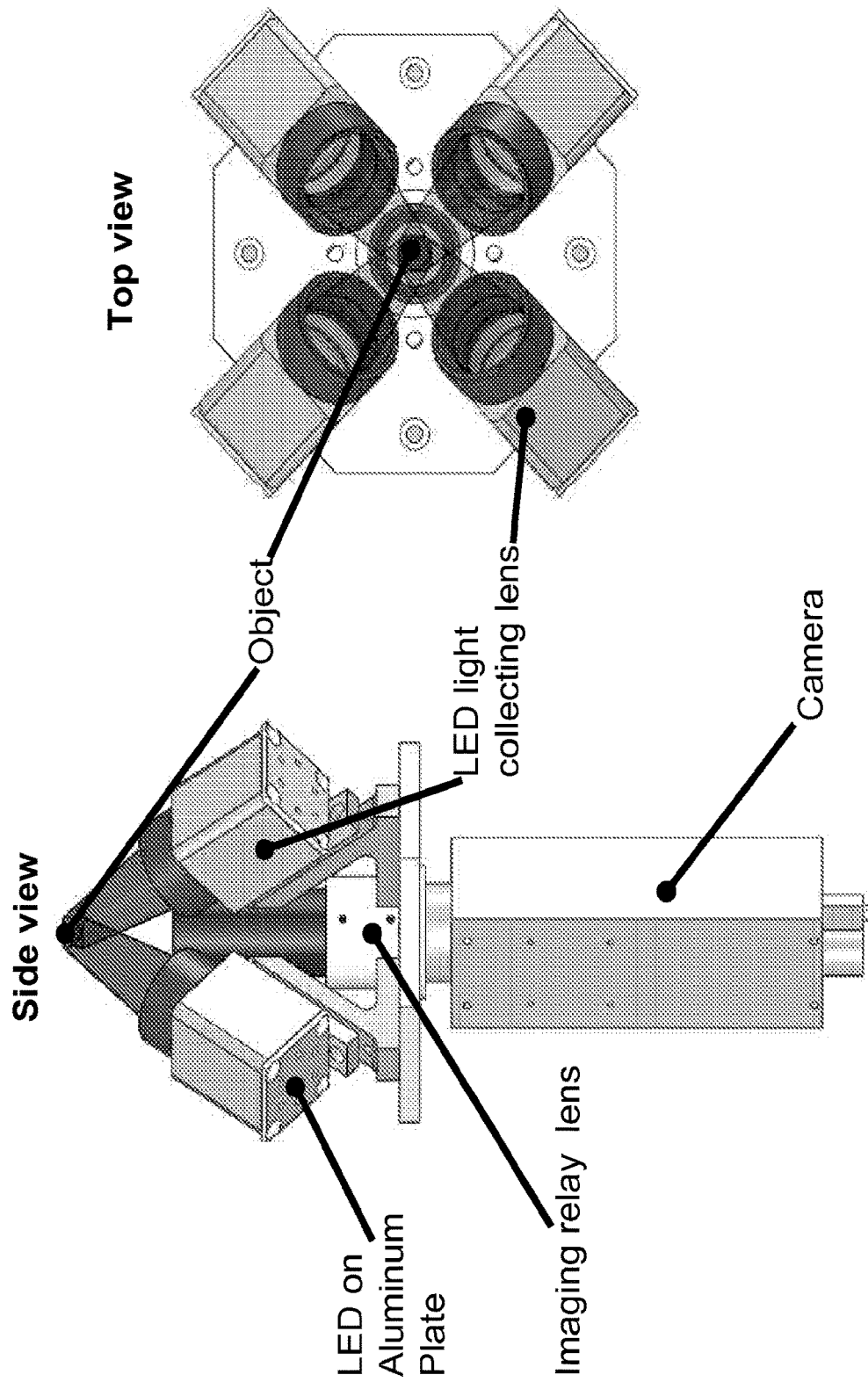
Fig. 73 Imaging optics system diagram automated analyzer. (Example 1 and Example 8)

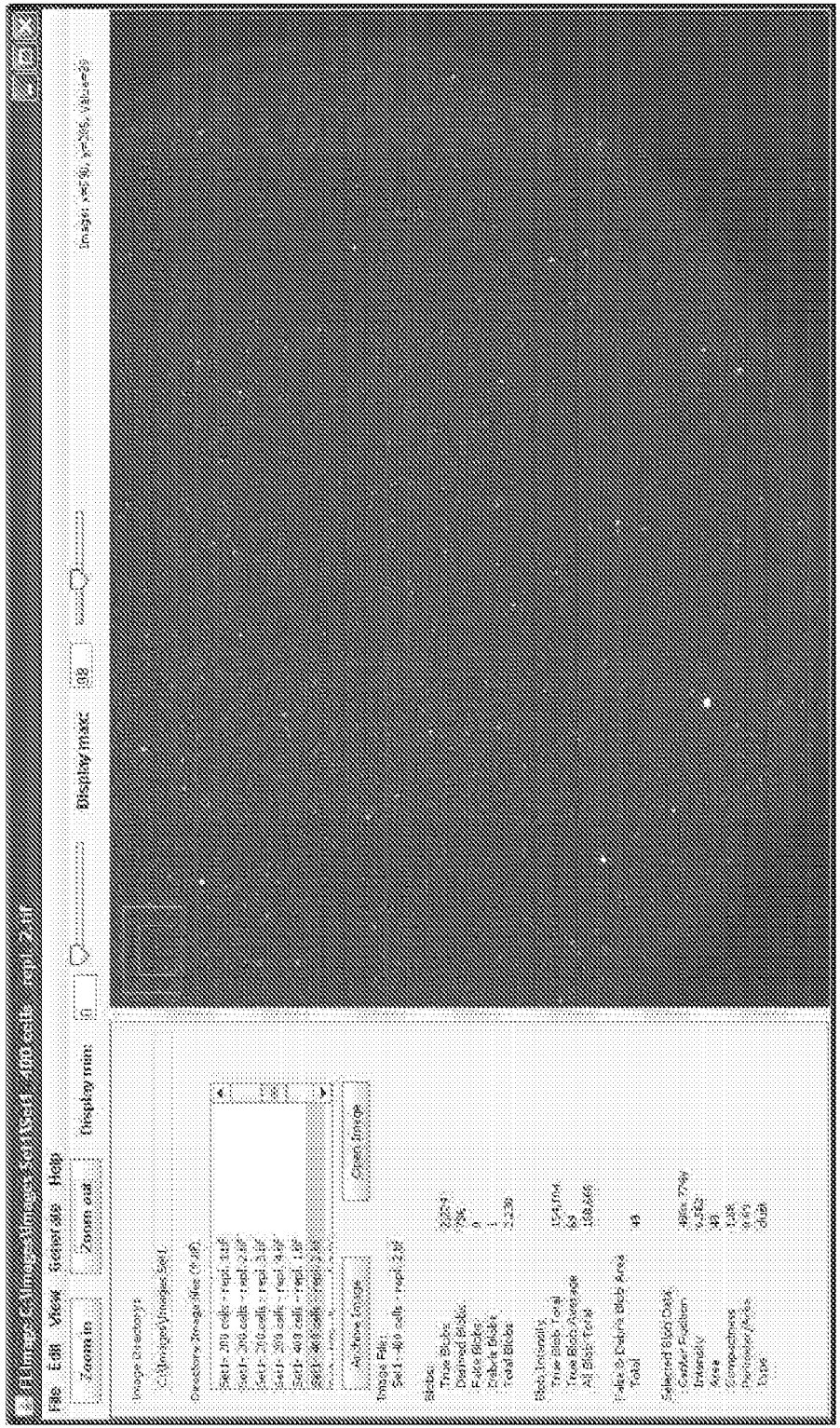
Fig. 74    Automated image analysis software. (Example 8)

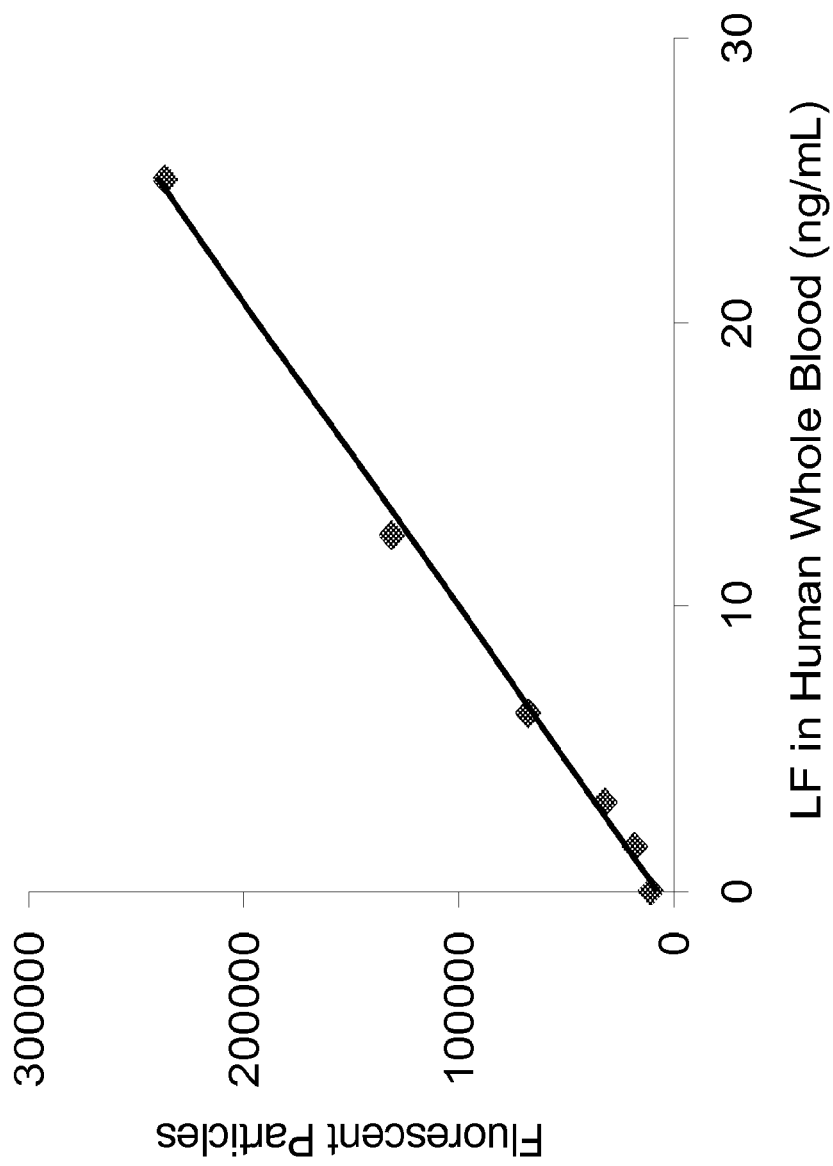
Fig. 75  Detection of bacterial *Bacillus anthracis* Lethal Factor protein in human whole blood by automated analysis. (Example 14

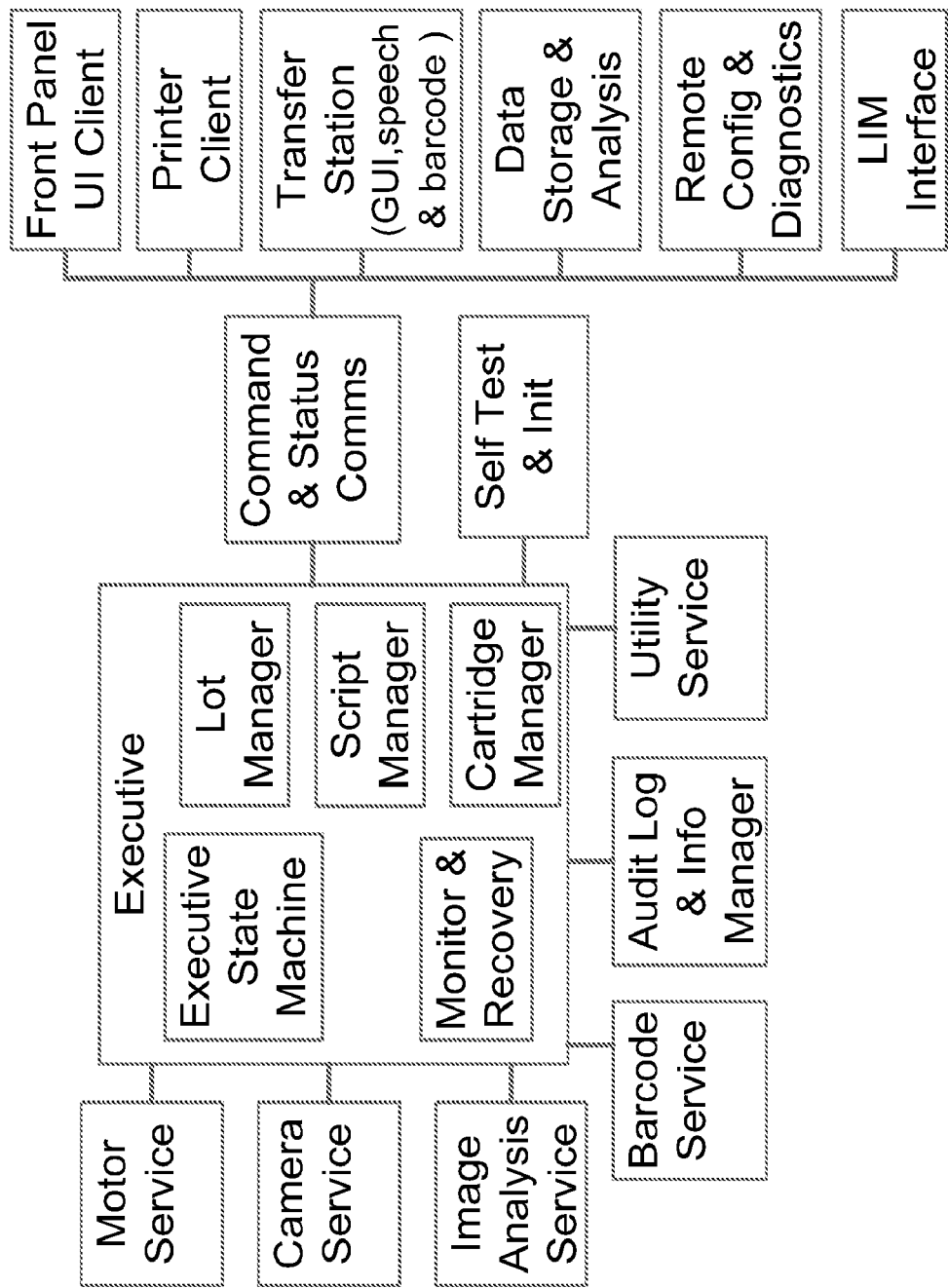
Fig. 76 Extended software architecture. (Example 6)

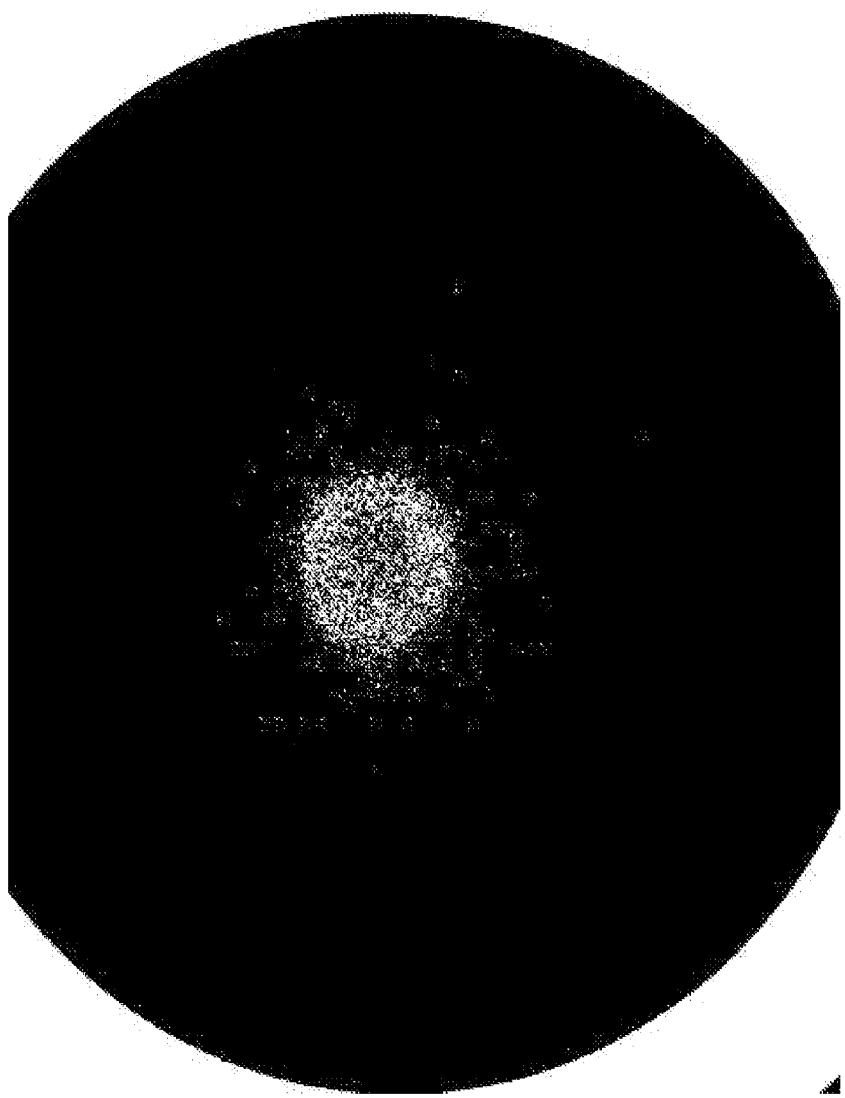
Fig. 77. Localized deposition of selected labeled targets. (Example 2)

IMAGING ANALYZER FOR TESTING ANALYTES

CROSS-REFERENCE TO RELATED APPLICATIONS

This application claims benefit of U.S. Provisional Application No. 61/099,830, filed Sep. 24, 2008, which is hereby incorporated by reference.

GOVERNMENT SUPPORT

This invention was made with government support under grant numbers AI055195, AI080016, and AI078695 awarded by the National Institutes of Health. The government has certain rights in the invention.

BACKGROUND

Importance of detecting specific targets. Methods for detecting specific molecular, cellular, and viral targets are fundamental tools for medical and veterinary diagnostics, environmental testing, and industrial quality control. Examples of methods for detecting specific targets in clinical medicine include over-the-counter rapid pregnancy tests, microbiological culture tests for determining the resistance of infectious agents to specific antibiotics, and highly automated tests for cancer markers in blood samples. Detecting pathogen contaminants in food, high throughput screening of candidate compounds for drug discovery, and quantifying active ingredients in pharmaceuticals exemplify industrial manufacturing applications that depend on methods for determining the presence of specific targets. Environmental applications requiring testing for specific targets include detecting water supply contamination, airborne biothreat agents, and household fungal contaminants.

Labeling targets. One important approach for detecting specific cells, viruses, or molecules is to tag the targets with optically detectable labels. Targets can be specifically labeled or non-specifically labeled. Targets can be specifically labeled by tagging with target-specific binding molecules that contain an optical label. Target-specific labels can have various types of binding moieties including macromolecules (e.g., antibodies, protein receptors, nucleic acids, carbohydrates, and lectins) and small molecules (e.g., hormones, drugs of abuse, metabolites). The detectable signaling moieties of the target-specific labels can use a variety of signaling characters including fluorescence, phosphorescence, chromogenicity, chemiluminescence, light-scattering, and Raman scattering.

Alternatively, targets can be labeled non-specifically—that is, they can be labeled along with other entities in a sample. For example, all cells in the sample can be labeled with a DNA stain or all lipoproteins can be labeled with a label that binds to all such molecules. Non-specifically labeled targets can then be specifically detected using a target-specific selection as described below.

Specifically selecting targets. Target-specific selection is usually important for detecting labeled targets. Specific selection is often used to physically isolate targets from other labeled entities and also from unbound label. For example, magnetic particles coated with target-specific antibodies can be used to complex with labeled targets. Applying magnetic force to the complexes can then deposit the labeled targets on a surface while labeled entities and unbound label are not deposited. Alternatively, specific selection can take place by capture, that is, by binding to a surface coated with target-specific binding moieties such as antibodies. Specific selection can occur either before or after target labeling.

Following specific selection and target labeling, the unbound label is generally removed from the reaction in successive washing steps while selection retains the specifically selected targets for subsequent detection. Washing steps require undesirable labor for the user in the case of manual test methods and may require sophisticated engineering for liquid handling in automated systems. Some technologies, such as lateral flow methods, use passive capillary action to wash unbound label and non-specifically bound label from labeled targets that have been specifically captured on a membrane or solid surface. Lateral flow methods simplify the washing function for manual tests, but these methods can be insensitive and are not appropriate for high throughput testing on automated platforms.

Using imaging to count labeled targets. Imaging is a powerful method for detecting specifically selected labeled targets on a detection surface. Imaging methods map the optical signal emanating from each point in the detection area to a corresponding point in the image. In contrast, non-imaging detection methods generally integrate the optical signal emanating from the entire detection area.

Some imaging methods can detect and count individual labeled targets. Enumerating specifically labeled targets can result in detection at very low target levels compared to detection area integration methods. The sensitivity advantage of imaged-based target counting methods stems chiefly from the fact that the optical signal to background stays essentially constant as target levels decrease. In contrast, for detection area integration methods the signal to background decreases as the target levels decrease.

One type of method builds an image by systematically scanning the detection area with a microscopic beam. Scanning methods are more time consuming than methods that use digital array detectors (e.g., CCD or CMOS cameras) to enumerate specifically labeled targets in the entire detection area simultaneously.

Large area imaging at low magnification for sensitive target counting. Some methods use high magnification microscopy to enumerate the individual microscopic targets. Microscopic imaging lacks sensitivity because each image only samples a small area. Larger areas can be successively imaged, but acquisition of many images can be laborious, expensive and time consuming. Alternatively, labeled microscopic targets can be individually detected and enumerated using large area imaging at low magnification. Low magnification imaging can allow enumeration of a small number of microscopic targets in a relatively large area in a single image.

Methods that do not require washing to remove free label from specifically labeled targets. Several methods that do not require washing have been developed that detect targets specifically complexed with labeled target-specific binding moieties. One type of method uses labels that do not emit signal unless they are bound to the target. These labels have the limitation that they do not emit a strong enough signal for efficient large area detection of individual labeled targets. Another method that does not require washes uses selection through a liquid phase barrier to separate labeled target complexes from unbound label. This approach uses detection area integration rather than sensitive image analysis and thus lacks high sensitivity.

Analyzers for tests that use imaging to detect specific targets. Analytical instruments for imaging individual labeled microscopic targets generally use high magnification to image targets. For example, an analyzer with microscope optics and a digital camera can detect individual labeled cells deposited on the optically transparent base of the well of a microtiter plate. Besides the inherent lack of sensitivity and imaging efficiency that comes from microscopic imaging of a small area, these analyzers generally require multiple wash steps to remove unbound label and non-specifically labeled entities.

Several imaging-based analyzers that use large area automated digital imaging have been developed for simultaneously detecting individual labeled targets. To detect individual targets these analyzers must either perform repeated wash steps or wash by capillary flow. Analyzers limited to tests that use devices requiring capillary flow are not can not efficiently test large volume samples (e.g., 1 ml) or be configured for automated high throughput testing.

SUMMARY OF THE INVENTION

The invention provides for improved analyzers that use large area imaging with optics capable of detecting individual optically labeled targets and that eliminate the need for wash steps. By providing imaging of individual labeled targets without wash steps, the invention provides sensitive and quantitative testing while lowering the cost and complexity of automated operation.

In one aspect, the invention features an imaging analyzer including a housing that accepts a sample container that contains a sample and has a detection area having a shortest linear dimension of 1 mm for detection of a target potentially in the sample; a component for applying a selective force to the sample container; a photoelectric array detector disposed for large area imaging of the detection area; and imaging optics that magnify less than 5 fold, e.g., less than 2 fold. In various embodiments, the selective force moves a magnetic particles with an average diameter of less than 0.5 mm and an average density of less than 2 $g/cm^3$n through a liquid in the sample container that is held a fixed position in the analyzer over distance of greater than 5 mm at an average speed of greater than 0.5 mm/min wherein the liquid is essentially equivalent in density and viscosity to saline. The device for applying a selective force may include a magnet that has a shortest overall linear dimension of greater than 10 mm and magnetization greater than 3.5 kilojoules per cubic meter. The analyzer may also include one or more of automatic focusing on the detection area; a mechanism for ensuring a fixed distance between the detector and the detection area; an illumination source for the sample container (e.g., light emitting diodes); automated liquid transfer devices; a mechanism that causes liquid flow inside the sample container; a robotic gantry that can move a sample container between locations on the analyzer; a carousel mechanism that can move a sample container between locations on the analyzer; a mechanical track mechanism that can move a sample container between locations on the analyzer; a bar code reader; an incubator that accommodates the sample containers in an enclosure that stably maintains and average temperature within 2 degrees Celsius of a temperature set point; a printer, electronic monitor, and/or system for connection to an external communication network; automatic sample container cleaner; one or more receptacles that accept sample containers after imaging on the analyzer; one or more receptacles for waste liquids; integrated image analysis software with object finding algorithms; and integrated scheduling software for managing the movement of one or more sample containers between different locations in the analyzer. Preferably, the analyzer accommodates introduction of the sample containers as single or as multiple units. The analyzer may also accommodate a sample container that has height greater than 8 mm.

Imaging analyzers and components thereof are also described in the examples and the figures.

By washing is meant a process for physically removing, from a container or a surface, liquid containing undesirable components from targets, which, in contrast to the undesired components, are either retained, selected, or captured in the container or on the surface.

By a test not requiring washing is meant a test in which targets are detected without using wash steps.

By an analyzer or imaging analyzer is meant an apparatus having an array photodetector and imaging optics allowing simultaneous imaging of a detection area, as defined herein. Analyzers can have many other functions for enhancing detection including modules for applying selective forces on selection moieties, conveyance, or incubation.

By a well is meant a vessel that can hold liquid. Wells generally have a well depth ≥1 mm.

By an imaging well is meant a well through which labeled targets can be detected by imaging. Imaging wells have a detection surface on which an imaging analyzer can detect labeled target particles. The material lying between the detection surface and the imaging analyzer's photodetector has optical properties for supporting imaging detection of labeled targets. For example, the material is generally transparent and has low optical background in the spectral region corresponding to the signal signature of the device's signaling moieties.

By imaging well depth is meant the distance of the imaging well along an axis that is perpendicular to the detection surface.

By cushion, density cushion, liquid cushion, cushion layer, or liquid density cushion is meant a substantially liquid layer which is denser than the overlying layer. In the invention, the cushion is found in the imaging well lying between the detection surface and the liquid layer including the sample and test reagents. This cushion provides a physical separation between the test's reagents and the detection surface. Using selection, labeled targets complexed with selection moieties are moved through the cushion and deposited on the detection surface for imaging. Signaling moieties which are not complexed with a selection moiety are excluded from the detection zone by the dense liquid layer of the cushion.

By dye is meant a substance or mixture added to the reaction which interferes with the production or transmission of light to or from signaling moieties. The dye reduces or eliminates signal originating outside of the detection zone while allowing detection of the signal derived from signaling moieties within the detection zone. For devices that include fluorescent signaling moieties, dyes can absorb light of the fluorescent excitation frequencies, the fluorescent emission frequencies, or both. Various dye properties can be useful for this purpose including light scattering and absorbance. In various embodiments, the dye reduces signal by at least 50%, 75%, 85%, 90%, 95%, or even 99%.

By dyed cushion is meant a cushion that includes dye. The dyed cushion simultaneously provides a physical exclusion of the bulk reaction from the detection zone (as a function of the density of the dyed cushion) while preventing or reducing the transmission of signal from the overlying reaction to the detector (as a function of the dye included in the dense layer).

By sampling device is meant a device used to collect a sample. Examples of sampling devices include swabs, capillary tubes, wipes, beakers, porous filters, bibulous filters, and pipette tips.

By target is meant a cell, virus, molecule, or molecular complex that is potentially present in a sample and the presence of which is tested by the invention.

By category of target is meant one or more features shared by multiple targets so that the multiple targets are considered identical for the purposes of a test constructed using the invention. For example, for a test designed to detect all HIV viruses, the category is HIV. Such a test would detect all HIV viruses, without differentiating the HIV-1 and HIV-2 variants. In this case, the category of the target includes both HIV-1 and HIV-2. The goal of another test might be to distinguish HIV-1 from HIV-2. In this case, each type of HIV would be considered a different category. If the goal of the test is to detect *C. albicans*, three probes considered identical for the purpose of the test because they share the common feature that they bind specifically to *C. albicans* would be considered to be in the same category of target molecules.

By category-binding molecule is meant a molecule or molecular complex that specifically binds to a category-specific binding site. Examples of category-binding molecules are nucleic acid probes that hybridize to genomic DNA; nucleic acid aptamers that have been selected or "evolved" in vitro to bind specifically to sites on proteins; antibodies that bind to cellular antigens or serum proteins; and ligands such as epidermal growth factor or biotin that bind specifically to hormone receptors or to binding molecules, such as avidin. Two category-binding molecules are distinct if they bind to distinct and non-overlapping category-specific binding sites. Category-binding molecules may be referred to according to their molecular composition, e.g., a category binding oligonucleotide, probe, antibody, ligand, etc.

By capture molecule is meant a category-binding molecule that is stably bound to a surface, membrane, or other matrix that is not a particle.

By a category-binding molecule that specifically binds to a category of target is meant a category-binding molecule that binds under defined binding conditions to essentially all targets that are members of a category scanned for by a test, but to essentially no other molecules that are likely to be present in the sample. The number of category-binding molecules that are bound by targets in a category scanned for as compared to the number bound by targets not in such a category, are typically two-fold, five-fold, ten-fold, or greater than fifty-fold greater.

By signal element is meant a molecule or particle that directly generates a detectable signal. The phrase "directly generates" refers to the fact that signal elements are the immediate source or critical modulator of the detectable signal. Thus, if the signal is photons that arise from a fluorophore, the fluorophore is the immediate source of the photons and, therefore, is a signal element. If the signal is photons scattered by an RLS particle, the RLS particle is a signal element. Alternatively, if the signal is the light transmitted or scattered from a chromogenic precipitated product of the enzyme horseradish peroxidase, the chromogenic product is the signal element.

A characteristic of a signal element is that such an element cannot be divided into parts such that each part generates a signal that is comparable (in character, not necessarily in intensity) to the whole. Thus, a 2 nM diameter quantum dot is a signal element, as dividing it changes the character (emission spectrum) of the resulting nanocrystals. A 5 µm particle impregnated with a fluorescent dye such as fluorescein, is not a signaling element, since it could be divided into parts such that each part has signaling characteristics comparable to the intact particle. The molecule fluorescein, in contrast, is a signaling element. The detectable products of signal generating enzymes (e.g., luciferase, alkaline phosphatase, horseradish peroxidase) are also considered signal elements. Such signal elements (or their precursors when there is a chemical conversion of a precursor to a signal element) may be diffusible substances, insoluble products, and/or unstable intermediates. For example, the enzyme alkaline phosphatase converts the chemiluminescent substrate CDP-Star (NEN; catalog number NEL-601) to an activated product, which is a photon-emitting signal element.

By signaling moiety is meant a molecule, particle, or substance including or producing (in the case of enzymes) one or more signal elements and that is or can be conjugated to a category-binding molecule. The signaling moiety can be attached to the category-binding molecule either covalently or non-covalently and either directly or indirectly (e.g., via one or more adaptor or "chemical linker" moieties or by both moieties being conjugated to the same particle). Examples of signaling moieties include carboxylated quantum dots; a fluorophore such as Texas Red that is modified for binding to a nucleic acid probe or an antibody probe; streptavidin-coated fluorescent polystyrene particles (which can be conjugated to biotinylated category-specific binding proteins); a rolling-circle replication product containing repeated nucleic acid sequences each of which can hybridize to several oligonucleotides tailed with fluorescently modified nucleotides and which contains a category-specific binding oligonucleotide at the 5' end. A signaling moiety can include physically distinct elements. For example, in some cases the signaling moiety is an enzyme (e.g., alkaline phosphatase) that is conjugated to a category-binding molecule (an antibody, for example). Signal is generated when a substrate of alkaline phosphatase (e.g., CDP-Star, or BM purple from NEN and Roche, respectively) is converted to products that are signal elements (e.g., an unstable intermediate that emits a photon, or a precipitable chromogenic product). It is not unusual for the category-binding molecules, enzymatic signaling moieties, and substrate to be applied to the reaction at distinct times.

By particle is meant a matrix which is less than 50 microns in size. The size of a population or batch of particles is defined as the mean measurement of the longest pair of orthogonal dimensions for a sample of the particles. The longest pair of orthogonal dimensions is the pair of orthogonal dimensions of a particle, the sum of the lengths of which is the maximum for all such sums for the particle. If a sample of two particles has a longest pair of orthogonal dimensions of 1 micron×2 micron and 2 micron×3 micron, respectively, the mean measurement of the longest pair of orthogonal dimensions is 2 microns [(1+2+2+3)/4=2 microns]. The mean measurement of the longest pair of orthogonal dimensions for a sample of particles is, e.g., less than 50 microns, less than 20 microns, or less than 5 microns.

Many particles have some characteristics of a solid. However, molecular scaffolds or complexes, which may not be rigid, are also defined as particles. For example, dendrimers or other branching molecular structures are considered to be particles. Similarly, liposomes are another type of particle. Particles can be associated with or conjugated to signal elements. Particles are often referred to with terms that reflect their dimensions or geometries. For example, the terms nanosphere, nanoparticle, or nanobead are used to refer to particles that measures less than 1 micron along any given axis. Similarly, the terms microsphere, microparticle, or microbead are used to refer to particles that measure less than one millimeter along any given axis. Examples of particles include latex particles, polyacrylamide particles, magnetite microparticles, ferrofluids (magnetic nanoparticles), quantum dots, etc.

By labeling particle is meant a particle that can specifically bind to targets and generate a signal. Labeling particles are conjugated to both signaling moieties and to category-binding molecules.

By target:labeling particle complex is meant a labeling particle to which one or more targets are specifically bound.

By signal character of a signal element or signal moiety is meant the aspect or aspects of a signal generated by the signal element or signaling moiety that is useful for distinguishing it from other signal elements or signaling moieties. For example, the signal character of a signaling moiety labeled with fluorescein and rhodamine is fluorescence. The character of a radio transponder is radio frequency. Examples of photonic signaling character are fluorescence, light scattering, phosphorescence, reflectance, absorbance, chemiluminescence, and bioluminescence. All but the latter two examples of photonic signaling character depend on external illumination (e.g., a white light source, a laser light source, or daylight). In contrast, chemiluminescence and bioluminescence are signaling characters that are independent of external light sources.

By signal signature is meant the distinctive signaling quality of the combination of signaling moieties that bind to a category of targets in a test. A target that is bound to four types of antibodies, one of which is conjugated to a fluorescein molecule, and three of which are conjugated with rhodamine molecules has a signal signature that is described by the combined weighted absorbance and emission spectra of fluorescein and rhodamine.

By selection force is meant a force that is used to capture, isolate, move, or sequester targets. Examples of selection forces include gravity, magnetism, electrical potential, centrifugal force, centripetal force, buoyant density, and pressure. Targets can be mobilized by a selection force acting on the targets alone. Alternatively, selection forces can act specifically on targets that are associated with selection moieties (see definition below).

Examples of the application of selection forces to mobilize targets include centrifugation of targets; magnetic selection of targets bound to magnetic particles; gravitational sedimentation of targets labeled with metallic particles; and deposition of targets on a porous membrane by vacuum filtration. Further instances of the use of selection forces are included in the examples below.

By selection moiety is meant an atom, molecule, particle, or other entity that can be conjugated to a category-binding molecule and that confers on the category-binding molecule the ability to be selectively captured, isolated, moved, or sequestered by a selection force. When a category-binding molecule:selection moiety complex is specifically bound to a target, the target can also generally be selectively captured, isolated, moved, or sequestered by the selection force. Selective refers to the preferential conferring of susceptibility to mobilization by the selection force on selection moieties and associated entities over entities not associated with selection moieties.

Paramagnetic particles and ferritin are examples of selection moieties. A dense silica particle that sinks in solution is another type of selection moiety. Such particles, when coated with category-binding molecules and bound to a microbial target will cause the target to sink in aqueous solution, thus resulting in separation of the bound target from other sample unbound constituents.

By a roughly planar surface or substrate is meant a surface that can be aligned in parallel to an imaginary plane such that when the distance is measured from points in any 1 mm×1 mm square on the surface to the closest points on the imaginary plane, the absolute value of the mean distance is less than 50 micrometers.

By detection surface is meant the surface of a roughly planar substrate onto which targets are deposited in some embodiments of the invention. In embodiments using photonic signaling character, if the detection surface is optically transparent, detection can be effected via either face of the detection surface. If the detection surface is opaque, detection is effected via the face of the detection surface on which the targets are deposited.

By detection area is meant the area of the detection surface or detection zone that is simultaneously analyzed by the invention. The detection area is typically greater than 1 mm, e.g., greater than 5 mm, 10 mm, or 15 mm, in its longest linear dimension. For example, the section of a glass slide that is simultaneously imaged by an optical device that includes a collection lens and a CCD chip might measure 0.8 cm×0.5 cm. The detection area is then 0.4 $cm^2$.

By detection zone is meant the volume in which targets can be detected. The detection zone has the same dimensions as the detection area but has a depth corresponding to the depth in which a labeling particle can be detected and identified. The depth of the detection zone is therefore dependent on the threshold criteria used to score for positive signal. When optical detection is used, the depth of the detection zone is dependent on the optical depth of field.

By the longest dimension of the detection area is meant the line of maximum length that can be drawn between two points on the perimeter of the detection area. For example, if the detection area is a rectangle measuring 0.3 cm×0.4 cm, the longest dimension of the detection area is the diagonal, 0.5 cm. If the detection area is an ellipse with semi-major axis of length 7 mm and semi-minor axis of length 2.5 mm, the longest dimension of the detection area is 14 mm.

By the shortest dimension of the detection area is meant the line of minimum length that can be drawn between two points on the perimeter of the detection area. For example, if the detection area is a rectangle measuring 0.3 cm×0.4 cm, the shortest dimension of the detection area is 0.3 cm. If the detection area is an ellipse with semi-major axis of length 7 mm and semi-minor axis of length 2.5 mm, the shortest dimension of the detection area is 5 mm.

By large area detection or large area imaging is meant a method for detecting microscopic targets in which the detection area (the area that is simultaneously analyzed by the detection device) is much larger than the target. The detection area for large area detection has linear dimensions 1 mm. In contrast, the microscopic targets are substantially smaller, typically measuring less than 50 µm in at least two orthogonal dimensions. Examples of large area detection include imaging a 9 mm diameter detection area with a CCD camera; imaging a 2 cm×1 cm rectangle by scanning with a CCD line scanner that has a long dimension of 1 cm; imaging a 4 cm×4 cm filter containing microbial targets using direct exposure on photographic film; and visual detection of colored spots corresponding to microscopic targets on a 1 cm×3 cm test area in a rapid lateral flow strip test.

By conjugated or stably associated is meant a physical association between two entities in which the mean half-life of association is least one day in PBS at 4° C.

By simultaneously detecting targets in a section of the detection area is meant detection of the signal from a section of a roughly planar detection surface in one step. Large area imaging of targets in a detection area using a CCD chip, visual detection, or photodiode-based signal integration are examples of simultaneous detection.

By sample is meant material that is scanned by the invention for the presence of targets.

By direct visual detection is meant visual detection without the aid of instrumentation other than wearable corrective lenses. For example, direct visual detection can be used to detect the reddish reflective signal of nanogold particles in some rapid lateral flow tests.

By photoelectric detector is meant a man-made device or instrument that transduces photonic signals into electric signals. Examples of photoelectric detectors include CCD detectors, photomultiplier tube detectors, and photodiode detectors, e.g., avalanche photodiodes.

By photoelectric array detector is meant a photoelectric detector that comprises an array of independent photosensitive pixel elements. Examples of photoelectric array detectors include CCD detectors and CMOS detectors.

By illuminating is meant irradiating with electromagnetic radiation. Electromagnetic radiation of various wavelengths can be used to illuminate. It includes, for example, radiation with wavelengths in the X-ray, UV, visible, or infrared regions of the spectrum. Note that illuminating radiation is not necessarily in the visible range. Illuminating preferably occurs with the range of 190 to 1100 nm.

By signal elements or signaling moieties with photonic signaling character is meant signal elements or signaling moieties that are detectable through the emission, reflection, scattering, refraction, absorption, capture, or redirection of photons, or any other modulation or combination of photon behavior. Some examples of signal elements or signaling moieties that have photonic signaling character include: the fluorophore Texas Red (fluorescent signaling character); CDP-Star (chemiluminescent signaling character); luciferase (bioluminescent signaling character); resonance light scattering particles (light scattering signaling character); BM purple (light absorption or chromogenic signaling character); and up-converting phosphors (absorption of two long wavelength photons and emission of one shorter wavelength photon).

PBS is a phosphate-buffered saline solution containing: 120 mM NaCl, 2.7 mM KCl and 10 mM phosphate buffer (sodium salt) pH 7.4.

CCD is charged coupled device.

hTSH is human thyroid stimulating hormone.

PSA is pressure sensitive adhesive.

RF ID is radio frequency identification.

Unless otherwise noted, microbiological strains described in the specifications are obtained from the American Type Culture Collection (ATCC), Manassas, VA

BRIEF DESCRIPTION OF THE DRAWINGS

FIG. 1. Imaging and optics system diagram. (Example 1)

FIG. 2. Image analysis: counter clockwise from top left-input, ROI, zoomed input, detected signal, detected debris. (Example 3)

FIG. 3. Bar magnetic assembly. (Example 2)

FIG. 4. Imaging between parallel bar magnets. (Example 2)

FIG. 5. Array of cylindrical magnets. (Example 2)

FIG. 6. Comparison of assay results from a device with integrated growth and reagent modules and a bench-top assay. (Example 9)

FIG. 7. System diagram of a simple non-automated analyzer. (Example 4)

FIG. 8. Photograph of a simple non-automated analyzer. (Example 4)

FIG. 9. Automated analyzer software diagram. (Example 6)

FIG. 10. Automated single sample instrument cartridge insertion. (Example 7)

FIG. 11. Automated single sample instrument sample addition. (Example 7)

FIG. 12. Automated single sample instrument system diagram. (Example 7)

FIG. 13. Automated single sample instrument results output. (Example 7)

FIG. 14. High throughput automated analyzer. (Example 8)

FIG. 15. On-demand analyzer CAD Subassemblies. (Example 9)

FIG. 16. On-demand analyzer photograph. (Example 9)

FIG. 17. Cartridge embodiment. (Example 9)

FIG. 18. On-demand analyzer electrical system. (Example 9)

FIG. 19. Exported spreadsheet from automated image analysis software. (Example 8)

FIG. 20. External view of On-Demand Automated Analyzer using a cleated belt drive. (Example 10)

FIG. 21. Internal view of On-Demand Automated Analyzer. (Example 10)

FIG. 22. Front view of conceptual drawing for Automated on-demand cartridge analyzer. (Example 11)

FIG. 23. Rear view of conceptual drawing for Automated on-demand cartridge analyzer. (Example 11)

FIG. 24. A single plane conveyor drive mechanism. (Example 12)

FIG. 25. Surge System Software Diagram. (Example 13)

FIG. 26. Cartridge used in automated cartridge analyzer for high throughput surge testing. (Example 15)

FIG. 27. Carrier for the cartridge in FIG. 26. (Example 15)

FIG. 28. Automated cartridge analyzer for high throughput surge testing. (Example 15)

FIG. 29. Internal view of high throughput surge testing analyzer. (Example 15)

FIG. 30. Processing steps on the high throughput surge testing analyzer. (Example 15)

FIG. 31. Fluidic containers. (Example 14)

FIG. 32. Sample rack with one sample consumable. (Example 14)

FIG. 33. Functional organization of the platform carousel. (Example 14)

FIG. 34. Commercial Surge detection Platform Architecture. (Example 16)

FIG. 35. Illustration of pipetting three patient samples at once. (Example 16)

FIG. 36. Loading a sample rack. (Example 16)

FIG. 37. Samples are delivered to the instrument by a sample track system. (Example 17)

FIG. 38. Simple architecture and small footprint relative to comparable machines. (Example 17)

FIG. 39. Functional organization of central lab analyzer. (Example 17)

FIG. 40. Key elements of central lab analyzer. (Example 17)

FIG. 41. Software state diagram. (Example 6)

FIG. 42. Pick and place robot layout.

FIG. 43. Example sample workflow.

FIG. 44. Queuing subassembly populated with sample racks. (Example 14)

FIG. 45. View of liquid handling and reagent handling subsystem. (Example 14)

FIG. 46. Transfer pipette assembly. (Example 14)

FIG. 47. Cup cleaning assembly. (Example 14)

FIG. 48. Surge detection prototype platform. (Example 14)

FIG. 49. Close up view of liquid handling subsystem. (Example 14)

FIG. 50. System control interface tab 1. (Example 8)

FIG. 51. System control interface tab 2. (Example 8)

FIG. 52. System control interface tab 3. (Example 8)

FIG. 53. System control interface tab 4. (Example 8)

FIG. 54. Plate position selection window for Auto 2. (Example 8)

FIG. 55. Bulk reagent container examples showing turbulence-inducing baffles and keying. (Example 14)

FIG. 56. Mixing cups and SAW transducer subassemblies. (Example 14)

FIG. 57. Magnet and optical subassemblies. (Example 14)

FIG. 58. Carousel top view. (Example 14)

FIG. 59. Methods for removing liquid from cups. (Example 14)

FIG. 60. Capillary sample collection consumable. (Example 14)

FIG. 61. Combination sample acquisition and dispense consumable. (Example 14)

FIG. 62. Four axis manipulator.

FIG. 63. Example of even magnetic selection. (Example 14)

FIG. 64. Fluid Handling Diagram. (Example 14)

FIG. 65. Photograph of surge testing cartridge. (Example 15)

FIG. 66. Images with various magnetic selections. (Example 2)

FIG. 67. Example of a deformable pouch with a frangible seal acted upon by a roller mechanism.

FIG. 68. Surge system sample collection. (Example 16)

FIG. 69. Mobile surge analyzer. (Example 16)

FIG. 70. Surge system secure crating, transport (left), and stacking storage (right). (Example 16)

FIG. 71. Liquid replacement utilizing quick disconnect fittings. (Example 16)

FIG. 72. Imaging optics system diagram of automated analyzer with robotics. (Example 1 and Example 9)

FIG. 73. Imaging optics system diagram automated analyzer. (Example 1 and Example 8)

FIG. 74. Automated image analysis software. (Example 8)

FIG. 75. Detection of bacterial *Bacillus anthracis* Lethal Factor protein in human whole blood by automated analysis. (Example 14)

FIG. 76. Extended software architecture. (Example 6)

FIG. 77. Localized deposition of selected labeled targets. (Example 2)

DETAILED DESCRIPTION OF THE INVENTION

Overview of invention. The invention is an analyzer that provides rapid and sensitive detection of targets in medical, veterinary, industrial, and environmental samples. The invention can test a variety of sample types for many types of targets including cells, viruses, and molecules. The invention achieves its sensitivity and efficiency by using low-magnification large-area imaging to detect and enumerate individual labeled target complexes following specific target selection. Embodiments of the invention can incorporate a range of mechanical complexity from analyzers with only a few moving parts to highly automated platforms. Automated embodiments minimize user-steps including sample preparation. The invention can provide high-throughput on-demand testing with automated sample input, processing, analysis, and results reporting. The imaging analyzer may be designed for use with kits or devices as described herein and in International Application No. WO/2010/036808, titled "Kits and devices for detecting analytes," filed Sep. 24, 2009, which is hereby incorporated by reference. The devices and kits may be employed in assays as described herein and in international Application No. WO/2010/036827, titled "Method for detecting analytes," filed Sep. 24, 2009, which is hereby incorporated by reference.

Some of the key functions and attributes of the invention are described in the following sections:

1. Sample input
2. Reagent processing
3. Processing container motion
4. Managing input sample information
5. Intermediate processing
6. Specific selection
7. Imaging
8. Image analysis
9. Results reporting
10. Post-processing
11. System control 1. Sample Input The analyzer may include one or more sample input subsystems that allow the analyzer to interact with one or more samples. The analyzer can accommodate a variety of different types of samples and modes of sample introduction, which may support a wide range of user workflows. Once added to the analyzer, a sample may also experience pre-assay treatments.

Types of samples. Samples may range in consistency from urine, feces, blood, serum, saliva, to mucus, food or water. Environmental samples can be collected off surfaces with a swab or wipe or from air or water. The sample volume may vary greatly. The volume could, for example be less than 1 µL for a fingerstick of blood (FIG. 26) to greater than 1 mL for an eluted nasal swab sample (FIG. 17). The sample may have been pre-preprocessed or not. For example, diluents or growth reagents may be added to the sample before being added to the analyzer, or sample growth may occur before addition to the analyzer. Also, one or more additives may be added to the sample. Anti-coagulant may be added to a sample of whole blood to prevent clotting before or after introduction to the analyzer. Specific analyzer embodiments may be designed to process one or more specific samples.

An analyzer may accommodate one specific assay type (FIG. 33) or many different assay types (FIG. 38). Multiple test types might be run in sequence (FIG. 33) or in a random-access manner (FIG. 38). The analyzer may store and manipulate reagents for testing or the reagents may be stored and manipulated outside of the analyzer or in a test device introduced into the analyzer (FIG. 28).

Sample introduction. Sample introduction may include any steps required to introduce a sample for analyzer processing. There can be many different possible modes of sample introduction. A sample can be introduced to the analyzer via a sample container (FIG. 10 and FIG. 17) or it may be added directly by pipette, sample collection bulb, swab, finger with drop of blood, syringe, capillary, cloth, or wipe, to provide a few examples. The mode of sample introduction may be automated, manual, or a combination of both. An example of manual sample introduction is shown in FIG. 7, in which a user places a sample container directly onto the assay tray for processing. One combination of manual and automated sample introduction is illustrated in FIG. 28 and FIG. 29 in which a sample container is placed into a loading carousel by a user where it is then automatically taken into the analyzer and processed. FIG. 37 illustrates one embodiment of fully automated sample introduction that utilizes an automated sample track system. Here, sample containers are delivered to the analyzer where an optical sensor detects when a new sample has arrived and meters sample for processing. This whole process occurs without user interaction.

The analyzer can accept a variety of different sample container configurations. Sample containers may vary widely in size, format and contents depending on the application, sample type, or analyzer format. Sample containers can range from a simple open container with specific optical properties in which the user performs many material exchange steps to a multifunctional analyzer with fluidics that are automated. Sample containers can be individual modules (FIG. 26) or stacks (FIG. 20). They can also be single (FIG. 31) or multi-sample containers. A rack could be accepted into the analyzer that contains one (FIG. 32) or multiple (FIG. 27) sample containers. The sample container may be taken into the analyzer to be processed with the sample remaining inside during processing (FIG. 29), or sample may be removed from the container and processed in a different vessel (FIG. 37 and FIG. 38).

There is a range of ways in which the analyzer might accept sample containers for test processing. Sample introduction can be as simple as a user directly placing a sample container onto an assay tray for immediate analysis such as in FIG. 7, or it can be as complex as the analyzer illustrated in FIG. 15 which utilizes optical sensors, a conveyor belt, and a three axis gantry robot. Sample container input may use one or more subsystems that utilize the effects of gravity (FIG. 22), linear actuation (FIG. 24), robotics (FIG. 15), or belts (FIG. 21) to mobilize one or more sample containers or sample container racks. External automation units, not associated with the analyzer may also deliver sample containers to the analyzer for processing such as an automated track system, which might be part of an independent hospital sample tracking system.

Sample pretreatment. Once inside the analyzer, the sample may experience pretreatment (e.g. contact with anticoagulant in a blood collection tube). The sample or sample container may be held temporarily in a queue to await processing or it may experience one or more pretreatments. Sample pretreatment may include, but are not limited to, heating, cooling, mixing, dilution, incubation, addition of additives or media. Pretreatment may occur automatically on the sample container or may be initiated by the analyzer.

2. Reagent Processing

To analyze samples, the analyzer may need to control the timing of sample reaction stages. This may involve the mobilization of reagents, including liquids. The invention may provide one or more means for mobilizing and metering various reagents, which may include movement of liquids, solids, and gasses in a precisely controlled manner.

The reagent processing analyzer subsystem can range in complexity. In the simplest cases, reagent processing is automatically metered and timed internally in an advanced sample container, such as FIG. 7. In this embodiment, the analyzer does not require any reagent processing functionality. However, in more complex analyzer embodiments, such as FIG. 39, numerous reagents additions and processing steps are performed by the analyzer. Here, multiple reaction reagents are added, mixed, and timed by the analyzer in the act of conducting an assay on the sample.

There are many types of reagents that may require controlled movement by the analyzer. Reagents that require mobilization and metering may include one or more assay reagents, diluents, eluents, additives, cleaning liquids, and waste liquids.

The reagent processing subsystem of the analyzer may utilize reagents management methods that are conducted entirely off-board the analyzer, entirely on-board the analyzer, or a combination of both. Off-board reagent processing includes the analyzer shown in FIG. 28 where a whole blood sample is mobilized automatically by internal capillary action and reacted with self-contained reagents already inside the disposable sample container (FIG. 26). This analyzer embodiment moves the sample containers for imaging and results processing, but it does not require any reagent processing subsystems. Alternatively, fluid management can be entirely controlled by the analyzer, such as in FIG. 40 where whole blood is mobilized and metered by a rotary pipetting robot. Other reagents are added by another pipette robot on the analyzer to start the reaction. Mixing and reaction timing also is handled by the analyzer's reagent processing subsystem. Reagent processing can also be managed partly by the analyzer, such as in FIG. 21, in which sample reaction is initiated by activation of a mechanical actuator on the analyzer, but all other reagent processing steps, including liquid movement, reaction reagent addition to the sample, and mixing occur internally to the sample container.

Methods of liquid mobilization. Liquids can be mobilized in a wide variety of ways that can be either passive or active. Passive movement of liquids can be done by, for instance capillary action, and can induce flows by molecular-level interactions of surface tension, as with the blood samples inserted into the narrow channels of the analyzer in FIG. 26 Other passive liquid handling methods include differences in osmotic pressure such as across a semi permeable membrane or by differences in electrical environment, among others. Fluid flow in a channel can be either passive, in the case of capillary action, or active if it is under pressure.

Active liquid mobilization requires a pressure gradient to be induced across the liquid. There are many ways to mobilize liquids in this manner. A fluid can be acted upon by a plunger as in FIG. 17, a screw as in the sample containers in FIG. 21, or by direct linear actuation as utilized in the analyzer in FIG. 22. Fluid can also be mobilized by a deflection of a solid analyzer, such as in the deformation membrane or diaphragm, or the collapse or expansion of a bellows or accordion.

Other means of active liquid mobilization include blister pouches, frangible seals, and combinations of the two. Liquids can be sealed into one or more blister pouches and released by adding pressure to a deformable region until it bursts. Likewise, a frangible seal can be designed to fail at specific pressures so that liquid is mobilized after specific forces have been applied behind a bolus of liquid. A liquid reagent contained inside a blister pouch that has been sealed by a frangible seal could be mobilized by a linear actuator or a roller mechanism, such as illustrated in (FIG. 67). By packaging reagents into modular pouches, longer shelf life and reliability may be achieved. Frangible seals can be used with or without a blister. The simplicity of the roller mechanism may ensure robustness. The possibility for controllable, directional motion using a roller-type mechanism could limit back flow and cross flows or even be used for mixing. The roller mechanism could be integrated into the sample container or placed as a subsystem on the analyzer. One specific embodiment of this module concept is illustrated in U.S. Pat. No. 5,254,479.

There are other active mobilization processes that integrate mechanical motions. In some cases, mechanical action can open a gate such as a valve. Valves come in a wide variety and include examples such as pinch, rotary, check, or duck bill valves to name a few. Other mechanical motions, such as expansion or compression of a deformable absorbent matrix can induce liquid motion, such as squeezing liquid out of or into a sponge. A wide variety of absorbent materials that have a specific absorbency and volume could be used to this effect. In another example of mechanical motion, two physically separated components are brought together and aligned that were previously non-contiguous.

Other methods of actively mobilizing liquids include removal of a solid or liquid or gas that is strategically blocking a channel. Such a component could be removed or melted or evaporated by elevated temperature, chemical reaction, absorption, or exposure to radiation, such as ultraviolet wavelength light. Samples can also be physically moved by direct liquid transfer, such as by pipetting. Liquid mobilizations by pipette are shown in FIG. 34 and FIG. 37. A mechanical actuator could interact with an interface on a sample container, such as the plunger in FIG. 17. The mechanical actuator could include movement of a pin, plunger, hook, hammer, roller, or other surface. Reagents could be mobilized by application of vacuum or pressure such as by a pumping action, such as with a syringe, peristaltic, impeller, or diaphragm pump.

Any combination of one or more of the above mobilization methods can be envisioned to create complex liquid handling schemes. One example is shown in FIG. 17, where liquid mobilization is activated by the analyzer. The reagent processing subsystem consists of a linear actuator that depresses the plunger the sample container cap, until sample interacts with growth media contained inside the sample container. The analyzer then times the incubated growth for a specific period. When the time has elapsed, the linear actuator depresses the plunger of the sample container further, mobilizing liquid in the growth wells to imaging wells where the assay proceeds automatically inside the sample container. Numerous alternative combinations of reagent mobilization methods can be envisioned to create any number of unique schemes.

Onset of flow. There are many ways to control onset and timing of reagent motion. A frangible seal, reseal-able membrane, or valve can prevent fluid from moving until the proper time. O-rings can be compressed or relaxed to control flow. And mechanically movable components that mate with one another in specific ways can be used to control flows. Examples include, but are not limited to, snaps, screws or augers, pressed fits, hinges, or slides.

Surface treatments can be used to modify flow characteristics by introducing hydrophobic or hydrophilic regions on the analyzer subcomponents, including pipette tips. Regions can be created by environmental treatments such as placing subcomponents in oxygen plasma, corona, ionically charged chambers. Modules can also be exposed to other types of treatments, including but not limited to, chemical etchings, vapor and liquid depositions, Teflon or other non- or low-stick coatings, including other chemical coatings. Onset and direction of flow can also be effected by material selection and processing, including surface texture and roughness.

Photo-reversible coatings can be used to create surfaces whose character, such as hydrophilicity or hydrophobicity, can be changed on demand.

Metering fluids. Fluid can be precisely metered and delivered to one or more parallel or serial vessels. Metering can be controlled through one or more analyzer subsystems or subcomponents that may include a variety of passive and active methods.

Fluids can be actively metered in a number of different ways. Active fluid metering can include moving a plunger, syringe or piston, compressing a blister pouch with or without roller, controlled rupturing of a frangible seal, turning of an auger or screw, deforming a membrane, diaphragm, bellows or accordion. Fluids can also be directly transferred by pipetting.

Passive metering can occur in several ways. A subcomponent or sample container may be in part or completely controlled by geometric designs that equalize resistance to flow, for example by surface tension or by capillary action. Metering also can be done with a fill to a hydrophobic or hydrophilic boundary region. In this case, liquid displaces gas or air, but stops at a hydrophobic membrane or boundary that it cannot readily pass. Another passive embodiment could include metering using a vacuum filled region. A self contained vacuum in a well or vessel could be opened to a fluid volume that was backed by a higher pressure, such as atmosphere. Releasing the boundary between the vacuum region and the liquid could result in a specific liquid volume being metered into the formerly evacuated region as the liquid rushes in to equilibrate the region of low pressure. The same features used for precisely metering can be used for timing.

Preventing leakage. The analyzer may have features that account for liquid containment and prevent leakage. This may include wells, vessels, and channels among other containment modules. Boundaries that contain fluid flows and prevent leakage may be made from a solid, liquid, or gas that controls the physical location and paths of movement of a sample.

There are many ways to prevent leakage before, during, and after pre-processing and assay reaction steps. Immobile solid containments include, but are not limited to, channels, wells, vessels, and chambers, including pipette tips and bulbs. There are also pads or membranes. Fluids can be used to keep another liquid contained, such as by focused flow, an emulsion, or a suspension of two immiscible fluids, to list a few examples. These liquids can be either static or in motion. Flows can be contained by mechanically movable solid parts which may include two parts that fit together by snapping or press fit, a screw, a hinge, slide, o-ring, valve, frangible seal or resealable membrane.

The fluid may need to displace trapped air; therefore venting methods may be included to minimize trapped gases inside wells or channels. There are many ways to vent air. A few examples include membranes such as hydrophobic membranes, vacuums or low pressure regions, displacement or compression of another liquid, gas, or deformable solid such as a diaphragm, a capillary or large hole open to atmosphere, or a porous solid, such as silicone.

During metering and after it is completed, there may be a need to minimize crossover or backflow. Preventing backflow may be achieved by using a membrane, a valve, or a bubble of air or immiscible fluid, such as oil with an aqueous sample, or a liquid plug. Crossover may be minimized by thorough washing of components, such as pipette tips and reaction cups (FIG. 40), between samples.

Mixing. The analyzer may have features for mixing of fluids with other liquid or dried reagents. Mixing may occur passively or actively. Passive mixing may include means such as turbulent flows, contorted paths, or low energy of solutions such as adding liquids to dried reagents. Active mixing may include, but is not limited to, physical motions such as a rotating or oscillating paddle or stir bar, repipetting such as pipetting up and down, vibrational such as ultrasonic waves, introducing bubbles, or by vortexing or nutating. One or more mixing method may be included on an analyzer.

3. Processing Container Motion

Container motion may be done in a wide variety of types. Containers can be a simple single unit with external liquid movement functions, or closed complex designs with fluid management and reaction infrastructure designed in and requiring external initiation of fluidic transfers. In an analyzer, processing container motions can be linear, random, none, or a combination of motions. In the model that fixes processing units (FIG. 7) a user places a container in a designated area and the system will move the processing subsystems (e.g. camera, magnets) while the container remains stationary. There are linear motion systems that perform serial process operations in many orientations. FIGS. 11, 14, 21, 22 and 24 use a linear with serial processing model. Sliding platforms sometimes referred to as stages, can also perform serial or random processing functions. FIG. 14 shows a platform subsystem.

Rotary motions include carousels. Carousels can be used in applications to conserve surface area or number of components, such as motors. Carousel processing can be serial or random and are featured in FIGS. 28, 30 and 35. Some of these are used in combination with liquid handling.

In applications that require random access several combinations of motions can be used. For example, Cartesian robots (in motorized grab, lift, vacuum lift or other models of container connection), pick and place robots (in motorized grab, lift, vacuum lift or other models of container connection) design provide motion functionality. FIGS. 15, 42 show random access robots. There are alternate designs for random motion as in the combination of a serpentine belt as primary motion device with reverse capability, and a transfer mechanism for movement off the main motion device.

Other types of container transfer can move containers between motion elements, between motion and processing functional units, and between processing containers. These models include ramps, actuators, trap doors, spring guide, gravity feed designs. FIGS. 15, 20, 23, 24, 29, make use of one or more transfer models in their designs in moving containers.

4. Managing Input Sample Information

An important aspect of the invention is the management of input sample information. This includes the management of test subject information and test analysis information.

Test subject information provides the ability to link test results with the test subjects. For example, in a clinical setting, the invention provides a mechanism to link test results to patients. In addition to linking test subjects and results, test subject information may provide additional data related to the test subject. For example, in an emergency surge testing application, patient contact and history information can be collected by the system to facilitate the next stage of patient care.

In addition to managing test subject information, invention embodiments can manage test analysis information which is information relevant to the test itself. Test analysis information includes the type or types of test to perform and analysis parameters associated with the test such as calibration information.

Test Subject Information. There is a range of embodiments for managing test subject information. The embodiment used often depends on the application and the workflows appropriate to that application. Some of the possible embodiments are described in the following paragraphs One example is manual entry of test subject information. Manual entry can include: the user writing test subject data on a log sheet, the user electronically entering the data in a Laboratory Information System (LIS) or a Hospital Information System (HIS), and entry of the test subject data on the instrument using the front panel, connected terminal, or other mechanism.

In many applications, there is a test or patient specific identifier generated by the institutional workflow system. This is used by the institution's data management system to track test results. In embodiments that support these applications, the test and test results are associated with the institutional identifier for reporting to the institution's data management system. This association can be done in a number of ways.

One way to associate the institutional identifier with the test is to add it to the test input container. For example a barcode or hand written label can be placed on a sample tube or test cartridge.

Another approach to tracking test results is to associate the institutional identifier with an identifier on the input sample container. For example, the input unit can have a factory installed identification device such as a barcode. This input container identifier can be associated with the institutional identifier. This can be done by reading or scanning the identifiers and storing them in a range of ways including: on the instrument, on the input container, and in a third party system.

Both the input unit identification device and the institution identification device can use a number of identification and identification reading techniques. This can be any combination of one or more input unit identification reading techniques with one or more institution identification reading techniques. Reading techniques include and are not limited to: optical scanned and converted to electronic ID format, Optical scanned and converted to image format, radio frequency scanning, infrared scanning, and manual reading and entered by keyboard/pointing device or voice interface.

When a test is complete, the results are associated with the institutional identifier and reported to the institution's data management system. This can be done automatically by the instrument. For example, the instrument can communicate with the LIS/HIS system.

As alternative to an institution-generated identifier to track test results, some applications may use the analyzer to provide a mechanism to associate the test with a patient. For example, when testing a large group for potential biohazard exposure, the analyzer may record patient information and provide a link between that information and the test sample. There are a number of approaches to associate a test with a patient. These include capturing patient information and contacting the patient with the test results, giving the patient an identification device, and a combination of these approaches Capturing patient data can be done in a number of ways. These include and are not limited to: entry of the data on the instrument panel, entry of the data on a web browser or other attached thin client interface, entry of the data on a direct or network attached computer, entry of the data using a voice interface system.

There are a number of identification devices that can be given to the patient. A patient may be given an identification item such as a tag, card, bracelet, for example. The patient can be given a pager or other signaling device that allows signaling through a unique code. Each of these devices has an identification mechanism. Possible mechanisms include: text identifier, barcode, radio frequency identifier (RFID), and blue tooth.

Once test is complete, the system will associate the test results with the patient. It will then signal the patient using the chosen signaling device and using the unique code notify the patient of the appropriate next stage treatment based on the results. Example embodiments of this process include:

Use human or Interactive Voice Response (IVR) contact by telephone at the phone number provided in the patient information. The patient is informed of the next stage of treatment.

Human or system contact via SMS text or instant message to the address provided in the patient information to inform patient of the next stage of treatment.

Locate individual by wearable device location function, then provide direct human consultation of next stage of treatment.

Page the patient on the signaling device provided. The patient is informed to contact the appropriate patient management personnel.

Announce patient name or ID via announcement system. The patient is informed to contact the appropriate patient management personnel. Announcement system can include voice, amplified voice and identifier display.

After sample is taken, patients move to awaiting area. They wait in line as tests are processed in order. Patient ID device is read at an output station. The patient is then informed of next step in treatment based on test results.

Patients contact system personnel after test is run. They are informed of the result and next stage of treatment.

Patient can electronically access results based on their identifier.

Any combination of two or more of the above approaches can be used.

Test analysis information. Analytical instruments that are embodiments of this invention accept and interpret information associated with the input samples to provide information on how to process and analyze the sample. This includes the type or types of test to perform, calibration information, and other analysis parameters associated with the test.

The input sample can be associated with test analysis information. Information from the input sample can be retrieved from the input device as a machine readable format such as a 1D barcode, 2D barcode, other optical format, magnet readable tag, or radio frequency identifier. It can also be manually entered by the user. Calibration and analysis parameter information is typically generated as part of the manufacturing process. It can be directly applied to the sample device. Another embodiment is to provide an identifier on the sample that links to separate media that provides the information. This media can refer to one or more samples and can be in any human or machine readable format.

The system may provide a mechanism to identify which test or tests to perform on each input sample. In many embodiments, the invention first retrieves the input container identifier using one of the mechanisms above, and then calculates the set of tests to run. Possible embodiments for this process include: running a single test type, using fixed test type codes, using loadable test codes associated with sample container lots, and looking up test type in an external system such as the LID/HIS.

An embodiment can process only a single test type at a time. In this case, the type of test to run is determined by the instrument alone.

The instrument can also use a fixed test type coding system. In this case, the test type is retrieved directly from the input container.

An embodiment can also use a loadable test coding system. Prior to running a test, information about the test is scanned or entered into the instrument. This establishes a new test code and relevant information to run the test. This new test code can be encoded on input containers.

This loadable test coding approach can work with sample lots where a lot card or other device is shipped with a set of sample containers. The lot card is scanned or entered into the instrument. This establishes a lot identifier and associated test parameters. These can include test type, calibration information, expiration date, and analysis parameters. Each sample container in the lot is encoded with the lot identifier which is read by the instrument when the sample is processed. The instrument can use this identifier to reference the lot data and retrieve test type and other parameters. The lot card system can also provide security. In this case, the lot card data is encoded so that only authorized lot cards will be accepted. Only test associated with authorized lots will be run.

In some embodiments, the test type can be determined from the institutional identifier associated with the input sample container. When the test is processed, the institutional identifier is read as described above. This identifier can be used to reference test type and other test analysis information. This information could have been previously entered into the system or electronically retrieved from a management system such as the LIS/HIS 5. Intermediate Processing The analyzer can facilitate intermediate processing before specific selection and imaging can occur. Intermediate processing may be as simple as waiting for ten minutes for a sample to reaction, or it may be as complex as adding antibiotic and growth reagents, incubating at elevated temperature at 37° C. for four hours, before adding reagent signaling and selection moieties, mixing with an ultrasonic mixer, and incubating for five additional minutes at 25° C. temperature before specific selection and imaging. Intermediate processing is important because some assays require additional assay steps, such as growth or incubation, to distinguish a positive sample from a negative one. For example in an MRSA diagnostic assay, bacterial cells growth in the presence of an antibiotic, such as methicillin, distinguishes a positive sample from a negative one.

Embodiments may include various subsystems that provide carefully controlled and maintained environmental conditions. This could include adding or removing reagents, diluents or additives in liquid, dried, or gaseous form at one or more time points, maintaining one or more samples at one or more range of temperatures or humidity, providing agitation by movement, or ensuring no agitation occurs for a specific period of time. Intermediate subsystems can include components for growth of cells or nucleic acid amplification. It may also include one or more mixers, agitators, aerators, shakers, heating or cooling elements, means to queue and move samples, or means to time and control subcomponents and samples. The subsystem for intermediate processing may include features that allow one or more samples to be moved into and out of the subsystem at specific times. The subsystem may be contained at a specified humidity between 0-95% or it may change over time. Likewise, the temperatures may range from less than room temperature to more than 37° C. The temperature inside the subsystem may be held at a static temperature or it may alternate periodically between one of more temperatures or temperature ranges. For example, detection of MRSA (FIG. 43) may require incubation for four hours at 37° C. in which the sample is agitated and provided with sufficient nutrients for cell growth as well as sufficient aeration to allow for aerobic respiration.

Temperature may be controlled in any number of ways. Temperatures can be affected by electrical resistance heaters or Peltier devices, which can be used for heating and cooling, as well as the materials used to fabricate the subsystem. These components may be integrated into the analyzer or may be included into an external component such as the sample container. For example, the subsystem can be fabricated out of copper when rapid conduction of temperatures is required, or it can be fashioned from an insulator, such as PVC foam, to minimize heat transfer times. Temperatures may be monitored by internal integrated probes. Control of dwell times of samples in the intermediate processing subsystem may range from those that are timed manually to those with serial queuing (FIG. 29 and FIG. 30) to those with random access queuing (FIG. 42).

6. Specific Selection

The analyzer may provide one or more subsystem for the selection of a specific target in an assay sample. Specific selection can be useful because it can dramatically lessen the background signal of unbound labels and non-specifically bound labels in the region of the sample that is to be optically interrogated. Selection is also advantageous because it can gather all targets signal moiety complexes into a specific location and orientation optimal for interrogation by imaging.

There are many different types of specific selection. Some methods may include capture on surfaces coated with a binding moiety, for example, antibodies or oligonucleotides. Magnetics can be applied to a sample where the physical and field properties of magnetic components result in mobilization of bound target moieties inside the sample container. Target moieties can be designed to possess certain magnetic susceptibilities optimal for magnetic selection. Magnetic selection may utilize one or more electromagnets or solid state magnets in particular orientations. For example, one or more solid state neodymium-boron-iron bar magnets may be placed in parallel adjacent to one another (FIG. 3) or in spaced to allow imaging while selection occurs (FIG. 4). Other configurations, such as, but not limited to, one or more disc, spherical, and cylindrical (FIG. 5) magnetic components can used to specifically select for target moieties. In some instances, the sample may be compatible with capture of target moieties that rapidly form a uniform monolayer. Other types of selection may include gravity, such as centrifugation or sedimentation, buoyancy, optical interrogation such as fluorescence, chemiluminescence, morphology, or white light microscopy). Other methods include, but are not limited to, diffusion, and size exclusions, for example those using a membrane or filter. One or more of these methods may be used together or separately in a single analyzer.

The analyzer may have a selection subsystem in which the targets in a reacted and bound sample are selected for by projection directly onto a detection area. Linear projection of a volume directly onto a surface can enhance imaging interrogation of the assay. For example, in (FIG. 66) reagents that include magnetic and fluorescent particles that are pulled down to the bottom of well in a single uniform layer where they can be imaged from below. Other embodiments can be envisioned, including selection to alternative surfaces, such as sides or top. The selection may be done in the absence of flow.

7. Imaging

The analyzer has a subsystem that includes imaging optics with a photodetector array that can acquire a wide area at low magnification. Low-magnification wide-area limiting imaging is important for sensitive and rapid detection of targets in samples. The analyzer imaging subsystem can image the whole assay sample with as few as one image. The imaging subsystem includes means for illumination, detection, image conditioning, image acquisition, and a photodetector array.

The imaging subsystem may include means for illumination. Illumination may include, but is not limited to, incandescent bulbs, lasers, or light emitting diodes (LEDs). One or more of each illumination source may be included. In some instances, multiple illumination sources are used to increase the intensity of excitation energy in a specific location for image detection. The illumination source may be broad band (a wide range of energy wavelengths) or a specific wavelength sources. Illumination sources may or may not be conditioned before or after they impinge on a sample. In some cases, such as chemiluminescence for example, no illumination is required. A chemical reaction induces emission of visual energy that can be detected directly. Before the image is acquired by the photodetector array, the image may be conditioned to enhance the resolution of the image. Optics, including lenses, diffraction gradients, and wavelength filters may be employed to condition the image. Lenses may focus or defocus the image so that when it arrives at the photodetector array it is less than 10-fold magnified from actual size. Lenses may also relay images, correct for chromatic aberrations, coma, or other optical effects. Wavelength filters may block certain wavelengths of light and allow other wavelengths to pass. Filters may be used on excitation or emission wavelengths, or both. In some cases, no conditioning of the image is required.

Image acquisition is done by use of one or more photodetector arrays. There are many different ways to capture images in this manner. Photodetector arrays can include, but are not limited to, charge coupled devices (CCDs), photodiode or avalanche photodiode arrays (APDs), single photon avalanche photodiode (SPAD) arrays, photon multiplying tube (PMT) arrays, or complimentary metal oxide semiconductor (CMOS) arrays. Photodetector arrays vary widely in price, resolution, and sensitivity, and can be selected for different performance properties depending on the assay requirements on the analyzer.

The imaging subsystem may include means of focusing to acquire an image. This may include passive methods, such as a physical geometry (e.g. v-groove or alignment pin) or active means such as a software autofocusing algorithm (e.g. focusing on a fiducial), a laser distance sensor (e.g. Keyence), or a physical distance sensor (Hall-effect probe) to name a few examples.

8. Image Analysis

The primary function of image analysis is to quantify the amount of signal present in the images produced by the imaging subsystem. The analysis output can be used to determine characteristics of the test, container. For instance, it is the basis for test rejection when signal is invalid, or it could detect non human readable code or fiducials for container validity check.

Image analysis may contain steps such as preprocessing, signal separation, and signal quantization.

Imaging preprocessing algorithms can optionally be applied to the image. There are a range of preprocessing algorithms including for example:

Region of interest (ROI) detection may be performed to limit subsequent analysis to the region of the image that contains the signal. There are a range of approaches for ROI detection. These include: using a fixed ROI based on consistent image acquisition mechanics, computation via edge detection analysis, matched filter analysis looking for knows signal elements such as the edge of the imaging well, fiducials or other know markings on the image, and detected with threshold and connectivity analysis.

Field flattening can be applied to the image to adjust for uneven lighting effects.

There are many standard image processing functions that can be applied. These include smoothing, sharpening, edge detection, contrast enhancement, noise reduction, rank filtering, mean filtering, and matched filtering to find signal or remove noise or debris (Oppenheim, A., Schaefer, R., Digital Signal Processing, Prentice Hall, 1974) A distortion correction algorithm can be applied to adjust for known distortion effects produced by the imaging system.

In addition to enhancing input images, preprocessing can decide what subsequent processing algorithms to use or determine image error conditions such as missing input, blocked input, no lighting, and damaged sample container.

The second general image analysis element is signal separation. This process removes background, noise, and debris components from consideration by the signal quantization step. Possible signal separation approaches include Some algorithms do not use signal separation. For example, a simple algorithm may produce a result by simple summing all image pixels.

Some algorithms use of one or more threshold ranges to consider only pixels that have a value within one of the ranges.

Some embodiments use the threshold analysis described above followed by connectivity analysis to associate adjacent pixels into blobs. Various blob parameters are measured, and based on those parameters, signal blobs are separated from other blobs. For example, a blob with a very large area may be considered debris and not counted as signal The final general image analysis element is signal quantization. This analysis uses the output of signal separation and produces a numeric, binary, or enumerated result. There are a range of signal quantization approaches. These include:

Some algorithms sum the intensity of all signal pixels to produce a result. The sum can be returned directly. The sum can also be scaled, thresholded, or otherwise processed to produce an final output.

Some algorithms base result on the statistics of individual signal components. For example, the result could be based on a count of the signal pixels. Or, if connectivity analysis is used in signal separation, the result could be based on the count of signal blobs or statistic such as the sum of signal blob intensity or area.

In addition to processing individual images, image analysis can use multiple images to produce a result. This can be the use of a statistical process such as averaging or median across the images. Multi image processing may also detect expected differences in the images. For example, magnetically tagged signal particles may move in the presence of a magnetic field from frame to frame. In this case, the analysis algorithm can use frame to frame motion to separate the signal components.

9 Results Reporting

Analyzer embodiments may provide a means to report test output data. Data includes elements related to tests results, test parameters, patient administrative, patient medical quality control data, calibration, and proficiency. Depending on the need of the user and the capability of the analysis system, test result data could include a "pass-fail" indicator, images, and partially processed data. The display of data can take many formats including simple alpha numeric on a visual display (e.g., LED) that is integrated into the analyzer, an integrated system display such as an LCD, or a thin client with web browser attached to the system. In some designs, an attached network personal computer running a thick client application. In addition to these volatile, real time, visual display, design could also incorporate options for printing; integrated on board, external through common communications connections (serial, usb, Ethernet, firewire), and they could be through physical or radiated media for record keeping. FIG. 13 is a analyzer that has an integrated printer and LCD to display results. For longer term record keeping, there could be a defined term of data storage on disk and other media in specific structures including databases for later access. These data could also be transmitted to other enterprise systems (e.g., LIS, HIS) in any of its forms. Finally any or all of the data could be reported in any or all of the designs and formats mentioned. FIG. 25 shows a system with a database, displaying to an on board system control panel, database storage, dedicated commend ad control link, web interface, and an interface to the LIS.

10. Post-Processing

Analyzer embodiments may perform one or more of post-processing steps after a sample has been imaged and analyzed. Post-processing may be done to prepare the analyzer another sample, protect the user from biohazardous materials, or enhance user friendliness of the analyzer by eliminating user steps.

There may be one or more actions that the analyzer may perform to prepare for next sample. These may include cleaning, waste disposal, or movement of one or more samples, reagents, components, or containers. Cleaning actions may include rinsing of one or more pipette tips (FIG. 46), imaging or reaction cups (FIG. 47). Waste disposal may include removal and storage of liquid wastes formed as a byproduct of running an assay (FIG. 48) or it may mean moving a unitized sample container to a dry waste disposal bin or container (FIG. 16). Waste disposal containers may or may not have manual or automatic sensing capabilities that allow the user or analyzer to determine when the waste container needs to be replaced. Waste containers or byproducts may provide visual cues (FIG. 13) that they require user interaction for clearance, or they many have an automatic sensing analyzer, such as an optical sensor (FIG. 38) that can communicate with the analyzer or user when the waste need be removed.

In many embodiments, post-processing involves preparation for another sample assay. This may include washing and cleaning components as already mentioned, but also might include resetting or homing subcomponent locations (FIG. 14), replenishing reagent volumes (FIG. 49), and moving components or sample containers off the imaging subsystem (FIG. 13 and FIG. 15).

11. System Control

In order to perform and report on analytical tests, the analyzer may have means to control the system and analyze the detected images. This function is provided by the system control element. It can be used to control and coordinate all activities of the system. Functions that can be provided by system control include, but are not limited to, instrument control, motion control, liquid handling control, incubation control, lighting and image acquisition control, reaction process timing, resource scheduling, user interface, data entry, system status display, system configuration and control, system maintenance and diagnostics, results display and output, data management, communication with external information management systems (LIS/HIS), and image analysis.

Typical instrument control implementations would perform tasks such as identified in FIGS. 9 and 25, controlling timing and motion of motors, actuators, pumps, mixing, display and external communication updates, (e.g., button pushes, mouse clicks), subsystem testing and diagnostics, data storage, analysis and retrieval. Those basic tasks could be combined with others, as needed for specific applications.

In many embodiments, system control consists of a microprocessor or other computation unit. This can include a non-volatile storage capability, system interface circuitry, and system control software. The embedded processor components and the interface circuitry are often located on a single circuit board, but can be deployed on multiple boards. The electronic interface between the system control subsystem and other system components can include one or more channels of both general propose industry and custom interfaces. General standards used include standards Universal Serial Bus (USB), IEEE 1394, 10/100 base T Ethernet and RS-232 standard serial interface. Where custom interfaces are used, the control system often provides low level component control. For example, system control can include a motor controller that interfaces to the motor with analog stepper control signals.

The system control subsystem hardware can be based on a commercial general purpose computer. This can be deployed as physically integrated component of the overall invention, as a separate dedicated unit, or a provided by the user. The electronic interface from the general purpose computer can be one or more industry standard interface connections. It can also be a custom connection provided by a custom card that is added to the general propose computer. When an embodiment uses a general purpose computer, it may use a standard interface to connect directly to a system element. In addition, there may be interfaces to integrated circuitry.

System control software may provide the logic that implements the system control functions listed above. System control software may consist of four or more elements, which may include executive, system services, data management, and user interface.

The system control software may have an executive component. The executive may provide the core logic the controls the runtime activities of the system. Possible embodiments of the executive software element include, but are not limited to, directly coded control logic, event handling state machine, script driven system, general purpose script language, custom script language, and likely implementations will include combination of one or more of these.

There may be a set of software system services that manage the inventions hardware components. In addition, major software capabilities are provided by system services. System services include, but are not limited to, motor and sensor management, camera control and interface, liquid handling management, mixing unit management, barcode unit interface, database interface, utilities and image analysis.

The system control software might include data management. The data management element may be responsible for tacking information related to pending, in process and completed analytical tests.

A user interface may be included in the system control software. The user interface element may drive a variety display and user input modalities. These include, but are not limited to, front panel display, attached thin client interface such as a web browser, attached thick client interface such as a application running on a network attached personal computer, printer output, and interface to other analyzers such as a Hospital Information System (HIS),

EXAMPLES

The invention is further described with respect to the following nonlimiting embodiments. Unless otherwise noted, any element of an analyzer specifically described in the examples may be employed generally with an analyzer of the invention.

Example 1

Imaging

Overview. Each embodiment of the analyzer has a subsystem that performs imaging of an assay. Images are acquired with a photo-detector array with optics that result in an image with magnification less than 5×. In most cases imaging is done without any magnification. Imaging is advantageous for rapid sample processing and analysis because it has a broad dynamic range. Samples that have only one or two targets can be analyzed by the same detection system that can visualize more than tens of thousands of targets. Wide area, low magnification imaging removes the complexity and cost of precision optics. It also eliminates complicated methods of interrogating a whole sample, such as scanning. The analyzer imaging subsystem can interrogate the whole assay sample with as few as one image. The imaging subsystem includes modules for illumination, detection, image conditioning, image acquisition, and a photo detector array.

Non-automated analyzer optics. The non-automated analyzer (FIG. 8) used an imaging subsystem illustrated in FIG. 7. In this case, imaging occurred on the top surface of the imaging well. A CCD photo detector array (Sony XCD SX-910) was used to perform non-magnified imaging on a large sample target area. Two LEDs (Luxeon Emitter 3W LED-Blue, Lumileds, LXHL-PB09) were arranged to focus on the sample as illustrated in FIG. 7. Each LED subassembly consisted of one LED, a LED 1A constant current power supply (Future Electronics, 3021-D-E-1000-LF), a LED focusing lens (focal length=50 mm, PCX, Edmund Scientific, 45-361), a LED collimator lens (Lumileds, LXHL_NX05), and a LED emission filter (Chroma, Z475/49X). The emitted light from the sample was collected by a non-magnifying 1:1 relay lens (Edmund Scientific, 45-760) and spectrally conditioned with an emission filter (Chroma, HQ535/50m).

Focus adjustment was accomplished by hand. The user used a linear stage slider with a fine pitched adjustment screw (Newport, AJS-02H) to bring images into focus. Mechanical tolerances of the imaging wells and length of travel on the vertical stage ensured imaging well targets were within the range of the optical systems depth of field. Image analysis was computed as described in Example 3.

Automated analyzer optics. The automated analyzer (FIG. 14) used an imaging subsystem illustrated in FIG. 73. In this case, imaging occurred on the bottom surface of the imaging well. A CCD photo detector array (Sony XCD SX-910) was used to perform non-magnified imaging on a large sample target area. Four LEDs (Luxeon Emitter 3 W LED-Blue, Lumileds, LXHL-PB09) were arranged to focus on the sample as illustrated in FIG. 73. Each LED subassembly consisted of one LED, a LED 1 A constant current power supply (Future Electronics, 3021-D-E-1000-LF), a LED focusing lens (focal length=50 mm, PCX, Edmund Scientific, 45-361), a LED collimator lens (Lumileds, LXHL_NX05), and a LED emission filter (Chroma, Z475/49X). The emitted light from the sample was collected by a non-magnifying 1:1 relay lens (Edmund Scientific, 45-760) and spectrally conditioned with an emission filter (Chroma, HQ535/50 m).

Focus adjustment was accomplished by moving the imaging platform assembly described in Example 8. FIG. 2 shows images captured from a typical assay. Image analysis was computed as described in Example 3.

Surge testing analyzer optics. The surge testing analyzer (FIG. 15) used an imaging subsystem illustrated in FIG. 1. In this case, imaging occurred on the bottom surface of the imaging well. A CCD photo detector array (2 Mpixel CCD camera, uEye, UI-2550-M) was used to perform non-magnified imaging on a large sample target area. Six LEDs (Luxeon Emitter 3 W LED-Blue, Lumileds, LXHL-PB09) were arranged to focus on the sample as illustrated in FIG. 72. Each LED subassembly consisted of one LED, a heat sink (Aavid Thermalloy, 374124B00035), a LED 1A constant current power supply (Future Electronics, 3021-D-E-1000-LF), a LED focusing lens (focal length=50 mm, PCX, Edmund Scientific, 45-361), a LED collimator lens (Lumileds, LXHL_NX05), and a LED emission filter (Chroma, Z475/49X). The emitted light from the sample was collected by a non-magnifying 1:1 relay lens (Edmund Scientific, 45-760) and spectrally conditioned with an emission filter (Chroma, HQ535/50m).

Focus adjustment was accomplished by moving the camera assembly on each cycle as shown in FIG. 57. A closed loop stepper motor with integrated amplifier (Oriental Motor, AS46A) was attached to a vertical linear axis (Deltron, DL26L-70-ST-C-PH) to mobilize the imaging system such that it lifted the imaging cup a fixed distance from the optics. Mechanical tolerances of the cup and the imaging unit are less then the optical system's depth of field. Image analysis was computed as described in Example 13. FIG. 63 shows images captured from a typical assay.

Automated analyzer with robotic optics. The automated analyzer (FIG. 48) used an imaging subsystem illustrated in FIG. 1. In this case, imaging occurred on the bottom surface of the imaging well. A CMOS photo detector array (Mightex BCN-B013) was used to perform non-magnified imaging on a large sample target area. Six LEDs (Luxeon Emitter 3 W LED-Blue, Lumileds, LXHL-PB09) were arranged to focus on the sample as illustrated in FIGS. 1 and 72. Each LED subassembly consisted of one LED, a LED 1 A constant current power supply (Future Electronics, 3021-D-E-1000-LF), a LED focusing lens (focal length=50 mm, PCX, Edmund Scientific, 45-361), a LED collimator lens (Lumileds, LXHL_NX05), and a LED emission filter (Chroma, Z475/49X). The emitted light from the sample was collected by a non-magnifying 1:1 relay lens (Edmund Scientific, 45-760) and spectrally conditioned with an emission filter (Chroma, HQ535/50m).

Focus adjustment was accomplished by moving the imaging platform assembly described in Example 14. Image acquisition and analysis was conducted as described in Example 3.

Results. FIGS. 2 and 63 show typical images captured from the imaging subsystem. Detailed experimental protocols and results are explained in Examples 4, 8, 9, and 14.

Conclusions. This example shows several embodiments of the imaging subsystem that included modules for illumination, detection, image conditioning, image acquisition, and a photo detector array. It allowed low magnification imaging for rapid sample processing.

Alternative embodiments. There are numerous alternative embodiments, including those listed in the detailed description. The CCD devices in this example could be replaced with an avalanche photodiode array or an array of photomultiplier tubes. The light source could be a xenon bulb, or it could be a defocused laser source. Different lenses could be used to change the relative focal distances and depths of focus. Also, the wavelengths of excitation and emission could be changed to accommodate different spectral regimes.

Example 2

Magnetics

The device may include of one or more subsystems for selection of labeled targets through the application of selection forces upon labeled target-selection moiety complexes in the sample. This example describes several methods used to apply magnetic force for selection. Magnetic selection of magnetically-responsive particles was accomplished by using magnet types and configurations that generate high magnetic gradients. Rare earth, solid state magnets such as neodymium-iron-boron magnets generate high magnetic gradients, are inexpensive and useful for many embodiments of the invention.

Different magnetic field and field generating magnet configurations (FIGS. 3-5) can be used to select magnetically responsive particles and deposit them in the detection zone. The configurations are used to address different imaging well geometries, and imaging subsystems used on different embodiments of the invention.

The parallel bar magnet assemblies (FIG. 4.) allow simultaneous selection and imaging in a fixed arrangement. This reduces the overall size of some embodiments of this invention since imaging and magnetic subsystems can be placed in close proximity to each other and there is no requirement for motion to transition between these subsystems.

Description. The Bar magnet assembly (FIG. 3) was manufactured by assembling five 22×22×100 mm neodymium-iron-boron magnets (grade N50, Dexter Magnetics) in an aluminum rack so that the N-S polarities were progressively rotated 90° from magnet to magnet (cross-sectional view FIG. 3.). This configuration results in magnetic field lines that generate a magnetic gradient perpendicular to the magnet assembly surface (cross-sectional view of magnetic field lines FIG. 3.). The magnetic gradient generated will rapidly select magnetic selection particles in a solution above the assembly and deposit them uniformly across an imaging surface parallel to the surface of the assembly.

Parallel bar magnet assemblies (FIG. 4.) were manufactured using 3.35×0.125×0.25 inch neodymium-iron-boron bar magnets (grade N50, Dexter Magnetics) glued into slots spaced 10 mm apart on custom manufactured 88×15×127 mm aluminum frames with lips. The assemblies were designed to accommodate standard commercially available 96- and 384-well microtiter plates. The configuration results in a magnetic gradient within specific wells of either a 96- or 384-well microtiter plate (cross-sectional view of magnetic field in a well FIG. 4.). The magnetic gradient generated rapidly selected magnetic selection particles in a solution above the assembly and deposited them uniformly across the bottom of the micotiter well (detection surface).

Pin array magnet assemblies (FIG. 5.) were manufactured using $1/16 \times 1/4$ inch neodymium-iron-boron cylinder magnets (grade N45K & J Magnetics). Pin magnets were inserted into $1/16$ inch holes drilled in 15×1×12 cm rectangular sheet of plexiglass. Four larger pins were also inserted as stops to position standard commercially available 96-well microtiter plates so that the center of each well registers with the center of the ends of the corresponding pin magnet.

Methods. An assay as described in example 14 was performed with the following modifications: all pipetting steps were performed manually into two separate 96 well black microtiter plate (Greiner, Cat. No. 675096). For magnetic selection one plate was magnetically selected on the bar magnet assembly. The other plate was mounted on a parallel bar magnet assembly.

In another experiment a similar assay was performed with the following modification: Optiprep® density agent was not included in the dye reagent. For this experiment magnetic selection was performed on a pin magnet assembly.

Results. FIG. 66 demonstrates the even deposition of selected target signal moieties across the imaging surface allowing enumeration of signaling moieties with non-magnified imaging using parallel bar magnets and bar magnet assembly.

FIG. 77 shows the image from an assay using the pin magnet. The deposition of selected moieties in a region of the imaging surface allows enumeration of signaling moieties with non-magnified imaging. Signal present in the area around the deposition zone allows assessment of the non-selected background.

Conclusions. Magnetic selection of magnetically-responsive particles was accomplished by using several types and configurations of the magnetic assemblies described. The magnetic assemblies can be used in different embodiments of the invention as the selection force described for the invention. Magnetic selection of labeled targets is specific and allows sensitive detection of targets by enumeration of targets by non-magnified imaging.

Alternative embodiments. In other embodiments of the invention magnets of different composition can be used and are known in the art.

The magnetic assemblies described can be incorporated as subsystems of the embodiment of the invention described in FIG. 14. In some embodiments the imaging vessels are moved across the magnetic assemblies.

Other embodiments can incorporate multiple magnetic assemblies in one analyzer.

This example describes several magnet configurations but others can be contemplated and are known in the art that address different imaging well geometries, and imaging subsystems used on different embodiments of the invention.

The parallel bar magnet assemblies (FIG. 4.) allow simultaneous selection and imaging in a fixed arrangement providing the ability to view the detection zone during the selection step. This feature could be used to reduce assay times.

Example 3

Image Analysis

Overview. A core function of the invention is to process analytical tests based on non-magnified imaging of targeted analytes. This example describes an embodiment of image analysis processing.

The features of the image analysis algorithm described in this example include: counting individual signal moieties, determining accurate moiety count over a very large range of signal performance when individual moieties can not be resolved, performance over large area counting of defocused objects, performance over a wide range of test types based on tests-specific analysis parameters, exclusion of various types of debris and detection of erroneous images (no lighting, image blocked, damaged sample container, missing sample container)

Description. The image analysis algorithm provided a fully automated analysis. An input image and information on the type of test that generated the image were provided and the analysis software produced a numeric result quantifying the number of signaling moieties present in the image. The type of image was specified based on both the assay that was run and the image acquisition system that was used. The algorithm used a set of preconfigured analysis parameters based on the input image type. Image analysis was performed using the following steps: Region of Interest (ROI) computation, frame analysis, field flattening, masking, connectivity analysis, parameter extraction, classification, and computation of results. Each of the algorithm's processing steps is described in the following sections.

Region of Interest (ROI) computation. The first step of image analysis was the computation of the Region of Interest (ROI). ROI is the portion of the frame that contains the signal (FIG. 2). For many test types, the signal was contained in a round well that is inside a rectangular image frame. Detection of the ROI allowed subsequent analysis steps to process only the pixels where the signal could be found.

ROI detection was controlled by configuration parameters based on the type of test that was input to the algorithm. For some test types, the ROI does not vary from image to image. In this case, a pre-configured ROI was used.

In cases where the test type required ROI detection, the analysis used an edge detection algorithm designed to detect the difference in background or peak signal level between the ROI and the image area outside the ROI. The use of background or peak signal was also based on the test type.

To compute the ROI, a set of linear arrays of pixels from the image were considered. These lines were chosen in the horizontal and vertical directions. Each line formed a one dimensional signal. A rank filter was run on each line to find the background or peak signal. Using a rank filter with length 20, a rank of 2 found the background, and a rank of 18 found the signal peak. Next, the output of the rank filter was correlated with a rising edge of length 80 where a rising edge was expected and the inversion of this where a falling edge was expected. For each line, the edge correlator output was added to a new blank image at the pixel positions that corresponded to the original line. Finally, a two dimensional correlation was applied to this image against the shape that matched the input well. The ROI position corresponds to the max output of the correlator. This approach was also used to search for different well sizes. This process was a three dimensional search that found the size, x position, and y position of the ROI with the maximum correlation.

The final ROI used was the well shape centered on the calculated ROI position. Based on the input image type, this shape could be configured to be a different size then the measured ROI. In some cases, it was slightly smaller.

Frame analysis. The purpose of full frame analysis was to determine if detailed analysis should be skipped. This was done in the following cases.

The signal level and area were too high for meaningful blob analysis. Since the assay had a very high dynamic range, it many not have been possible to identify individual blobs. In this case, the analysis result was based on total intensity and area. While it was not possible to remove debris in this case, the signal was so high that the overall result had a good signal to noise ratio.

Frame analysis also checked for a valid frame by looking for the presents of markers. This included features of the imaged object such as the edge of a well or fiducials. If features did not appear as expected, analysis was curtailed and an error was reported. Conditions that were checked include features that are missing, obscured, not properly lighted, and badly out of focus, Field flattening. Field flattening was used to correct the image for differences in background level. It was designed to compensate for uneven lighting. This could occur if the lighting system had a defect such as a broken LED. Field flattening was also helpful when image conditions were not known prior to analysis. This often occurred in scientific analysis applications where assay conditions were varied. The use of field flattening is a configuration parameter based on the type of test being analyzed.

When field flattening was used, the background level inside the ROI was first estimated by running a rank analysis on all pixels in a section inside the ROI. A pixel value at the $10^{th}$ percentile was used as an estimate of the image background. All pixels outside the ROI were set to this value.

Next, the image was divided into a 10 by 10 array of rectangular sections. A portion of each section was applied to a rank analysis as described above to determine a background estimate for the section. The mean and standard deviation of all the section background estimates were measured. If any estimate value exceeded the mean by more then 3 times the standard deviation it was replaced by that limit. Similarly, if any value was less then the mean minus 3 times the standard deviation, it was replaced by the lower limit. The limited estimate values were formed into a 10 by 10 pixel image with one pixel for each limited background estimate from the corresponding section.

A lowpass filter was applied to the image from the previous step. The resulting image was then expanded using interpolation to the size of the original image. This background image was then subtracted from the original image. Any pixel value less then zero was set to zero. This formed the output image of the field flattening process.

Masking. The flattened image was thresholded to separate detected signal from background. This was done with a fixed threshold that was based on the type of image being processed. A mask image was formed as follows: If a pixel value was less then the threshold, the mask pixel was set to zero, otherwise the mask pixel was set to 1.

Connectivity analysis. A connectivity analysis was run on the mask from the previous step. This produced a list of image blobs where each pixel in the blob had a mask value of one and was directly adjacent to at least one other pixel in the blob. Also, no two pixels from different blobs were directly adjacent.

In addition to the blob list, an image was formed with the same dimensions as the original image. Each pixel in this image was set as follows. If the mask value for that pixel was zero, it was set to zero. Otherwise, the pixel value was set to a reference to the blob structure to which it belongs.

Parameter extraction. A number of parameters were measured for each blob. These included center position, area in pixels, intensity (total pixel value), mean intensity, perimeter, minimum pixel value, maximum pixel value, width, height, aspect ration, and compactness.

Classification. Blobs were then sorted into several categories based on blob parameters. The categories included signal, blobs too small to be signal, and various categories of debris.

For each type of image being processed there were a set of rules for blob sorting. Each rule considered both blob parameters and image wide parameters that where measured in the frame analysis stage.

Debris was classified by shape, size, total intensity, and variation in intensity. Rules varied based on image type and the total amount of signal in the image. If there was high signal present, signal blobs were more likely to be adjacent to each other and look like a large blob. In this case, using larger debris thresholds was desirable to insure that these large signal blobs were correctly labeled. The sorting rules were based on the type of image. A common configuration was to use 3 sets of rules: One for the low signal case with tight debris settings, one for the moderate signal case with average settings, and one for the high signal case with loose debris settings. This type of approach maximized the signal to noise ratio, it limited debris on low signals where it had a large effect as a percentage, and properly counted signal in high signal cases.

Computation of results. Computation of the number of signaling moieties present in the image was based on image type and total signal level. There was a results counting threshold configured for each type of image. If the total signal level was less then or equal to this threshold, then the algorithm set the result to the count of blobs that were labeled as signal. Otherwise, the result was set to the total intensity of each blob that was labeled as signal divided by the signaling moiety intensity configured for the image type.

Conclusion. This example demonstrates reduction to practice of an imaging analysis algorithm that automatically computes the number of signaling moieties present in an image that was created using a non magnified photodetector array. This example describes an algorithm that can separate signal from background, compensate for lighting effects, ignore debris, detect erroneous images, and work over a wide range of input test types.

Alternative embodiments. The processing steps described in this example provide a general outline for image analysis. It is possible to bypass many of these steps and still produce a usable result. Additional steps can also be added. For example, a preprocessing stage may be needed to adjust for distortion that is introduced in a particular detection system.

An alternate approach for ROI detection is to search for one or more fiducials if they are used in the application.

Another approach to image analysis is to simply sum the values of all pixels above a configured threshold.

Image analysis can also be performed manually with an imaging tool such as Image Pro. The user can manually set the ROI and then threshold and perform connectivity analysis with the counting tool. They can also use this tool to select area and intensity range filters on the blob list produced by the counting tool. Finally, the user can manually indicate which blobs are debris and should be ignored. The total intensity of all signal blobs can be displayed by the tool and recorded as the result.

Example 4

Simple Non-Automated Analyzer

This example describes an extremely small analyzer designed to image sample vessels with the dimensions of a microscope slide. This analyzer provides powerful but cost-effective analysis for low throughput applications. The analyzer of this example provided the following features: support for multiple test types, accommodated microscope slides, imaged from above to support top selection assays, accommodated formats that do not require external selection such as lateral flow assays.

Description. This analyzer was designed to accommodate samples that were prepared on a standard microscope slide or in a similar format. FIG. 7 is a diagram of the analyzer, FIG. 8 shows a photograph.

The system was used to perform lateral flow assays where a capture antibody was anchored at a fixed position on the slide assembly. Labeled targets were captured as they flowed past. Labeling was done using fluorescent particles coated with an antibody.

To use the system, the user prepared a capture assay in a 1 inch×3 inch or smaller format and placed the assay support on the platform where imaging occurs.

The system allowed the user to manually move the input slide. The user also controlled focus using a thumbscrew that moved the imaging stage.

The imaging subsystem was designed to detect fluorescent signaling moieties (~475 nm excitation/~535 nm emission). See Example 1 for details on imaging. The imaging subsystem was built with a CCD camera (Sony XCD SX-910) that produces an 8 bit grayscale image. Two Luxeon LXHL-PB09 blue LEDs (Lumiled LXHL-PB09) were used to illuminate the image. These produced a Lambertian radiation pattern for the maximum spot intensity at the target.

Image acquisition control and analysis was provided by the Image Pro software application from Media Cybernetics. This ran on a personal computer that was connected to the camera with an IEEE 1394 (FireWire) interface. Image capture was initiated by the user with the Image Pro Interface. Image analysis was also performed in Image Pro using the blob counting tool. Image analysis is described in example 3.

Conclusion. This example demonstrated an embodiment of the invention that uses a photodetector array with light emitting diodes for illumination to image individual labeled targets on a microscope slide after they are selected by a capture moiety. This embodiment shows reduction to practice of a simple analyzer.

Alternative embodiments. The analyzer can have a motorized stage that could move left or right (parallel to the front of the system) using a screw drive. This motor can be used to move the stage during image acquisition to allow imaging of an area larger then a camera frame.

The analyzer can have an associated selection module that uses top selection magnetics to apply a selection force to the assay prior to imaging.

The analyzer can be reconfigured to image from the bottom and use an associated bottom selection magnetics module to apply a selection force to the assay prior to imaging.

Example 5

Simple Non-Automated Analyzer for Detection of Multiple Signaling Moieties

Overview. This example describes a single-sample manually operated imaging module that uses non-magnified imaging to detect two different fluorescent signaling signatures within a single sample. This analyzer is useful for imaging manually assembled and selected multiplexed assays which incorporate two different signaling moieties with distinct signal characters, for instance, two different fluorophores, as their labels. It also can be used for imaging of other types of samples containing labels of two different signal characters, for example an assay detecting cells where the cell is internally labeled with a red nucleic acid stain like hexidium iodide and externally labeled with yellow-green fluorescent particles bound to a cell surface antigen.

The analyzer uses commercially available or custom manufactured sample vials to contain the reaction. The sample is prepared offline. This includes contacting labeling moieties and selection moieties with the target, and depositing labeled targets in the detection zone. After preparation, the well containing a sample to be imaged is manually placed in an imaging fixture. Two different excitation light sources can be manually selected to illuminate the sample, and emission filters mounted on the imager can be changed by hand as required. Operation of the data acquisition function is manual via a personal computer interface for control of the imaging functions.

Description. This example is a specific embodiment of the imaging module of an analyzer, adapted to detect two signaling characters. The optical assembly is shown in FIG. 1. This embodiment is designed to detect fluorescein-like fluorescent moieties (excitation peak 488 nm, emission peak 520 nm) as well as Cy5® or Alexa® 647 fluors (excitation peak 650 nm, emission peak 668 nm)

The sample in a well with an optically clear bottom detection surface was placed into the imaging fixture by hand (not shown in the Figure). The imaging fixture consisted of a support for the sample well which by its design aligns the well in the appropriate position for detection by the camera and a system for moving the support along the imaging axis to allow the image to be focused.

The illumination module was identical to that described in Example 1 except that, instead of six identical LED's for illumination. It used illumination in each wavelength regime provided by alternating two different types of LED's. In each wavelength regime, three LED's were used in an evenly distributed circular array. In this embodiment, LED's for the fluorescein spectral regime were Luxeon Emitter 3 W LED-Blue, Lumileds, LXHL-PB09, which produced light in the blue spectrum. Each LED was paired with an excitation bandpass filter (20 mmD, Chroma, Z475/49x). LED's for the Cy5®/Alexa®647 regime were Luxeon LXHL-PD09 red. Each LED was paired with an excitation bandpass filter (Chroma HQ620/60x).

The imaging system includes a Mightex, Inc. BCE-BO13US camera, interfaced through a USB 2.0 connection to a personal computer, a non-magnifying lens (Relay Lens, Edmund Scientific, 45-760) to project the image onto the CMOS imager, and a manually interchangeable emission filter. For the fluorescein spectral regime, a Chroma HQ535/50m emission filter is used. For the Cy5® regime, a low pass Chroma HQ665LP filter is used.

Operation. The operator placed the prepared sample into the imaging fixture. A first signaling regime was selected by installing the appropriate emission filter, and switching on the appropriate set of LED's. Data acquisition in a real-time mode was initiated, and the image was focused by manually adjusting the distance between the detection surface and the lens. Images in the first spectral regime were acquired by frame capture, adjusting the exposure time so that signaling moieties were detected without saturating the camera. A second signaling regime was selected by installing the appropriate emission filter, and switching on the appropriate set of LED's. Focusing was not necessary, as it was performed under the illumination of the first signaling regime. Images in the second spectral regime were acquired by frame capture, adjusting the exposure time so that signaling moieties were detected without saturating the capacity of the camera. In the case where the two signaling moieties have a differential susceptibility to photobleaching, the most photostable signaling moiety was imaged first, so that the manual focusing operation does not affect the sensitivity of signal detection.

Conclusion. This imager is useful for two color detection. It can be used for detection of dually labeled single targets, or for multiplexing of assays. This device can be seen as the optical assembly for an automated image acquisition system.

Alternative embodiments. Light sources and filters can be designed for any desired pair of signaling moieties Emission filter exchange can be automated by use of a motor driven filter bar or wheel. The presentation of the sample to the imager can be automated by use of robotics, including moving a sample to acquire multiple images from a single detection surface, and the focusing operation can be automated through software adjustment of the distance between the sample and the camera, combined with image analysis to detect the best plane of focus. This operation can performed on by imaging the sample itself or by imaging a fiducial present on the detection surface of the sample well. Alternatively, focus can be fixed by the design of the sample mounting system, so that when the sample is placed in the imager by automated or manual placement, the sample is always in focus.

Example 6

Automated Analyzer Software Architecture

Overview. This example details a software architecture embodiment that was used to control automated analyzers.

The example used an analyzer control executive that was based on a full featured script implementation. The execution scripts were controlled with a state machine design that used well defined analyzer states of start, homing, initialization, kickoff, pause, and end.

In addition, this example provides a flexible architecture that can be extended via control scripts and additional services. Multi-channel user interface clients can also be added through a command and status interface.

Description. FIG. 9 shows the software block diagram for this example. The major system elements of executive, system services, data management, and user and communications interface are described in the following sections.

Executive. The executive element was responsible to runtime control of the analyzer. This example used a control executive written in Java. This element managed the execution of individual control routines which provided a sequence of commands to the system. The control routines were written in the Groovy scripting language. This system was efficient since the Groovy code was compiled into Java byte code when loaded and ran in the same Java virtual machine as the executive.

The executive's script manager shown in FIG. 9 was responsible for loading and executing scripts. To support parallel control activities, a script could have one or more script processes, each of which ran in a separate thread. The scripts controlled the analyzer by issuing commands to the system services. System services also provided script support functions such as delay services and script process synchronization. In addition to accessing system services, the scripts had access to various memory contexts including sample data, lot data, and global data.

To manage script execution, the executive used a state machine architecture as shown in FIG. 41. The operation of the state machine is described in the following paragraphs.

The homing state was the first state that was run after startup. The executive ran the homing script during this state. This performed one time initialization activities such as homing the system motors so that the motor controller positions correspond to actual positions. When the homing script was complete, the executive moved to the initialization state.

The initialization script was run in the initialization state. This performed general setup functions such as moving motor stages into their start positions. In addition, the implementation of certain diagnostic features used the initialization script to perform a series of diagnostic commands. When the initialization script was complete the executive moved to the kickoff state.

During the kickoff state the executive repeatedly ran the kickoff script which checked for startup conditions. For example, the kickoff script could check the input sensor and the incubator queue to see if an input sample had been added to the system or if a sample container was ready to come out of the incubator. When the proper conditions were found, the kickoff script signaled the executive which moved to the run state.

The run state provided a cyclic processing capability. It invoked the run script at a fixed interval that was based on system configuration. In typical applications, the run script provided control of the main processing elements. The executive remained in the run state until a pause or stop command was received form the command and status interface. On a pause command executive moved to the pause state. On the stop command it executed a shutdown sequence and terminated the system.

The pause state was used to support diagnostics and software development. As shown in FIG. 41, the pause state was entered from the run state when a pause command was received from the command and status interface. When paused, the system did not run any scripts. However, system data could be accessed through the command and status interface.

In addition, new scripts could be loaded or existing scripts modified. The pause state was exited when a continue command was received. If there were active samples that require processing, the executive moved to the run state. Otherwise it moved to the initialization state.

In addition to the current state, the executive tracked the status of all samples that are in process using the sample manager. The lot manager was used to track information on active sample lots. Each lot contains test type, processing, expiration and calibration information for all samples in the lot. Lot data was linked to a sample by the lot identification that was encoded in the sample barcode.

When there was a change to the status of the executive state, the sample manager, or the log manager, the executive saved the current status in non-volatile memory. This information was used at startup to reestablish current system operation after a power failure or other system error.

System services. There were a set of system services that correspond to major hardware elements in the system. These provided a simple interface that the script could use to control the hardware. An extensible architecture made it easy to introduce additional services.

Data management. Data management was provided by the sample manager and the lot manager (FIG. 9). To support configuration and status user interfaces, these systems were accessed through the command and status communications interface.

User and communications interface. As shown in FIG. 9, user interface clients communicate through the command and status interface. This interface supported connections from a remote computers. The system could support multiple clients.

Conclusion. This example shows reduction to practice of a control system that supports an automatic analyzer. It is extensible, flexible, robust, and supports rapid development of additional analyzer functionality.

Alternative embodiments. FIG. 76 shows an extended architecture that incorporates several user interface and data management systems. There are a number of user and system interface clients. The front panel is used to control the system and report results. The printer provides another form off system output. The transfer station is one or more client interfaces that allow entry or scanning of lot card information. The transfer station also provides a mechanism to enter or scan institutional identifiers and associated sample identifiers. The HIS/LIS interface is used to report results to the institutions information management system. In addition to management of runtime data provided by the sample manager and the lot manager, there is a data storage and analysis element as shown in FIG. 9. This element stores data for processed samples and lot information that has been scanned into the system. It uses the command and status interface to receive sample results and to initialize and inform the lot manager of changes in the lot card database. User and external system interfaces can also access the data storage and analysis element. Implementation options for this element include relational and flat file databases.

The architecture of this example facilitates the integration of services to provide additional functionality. These could include the support of a new system hardware element and the addition of a new software service such as a redundancy interface to an external computer.

The architecture is also structured to easily support user interface extensions. This could include support for a new scanner and an interactive voice response interface with voice recognition.

In addition to the Groovy scripting language, the system can run scripts written in any Java-JSR 223 supported scripting language. These include JavaScript, Ruby, Python, and over 20 other scripting languages.

In an alternate embodiment, there could be an additional stopping state the runs a stopping script to provide fixable control of the termination sequence.

Example 7

Automated Single Sample Analyzer with Integrated Selection Module

Overview. The automated single sample analyzer described in this example accepts a sample container, which is a proprietary cartridge, accommodates assay formats using various methods for specific capture of targets, and incorporates means for imaging captured targets. This embodiment is ideal for clinical point of care testing. In addition, it can be used for food manufacturing and veterinary applications.

This example uses a proprietary cartridge to process one sample at a time. The cartridge contains the reagents required to run a single assay or a series of parallel assays, and automatically initiates the assay when the sample is added.

The cartridge is inserted into the analyzer and the sample is added to a sample well of the cartridge. The analyzer then automatically performs all required assay processing steps to produce a result that is displayed and printed. These steps include the following functions: start of reaction detection, assay timing, magnetic selection, image acquisition, image analysis, and results reporting. From the standpoint of the user, operation is very simple: insert the cartridge into the analyzer and introduce the sample to the cartridge. All other operations are carried out by the analyzer. The user removes the cartridge after testing is complete, and disposes of it.

The system supports multiple the performance of an array of assays in a single cartridge.

Description. This example is an embodiment that uses self-contained cartridges to automatically process a single sample at a time. Once the container is inserted into the analyzer and the sample is added to the container, the analyzer automatically performs all required assay steps to produce a result that is displayed and printed. The user reads the result on the display, receives a printed copy from the integrated printer, and can send the results to the Hospital Information System.

This embodiment can be used ideal for clinical point of care testing, where low throughput on demand testing is desired. In addition, it can be used for food manufacturing and veterinary applications.

FIG. 10 shows an embodiment that is intended for a point of care application. The analyzer shown interacts with one cartridge at a time for a variety of applications based on the design of the cartridge that is used. One sample can be used to run a single test in the cartridge, or the cartridge can split the sample and a panel of tests can be run in parallel.

Sample input. The user first places a new cartridge on the analyzer shown in FIG. 10. Next, the test sample is added to the cartridge as shown in FIG. 11. The system detects when adequate sample volume has been added by using an optical sensor (OMRON, E3T-SR21R2M) that detects a change in a special well and uses this signal to start timing the reaction (FIG. 10). Once the presence of input sample is detected, the system waits for the reaction to occur within the container. The wait time is based on the type of test that is encoded in the barcode.

Handling Reagents and Other Liquids. Because the reagents are internal to the input container, reagent and liquid handling happens inside the container. No other reagents are required.

Processing Container Motion. Containers are added manually to the system, processed one at a time, and manually removed from the analyzer. Once in the analyzer, the cartridge remains stationary throughout the processing cycle. In FIG. 12, after the assay incubation is complete, the analyzer uses linear actuators (Firgelli, L12-50-100-12-1) to move magnets (NdFeB magnets 22×22×100 mm, AllStar Magnets) into position below the cartridge to perform magnetic selection of the reaction. The process of magnetic selection is described below.

Managing Sample Input Information. The embodiment was designed for a point of care application where the sample is collected and added to the system in direct sequence. Tests are processed one at a time using a new cartridge for each test. When each test is complete, the results for the current patient are printed on a thermal printer (Seiko, DPU-30) and displayed on a liquid crystal display (LCD monitor, AEI, ALCDP7WVGATS) in FIG. 13. The user then manually updates the written or electronic patient record with the new results.

Each cartridge is labeled with a 1D barcode that encodes the container's test type. This is read by the system processor using a barcode reader (Bar Code Scanner, Miniscan, MS1207FZY) shown in FIG. 12. The system processor (AMPRO, RB800) performs its analysis process based on the test type scanned. The barcode also encodes the container ID and lot number.

This embodiment allows for patient information to be entered using the front panel or scanned directly from a test identifier barcode using a hand held barcode reader.

The embodiment also supports an alternate approach for sample—patient association. This alternate approach integrates the embodiment directly with the hospital information system (HIS) via a standard network interface (IP connection over 10 or 100 baseT Ethernet). In this case, the user enters the institution test identifier into the embodiment and this information is stored by the system processor.

To insure that the user has entered the test identifier correctly, the system queries the HIS for the patient identifier and displays this information to the user. The user checks that this identifier matches the patient.

When the test is complete and the information is fully entered, the system processor communicates to the institution's hospital information system (HIS) to report the test results When a new cartridge is inserted to the analyzer, the previous test ID information is cleared and new identification data for the new test can be entered.

Barcode information along with the test results and any institution test ID are archived in the system and can be retrieved by the user using the front panel and printer.

Selection. The embodiment uses magnetic selection. This is achieved by moving a magnetic assembly (NdFeB magnets 22×22×100 mm, AllStar Magnets) into position under the cartridge using a solenoid as shown in FIG. 12. The system then waits for a magnetic selection time that is based on the type of test. Once selection is complete, the magnets are moved into their disengaged position using the solenoid.

Imaging. Once the magnets are retracted, imaging begins. Imaging components are in FIG. 12. The imaging subsystem was designed to work with fluorescent assay labels that are excited with blue light at 475 nanometer wavelength and emit green light at 535 nanometer wavelength (example 1). The lighting components, detection optics, and camera are all positioned under the cartridge where they can image the detection surface of the cartridge. The system uses a 5 mega pixel CMOS (Camera, Mightex, BCN-B013) camera that produces an 8 bit monochrome image.

A series of 10 frames are taken and summed to produce a single 16 bit monochrome image for analysis. This process increases the measurement dynamic range by a factor of 10 over a single image.

Lighting is achieved using 2 light emitting diodes (LED) (Luxeon Emitter 3 W LED-Blue, Lumileds, LXHL-PB09) that produce light in the blue spectrum. Each LED is paired with an emission filter (Filter-20 mmD, Chroma, Z475/49X) that passes light at 475 nanometer wavelength.

In FIG. 10, the imaging subsystem detects the presence of fluorescent material through a set of transparent windows in the bottom of the input container. The fluorescent signal passes through an emission filter tuned to a 535 nanometer wavelength. It is focused by a non magnifying lens (Relay Lens, Edmund Scientific, 45-760) onto the camera detector.

This example embodiment was designed to use a single image to collect data on a set of up to 25 sub assays depending on the type of container. The use of an inexpensive high resolution camera is designed to resolve individual signaling moieties. With an array of 25 sub assays, there are about 40,000 pixels in each sub assay.

The container is held in the input slot at the correct position to insure proper focus. The total manufacturing tolerances of the container and the analyzer's container holder are less then plus or minus 150 microns. This tolerance is within the depth of focus of the imaging system. In addition, the container has a set of fiducial marks that are optically visible. These are used to verify focus, correct container placement, and confirm absence of debris that would interfere with image acquisition. If the fiducials are not detected as expected, the user is informed to re-initiate the test with another container.

Results reporting. Results are reported on the liquid crystal display and the printer as in FIG. 13, and can also be reported automatically using a direct connection to a hospital information system. See the "Managing Sample Input Information" section above.

Post processing. Once the test is complete and the results are shown, the user removes the cartridge. When the previous cartridge has been removed, the system is ready for the next test.

System Control. As in FIG. 12, the example embodiment was developed to use an embedded computer to perform all system control and processing. This single circuit board contains an Intel Atom micro-processor along with motor controllers, display controllers, 10/100 base T network interface, and other required interface circuitry.

Conclusion. This example demonstrates an embodiment of the invention that uses a cartridge design to automatically process a single sample and report an array of up to twenty-five test results. The testing process includes a timed incubation of the reaction within the cartridge, magnetic selection of the reaction array, and imaging of the capture results using a CMOS camera and LEDs for illumination. Assay results are linked to the patient information using the barcode scanner attached to the container. The analyzer will output results on the display, print a copy from the integrated printer, and send results to the Hospital Information System.

Alternative Embodiments. A modification of this embodiment would allow the addition of a sample queue, so that multiple cartridges could be processed without further user input. This would require addition of cartridge handling capacity for moving cartridges into position on the analyzer, as well as modification of the cartridge-analyzer interface to permit an instrumented start of the reaction on the cartridge.

Example 8

Automated Analyzer Capable of High Throughput Analysis

Overview. The high throughput automated benchtop analyzer described in this example accepted microtiter plates (96 and 384 well configuration) as sample containers, includes an associated magnetic selection module for depositing moieties on the detection surface. It incorporated a CCD camera for imaging targets and had custom software and hardware for focusing, image analysis, and results reporting. The flexibility and features of this device provide powerful but cost-effective analysis for high throughput applications. The device can be used for drug screening and in scientific, clinical, environmental and manufacturing quality laboratories.

Description. Assay preparation and assembly in the microtiter plates was done externally to the analyzer with manual liquid handling steps. The exact steps involved depend on the assay being performed, but typically followed the procedure below.

An assay standard was diluted to a set of specific concentrations (assay dependent). Three measured aliquots of each standard concentration and test sample were pipetted into a set of mixing containers, one aliquot per container. Equal volumes of one of the following was added to each aliquot and mixed thoroughly. There were three tests that included a reagent that will give a positive assay result (positive control), a reagent that inhibits the assay (negative control), buffer diluent (experimental result).

The assay mixture was then incubated at room temperature for a specific amount of time (assay dependent). While the incubation occurred, a dye cushion was pipetted into the microtiter wells used for imaging. When the reaction was completed, the reaction mixture was pipetted on top the dye cushion.

The microtiter plate was then placed on top of the magnetic capture assembly at room temperature for target deposition for five minutes. When magnetic capture was complete, the microtiter plate was inserted into the analyzer for imaging. The image set generated was then analyzed to determine the results of the assays.

When the image analysis was complete, the microtiter plate was removed from the analyzer and placed into a biohazard waste container.

Sample input. The analyzer was built with a flexible sample container nest that accepted microtiter plates of either 96 well or 384 well configuration (FIG. 14). The analyzer accepted one microtiter plate, but multiple assays were placed into a single plate. This allowed the analyzer to analyze any number of assay reactions up to the plate's capacity.

Handling reagents and other liquids. Liquid handling, including assembly of the assay, were performed off the analyzer. The steps followed the procedure below.

An assay standard was diluted to a set of specific concentrations (assay dependent). Three measured aliquots of each standard concentration and test sample were pipetted into a set of mixing container, one aliquot per container. Equal volumes of one of the following was added to each aliquot and mixed thoroughly: a reagent that will give a positive assay result (positive control), a reagent that inhibits the assay (negative control), buffer diluent (experimental result).

The assay mixture was then incubated at room temperature for fifteen minutes. While the incubation occurred, a dyed density cushion was pipetted into the microtiter wells used for imaging. When the reaction was completed, the reaction mixture was pipetted on top the dye cushion.

The microtiter plate was then placed on top of the magnetic capture assembly at room temperature for moiety separation for five minutes. When magnetic capture was complete, the microtiter plate was inserted into the analyzer for imaging. The image set generated was then analyzed to determine the results of the assays.

When the image analysis was complete, the microtiter plate was removed from the analyzer and placed into a biohazard waste container.

Processing container motion. Motion in the analyzer was accomplished by two motorized stages (FIG. 14). Movement in the X (forward and backward) and Y (left and right) axis used accomplished using a two-directional motorized stage (Prior H138A) and was used to position the sample for imaging. Movement in the Z axis (up and down) was accomplished by a single motorized stage (Micos MT-40) and was used for image focusing. The X-Y stage has a resolution of 0.2 microns in both axes. The Z stage has a 0.5 micron movement resolution. All movement was done manually or using premeasured movements (for the X-Y stage only).

Managing sample input information. Sample information, assay information, and position in the container were recorded by the user in a laboratory notebook. Analysis results were linked to the sample information by labeling the images with the container position where the image was taken, along with the image set name the user input into the analyzer (FIG. 52). This is described in detail in the System control section below.

Selection. The target analyte was selected by magnetic capture using neodymium (NdFeB) magnets (22×22×100 mm AllStar Magnets—see Example 2 Magnetics). An associated magnetic selection module was used to deposit labeled target on the detection surface (FIG. 3).

Imaging. The imaging subsystem was designed to detect fluorescent signaling moieties (~475 nm excitation/~535 nm emission). See Example 1 for details on imaging.

The imaging subsystem was built with a CCD camera (Sony XCD SX-910) that produced an 8 bit grayscale image. Four Luxeon Emitter 3 W Blue LEDs (Lumiled LXHL-PB09) were used to illuminate the imaging area. A distance sensor (Keyence LK-G37) was used for imaging focus adjustment. The system was built with the lighting components, detection optics, and camera positioned under the container (FIG. 14).

The image capture software used was programmed with two modes. Interactive viewing mode (also called Live mode) was designed to capture a continuous stream of images from the camera. A button in the software interface was programmed to save a single image from the stream when pressed (FIG. 50).

Automatic image collection mode was programmed such that a target well containing an assay needed to be focused first. The program then requested the well positions to be imaged, starting with the target well (FIG. 54). Once the wells were selected, the software controlled the analyzer to move the microtiter plate over the Keyence where each selected well's distance was measured. Using the focused well's distance as a reference, the program calculated the focus correction factor for each well to be imaged. Once all the correction factors are found, the program moved the plate over the camera and imaged each well, after adjusting the Z axis for each well. The software was programmed to save each image as an individual file using the well position, image set name, current date, and current time as the file name (FIG. 52).

Once the images had been acquired, the images were analyzed by custom automated software developed in house (Example 3).

Results reporting. The automated analysis software was programmed to display the results of a single image analysis on the computer screen (FIG. 74). The program also designed to analyze a directory of images and export the result to an excel spreadsheet or csv file (FIG. 19). The results were reported according to the position the image was taken. These image results were then mapped to the actual sample information.

System control. The analyzer was built such that components connected directly to the PC or were connected via a controller board. Components connected directly to the computer include: a motor controller board (Galil DMC-2134) connected through an RS232 serial port, the distance sensor (Keyence, LK-G37) connected via an RS232 serial port, and the CCD camera (Sony XCD SX-910) connected via a firewire connection (IEEE1394).

Components connected to the motor controller board include: the X and Y motorized stage (Prior H138A), the Z stage motor (Micos MT-40), and the four Luxeon Emitter 3 W LED-Blue (Lumileds, LXHL-PB09).

The analyzer's control program custom software was written in LabView (National Instruments). Device drivers required by the control program were provided by the device manufacturers.

The software worked by homing the motors upon program start up. The motors were homed by moving backwards until they reach a home or limit switch. At that point, the motor position was set as the origin. The program was designed to allow the origin point to be reset to any point by adjusting the program parameters in the user interface (FIG. 53). Once started, the program presented the user with four tabbed interfaces as shown in FIGS. 50-53.

The first tab, controlled the Live mode operation. It allowed the user to manually position the container over the camera at any point (FIG. 50). This tab was used for initial focusing before initiating Auto capture mode as well as manual image capture.

The third tab, shown in FIG. 52, controlled Auto capture mode. The directory where the images were to be stored was entered in the uppermost text box. An identification tag for the set of images was entered in the box below. The program was built to create a subdirectory in the selected directory with this tag name plus the date and time. The image set name was also used as part of the image filename that will be saved.

The 'Select Wells' button was programmed to bring up a popup window with a graphical representation of the microtiter plate to be imaged as shown in FIG. 54. On the popup window, the user selected the wells to be imaged, starting with the focus control well. Once the wells were selected, the user closed the popup window to initiate Auto capture. The analyzer then performed the image capture as described above and saved the files with the user designated prefix plus the well position, date and time added to the file name.

The fourth tab, called 'Setup', was designed to allow the user to change where the origin of the stage will be by entering the X, Y, and Z offsets in motor steps. The user was also allowed to change the number of steps required to move from one well position (called 'tile' in the program) as well as which type of plate is being used.

Conclusion. As shown above, this benchtop analyzer can automatically analyze multiple samples in microtiter plates to detect individual labeled target complexes deposited by magnetic selection. Using the imager assembly, comprised of the CCD camera and LEDs, the deposited fluorescent materials are automatically focused, imaged at low magnification, and analyzed to produce quantifiable results. This analyzer can be useful for high throughput drug screening and in scientific, clinical, environmental and manufacturing quality laboratories.

Alternative embodiments There are a number of variations available for this analyzer. The adaptor nest can accept various types of sample containers including 96- and 384-well plates and microscope slides.

Alternative embodiments can use different spectral regimes by using different optical filters and LEDs to alter the wavelength used for analyte detection. This would allow for multiple analyte detection in a single assay. See Example 5 for a detailed description of how this can be accomplished.

The device has an on-board magnetic selection module that provides imaging while the sample container is positioned for magnetic selection (FIG. 4). Alternatively, the associated magnetic station (FIG. 3) used in the embodiment above could be integrated into the analyzer as a station to which the sample container could be moved by the motorized stages. Other methods for capture could also be used in the context of an analyzer similar to the one described above.

For image capture, an alternate version of focusing involves finding the slope of the plane of the container. This is accomplished by using the distance sensor to measure three distant points on the bottom of the container. From these measurements, the slope of the plane is calculated. As with the current focus method, this method requires a target well to be focused first, but this method uses the slope to correct the focus distance. This version has been reduced to practice as shown in FIG. 53.

Example 9

Automated Analyzer with on-Demand Sample Input Using Robotic Gantry Motion Mechanism Overview. In this example the sample container (FIG. 17) interacts with an automated analyzer (FIG. 16) to process an assay and image targets, if present, in a sample. The analyzer incorporates a CMOS camera for imaging targets and has custom software and hardware for sample container conveyance, incubation, focusing, image analysis, and results reporting. The analyzer has a throughput of up to 40 samples per hour, which is useful in high volume clinical laboratory testing applications. It could also be used in food processing and veterinary testing applications.

Description. The sample container was prepared by pipetting an eluted nasal swab sample into the sample well (FIG. 17). The cap was then closed and inserted into the analyzer input queue as a single sample container for automatic processing. When the sample container was placed in the conveyor belt queue, a sensor was tripped. This signaled the analyzer to move the conveyor belt with the sample container on it. The gantry robot system carried the sample container from the conveyor belt through each station required for processing. Processing stations included barcode reading, initiation of growth, fixed temperature incubation, initiation of assay reaction, reaction incubation at ambient temperature, magnetic selection, and imaging of the magnetically selected reaction. Once the analyzer finished analyzing the sample, results were displayed on the LCD screen, printed on the printer, and sent to the LIS via network connection. The sample container was automatically disposed of in the integrated biohazard waste sample container. The processing of the sample container is explained in detail in the sections below.

The analyzer was designed and built with two queues to accept stacks of sample containers (FIGS. 15 and 16). The queue was designed to accept a stack between one and eight sample containers. When a stack was placed in either input queue opening, a photoelectric sensor (Omron photoelectric retro-reflective sensor E3T-SR21) was triggered and signaled the control software to activate a stepper motor (Arcus DMAX-KDRV-23) to move the stack into the analyzer for processing.

When a stack was ready to be processed in either queue, the analyzer processed the top sample container in the stack first. The top of the stack was found with a photoelectric sensor (Omron photoelectric retro-reflective sensor E3T-SR21) mounted to the gantry robot (FIG. 15). The robot scanned each queue with the sensor starting at the maximum stack height and moved down until a sample container triggered the sensor. Once found, the gantry robot removed the top sample container.

Movement of the sample container in the system was accomplished by three motor systems (FIGS. 15 and 16). These systems were called the input system, the main gantry system, and the imager gantry system. Each system is described in detail below. The systems were capable of operating independently, and occasionally required synchronization for specific operations.

The input system consisted of a single conveyor belt powered by a stepper motor (Arcus DMAX-KDRV-23) as mentioned above (FIGS. 15 and 16). The belt moved the sample container from the initial entry point to the space designated for gantry robot pickup. When a previous sample container was already in the pickup position, a new sample container moved with the belt until it contacted the sample container ahead of it. At that point, the belt slid under the sample containers that were queued in the pickup position.

Three stepper motors (Arcus DMAX-KDRV-17) were present in the gantry system (FIG. 15). Each motor was connected to linear stage (Automation Solutions, DL20DW-XZ) of a different length. The longest stage controlled the gantry Y (left and right) directions. This stage was anchored to the base plate. Attached to Y stage platform was the shortest stage which controlled the gantry X (forward and backward) directions. Attached to the X stage platform was the stage used to control the gantry Z (top and bottom) directions. Attached to the Z stage was a pair of forks. The forks had features that allowed alignment with features (FIG. 17) molded in the sample container. Also attached to the Z stage platform was a photoelectric sensor (Omron photoelectric retro-reflective sensor E3T-SR21). The sensor was used to measure the stack height, as described above.

The gantry picked up the sample container using the forks by adjusting the X and Z stages. Once the sample container was held by the forks, the X stage would move backwards to give clearance to the Y stage. In this position, the Y stage could move the sample container to any station for processing without colliding with structures in the analyzer.

The imager gantry system consisted of two stepper motors (Arcus DMAX-KDRV-17) attached to two linear stages (Automation Solutions, DL20DW-XZ). The longer stage was called the imager X stage. This stage controlled the forward and backward motions of the imager gantry. Attached to the imager X stage was the imager Z stage, which controlled the imager gantry's vertical motion. Attached to the Z stage was a platform that had alignment features on its surface that coincided with similar alignment features on the sample container (FIG. 17).

The imager Z stage differed from the other stages by having a fine pitched screw mechanism. It had a resolution of 5 microns, as opposed to the 50 micron resolution of the other stages on the analyzer. This difference permitted fine focus adjustments as well as fine control of height for initiating the reaction assay. These features are discussed in detail below.

After the sample container was picked up from the input position by the main gantry robot, it was taken to a barcode reader (Microscan MS1). The 1D barcode on the sample container encoded information including lot number, test type, and test parameters. When read, the control program stored the information in a data structure for tracking the sample container and holding the analysis results.

Two types of incubation occurred in this analyzer. They were fixed temperature incubation for sample growth and ambient temperature incubation for the assay reaction. After the sample container barcode was scanned, the initiation of the sample into the growth wells occurred. The main gantry robot moved the sample container to the imager gantry platform (FIG. 15). After the gantry placed the sample container onto the platform, the imager gantry raised the imaging platform until the plunger cap on the sample container (FIG. 17) was pressed by a feature at the top of the imager Z stage. By depressing the plunger, the liquid sample was mobilized from the sample input reservoir to the growth chambers were growth reagents were lyophilized. Next, the sample container was placed in the on-board fixed temperature incubator by the main gantry robot (FIG. 15). The sample containers were incubated at 35° C. for four hours to allow bacterial cell growth.

The incubator consisted of a shelf constructed of custom machined parts (top, bottom, left, right, back, and front sides). The shelf bottom contained features that mated with the feature on the bottom of the sample container (FIG. 17). The incubator walls were constructed using insulation foam which divided the incubator into four chambers. The rear wall of the incubator was shaped to fit four custom machined doors in front of the four chambers. The doors were opened and closed using actuators (Firgelli L12-50-100-12-l). Heating of the incubator used heating strips (OMEGA, SRFG-310/10-P) across the outside top and bottom of the incubator. Heating strips, as well as any exposed outside surface, were covered in insulation foam with the exception of the doors.

Initiation of the assay occurred after growth incubation was completed. The main gantry robot removed the sample container from the growth incubator and moved it to the imager gantry platform (FIGS. 15 and 16). After the gantry placed the sample container onto the platform, the imager gantry initiated the assay by raising the platform until the plunger cap on the sample container (FIG. 17) was completely pressed in by a feature at the top of the imager Z stage. By pressing down on the plunger a second time, the liquid sample was forced to move from the growth chambers into the imaging chambers where the assay reagents were lyophilized. As soon as the liquid entered the imaging chamber, the reagents were rehydrated and the assay reaction began. The imager gantry returned to the pickup position and the main gantry robot moved the sample container to the reaction incubation station. This incubation lasted fifteen minutes and occurred at room temperature.

The reaction incubator consisted of a system of fifteen shelves. The individual shelves had a feature that mated with the feature on the bottom of the sample container for positioning alignment.

After the reaction was complete, selection of the targets occurred by magnetic selection. The main gantry robot moved the sample container from the shelf to the magnet station (FIGS. 3, 15 and 16). Magnetic selection was performed for five minutes before the main gantry moved the sample container to the imaging platform. As shown in FIG.

15, the magnetic capture station consisted of two identical magnet assemblies. The assemblies contained rare earth, solid state type magnets (neodymium-iron-boron N48 NdFeB, 22×22×100 mm bars) as shown on the FIG. 3. This allowed for magnetic selection to occur for two sample containers during overlapping time periods.

After magnetic selection, imaging was performed. The imaging subsystem (FIGS. 1 and 72) was designed to work with fluorescent signaling moieties. The signaling moieties were excited with blue light filtered through a band pass filter centered around a 475 nanometer wavelength. Emission light was collected after filtering the light through a band pass filter centered around a 535 nanometer wavelength. The illumination components, detection optics, and camera were all positioned under the sample container in the imaging assembly (FIG. 15). The imaging subsystem is further detailed in Example 1.

After magnetic capture was complete, the main gantry robot moved the sample container from the magnet station to the imager gantry robot (FIG. 15). The imager gantry robot moved the sample container over a distance sensor (Keyence LK-G37). The distance to each imaging well was measured and the focus distance was calculated. The imager gantry robot positioned above the CMOS camera (Mightex BCN-B013) which acquired an 8 bit grayscale image of each well. Each well was imaged ten times and summed to result in a higher bit grayscale image for analysis.

Image analysis occurred using a custom in-house algorithm described in Example 3. Once the analysis was completed, the imager gantry robot moved the sample container to the ejection system. The sample container was then pushed off the platform and into the biohazard waste container (FIG. 16). Once the data was analyzed, the results, along with the cartridge information, were stored on a computer, printed (Seiko, DPU-30) and displayed on the LCD touchscreen monitor (AEI, ALCDP7WVGATS) (FIG. 16).

The system was designed to be controlled by a single small board computer (Ampro, RB800R) running Ubuntu Linux 2.6. All components were connected to the computer either directly or through controller boards. Components connected directly to the computer included the motor controller (Galil, DMC-2183-DC24-DIN), LCD monitor (AEI, ALCDP7WVGATS), CMOS camera (Mightex, BCN-B013), distance sensor (Keyence LK-G37), and printer (Seiko, DPU-30). The components connected through the motor controller included photoelectric sensors (Omron, E3T-SL22), stepper motors for the main gantry and imager gantry (Arcus, DMAX-KDRV-17), stepper motor for the input bay conveyor (Arcus DMAX-KDRV-23), and LEDs (Lumileds, LXHL-PB09).

Comparison with benchtop assay. An assay was run in the analyzer and compared to a hand prepared assay, run on the benchtop. The procedure follows. A culture of *S. aureus* (ATCC strain 29213) was grown in growth media TSB (Tryptic Soy Broth, Acumedia cat #7164A) at 32.5° C. for 2 hours to achieve log-phase growth ($OD_{600}$=0.3). The *S. aureus* cells were counted in a Petroff-Hausser counter on a Zeiss microscope and cells were diluted to 0, 700, 2100, and 8400 cells per every 35 μL solution in fresh TSB for the assay. A reaction mixture containing 100 μL SYBR® Green I (Invitrogen, Catalog No. S-7563) was diluted 1 part in 2000 parts with 0.9% sodium chloride, 25 μL of 0.005% w/v chicken anti-*S. aureus* protein A magnetic particles (manufactured as described in Example 1 with the following modification: chicken anti-protein A (Meridian OEM cat #C5B01-296 antibody was used) in 10 mM phosphate, 140 mM sodium chloride, 3 mM potassium chloride (Calbiochem cat #524650), 0.05% w/v Tween 20 (Acros cat #2333600010), 2 mg/mL bovine serum albumin (Sigma-Aldrich cat #A3059), 0.05% w/v ProClin 300 (Supelco, Catalog No. 48912-U) pH 7.4 and 125 μL of the *S. aureus* dilutions in TSB described was mixed well by pipetting and incubated for 15 minutes at ambient temperature in the dark. After incubation, the reaction mix was spilt into 6 equal portions, 35 μL of reaction mixture was overlaid on 65 μL of dye-cushion solution 15% v/v OptiPrep® (Sigma Cat. No. D1556) and 2 mg/mL Chromotrope 2R (Sigma-Aldrich C3143) pre-aliquoted in 3 wells in a 96-well half-area diameter clear bottom black plate (Grainer, Cat. No. 675096) and in 3 imaging wells of the device. Cell-particle complexes were deposited on the bottom of all wells by magnetic selection. Wells in a 96 well plate were placed on a bar magnet for 4 minutes. The bar magnet used a configuration of 22×22×100 mm permanent magnets depicted in FIG. 20. The plate was then removed from the magnet and placed in a high throughput automated imaging analyzer (Example 8 and FIG. 14). The wells were imaged on the analyzer at a 0.1 second exposure time. Individual fluorescent cells were then enumerated using software as described above. Wells in the device were placed in an alpha analyzer which automatically moves the cartridge to a magnetic selection station and then to the imaging station. The wells were then imaged at a 0.1 second exposure time. Individual fluorescent cells were enumerated using imaging software (Example 3).

Results. FIG. 6A shows the comparison of fluorescent counts in the *S. aureus* assay as run on the high throughput automated imaging analyzer and alpha analyzer. The results are similar within experimental error. FIG. 6B shows a digital image of individual stained *S. aureus* cells without magnification and comparison to a sample without cells. The results demonstrate that reagents in imaging wells of the device analyzed on the analyzer and by hand yield similar results.

Conclusion. This analyzer can automatically process sample containers with minimal user interaction. The sample container interacts with an analyzer that supports on demand processing, sample growth, non-magnified imaging and integrated waste disposal. It allows for detection of individual targets that have been bound to signaling and selection moieties to be analyzed using a standard CMOS camera at low magnification.

Variations. One variant of analyzer includes a high capacity growth incubator. Such a large incubator would allow the analyzer to process sample containers at least 40 per hour. With its small footprint it would make an ideal high throughput machine for clinical laboratory, food processing and veterinary testing applications.

Example 10

Automated Analyzer with On-Demand Sample Input Using a Cleated Belt Drive Motion Mechanism The automated analyzer described in this example accepts a sample container, uses magnetic selection on a sample container to capture targets, and incorporates a photo detector array for non magnified target imaging. The container design segregates the user liquid input samples from the test type specific reagents. This embodiment fully automates all steps required to produce a test result from each input container and supports multiple test types based on type of container and lot code.

This example supports on-demand sample input using a gravity fed queue. This capability allows the user to add input containers to the analyzer whenever they are ready, up to the queue capacity of 8 containers.

An embedded processor controls the system and data analysis functions. Sample advancement and processing is fully automated from user input to disposal of used containers into integrated biohazard waste container at completion of test.

This embodiment might be used for moderate volume (12 per hour) clinical laboratory testing applications. It can also be in food processing and veterinary testing applications.

Methods. The user pipettes samples from a hospital collection device to the container, closes the lid, seals the container input sample well, and applies an institutional bar code to the container. The user then places the container in a stack with other containers, or a single sample container into the queue (FIGS. 20 and 21). The analyzer processes each container per the sequence below.

Processing container motion. Containers placed in the input queue stack are gravity fed into the analyzer on to a toothed belt. An optical detector (Omron photoelectric convergent-reflective sensor E3T-SL22), set at the belt top level, detects when a container is placed on the belt. The sensor activates the system control software which moves the tractor toothed belt with a stepper motor (Arcus DMAX-KDRV-17). The belt pulls the bottom container forward for the barcode scanner (microscan, MS1 FIS-0001-000XG) to read the attached bar code. From the barcode, the system determines the lot information and container validity. The belt and container are designed with matching registration features so the system control can move the container in a specifically timed, serial sequence through incubation, imaging, and biohazard trash positions (FIG. 21).

Managing input sample information. As the container proceeds to the assay initiation, a barcode scanner (Barcode Scanner, Microscan, MS1 FIS-0001-000XG) reads the attached barcode to determine lot information and container validity.

Handling reagents and other liquids. After reading the barcode, the container proceeds to the subsystem that initiates the assay in the container. An actuator (Firgelli L12-50-100-12-l) engages the screw cap on the container (FIG. 21) and through a screw motion, applies pressure to the sample well to push the liquid sample into the chambers containing the dried reagents. The liquid in the sample rehydrates reagents located inside the sample container and starts the assay reaction.

Incubation. Incubation for sample growth is performed prior to user loading of the containers. Incubation of the assay relies on the timed movement of the conveyor. The conveyor is set to precisely move the container at a rate optimal for the test type is reaction incubation before reaching the selection stage.

Selection. Selection of the target occurs as the belt moves the test container over the magnet assembly. The parallel magnets (NdFeB magnets 22×22×100 mm, AllStar Magnets—see Example 2 Magnetics) perform the selection of tagged target. The time for magnetic selection depends on the belt movement rate. The rate depends on test type.

System control, imaging, results reporting, processing container motion, and managing sample input information are explained in detail in Example 9.

Conclusion. This example shows one design for a device that has on-demand sample processing using magnetic separation methods and non magnified photo array imaging for specific targets.

Alternative embodiments. For a assays requiring growth, the configuration could include an elevated temperature controlled incubator serially feeding incubated containers into the stack queue. Additional signal moieties could be imaged using dual color imaging as described in Example 5. Overall size could be reduced with addition of imaging through magnets as in Example 2.

Example 11

Automated Continuous Sample Container Analyzer with Screw Drive Mechanism

The automated analyzer described in this example accepts a sealed sample container, accommodates assay formats using magnetic methods for specific capture of moieties, and incorporates means for non magnified moiety imaging.

This example supports on-demand sample input. This is a capability that allows the user to add an input sample to the analyzer whenever they are ready.

The functionality of this embodiment is similar to the previous Example 10, but highlights the use of alternate implementations in the following areas:

Methods. The analyzer interfaces with sample containers that contain on-board reagents and fluidics (FIGS. 22 and 23). After sample collection, the user places the sealed sample containers (in stacks of up to 8) in the input (FIG. 22) position closest to the input chute. The sample containers in the input chute proceed through the elements of analysis processing detailed below. Once analysis is complete, the container is deposited in an internal biohazard waste container (FIG. 22).

Sample input. This analyzer accepts containers on demand in singles or stacks (FIGS. 22 and 23). The containers are manually moved towards a chute where they are gravity fed down into the analyzer and queued to await initiation of the assay. The barcode is read at this position by a subsystem as detailed in Example 10.

Handling reagents and other liquids. Initialization of reaction occurs while the container is in the chute (FIG. 22). A separate lead screw pulls the container partially out of the stack. A plunger head on an actuator (Firgelli L12-50-100-12-1) is moved downward, pushing the matching feature on the container and forcing liquid sample into the chamber with reagents. The plunger retracts and the lead screw replaces the container into the stack where it waits to be engaged by the main lead screw (5 micron pitch, custom design). All containers afterward simply drop down one queue position when the main motion screw moves the initialized container toward the magnet.

Incubation. Incubation for sample growth is performed prior to inserting the container into the queue. Once the reaction is started, the container is held in a vertical queue that allows the required processing time. At the bottom, the main motorized lead screw moves the container through the rest of the analyzer.

Processing container motion. Sample containers from the input chute are moved by an elevator platform using an actuator (Firgelli L12-50-100.12-1) (FIG. 23). Containers are moved by motorized lead screws and an actuated platform (FIG. 23).

Post-processing. After imaging, the containers are moved by screw drive to an integrated trash container (FIG. 22).

Conclusion. As with the Example 10, this example demonstrates on-demand sample input of sample containers. It accepts a sample container, accommodates assay formats using a magnetic selective force for specific capture of targets, and incorporates a non magnified optical system and photo detector array for imaging targets.

Alternative embodiments. Multiple test targets could be identified with the addition of a multicolor imaging subassembly, as in Example 5. A growth incubator could be added to allow for sample growth prior to the internal analysis stages. Additionally, a moving belt input could replace the chute, as in Example 9, so that advancement to the input queue would be automatic.

Example 12

Automated Continuous Sample Cartridge Analyzer with a Single Plane Conveyor Drive Mechanism Overview. The automated analyzer described in this example uses subsystems for separation, non-magnified image detection in sample containers as described in Example 10. This embodiment automates all steps required to produce a test result from each input container and supports user input of single samples. This example supports serial processing of containers at a rate based on the test type. A test takes 15 minutes to process and the throughput is 4 per hour.

As with Example 10, an embedded processor performs the automation through system control and data analysis functions. Sample advancement and processing is fully automated from user input to disposal of used containers into integrated biohazard waste container.

This embodiment may be used in low volume (4 per hour with attended single container loading) clinical laboratory testing applications. It can also be in food processing and veterinary testing.

Description. The user receives a sample that has been collected and closed inside a sample container with on-board reagents and fluidics. The user places the container in the input area (FIG. 24). The container proceeds through the elements of analysis processing detailed below. Once the analysis is complete, the container is deposited in an internal biohazard container.

Sample input. Containers are input directly on the container processing motion system by placing each into special designed carriers. Carriers have matching tolerance and mechanical registration features with the sample containers for simple placement and user positioning.

When a new container is placed in an empty carrier, it is detected by an optical detector (Omron photoelectric convergent-reflective sensor E3T-SL22). The sensor activates the system control software which activates the stepper motor (Arcus DMAX-KDRV-17 stepper motor) to move the drive cable. The drive cable pulls the attached carriers over a flat surface, advancing the containers through the processing sequence. The system control moves the container via the cable and carrier in a specifically timed, serial sequence through incubation, imaging, and trash positions.

Handling reagents and other liquids. After reading the barcode, the container proceeds to the subsystem that moves liquid (FIG. 24). An actuator (Firgelli L12-50-100-12-l) is mounted above the initiation of target labeling, and another optical sensor (Omron photoelectric convergent-reflective sensor E3T-SL22) senses when the container is in the correct position for initiation of target labeling. When the sensor alerts system control of correct position, the actuator depresses a plunger feature on the container. The plunger mobilizes the liquid sample into imaging wells containing dried reagents. The liquid sample rehydrates the reagents, starting the assay reaction. The actuator then retracts and the container is ready for further processing.

Transfer systems. The container is moved through the system using a stepper motor (Arcus DMAX-KDRV-17 stepper motor) attached to cable. There are also two types of transfer systems. First, a bumper guide is used to transfer cartridges to the imager. This isolates the imaging subassembly and reduces the effects of system vibration. A linear actuator (Firgelli L12-50-100-12-l) moves independently from the main drive, keeping the main system timing deterministic. The linear actuator moves the cartridge from the imager into the trash (FIG. 24).

Managing input sample information. When the container is moved from input to the initiation of the assay (FIG. 24), a barcode reader (Barcode Scanner, Microscan, MS1 FIS-0001-000XG) scans the barcode as the container moves past it. The barcode is used to determine lot information and container validity—see Example 10 managing input sample information Incubation. Incubation for sample growth is performed prior to user loading of the containers. Incubation of the assay relies on the timed movement of the conveyor system. The conveyor is set to precisely move the container at a rate optimal for the test type reaction incubation before reaching the selection stage.

Selection. Selection of the target occurs as the test container is moved over the magnet assembly. The parallel magnets (Example 2 Magnetics) perform the selection of tagged target. The time for magnetic selection is determined by the belt movement rate. This rate is adjusted to the requirements of the test type.

The imaging and results reporting processes are explained in Example 9. After imaging is completed, the container is deposited in the integrated biohazard waste bin (FIG. 24). The now empty carrier returns to the user input position.

Conclusion. This example highlights a low throughput analyzer with a simple motion and transfer system. It performs the key processing functions of sample target selection and non-magnified image detection in sample containers.

Alternative embodiments. Direct input replaced by queuing (such as in Example 11) would allow for an on-demand input model. Combining selection and imaging as co-resident stations, as in Example 2, would provide the benefit of double throughput. Finally, additional targets could be imaged using dual color imaging as described in Example 5.

Example 13

Surge System Software Architecture

Overview. This example details a software architecture embodiment that can be used to control automated analyzers.

In addition to direct control of the analyzer, this embodiment provides features specifically required in the surge testing application. These include a command and control interface to centralized situation command, and a patient management web application.

The example uses an analyzer control executive that is based on a custom script implementation that builds an execution object model from an extensible markup language (XML) script.

The embodiment uses a relational database to store and manage patient and test results data.

Description. The system is implemented to run on a Microsoft Windows compatible operating system. It consists of a set of windows processes that communicate over a Transmission Control Protocol/Internet Protocol (TCP/IP) interface with a custom message set. Standard data base interfaces are used where data base access is required. This design allows the system to be deployed on multiple computers for very large scale applications.

This example's software architecture is diagramed in FIG. 25. An overview of the major software functions of executive, system services, data management, and user and communications interface is provided in the following paragraphs.

Executive. The analyzer control element provides the executive function of controlling the execution of an automated analyzer. It includes an interface to the analyzer console, image analysis, interface to a relational database system, and a TCP/IP interface to a set of service processes.

The executive controls an analyzer that works as an assembly line where reactions travel through stations and processing occurs at each station. The system uses a cycle based strategy where all processing activities on all stations happen within the current cycle. The system then moves to the next cycle, and repeats the cycle processing steps with the new system state. The following is a simplified high level example of the type of processing that can occur during a cycle. Note the progress of each test is tracked; an operation is performed only if it is required by an active test.

Perform the following in parallel
- Carousel and station processing
  - The cycle begins by advancing the carrousel. This moves each reaction to then next processing stage.
  - Next, process station sequences in parallel
    - Reagent station: Move reagents robots to reagent input, pickup appropriate reagents with the correct channel with the liquid handling system, move reagent robot to the set of appropriate mixing cups, deposit reagents
    - Cushion station: Move cushion pipetter into cushion reservoir, aspirate cushion, move to empty imaging cup, dispense cushion.
    - Transfer station: If this is an even cycle, move the transfer robot into completed mixing cups, pickup reaction liquid form two cups and remove the pipetter. If this is an odd cycle, move to imaging cups, deposit liquid into two cups, and raise the pipetter.
    - Sample station: Samples are taken from a new input tube every six cycles and used for 6 tests. If a new sample is needed, move the sample pipetter into the sample tube and aspirate enough liquid for 6 samples. Next, on each cycle, move the sample pipetter into the mixing cup and dispense the sample, and then raise the sample pipetter.
    - Sample cleaning station: The system is designed with two sets of sample pipettes. While one is in use, the other is cleaning. If this is the first of the 6 cleaning cycles, move the unused sample pipetter into the sample pipette cleaning module, start cleaning. If this is the last cleaning cycle, stop cleaning and move the sample pipetter into the ready position.
    - Mixing station: Move the mixing transducer to contact the mixing cup, run transducer, retract the transducer
    - Imaging station: Move the imager assemble to contact the imaging cup, turn on lighting, acquire image, turn off lighting, retract imager assemble, analyze image, and output analysis result to data base.
    - Cup cleaning station: Move cup cleaning assembly into cups, Start cup cleaning fluidics, wait, stop cup cleaning fluidics, retract cup cleaning assembly.
- Bulk reagents are rocked to insure consistency.
- Input sample processing: If this is the last of the six cycle sample sequence, move the input queue to the next sample. If the current input rack is finished, eject the rack and load the next rack.

The executive is driven by a flexible set of scripts that are defined with a custom XML schema. This schema defines three classes of nodes: configuration, organization, and execution. At system startup, the scripts are compiled into an object model where each object corresponds to an execution node in the XML script. These objects are organized in task lists which are ordered lists of tasks that are executed in sequence. Execution is performed by synchronously calling the execute method on each object in turn.

In addition, node execution can also occur in parallel. This is supported by using a thread for each parallel task list.

As the simple example described above shows, the required operation is dependent on the cycle and the state of the system. Support of this is accomplished through the use of an expression language in the script object model.

The expression language supports standard compound arithmetic and logic operations that can access memory contexts associated with:
- The system. This includes current cycle number. This is incremented by the executive each cycle prior to script execution. Script nodes can use the cycle number and the modulus operator as a conditional to control multicycle activity.
- The current test being processed by the node
- The current system cycle
- The current node Each executable node can have a configuration and/or a conditional expression defined as a text string. This is complied at startup and run when the node is executed.

The configuration expression can set zero or more variables in any memory context.

The node is executed only if conditional expression returns true (non zero).

In processing scripts, it may be necessary to synchronize the activities of parallel script processes. For example, bulk reagents should stop rocking when the reagent pipette is moved to and from the aspirate position or the input sample tube should not be moved until the current sample is taken. To accomplish script process synchronization, the embodiment uses a set of specialized script node types that support setting, clearing, and waiting form named conditions. In this way one script process can wait for another to set a condition.

System services. There is a system service corresponding to each major hardware element in the system. These are shown in FIG. 25. Each service is implemented as a separate Windows process. They use a TCP/IP interface with a custom message set to communicate with the executive. This architecture simplifies software maintenance and facilitates addition of new functions. The use of TCP/IP allows services to run on a separate computer.

Data management. The data management subsystem provides patient tracking, remote tasking, and automatic data analysis. It has the following features:

Database stores all relevant sample and system information including analysis results, system configuration, and software version.

Integrated barcode reader tracks samples.

Software can recognize controls and automatically build calibration curves.

Web interface provides local or remote data entry and data analysis

Command & control interface provides remote management, tasking, and maintenance.

User and Communication Interface. This embodiment supports several user and communications interfaces including the following.

Analyzer console. The Analyzer console displays system status and results summary information. It is used to support system configuration, diagnostics, maintenance, and operations.

The console is implemented as an independent operating system process that communicates to the executive with using TCP/IP with a custom message set. This interface is setup as a client/server model where the analyzer control server can support one or more analyzer console clients. This approach provides both integrated console displays that run on the same computer as the executive and consoles running on remote computers.

Command and control interface. The command and control interface provides a connection to external situation control that is managing the overall response to the emergency situation associated with the surge testing. The Command and Control Interface uses the TCP/IP console interface described above to communicate with analyzer control. It also has access to data management system through a standard database interface.

Patient Management Web Application. The Patient Management Web Application is used to collect and manage patient information. This is typically used to enter patient contact and history information as part of the sample collection process. This application communications with the data management system, but does not need to interface with the executive.

Data Analysis Web Application. The Data Analysis Web Application provides various reports that summarize the overall data results. This application communications with the data management system, but does not need to interface with the executive.

Laboratory Information System/Hospital Information System Interface (LIS/HIS) interface. The LIS/HIS interface provides a connection to standard health care systems. It is used to report test results directly to the institutions data management system.

Conclusion. This example shows reduction to practice of a control system that supports an automatic analyzer and is capable managing a surge testing workflow. It is extensible, flexible, robust, and supports rapid development of additional analyzer functionality.

Alternative embodiments. An alternate to using a conditional expression on each node is to have specialized nodes that process expressions. This would include a condition node that evaluates an expression and only invokes its child nodes if the expression is true. It would also include a "set" node that can write to a variable in a memory context.

The architecture of this example facilitates the integration of services to provide additional functionality. These could include: the support of a new system hardware element and the addition of a new software service such as a redundancy interface to an external computer.

The architecture is also structured to easily support user interface extensions. This could include support for a new scanner and an interactive voice response interface with voice recognition.

Example 14

Automated Analyzer for High Throughput Surge Testing with on-Board Liquid Handing Overview. The automated surge analyzer is designed to provide high throughput automated testing for a single test panel run on a large series of specimens. It is designed to accommodate the requirements for testing in a biodefense or public health emergency where many thousands of people may have been exposed to a single pathogen or other agent. This type of scenario requires extremely high throughput, and simple analyzer setup and operation at peak capacity for an extended period of time.

The analyzer is self-contained, portable and rugged since the environment of operation varies from a hospital emergency room to an impromptu established field hospital. The device may be used outside in a field, parking lot, or high school gymnasium, for example.

The automated surge testing analyzer accepts a queue of specimen containers, logging each specimen as it is processed. The analyzer assembles test reactions in a serial fashion by transferring the sample and a series of onboard reagents into a mixing cup, incubates the test reaction and then transfers the test reaction into an imaging cuvette. The imaging cuvette containing the test reaction is held over a magnet to apply selective force to the reaction, depositing signal into a detection zone, and then an unmagnified digital image of the detection zone is captured with a CCD camera. Onboard image analysis provides a readout of the level of target(s) in each specimen.

The need for a high throughput, cost-effective, ultra-sensitive test for molecular targets results in a need for low trash generation by the platform. Minimizing the volume of solid consumable waste decreases the volume of biohazardous waste streams and the overall cost to the consumer. Trash is reduced by recycling and reusing components, including the mixing (also called reaction cups) and imaging cups and pipette tips. These components are thoroughly cleaned between samples to ensure low carryover and cross-contamination of samples and reagents. Trash streams are also minimized by decreasing sample contact, such as utilizing non-contact mixing and non-contact reagent dispensing. Since these components never contact the sample, they can be reused indefinitely without need for cleaning or replacement. Surface treatments and materials are also selected to minimize sample and reagent carryover. For example, custom manufactured pipette tips (Cadence Science) were coated in Teflon® and syringe line tubing was polytetrafluoroethylene (PTFE) tubing which has one of the lowest coefficients of friction of any plastic. Internal liquid handling of bulk reagents is used for a very low per test cost.

Low sample volume is important for minimizing reagent consumption, increasing patient throughput, and where patients may include infants, elderly, or other low sample-yielding persons. Collection of a small sample volume that also minimizes or eliminates the need for sample preparation is beneficial in a potentially disorganized and chaotic environment where a large number of patients need rapid screening.

The analyzer manages patient information in a secure manner and wirelessly communicates between hospital database systems, central command, and the vendor for diagnostic and bulk reagent resupply. Maintenance and service requirements are minimized to a regular routine in which the device is operational with short set-up time and can run continuously for several days.

Description. The device (FIG. 48) accepted and processed samples in a manner similar to an assembly line system. A lock stepped cycle carousel mobilized sample processing in a specific sequence, in which one or more sample processing steps occurred at each carousel location. The carousel motion system (FIG. 45) had receptacles for 100 pairs of mixing and imaging cups (FIG. 31). The carousel advanced one position at the start of each cycle using a stepper motor (Oriental Motor Co., DG130R-ASAA). Subsystems access one or multiple cups during each cycle (FIG. 33). The system used a six second cycle time.

Cups rotate counter clockwise one step per cycle where samples were assayed in a specific sequence of processing steps. First, the reagent subsystem deposited a diluent into the mixing cup. Next, a pipettor (FIG. 49) metered sample out of the sample container and into the mixing cup. Final reagents including signaling and selection moieties were added and the combination was mixed. Cushion was dispensed into the imaging cup and the mixed sample was incubated with reagents for five minutes. The reacted sample was carefully transferred from the mixing cup to imaging cup so that it remained floating on top of cushion. A one minute magnetic selection deposited any magnetic selection moieties onto the bottom surface where it was then imaged. After the assay was complete, both mixing and imaging cups were thoroughly cleaned and prepared for reuse. Waste liquids were sent to on-board biohazardous satellite storage tanks.

Sample input. The first step in assaying a sample included the user collecting a sample, inserting it onto the device, and the device automatically sensing and metering the sample into a reaction cup. The user collected a sample in a sample container, as illustrated in FIG. 31. Sample containers were added to racks in sets of up to 6 as shown in FIG. 32. Racks were placed into a gravity-fed queuing system (FIG. 44). Up to 16 racks, or 96 sample containers, were queued at one time in the device.

The gravity-fed queuing system included several functional subcomponents. Photoelectric sensors (Omron, E3T-FT12) detected the addition of new racks as well as monitored the position of other racks in the queue. The racks were advanced by a double-sided drive belt (Stock Drive Products, A6B3-D188025) with timing belt pulley (Stock Drive Products, A6A3-12NF03706) driven by a stepper motor with a closed loop amplifier, (Oriental Motor Co., AS46AA) and then by linear dual actuators (Firgelli, L12-50-100-12-1). A barcode reader scanned sample information from the sample container and transmitted the information to the on-board computer for assay tracking.

Racks were added to gravity feed queue as shown in FIG. 44. Racks were added by placing one rack on top of the next in the vertical queue. If no racks were present, the rack was moved to the bottom most position. The system supported stat processing of racks placed in the right side of the horizontal queue. These racks were always processed prior to racks from the vertical queue.

Input queue movement details. The sample container input queue movement occurred in a series of steps. First, the optical sensor detected a rack and lowered it with the dual actuators. The belt teeth engaged with features on the bottom of the in-process rack and the belt was moved to left till the first actuator was clear. An optical sensor determined when the in-process rack was clear of the first actuator. Other racks in the queue were held by the rack that dropped. The first actuator was then raised to hold the next rack in the queue and the belt was moved until the in-process rack was clear of the second actuator. The second actuator was then raised to hold the above rack queue. The in-process rack moved to left until the first sample container was aligned with the sample input position. An optical sensor was used to determine the precise location of the in-process rack and sample containers held within. As the system was ready for subsequent sample containers, the belt was moved until the next sample container was at the sample input position. After all sample containers in a rack were processed, the in-process rack was moved into the sample container biohazard trash. The process was repeated with the next rack until all that were loaded had been processed.

The final components of the sample input subsystem include a pair of rotary sample pipettes. FIG. 58 illustrates a top view of the system in which two sample pipettors access the sample containers. In this configuration, one pipette was cleaned in the cleaning station (FIG. 49) while the other metered sample into reaction cups. After each sample dispense, the pipettes switched tasks so that the pipette that had just dispensed sample would be cleaned and the freshly cleaned pipette would process the next sample.

Six tests were performed on each sample. The experiment below details an instance. The sample pipette aspirated a sample volume for all six tests at the same time. In each cycle, the sample pipette dispenses ten micro liters of sample into the current input mixing cup. After the six dispenses, the next sample tube in the input rack was moved into position as described in input queue movement detail above and processed in a similar manner.

Liquid handling. There were a number of liquid handling functions on the system. These included input pipetting, reagent pipetting, cushion pipetting, and sample transfer pipetting, cup cleaning, and mixing. FIG. 64 shows the liquid handling component diagram. Components of the liquid handling system included single syringe pumps for the sample, cushion, and transfer stations (Tecan part number 20738291 here), two multi-syringe pumps (XMP 6008 8-channel digital syringe pump, Tecan, 20737367) to deliver all twelve reagents, rotary valves (XLP 3-port, Tecan, 20738291), passive check valves, PTFE tubing (Upchurch Scientific) for reagents and carrier fluids and Tygon® formulation R-3603 tubing for other tubings, such as cleaning and waste. Other pumps included in this analyzer included 8 Mini-Wash diaphragm pumps (MiniWash full panel, Tecan, 20739017) for cleaning and washing with clean water and 10 diaphragm pumps (KNF Neuberger, NF5RPDC B-4) that were compatible with specific concentrations of NaOH, bleach, detergents used for cleaning and biohazardous decontamination.

A syringe system was used for each of the pipetting stations. Each syringe system was associated with a motion system where first the pipette was moved to the source container. Liquid was aspirated and then pipette was moved into the destination container where the liquid was dispensed. Syringe pumps (listed above) were used to move liquid for each pipetting station, and each syringe pump had an integrated valve that could select one of three positions.

The operation of the valve allows for one of three pumping actions. One position opened the line between the pump and pipette tip, which allowed the pump to aspirate and dispense liquids or air bubbles. Another position opened the line between the pump and the system fluid, which allowed priming of the pump by aspirating from system fluid and dispensing to the pipette tip which was positioned over a cleaning station. This setting also was used to disable aspiration and dispensing while the pump is moved. For example, this allowed individual channel control in gang pipettors that moved all channel pumps at the same time. The third position opened the line between the system fluid and the pipette tip. This setting was used for cleaning the pipettors and priming the lines. The system fluid side of the syringe pump had the option to be also driven with a diaphragm pump through the valving system. This was used for priming lines and cleaning pipette tips.

Pipette cleaning was important to minimizing carryover and cross-contamination. Pipette cleaning was performed by first moving the pipette tip to a cleaning station where the system liquid was flushed through it. Waste liquid was removed from the fixture with a diaphragm pump and sent to an on-board satellite waste storage container. The sample and transfer stations used an additional pump connected to the cleaning station that flushed system fluid external to the pipette tip to thoroughly wash the outside of the tip in addition to the inside.

There were several liquid handling stations included in the analyzer. FIG. 49 shows the sample pipettes from the front two sample pipette assemblies. These assemblies include pipette tips, tubing to syringe pump system, rotary motors, vertical motors, sample pipette cleaning stations, and mixing cups that received the sample aliquots.

The system used one sample pipettor to move the in-process sample from the in-process sample container to the six mixing cups as explained in the sample input section above. While one pipettor transferred sample, the other washed. They switched functions with every new sample. Works by first aspirating enough volume for each sample and then dispensing into a new mixing cup each cycle.

The reagent pipetting unit used is shown in FIG. 45. The twelve-channel system transferred liquid from reagent containers (FIG. 55) to mixing cups. It was moved by vertical and horizontal motor stages (FIG. 58) and liquid was mobilized by two multi-syringe pumps (see detail above). During each cycle, each reagent channel was able to dispense into the mixing cup that was in the channel's position. During each cycle, software controlled the syringe pump valves so that only the required reagents were aspirated from reagent containers and dispensed into the mixing cups.

The cushion dispensing unit was an additional channel on the reagent assembly (FIG. 45). The system used a dye cushion that was positioned under the reaction prior to the selection step. Selection pulled targets labeled with selection and signaling moieties through the cushion. This reduced imaging background by keeping free signaling moieties out of view of the imaging system. The cushion dispensing unit was driven by a syringe pump that dispensed cushion reagent into the imaging cup every cycle.

Another pipetting system was used to transfer sample after reaction incubation onto the cushion in the imaging cups (FIG. 46). The sample transfer pipette assembly consisted of two pipette tips, tubing to syringe pump system, a rotary and vertical motor. Sample transfer was a two cycle operation. During the first cycle, the liquid from the two adjacent mixing cups in the transfer position was aspirated by the two transfer pipettes. Next the liquid was dispensed on top of the cushion in two imaging cups. During the second cycle, the transfer pipettes were cleaned.

After reaction, selection, and imaging, the assay was completed and the cups required cleaning to prepare for a new sample. The cup cleaning station used is shown in FIG. 47. Each mixing and imaging cup was cleaned in a sequence that spanned seven stages, one per cycle. There were six cleaning stages and one drying stage. At the start of each stage, the cup cleaning unit was lowered into seven pairs of cups. Next, diaphragm pumps were engaged to dispense and aspirate cleaning liquid. Finally, the pumps were disengaged and the clearing unit was raised at the end of the cycle. The cup cleaning assembly (FIG. 47) consisted of six pairs of cleaning units and one pair of drying units. Each cleaning or drying unit was used for one cup at a time. Cleaning units were made of two concentric tubes in which the outside tube dispenses cleaning liquid and the inside tube aspirates. The final cleaning stage was a drying aspirator that consisted of a single aspirator tube.

In some cases, the liquid reagents required thorough mixing to satisfy assay performance requirements. The system used three ultrasonic surface acoustical wave (SAW) mixing units (Advalitix) as shown in FIG. 56. Mixing occurred as the sample was added. During a cycle, the mixing unit was raised such that its liquid reservoir contacted a mixing cup. A closed loop stepper motor with integrated amplifier (Oriental Motor, AS46A) was attached to a vertical linear axis (Deltron, DL26L-70-ST-C-PH) to mobilize the mixing apparatus. The transducer was engaged after contact was made with the liquid reservoir and turned off at the end of the cycle as the mixing unit was lowered.

Bulk liquids and waste containers were accessed by the user when the analyzer was powered down into a stand-by mode through either lower or upper doors that included electronic safety interlocking mechanisms.

Incubation. Once the reaction was fully mixed as described above, incubation began. Incubation time was five minutes, which was based on a cycle time of six seconds. Incubation was terminated by the reaction transfer pipettor followed by application of magnetic selection.

Managing Sample Input Information. The management of input sample information was designed to work in a surge testing application. Since surge testing often occurs in the result of an emergency, the system is designed to be fully automated. This minimizes complexity to the user and reduces the chances of errors.

The system uses a web server to provide a web interface for capturing patient information. This allows the simultaneous use of many patient input stations. At each patient input station sample was taken and stored in a barcodes sample container. The patient is given an identification (ID) unit (e.g. bracelet, FIG. 68) that matches or corresponds to the ID of the sample container. The ID information is scanned or entered into the patient record along with patient information. Sample tubes are added to the system as described above.

At the start of sample processing, the sample barcode is read. The sample barcode is stored as part of the sample record. At the end of processing, the final analysis result is computed and stored in the sample record. This information is associated with the patient record by the sample ID that was recorded during sample collection. The system uses a relational database to track patient and sample data.

Selection. Specific selection of targets is an important step of assay processing. This analyzer used magnetic selection to capture magnetic selection moieties that were given an opportunity to bind to possible targets in a sample. Magnetic selection occurred when the imaging cups were moved over the magnets as shown in FIG. 57. Selection time was 1 minute and included discrete spatial motions over the magnets during the capture time by the sample liquid being captured. The system uses a specific bar magnet configuration described in Example 2

Imaging. The system used an imaging system as described in Example 1. It used a CCD photo detector array (2 Mpixel CCD camera, uEye, UI-2550-M) to perform non-magnified imaging on a large sample target area.

Focus adjustment was accomplished by moving the camera assembly on each cycle as shown in FIG. 57. A closed loop stepper motor with integrated amplifier (Oriental Motor, AS46A) was attached to a vertical linear axis (Deltron, DL26L-70-ST-C-PH) to mobilize the imaging system such that it lifted the imaging cup a fixed distance from the optics. Mechanical tolerances of the cup and the imaging unit are less then the optical systems depth of field. Image analysis was computed as described in Example 3. FIG. 63 shows images captured from a typical assay.

Results reporting. Results are reported to multiple clients using a web interface. This interface supports various reports and analysis queries. The results are also shown on the system console. In addition, the system is designed to send results to an emergency command system through the command and control interface.

System Control. System control hardware included a system computer, a motion controller (8-axis Stepper Controller Ethernet, Galil, DMC-2183-DC24-DIN), and fluidics control system that included a Smart IO board (Cavro, PN 740029). Fluidics control system contains Fluidics control board, interfaced with the system computer via RS 485 serial bus. All syringe pumps and Cavro smart valves are controlled via this board. Diaphragm pumps are controlled via Smart IO board.

Surge testing software is described in Example 11. Software scheduling included the high level processing that ran during each cycle. The progress of each test was tracked such that an operation was performed only if it was required by an active test. A number of actions were performed in parallel, including carousel and station processing.

A cycle began by advancing the carousel. This moved each reaction to the next processing stage. The rest of the processing station sequences occurred in parallel. Reagents robots were moved to the reagent input where appropriate reagents were picked up. Then the reagent robots moved to mixing cups where reagents were deposited. The cushion pipette was moved into cushion reservoir, aspirated cushion, moved to an empty imaging cup, and then dispensed cushion. During even cycles, the sample transfer station robot moved into the completed mixing cups, picked up reaction liquid form two cups. During the odd cycles, the transfer robot moved to the imaging cups, deposited liquid into two cups. The sample robot aspirated sample from a new sample container every six cycles and was dispensed into six adjacent mixing cups for six sequential tests. The sample pipettor was moved into the sample container and aspirated 60 μL. Next, on each cycle, the sample pipettor was moved into a mixing cup and 10 μL of the sample was dispensed before the sample pipettor was raised. The sample cleaning station was designed with two sets of sample pipettes. While one was pipetting samples, the other was being cleaned. For the first six cleaning cycles, the unused sample pipettor was moved into the sample pipette cleaning module at which time cleaning commenced. During the last cleaning cycle, cleaning was stopped and the pipettor was moved into the ready position. Mixing transducer was moved into fluidic contact the mixing cup, the transducer was run, and then retracted upon completion of mixing. Imaging station assembly was moved into contact the imaging cup, LEDs were turned on, an image was acquired, the LEDs were turned off, the imaging assembly was retracted, the image was analyzed, and the analysis result was reported to the database. Cup cleaning station operation occurred by movement of the cup cleaning assembly into cups, the cup cleaning fluidics were started, cleaning ran for four seconds, the cup cleaning fluidics were stopped, and then the cup cleaning assembly was stopped. Bulk reagents were rocked once each cycle to insure consistency and prevent sedimentation. Input sample processing moved during the last of the six cycle sample sequence, to the input queue to the next sample container. When all sample containers in a rack were processed the rack was ejected into the biohazard trash container and the next rack in the queue was advanced as described above.

Experiment. Detection of *Bacillus anthracis* (Anthrax) Lethal factor in Human Whole Blood by Automated analysis on Surge testing analyzer.

This experiment describes the use of a fully automated high-throughput surge testing analyzer for assaying a bacterial toxin, the lethal factor of *B. anthracis*, in human whole blood. The assay uses mouse monoclonal anti-Anthrax lethal factor-coated fluorescent and magnetic particles to bind signaling moieties and selection moieties to lethal factor molecules contained in the human plasma sample. The fluorescent particle-lethal factor-magnetic particle complexes are deposited into the detection zone using magnetic selection through a dye cushion. A sample carrier containing whole blood samples spiked with different concentrations of lethal factor was presented to the analyzer. The analyzer assembled and incubated the reactions in reaction wells, and then overlaid each reaction on dyed cushion in an imaging well, transported the wells to a magnetic selection station, and imaged the wells automatically.

Method. All reagents were loaded into the reagent cups of a prototype high throughput surge testing analyzer. All pipetting steps described below were carried out by fully automated robotic pipettors under computer control. First, 10 μL of 200 mM EPPS (Sigma-Aldrich Catalog No. E9502) buffer containing 400 mM 1,3 Diaminopropane (Sigma-Aldrich Catalog No. D230807) pH 7.8 was added to the reaction cup followed by pipetting of 10 μL of a reagent containing 1 mg/mL Alginic acid (Sigma-Aldrich Catalog No. A2158), 2.5% w/v Polyvinylpyrrolidone (Sigma-Aldrich Catalog No. PVP40), 0.5 mg/mL bovine gamma globulin (Lampire Laboratories Catalog No. 7400805) and 1 mg/mL mouse gamma globulin (Jackson lmmunoresearch Catalog No. 015-000-002) in PBS). Ten μL of human whole blood spiked with Anthrax lethal factor ((List Laboratories, Catalog No. 172b) was added. Subsequently, 10 μL of a 0.007% w/v dilution of anti-Anthrax lethal factor fluorescent particles (Anti-hTSH antibody labeled fluorescent particles (Anthrax LF-FP) were prepared by chemically linking carboxylated 500 nm fluorescent particles (Invitrogen cat #8813) with free amino groups on mouse monoclonal anti-Anthrax LF (IQ Corp., Catalog No. LF-IQ) antibodies using a two step carbodiimide and N-sulfohydroxysuccinimide reaction using a standard method (Bioconjugate Techniques, Herrmanson Academic Press, 1996)) and 10 μL of a 0.05% w/v dilution of anti-Anthrax lethal factor magnetic particles (prepared using the same methods as the fluorescent particles above with this modification: the antibody was a mouse monoclonal antibody) were added, mixed by an onboard mixer, and incubated for 6 min. During the incubation 90 μL of dyed cushion reagent (30% Optiprep® (a 60% w/v solution of iodixanol) (Sigma-Aldrich D1556) 10 mg/ml Chromotrope 2R) was added to separate imaging cups automatically. After incubation, 40 µL of reaction mixture was layered on top of the dye-cushion layer in imaging wells of the analyzer. The imaging cups were then automatically moved over magnets within the analyzer and magnetic separation was carried out for 1 min. After the deposition of magnetic particles into the detection zone, the imaging cups were automatically moved to imaging stage and were then imaged on the analyzer using a 0.1 sec exposure time. Individual fluorescent particles were then enumerated and the sample results analyzed in an automated manner using software on the analyzer.

Results. The data generated using a fully automated surge-testing analyzer is presented in FIG. 74). The graph shows the dose response curve generated by automated analysis of the acquired images using software. These results demonstrate fully automated, specific and sensitive, detection of *B. anthracis* lethal factor from a complex matrix like human blood using non-magnified imaging without any washing steps. FIG. 63 shows images captured from a typical assay.

Conclusion. This example shows one device embodiment in which a one or more sample containers can be accepted directly into the device for high throughput surge testing. The device integrates a custom magnet array for application of selective forces and a CCD camera for unmagnified imaging. Liquid handing with bulk reagents and recycling of pipette tips and cups provides low per test cost while also minimizing accrual of solid waste.

Variations. There are many potential variations, including those listed in the detailed description of the device above. The cycle time can be adjusted to more or less than six seconds to suit the parameters required for a specific test. The device could use disposable cups or pipette tips, which may be beneficial to minimizing carryover and cross-contamination. The device could include more or fewer reagent pipettes that each can each access one or multiple reagents. An alternate drying tip design shown in FIG. 59 could be utilized or an alternate sample collection consumable could be used that employs capillary action (FIG. 60). The sample input could replace sample pipettors with an assembly that deposits samples directly from a sample container, such as shown in FIG. 61.

Example 15

Automated Cartridge-Based Analyzer for High Throughput Surge Testing

Overview. This example describes an analyzer which provides automated testing with ultra high throughput. The system is designed for use in biodefense or public health emergencies that require testing of many thousands of people who may have been exposed to a pathogen or other agent. The analyzer accepts single-sample assay cartridges. Each cartridge includes a lancet for drawing a capillary blood sample, Capillary blood is collected directly from the patient into the cartridge. The cartridge includes all reagents required to perform a panel of six assays. This embodiment fully automates all steps required to produce a test result from each input cartridge.

Description. FIG. 28 is the side view of the cartridge-based surge testing system. The Mobile analyzer has wheels for rapid deployment and set-up in emergency surge testing situations. Access to user functions is on one side of the analyzer, including loading of sample container input, LCD readout and controls, access to waste and front console, and storage.

Sample input. The sample is collected directly into the assay cartridge (FIG. 26) using the onboard lancet for drawing capillary blood, and the cartridge is loaded into a portable cartridge carrier (FIG. 27) for transport to the instrument. As they are filled, carriers are loaded into vacant slots at the top of the instrument. FIG. 29 illustrates the design of the analyzer.

Processing. The cartridges are dropped one by one from the loading racks into the activation slot of the reaction carousel, where the reaction is initiated on the cartridge. The carousel rotates stepwise in a counterclockwise direction so that after a six minute incubation, the cartridge passes over a magnetic selection device for a total of one minute. It then steps into the imaging station, where the reaction is imaged through a transparent detection surface. The timing scheme which uses cartridge rotation is illustrated in FIG. 30. Finally, the container is ejected to an onboard waste container (FIG. 29) and the next cartridge in the loading carousel replaces it at the same position. The waste bin is capable of holding the used cartridges consumed in one day.

The analyzer uses elements of other examples. Example 1 provides a description of the imaging subsystem. The 5 mega pixel CMOS camera takes an image of the viewing window. This captures all six reaction wells in an image. A final image is formed from a sum of 10 image frames. This increases the system dynamic range by a factor of ten. Proprietary software in the onboard computer analyzes the final image as described in Example 3. Focusing is based on fixed camera and container position. The total machine and container tolerances are less then the depth of focus.

Management of input sample information and results reporting operate the same as those described in Example 14

System Control: All analyzer operations, including system timing and scheduling, error handling and recovery, data storage, data transmission, system diagnostics, and image analysis are controlled by a small onboard computer. The onboard computer also controls the operations of subsystem components including the motor controller board, reaction carousel, loading carousel, LED control, camera functions, and the display panel. System software is described in Example 13.

Conclusion. This example demonstrates a cartridge-based high-throughput analysis system that accommodates assay formats using magnetics as a selective force for specific capture of targets, and incorporates a photodetector array for non magnified imaging of targets. It is designed for use in surge applications which require portability and easy set-up when used in alternative locations like a local gym or auditorium. It employs a system which does not require liquid handling or externally provided liquid reagents.

Alternative embodiments. Many other sample loading designs could be envisioned to replace the cartridge rack loading system. A complete alternative surge testing system design which substitutes liquid handling devices for the cartridge system is described in Example 14.

Example 16

Mobile, High Throughput Automated Analyzer with Liquid Handling for High Throughput Surge Testing Overview. The mobile automated surge testing analyzer is a device that accepts a queue of sample containers containing a liquid sample, performs several processing steps on each sample in series before a selective force is applied to the assay, and captures an unmagnified image with a photodetector array. The device provides automated testing with ultra high throughput of a single test type.

The system combines the high throughput architecture, with liquid handling, of the system described in Example 14, with the design for mobility and transport of the system described in example 15. High throughput is provided with internal liquid handling of bulk reagents for low cost per test; reagent packs can be added without stopping the system. The liquid handling, reaction carousel (FIG. 35), and other sub assembly allow for testing of 3 samples simultaneously. Storage, transport and setup are facilitated by a system that is both rugged, and designed to fit into stackable wheeled storage containers (FIG. 70). Thus, the mobile high throughput analyzer can be used for bio-defense or public health emergencies that require testing of many thousands of people that may have been exposed to a pathogen or disease, and where there is a need to rapidly increase the ability to do tests in a given locality, i.e., when an outbreak occurs in a particular city or locality, the installed, available base of analyzers may not be sufficient to handle the sudden surge in test demand; the analyzer described in this example is both mobile and has high throughput, so new analyzers can be moved to the locality as needed. Further, the analyzers are designed so that transport, installation and use can be performed rapidly, in a crisis situation, where personnel with previous experience may not be available.

Description. The analyzer in FIG. 69 is a front view of the high throughput, mobile, container based surge testing system. FIG. 70 shows a unit in a container, and how containers may be stacked. The Mobile analyzer is mobile with wheels for rapid deployment and set up in emergency surge testing situations. Access to user functions is from this side; loading of bulk reagent containers, LCD readout and controls, access to waste and front console, and storage.

Analyzer system operation is based a loading carousel and a reaction carousel (FIG. 29). The processing is an assembly line model, discussed in Example 14.

Sample input. User collects sample from patient in proprietary container. There is a lancet included for blood sample collection (FIG. 26) A user loads sample from one patient into one container. In the container, lyophilized reagents sit in chambers covered by an optically clear non-fluorescent viewing window to allow for imaging. One or more containers with sample are loaded into the rack seen at the top of FIG. 29. The rack is lowered into an empty position (carousel advances 1 rack position at the start of each cycle). The analyzer top level input carousel moves counter clockwise until a sample container reaches the start position. If it is empty, a sample container drops into a container to the reaction carousel at the activation station.

Processing container motion. FIG. 30 is the process model. In the activation station, the below mounted actuator (Firgelli L12-50-100-12-1) is aligned to the container so that a plunger in the container applies pressure to the liquid sample. This pressure will force the liquid sample into the reaction area, where it combines with reagents. This begins the reaction stage. The carousel rotates counterclockwise from the activation station, leaving a space for the next container to drop form the input carousel. In the reaction, separation selection and signaling moieties combine with targets of interest. The reaction incubates for 6 minutes in rotation. Then it enters the magnetics area, where the selection force will separate targets of interest from the reacted sample. This selection is one minute. After magnetic selection, the container is imaged, analyzed, and results displayed. Finally, the container is ejected to on board hazardous waste (FIG. 29) and the next input container (form the top carousel) replaces it at the same position. The waste bin is capable of a day's throughput for storage.

The analyzer uses elements of other examples. Example 1 provides a description of the imaging subsystem. The 5 mega pixel CMOS camera takes an image of the viewing window. This captures all six reaction wells in an image. A final image is formed from a sum of 10 image frames. This increases the system dynamic range by a factor of 10. Proprietary software in the onboard computer analyzes the final image as described in Example 3. Focusing is based on fixed camera and container position. The total machine and container tolerances are less then the depth of focus.

Managing input sample information and results reporting operate the same as described in Example 14.

Getting Ready for Next Sample. After ejecting the container, the reaction carousel is ready to accept a new sample container. The new container drops from the loading carousel into the open space on the reaction carousel.

System Control: All analyzer operations are controlled by the small onboard computer including system timing and scheduling, error handling and recovery, data storage, data transmission, system diagnostics, and image analysis. The onboard computer also controls the operations of subsystem components including the motor controller board, reaction carousel, loading carousel, LED control, camera functions, and display panel. System software is described in Example 13.

Conclusion. The analyzer shows development of system that accommodates assay formats using magnetics as a selective force for specific capture of targets. It incorporates a photodetector array for non magnified imaging of targets with LED illumination and on-board image analysis. It provides ultra high throughput and waste containment. It can be used for surge applications and increase the portability of the analyzer by using containers with on board liquid handling and no external liquids are required.

Alternative embodiments. Extend support to single test run by implementing direct input of individual containers. Addition targets could be imaged using dual color imaging as described in Example 5. Use single serpentine belt rather then separate loading and reaction carousel to reduce height and weight of a second carousel.

Example 17

Automated High Throughput Analyzer with a Large Menu of on Board Tests

Overview. The automated analyzer described in this example is a device that accepts sample containers, and has numerous tests for multiple targets using on board reagents. In the embodiment described in this example, the analyzer has on board reagents to carry out tests for 100 different analytes. The analyzer automatically processes each sample, applies a selective force, and uses low magnification large area imaging with a photodetector array to detect labeled targets. The ability to accept a wide array of samples, rapidly perform a wide array of tests with on board reagents, provide low cost per test, and use software to provide test information to users, makes this analyzer well suited for situations where very high throughput may be needed, as in a clinical laboratory.

The analyzer minimizes user costs by minimizing biohazardous solid trash generation, which is particularly important for high volume users. Solid waste is reduced by recycling and reusing components, including the mixing and reaction cups and pipette tips. These components are designed with materials and surface treatment so as to have minimal carry over, which facilitates cleaning. Trash streams are also minimized by decreasing sample contact, such as utilizing non-contact mixing and non-contact reagent dispensing. Since these components never contact the sample, they can be reused indefinitely without need for cleaning or replacement. The analyzer also minimizes costs by minimizing the volume of test reagents used.

Low sample volume is important for minimizing reagent consumption, increasing patient throughput, and facilitates testing when patients include infants, elderly, or other low sample-yielding persons. Collection of a small sample volume that also minimizes or eliminates the need for sample preparation is beneficial in a potentially disorganized and chaotic environment where a large number of patients need rapid screening.

The analyzer manages patient information in a secure manner and communicates between hospital database systems, central command, and the vendor for diagnostic and bulk reagent resupply. Maintenance and service requirements are minimized to a regular routine in which the device is operational with short set-up time and can run continuously for several days.

Description. Samples are delivered by a sample track system (FIG. 37). The analyzer (FIG. 38) has two circular, rotating carousels (FIG. 40). One carousel is for samples and one is for reagent packs. Beneath the carousels are sub assemblies for mixing, temperature control, imaging and magnetic selection. The analyzer also provides space for analyzer subassemblies such as pumps, electronics and power supplies, and storage for waste and bulk liquid reagents (e.g. water and cleanser). Key functional elements are shown in FIG. 40 and FIG. 39. The sample carousel has two concentric circles of reusable cups, mixing cups, where sample is contacted with reagents, and reaction cups, where the mixture of sample plus reagents (the reaction mix) is overlaid on a dye cushion. The reaction cups pass over the magnet, for selection. After magnetic selection, the reaction cups pass over an imaging system, which acquires a low magnification image using a photodetector array. The imaging system is a high resolution focusing system with LEDs as a light source, and emission and excitation filters to allow imaging of fluorescent signaling moieties, e.g., fluorescent micro particles (Invitrogen, catalog number F-8813). After image acquisition, an onboard computer with custom software processes the image, and delivers results as required by the user.

Both the reaction and mixing cups are reusable; cleaning of the reaction cup occurs after imaging. Cleaning of the mixing cup can occur at any point after transfer of the reaction mix to the reaction cup. A cup cleaning system (FIG. 40) uses pipetting robots with a single axis of movement to reduce carry over. A drying station ensures that a reproducible amount of liquid is present in each cup prior to addition of sample.

The overall scheme is conceptually similar to the scheme shown for the analyzer in Example 14, in that a rotating carousel with fixed cups allows for high throughput, sequentially processed reactions. The most significant difference is the provision for a second rotating carousel, which can hold reagents for 100 different tests, e.g. the analyzer has all of the reagents needed, on board to perform multiple tests.

Reagent packs are labeled with a barcode. Scanning of the barcode provides information to the analyzer software, such as the location of the reagent pack, the identity of the reagent, and calibration files that need to be used, and so forth. On board software informs user in a timely manner to change reagent packs as needed. The reagent pack carousel provides for temperature control of reagents.

Conclusion. The analyzer shows development of system that accommodates assay formats using magnetics as a selective force for specific capture of targets. It incorporates a photo detector array detector for non-magnified imaging of targets with on-board image analysis. It provides ultra high throughput and waste containment.

Alternate embodiments. There are many potential variations, including those listed in the detailed description of the device above. The cycle time can be adjusted to suit the parameters required for a specific test. The device could use disposable cups or pipette tips, which may be beneficial to minimizing carryover and cross-contamination. The device could include more or fewer reagent pipettes that each can each access one or multiple reagents. An alternate drying tip design shown in FIG. 59 could be utilized or an alternate sample collection consumable could be used that employs capillary action (FIG. 60). The sample input could replace sample pipettors with an assembly that deposits samples directly from a sample container, such as shown in FIG. 61.

Sample input. After samples are placed in the sample track system by the user, the analyzer scans sample barcodes, and checks for what tests are required. If necessary, stat samples with manual data entry are allowed. If more then one test is required for a sample, the sample subsystem can deliver aliquots of the same sample to multiple wells.

Mixing and incubation. Sample is contacted with reagents in the mixing cups. Reagents other than sample are added by pipetting robots. Depending on the assay, one or more reagents may be added, and the order of addition may vary. The analyzer has a mixing capability, to effect mixing of sample with reagents and temperature control, to maintain the reaction at a fixed temperature.

Cleaning. Cleaning may be affected by plasma cleaners, which can be used to clean both pipette tips and cups. To ensure minimal carryover, cleaning may include a step of preconditioning or coating a surface; this coating or preconditioning step may also serve to increase or decrease the wet ability of a surface.

The invention claimed is:

1. An automated imaging analyzer for detecting individual microscopic targets at low magnification, the automated image analyzer comprising:
   a sample cartridge, the sample cartridge comprising a sample input reservoir having a sample therein, a first plurality of wells configured for fluid communication with the sample input reservoir, and a plurality of imaging wells, wherein each imaging well of the plurality of imaging wells is configured for fluid communication with a respective well of the first plurality of wells, each imaging well comprising a detection surface;
   a housing configured to accept the sample cartridge;
   a reagent processing subsystem operable to:
      mobilize the sample within the sample input reservoir of the sample cartridge to disperse the sample into the first plurality of wells through a first plurality of channels of the sample cartridge, and
      mobilize the sample from each well of the first plurality of wells of the sample cartridge into a respective imaging well of the plurality of imaging wells of the sample cartridge through a second plurality of channels of the cartridge,
   wherein the reagent processing subsystem is configured to actuate at least one valve of the sample cartridge and apply a pressure gradient to the sample cartridge to cause flow of the sample within the sample cartridge to disperse the sample into the first plurality of wells, and a magnetic station comprising a magnet connected to the housing and disposed to apply a selective force to move magnetic particles in each respective imaging well to deposit the magnetic particles on said detection surface of the respective imaging well;

an imaging station comprising a collecting lens arranged to collect optical signal from the detection surface;

a photoelectric array detector connected to the housing and disposed to receive the optical signal and produce an image of individual particles deposited on the detection surface; and a conveyor operable to move the sample cartridge between a plurality stations within the housing, the plurality of stations comprising the imaging station and the magnetic station, wherein the image has lower than 5-fold magnification, and wherein the individual microscopic targets are detectable within the image.

2. The analyzer of claim 1 wherein the collecting lens has lower than 5-fold magnification.

3. The analyzer of claim 1 wherein the analyzer comprises a motor that is configured to adjust the distance between said photo array detector and the sample cartridge.

4. The analyzer of claim 1 wherein said analyzer comprises a light source positioned within the housing, wherein the light source is configured to illuminate said sample cartridge when the sample cartridge is positioned at the imaging station.

5. The analyzer of claim 4 wherein said light source comprises light emitting diodes for illuminating said sample cartridge.

6. The analyzer of claim 1 wherein the housing of said analyzer is configured to accept a rack that contains multiple sample cartridges into the analyzer.

7. The analyzer of claim 1 wherein one station of the plurality of stations comprises a bar code reader.

8. The analyzer of claim 1 wherein one station of the plurality of stations comprises an incubator, wherein the incubator comprises an enclosure that accommodates said sample cartridge, wherein the incubator is configured to stably maintain an average temperature within the enclosure within 2 degrees Celsius of a temperature set point.

9. The analyzer of claim 1, further comprising a system processor, wherein said analyzer comprises a printer, electronic monitor, and/or system for connections to an external communication network, wherein said printer, electronic monitor, and/or system is in communication and operably associated with the system processor and the photoelectric array detector.

10. The analyzer of claim 1 further comprising a system processor and non-volatile, non-transitory memory in communication and operably associated with the conveyor, the system processor operable to run integrated scheduling software stored in the non-volatile, non-transitory memory for managing the movement of the sample cartridge between stations of the plurality of stations in said analyzer using the conveyor.

11. The analyzer of claim 8, wherein the incubator is configured to receive therein and simultaneously incubate the first plurality of wells of the sample cartridge.

12. The analyzer of claim 1, wherein one or more test reagents and growth media contained within the sample cartridge are dried before the sample cartridge enters the housing.

13. The analyzer of claim 1, wherein each imaging well of the plurality of imaging wells of the sample cartridge, upon receiving a sample from the respective well of the first plurality of wells, is configured to provide a dye cushion comprising a dye and a liquid layer overlying the dye cushion, the liquid layer including the sample and test reagents, the dye cushion being denser than the overlying liquid layer, wherein all test reagents and growth media are contained within the sample cartridge before the sample cartridge enters the housing.

14. The analyzer of claim 11 wherein said sample cartridge has a height greater than 8 mm.

15. The analyzer of claim 8, wherein the plurality of stations comprises an incubation station that comprises the incubator, wherein the analyzer is configured to incubate the cartridge for a predetermined time.

16. The analyzer of claim 1, wherein the conveyor comprises at least one of a carousel, a gantry, a conveyor belt, or a drive cable.

17. The analyzer of claim 1, further comprising a system processor and non-transitory memory in communication and operably associated with the system processor, wherein the non-transitory memory comprises instructions that, when executed by the system processor, cause the system processor to perform a field flattening of the image to adjust the image for uneven lighting effects.

18. The analyzer of claim 1, further comprising a system processor and non-transitory memory in communication and operably associated with the system processor, wherein the non-transitory memory comprises instructions that, when executed by the system processor, cause the system processor to analyze the image to determine at least one error condition based on at least one of a missing sample container, a blocked image, inadequate lighting, or a damaged sample cartridge.

19. The analyzer of claim 1, wherein the image comprises a plurality of pixels, the analyzer further comprising a system processor and non-transitory memory in communication and operably associated with the system processor, wherein the non-transitory memory comprises instructions that, when executed by the system processor, cause the system processor to associate a plurality of adjacent pixels of the plurality of pixels as a blob.

20. The analyzer of claim 19, wherein the non-transitory memory comprises instructions that, when executed by the system processor, cause the system processor to associate the plurality of adjacent pixels as a blob based on at least one of center position, area in pixels, intensity, mean intensity, perimeter, minimum pixel value, maximum pixel value, width, height, aspect ratio, and compactness.

21. The analyzer of claim 20, wherein the non-transitory memory comprises instructions that, when executed by the system processor, cause the system processor to assign the blob as one of signal or debris.

22. The analyzer of claim 1, wherein the photoelectric array is configured to produce a plurality of images of individual particles deposited on the detection surface, the plurality of images comprising the image, the analyzer further comprising a system processor and non-transitory memory in communication and operably associated with the system processor, wherein the non-transitory memory comprises instructions that, when executed by the system processor, cause the system processor to compare frames of a plurality of images to detect motion of signal components between the plurality of images.

23. The analyzer of claim 1, further comprising a system processor and non-transitory memory in communication and operably associated with the system processor, wherein the non-transitory memory comprises instructions that, when executed by the system processor, cause the system processor to:

determine, based on an algorithm, a region of interest; and exclude at least one pixel from analysis of the region of interest based on the at least one pixel having an intensity outside of a predetermined range.

24. The analyzer of claim 1, wherein the sample cartridge comprises optical labels that are configured to bind with targets to form optically labeled targets, wherein the image of individual particles deposited on the detection surface is an image of optically labeled targets, wherein the imaging station is configured to detect individual optically labeled targets by detecting pixels that correspond to respective locations of the optically labeled targets.

25. The analyzer of claim 1, wherein the image is non-magnified.

26. The analyzer of claim 19, wherein the system processor and non-transitory memory in communication and operably associated with the system processor are remote to the housing.

27. The analyzer of claim 19, wherein the system processor and non-transitory memory in communication and operably associated with the system processor provided within the housing.

* * * * *